US010624586B2

(12) United States Patent
Noguchi et al.

(10) Patent No.: US 10,624,586 B2
(45) Date of Patent: Apr. 21, 2020

(54) PULSE WAVE MEASURING DEVICE, MOBILE DEVICE, MEDICAL EQUIPMENT SYSTEM AND BIOLOGICAL INFORMATION COMMUNICATION SYSTEM

(71) Applicant: Asahi Kasei Kabushiki Kaisha, Tokyo (JP)

(72) Inventors: Yoshihiro Noguchi, Tokyo (JP); Shimpei Ogawa, Tokyo (JP); Masaya Yamashita, Tokyo (JP); Akihiro Okamoto, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/189,207

(22) Filed: Jun. 22, 2016

(65) Prior Publication Data

US 2016/0302735 A1 Oct. 20, 2016

Related U.S. Application Data

(63) Continuation of application No. PCT/JP2014/084177, filed on Dec. 24, 2014.

(30) Foreign Application Priority Data

Dec. 25, 2013 (JP) .................................. 2013-267106
Oct. 17, 2014 (JP) .................................. 2014-213213

(51) Int. Cl.
*A61B 5/00* (2006.01)
*A61B 5/029* (2006.01)
(Continued)

(52) U.S. Cl.
CPC .......... *A61B 5/7278* (2013.01); *A61B 5/0022* (2013.01); *A61B 5/0077* (2013.01);
(Continued)

(58) Field of Classification Search
CPC . A61B 5/0022; A61B 5/0077; A61B 5/02108; A61B 5/02125; A61B 5/02416;
(Continued)

(56) References Cited

U.S. PATENT DOCUMENTS

2005/0075553 A1 4/2005 Sakai et al.
2007/0016085 A1 1/2007 Inukai et al.
(Continued)

FOREIGN PATENT DOCUMENTS

CN 101394785 A 3/2009
JP H5-285218 A 11/1993
(Continued)

OTHER PUBLICATIONS

Maeda et al., "Implementation of FFT by Interpolation", High Performance Computing 93-16, Mar. 12, 2003, pp. 89-94.
(Continued)

*Primary Examiner* — Paula J Stice
(74) *Attorney, Agent, or Firm* — Morgan, Lewis & Bockius LLP

(57) ABSTRACT

A pulse wave measuring apparatus is provided, the pulse wave measuring apparatus including: a cardiac pulse waveform information acquiring unit that optically acquires cardiac pulse waveform information from a region of a living body; and a pulse wave feature amount calculating unit that calculates a pulse wave feature amount based on the pulse waveform information, wherein the pulse waveform information acquiring unit has a video input unit that receives an input of a video of the region of the living body, and the pulse waveform information acquiring unit outputs a window signal that includes first sample data from the pulse waveform information, and outputs, from the video, the window signal whose sampling rate is fixed to a predetermined rate based on a reference signal indicating time.

49 Claims, 99 Drawing Sheets

(51) Int. Cl.
  *A61B 5/021* (2006.01)
  *A61M 1/16* (2006.01)
  *A61B 5/02* (2006.01)
  *A61B 5/024* (2006.01)
  *A61B 5/117* (2016.01)

(52) U.S. Cl.
  CPC .......... *A61B 5/02007* (2013.01); *A61B 5/029* (2013.01); *A61B 5/02108* (2013.01); *A61B 5/02125* (2013.01); *A61B 5/02416* (2013.01); *A61B 5/117* (2013.01); *A61B 5/4836* (2013.01); *A61B 5/6819* (2013.01); *A61B 5/6826* (2013.01); *A61B 5/6898* (2013.01); *A61B 5/7246* (2013.01); *A61B 5/742* (2013.01); *A61B 5/746* (2013.01); *A61M 1/1601* (2014.02); *A61M 2230/005* (2013.01)

(58) Field of Classification Search
  CPC ..... A61B 5/029; A61B 5/3836; A61B 5/6819; A61B 5/6826; A61B 5/6898
  See application file for complete search history.

(56) References Cited

U.S. PATENT DOCUMENTS

| | | |
|---|---|---|
| 2008/0306372 A1 | 12/2008 | Ohki et al. |
| 2009/0043210 A1* | 2/2009 | Kitoh ................. A61B 5/0059 600/476 |
| 2009/0050544 A1 | 2/2009 | Zhang |
| 2012/0022382 A1 | 1/2012 | Daisuke et al. |
| 2012/0266742 A1 | 10/2012 | Touyama et al. |
| 2013/0281868 A1 | 10/2013 | Kawachi et al. |
| 2013/0322729 A1 | 12/2013 | Mestha et al. |
| 2014/0012142 A1 | 1/2014 | Mestha et al. |
| 2015/0011851 A1* | 1/2015 | Mehta ................. A61B 5/7221 600/324 |

FOREIGN PATENT DOCUMENTS

| | | |
|---|---|---|
| JP | H10-295657 A | 11/1998 |
| JP | H11-113863 A | 4/1999 |
| JP | 2002-320593 A | 11/2002 |
| JP | 2005-160640 A | 6/2005 |
| JP | 2006-006897 A | 1/2006 |
| JP | 2007-125151 A | 5/2007 |
| JP | 2008-279185 A | 11/2008 |
| JP | 2010-094410 A | 4/2010 |
| JP | 2010-187993 A | 9/2010 |
| JP | 2010-220690 A | 10/2010 |
| JP | 2011-101698 A | 5/2011 |
| JP | 2012-081063 A | 4/2012 |
| JP | 5067024 B2 | 8/2012 |
| JP | 2012-226106 A | 11/2012 |
| JP | 2013-226189 A | 11/2013 |
| JP | 2013-248386 A | 12/2013 |
| WO | 2007/043328 A1 | 4/2007 |

OTHER PUBLICATIONS

International Search Report dated Mar. 17, 2015, for International application No. PCT/JP2014/084177.

International Preliminary Report on Patentability and Written Opinion dated Jul. 7, 2016, for International application No. PCT/JP2014/084177.

\* cited by examiner

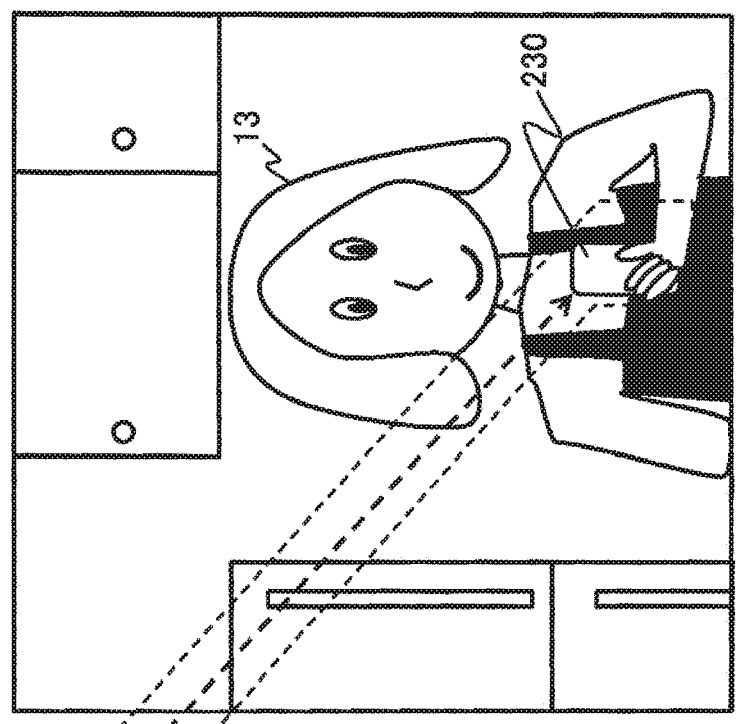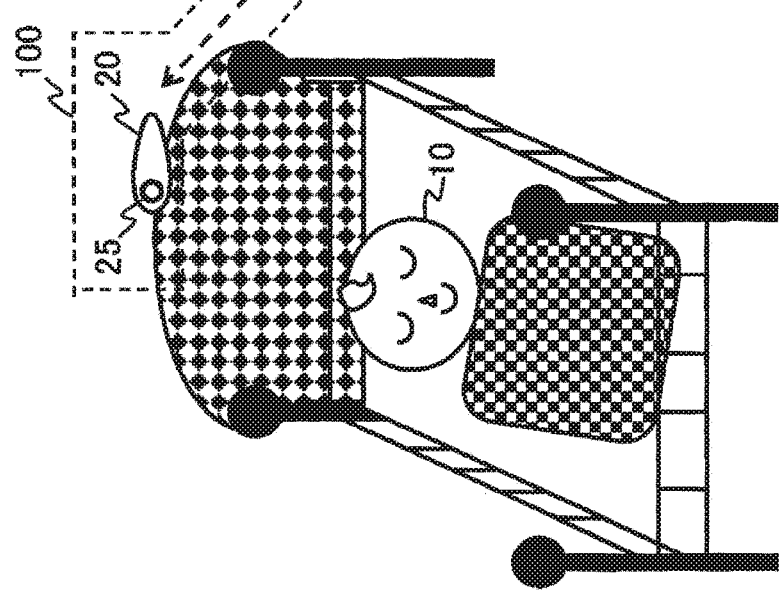
FIG. 9

320

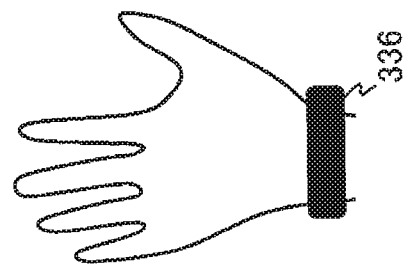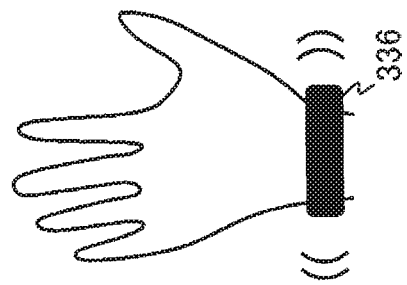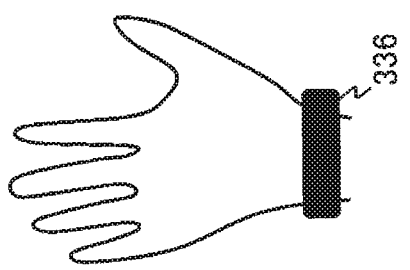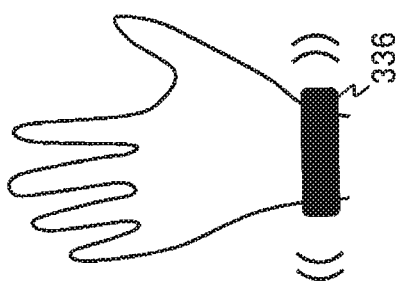
FIG. 99
NORMAL STATE
WHEN EMPATHY OCCURRED

PULSE WAVE MEASURING DEVICE, MOBILE DEVICE, MEDICAL EQUIPMENT SYSTEM AND BIOLOGICAL INFORMATION COMMUNICATION SYSTEM

The contents of the following Japanese patent application(s) are incorporated herein by reference:
NO. 2013-267106 filed in JP on Dec. 25, 2013
NO. 2014-213213 filed in JP on Oct. 17, 2014, and
NO. PCT/JP2014/084177 filed on Dec. 24, 2014

BACKGROUND

1. Technical Field

The present invention relates to a pulse wave measuring apparatus, a mobile device, a medical equipment system and a biological information communication system.

2. Related Art

Conventionally, a sheet called a cuff that is swollen by air pressure has been used in a blood pressure measuring apparatus that measures human blood pressure. The cuff is wrapped around an arm of a human, is swollen by air pressure, and applies a large pressure to the arm. Conventional blood pressure measuring apparatuses measure blood pressure based on the repulsive force of blood vessels in an arm when pressure is applied thereto (see, for example, Patent Document 1).

Patent Document 1: Japanese Patent Application Publication No. 2010-94410

However, because conventional blood pressure measuring apparatuses apply large pressures to living bodies by using cuffs, the burden on the living bodies is significant.

SUMMARY

Therefore, it is an object of an aspect of the innovations herein to provide a pulse wave measuring apparatus, a mobile device, a medical equipment system and a biological information communication system, which are capable of overcoming the above drawbacks accompanying the related art. The above and other objects can be achieved by combinations described in the claims. That is, a first aspect of the present invention provides a pulse wave measuring apparatus comprising: a pulse waveform information acquiring unit that optically acquires pulse waveform information from a region of a living body; and a pulse wave feature amount calculating unit that calculates a pulse wave feature amount based on the pulse waveform information.

A second aspect of the present invention provides a mobile device comprising the pulse wave measuring apparatus according to the first aspect; and a display that displays at least either of attribute information and health information.

A third aspect of the present invention provides a medical equipment system comprising: the pulse wave measuring apparatus according to the first aspect; and medical equipment controlled based on health information.

A fourth aspect of the present invention provides a biological information communication system comprising a correlation judging unit that has a plurality of the pulse wave measuring apparatuses according to the first aspect, and judges respective correlations of a plurality of the pulse wave feature amounts or pieces of health information calculated by the plurality of the pulse wave measuring apparatus, wherein when there is a correlation that is higher than a predetermined value among the respective correlations, the correlation judging unit transmits, to a pulse wave measuring apparatus that calculates a corresponding pulse wave feature amount among the plurality of pulse wave feature amounts, information indicating that the correlation is higher than the predetermined value.

The summary clause does not necessarily describe all necessary features of the embodiments of the present invention. The present invention may also be a sub-combination of the features described above.

BRIEF DESCRIPTION OF THE DRAWINGS

FIG. 9 shows the blood pressure information output apparatus 100 according to Embodiment 9.

FIG. 99 shows one example of the empathy detection system 500 according to Embodiment 25.

DESCRIPTION OF EXEMPLARY EMBODIMENTS

Hereinafter, (some) embodiment(s) of the present invention will be described. The embodiment(s) do(es) not limit the invention according to the claims, and all the combinations of the features described in the embodiment(s) are not necessarily essential to means provided by aspects of the invention.

Embodiment 1

Figure 1:
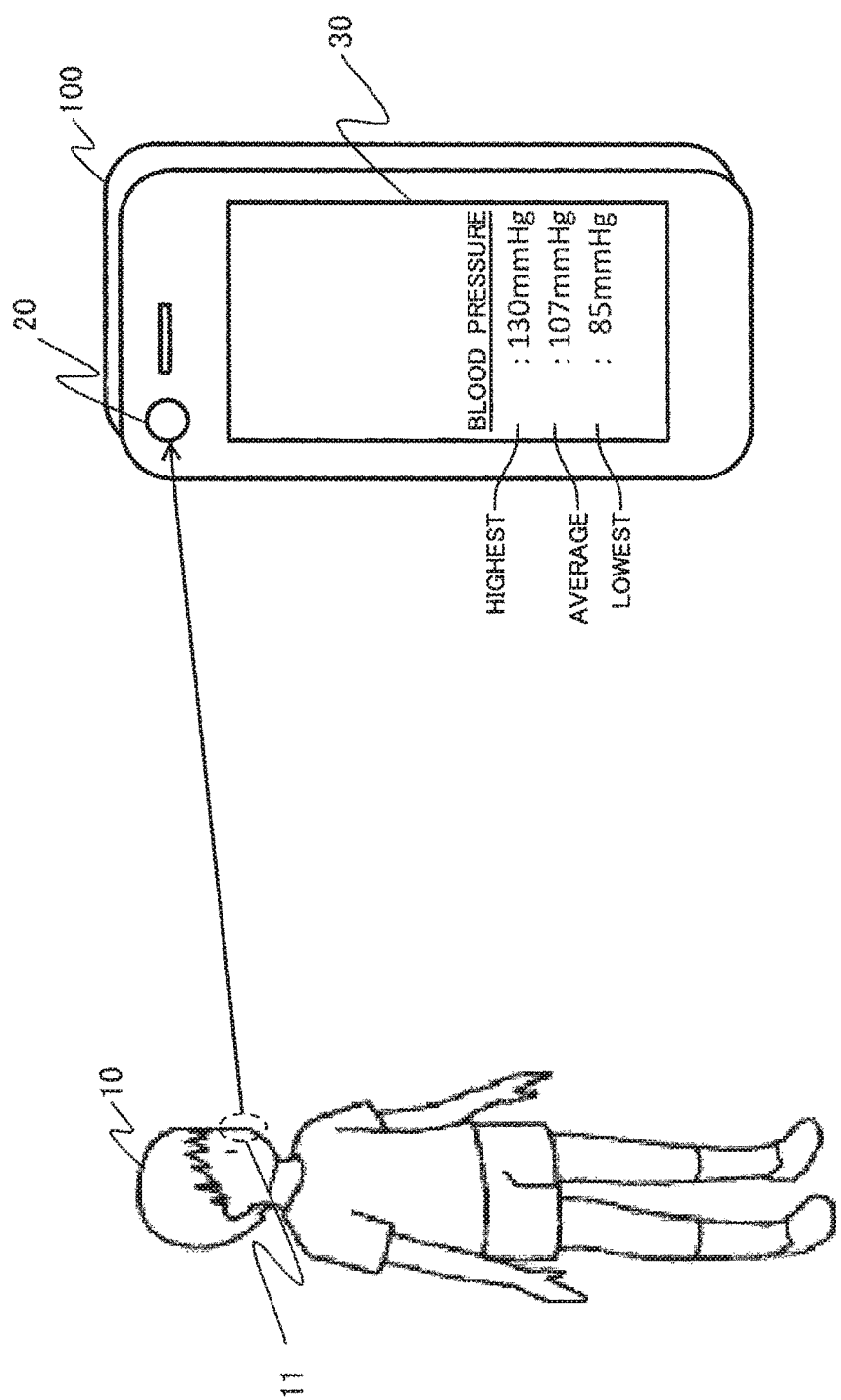
FIG. 1 shows a blood pressure information output apparatus 100 according to Embodiment 1.

FIG. 1 shows a blood pressure information output apparatus 100 according to Embodiment 1. The blood pressure information output apparatus 100 according to the present example is implemented in a smartphone. The blood pressure information output apparatus 100 comprises a video input unit 20 and a blood pressure information output unit 30.

The video input unit 20 receives an input of a video of a single region of a living body 10. The video input unit 20 comprises a camera, and captures a video of the living body 10. The video input unit 20 according to the present example acquires a video including a single region in the living body 10. Thereby, a video having pulse waveform information of the living body 10 is optically input to the video input unit 20. A pulse wave is a temporal waveform showing pulsation of blood vessels at a region of the living body 10. pulse waveform information is information related to the temporal waveform. For example, pulse waveform information includes information related to timing at which a pulse wave shows a peak. In the present example, a video of the nose 11 of the living body 10 is input to the video input unit 20 via the camera. Note that in the present specification, when the phrase "video of the living body 10" appears, it refers to a video including a single region in the living body 10. This applies similarly to a case where a video is a previously recorded moving image or the like.

The blood pressure information output unit 30 outputs blood pressure information of the living body 10 based on a video input to the video input unit 20. The blood pressure information output unit 30 comprises a display that displays blood pressure information. Here, blood pressure information is about blood pressure BP, states of blood vessels such as a high blood pressure state, a normal blood pressure state, a low blood pressure state or arteriosclerosis, a vascular age, or information related to the blood pressure BP such as a predisposition to stroke or the like. In the present example, a systolic blood pressure (Highest: 130 mmHg), an average blood pressure (Average: 107 mmHg), and a diastolic blood pressure (Lowest: 85 mmHg) of the living body 10 are being displayed on the blood pressure information output unit 30.

According to the hemoglobin concentration of the blood of the living body 10, its light absorbing property for G components (green components) among RGB components in light changes. Because a pulse wave corresponds to variation in a blood flow amount, the cycle of variation in G components in light transmitted through or reflected by the living body 10 corresponds to the cycle of a pulse wave of the living body 10. That is, a video of the nose 11 of the living body 10 in the present example includes a variation waveform of G components according to a pulse wave.

The blood pressure information output apparatus 100 extracts a pulse wave component signal of blood vessels in the nose 11 from a video of the nose 11. The pulse wave component signal is a RGB signal or a YCbCr signal of a video including pulse waveform information. The blood pressure information output apparatus 100 calculates a pulse rate HR of the living body 10 and temporal information of a pulse wave of the living body 10 from a video of the living body 10. Temporal information refers to rising time TR or falling time TF of a pulse wave. The blood pressure information output apparatus 100 estimates and outputs blood pressure BP from a pre-calculated relational expression among a pulse rate HR, temporal information of a pulse wave and blood pressure BP, and the pulse rate HR and the temporal information of a pulse wave.

The video input unit 20 may detect motion of a single region in the living body 10, and capture images by tracking the region. When a single region of the living body 10 is moving toward the outside of an image-capture region of the camera while a pulse wave is being detected, the video input unit 20 may perform control so that the single region is within the image-capture region of the camera by controlling pan, tilt, zoom or the like of the camera. Also, the blood pressure information output apparatus 100 may calculate pulse information based on pulse waveform information acquired in a period during which the moving speed of a region of a single portion is equal to or lower than a predetermined value.

Although the blood pressure information output apparatus 100 according to the present example uses a video of the nose 11 of the living body 10, it may use a video of a fingertip of the living body 10. For example, the blood pressure information output apparatus 100 acquires a video of a fingertip by using an optical fingerprint sensor provided on the rear surface of a smartphone. Also, the region a video of which is to be captured is not limited to the nose 11 and a fingertip, and the blood pressure information output apparatus 100 may acquire a video of a single region of the living body 10. The nose 11 and a fingertip are where capillaries concentrate; thus, the hemoglobin concentration is high. For this reason, by using a video of the nose 11 and a video of a fingertip, the sensitivity of extracting the pulse waveform information and the accuracy of calculating the pulse information become high. Furthermore, the pulse waveform information may be extracted by using a single photoelectric plethysmogram wave meter worn on a fingertip.

Because in this manner, the blood pressure information output apparatus 100 according to the present example optically extracts the pulse waveform information and outputs the blood pressure information, the burden on the living body 10 is small. Also, because the blood pressure information output apparatus 100 does not require time for pressurization and depressurization that are required when a cuff is used, real-time blood pressure information can be output. Real-time blood pressure information refers to real-time blood pressure information that is detected continuously in every predetermined period. Furthermore, because the blood pressure information output apparatus 100 according to the present example is configured to extract pulse waveform information from a video, blood pressure information can be estimated without contacting or binding a living body. Note that if a plurality of people is present in a video from the camera, the blood pressure information output apparatus 100 can estimate blood pressure information of the plurality of people simultaneously.

Embodiment 2

Figure 2:
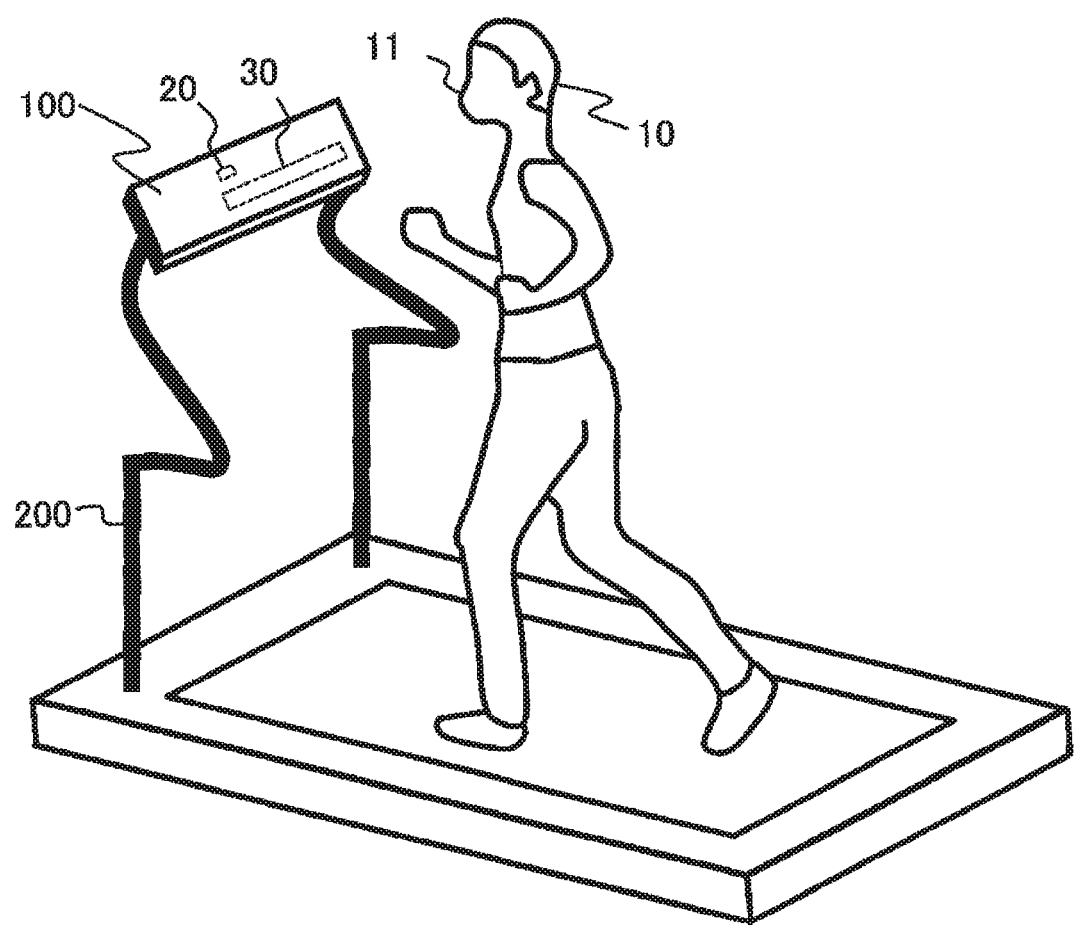
FIG. 2 shows the blood pressure information output apparatus 100 according to Embodiment 2.

FIG. 2 shows the blood pressure information output apparatus 100 according to Embodiment 2. The blood pressure information output apparatus 100 comprises the video input unit 20 and the blood pressure information output unit 30. The blood pressure information output apparatus 100 according to the present example is implemented inside a treadmill 200. The treadmill 200 is an exercise machine such as a running machine, a walking machine, an exercise bike at a fitness gym or the like. The treadmill 200 according to the present example is a running machine.

The video input unit 20 comprises a camera, and captures a video of the nose 11 of the living body 10 who is exercising on the treadmill 200. The blood pressure information output unit 30 comprises a display, and displays blood pressure information on the display. Thereby, the living body 10 can check the blood pressure information of himself/herself while exercising. Note that the blood pressure information output unit 30 may display a pulse rate HR in addition to the blood pressure information.

Embodiment 3

Figure 3:
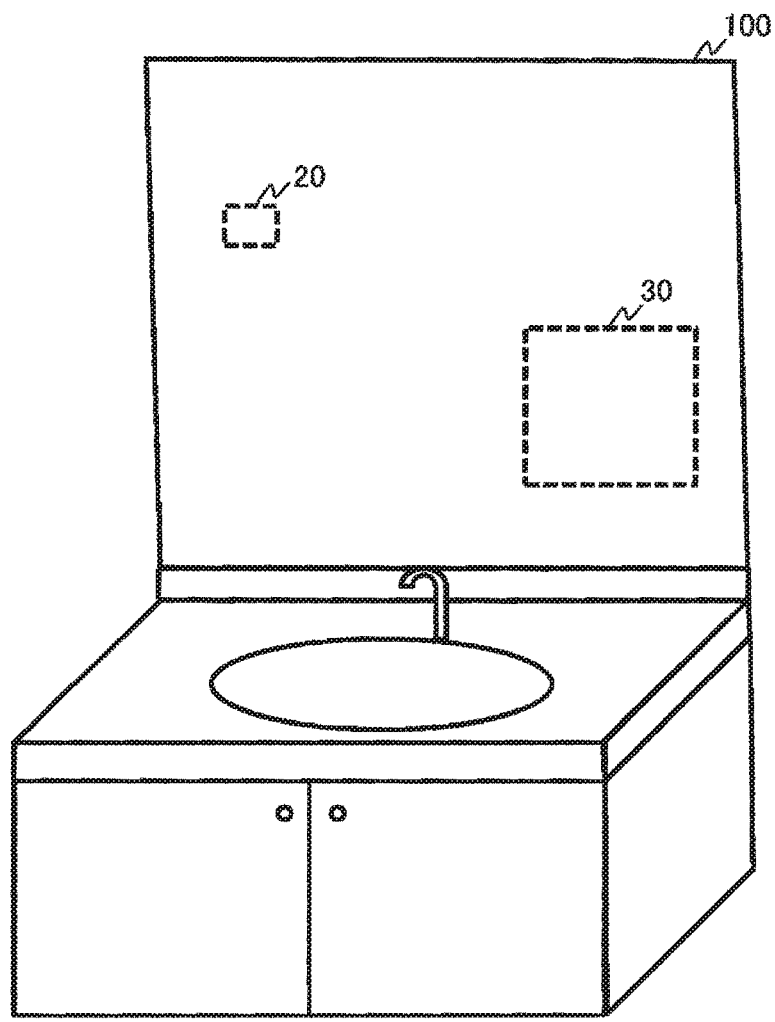
FIG. 3 shows the blood pressure information output apparatus 100 according to Embodiment 3.

FIG. 3 shows the blood pressure information output apparatus 100 according to Embodiment 3. The blood pressure information output apparatus 100 comprises the video input unit 20 and the blood pressure information output unit 30. The blood pressure information output apparatus 100 is implemented in a mirror of a washstand.

The video input unit 20 comprises a camera, and captures a video of the nose 11 of the living body 10 who is washing hands, brushing teeth or doing other things in front of the washstand. The blood pressure information output unit 30 comprises a display, and displays, on the display, blood pressure information of the living body 10 according to the video captured by the video input unit 20. Thereby, the living body 10 can know blood pressure information of himself/herself while washing hands, brushing teeth, or doing other things. Because the blood pressure information output apparatus 100 according to the present example can measure the blood pressure information simply and effortlessly, the blood pressure BP can be monitored constantly.

Embodiment 4

Figure 4:
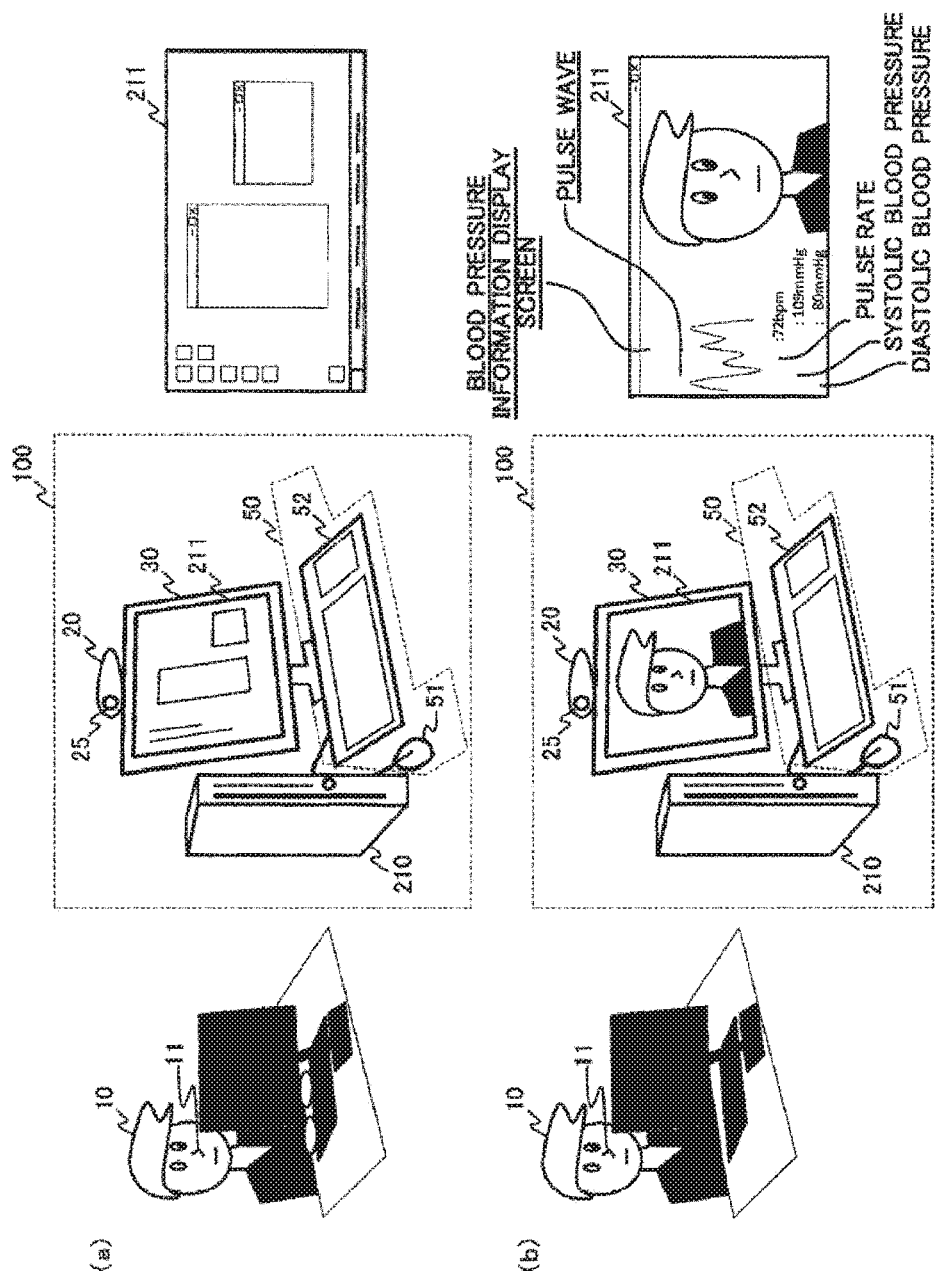
FIG. 4 shows the blood pressure information output apparatus 100 according to Embodiment 4.

FIG. 4 shows the blood pressure information output apparatus 100 according to Embodiment 4. The blood pressure information output apparatus 100 comprises the video input unit 20, the blood pressure information output unit 30, an information input apparatus 50 and a PC main body 210. The blood pressure information output apparatus 100 is implemented in a personal computer (PC), and functions as a healthcare screen saver computer that displays blood pressure information on a screen saver.

The video input unit 20 comprises a camera 25, and captures a video of the living body 10 who is operating the PC. The information input apparatus 50 comprises a mouse 51 and a keyboard 52. The living body 10 operates the mouse 51 and the keyboard 52 to transmit an instruction or input information to the PC main body 210.

The PC main body 210 is connected to the video input unit 20, the blood pressure information output unit 30 and the information input apparatus 50. The PC main body 210 estimates blood pressure information based on a video input from the video input unit 20. Also, based on the information input from the information input apparatus 50, the PC main body 210 determines whether or not to display the estimated blood pressure information on the blood pressure information output unit 30.

The blood pressure information output unit 30 comprises a monitor display 211. The monitor display 211 displays information that has been transmitted from the PC main body 210 and corresponds to operation by the living body 10. Also, the monitor display 211 displays blood pressure information as a screen saver. In other words, the monitor display 211 functions as a display for displaying blood pressure information.

(a) of FIG. 4 shows the blood pressure information output apparatus 100 in a case where the living body 10 is operating the information input apparatus 50. The PC main body 210 transmits, to the blood pressure information output unit 30, information according to operation of the PC when the living body 10 is operating the information input apparatus 50. In other words, the PC main body 210 outputs, to the blood pressure information output unit 30, information according to usual PC operation when the living body 10 is operating the information input apparatus 50.

(b) of FIG. 4 shows the blood pressure information output apparatus 100 in a case where the living body 10 has not operated the information input apparatus 50 for a predetermined length of time. When the living body 10 has not operated the information input apparatus 50 for a predetermined length of time, the PC main body 210 estimates blood pressure information of the living body 10 based on a video of the living body 10, and transmits the blood pressure information to the blood pressure information output unit 30. The blood pressure information output unit 30 displays the blood pressure information on the monitor display 211.

For example, the monitor display 211 displays a pulse wave, a pulse rate (Pulse rate: 72 bpm), systolic blood pressure SBP (Highest: 109 mmHg) and diastolic blood pressure DBP (Lowest: 80 mmHg) based on a video of the nose 11 of the living body 10. Also, information displayed on the monitor display 211 is not limited to pulse rate HR or blood pressure BP, and the monitor display 211 may display information such as a vascular age or arteriosclerosis. Thereafter, when the living body 10 has operated the information input apparatus 50, the blood pressure information output apparatus 100 switches contents displayed on the monitor display 211 from those displayed on the screen in (b) of FIG. 4 back to those displayed on the screen in (a) of FIG. 4, and ends outputting the blood pressure information.

Embodiment 5

Figure 5:
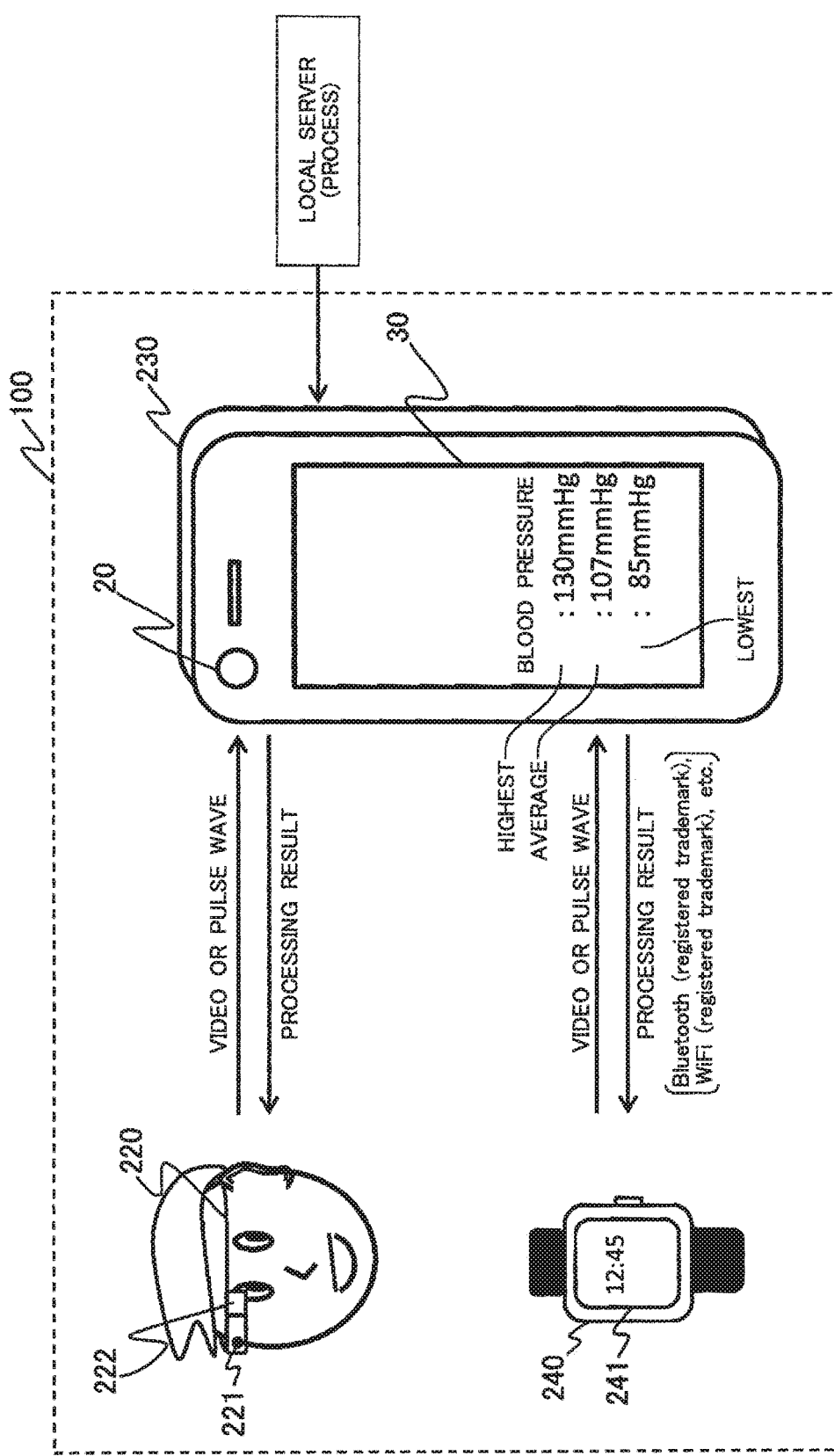
FIG. 5 shows the blood pressure information output apparatus 100 according to Embodiment 5.

FIG. 5 shows the blood pressure information output apparatus 100 according to Embodiment 5. The blood pressure information output apparatus 100 comprises a HMD 220 (head mount display) such as "GOOGLE GLASS" (registered trademark), a smartphone 230 and a wristwatch 240.

The HMD 220 comprises a HMD camera 221 and a display glass 222 (blood pressure information display unit). The HMD 220 acquires a video of the living body 10 from the HMD camera 221. In other words, the HMD camera 221 is one example of the video input unit 20. The HMD 220 transmits an acquired video or pulse waveform information to the smartphone 230 wirelessly. The smartphone 230 according to the present example may cause the video input unit 20 to function as a video receiving unit, and receive a video from the HMD 220.

The smartphone 230 functions as a local server. The smartphone 230 estimates real-time blood pressure information based on the received video or pulse waveform information. The estimated blood pressure information is displayed on the blood pressure information output unit 30. Also, the smartphone 230 may transmit the blood pressure information to the HMD 220 and the wristwatch 240.

The wristwatch 240 comprises a clock display 241 (blood pressure information display unit) that displays time or the like. Also, the wristwatch 240 displays, in real time on the clock display 241, the blood pressure information transmitted from the smartphone 230. The HMD 220 displays, in real time on the display glass 222, the blood pressure information transmitted from the smartphone 230.

The smartphone 230 and the wristwatch 240 may have a camera or a photoelectric plethysmogram wave meter that functions as a pulse waveform information acquiring unit instead of the HMD 220. When the wristwatch 240 has a camera or a photoelectric plethysmogram wave meter, the smartphone 230, by having a pulse waveform information receiving unit built therein, receives a video or pulse waveform information of the living body 10 from the wristwatch 240. The smartphone 230 estimates blood pressure information based on the received video or pulse waveform information, and transmits the blood pressure information to the wristwatch 240 or the HMD 220 through a wireless network such as BlueTooth (registered trademark) or Wi-Fi (registered trademark).

In other words, the blood pressure information output apparatus 100 may acquire a video of the living body 10 from any of the HMD 220, the smartphone 230 and the wristwatch 240. Also, the blood pressure information output apparatus 100 may display pulse waveform information on any of the display glass 222, the blood pressure information output unit 30 and the clock display 241. Thereby, a user can check pulse waveform information casually irrespective of situations. Note that the blood pressure information output apparatus 100 may cause the HMD 220 or the wristwatch 240 to function as a local server.

Embodiment 6

Figure 6:
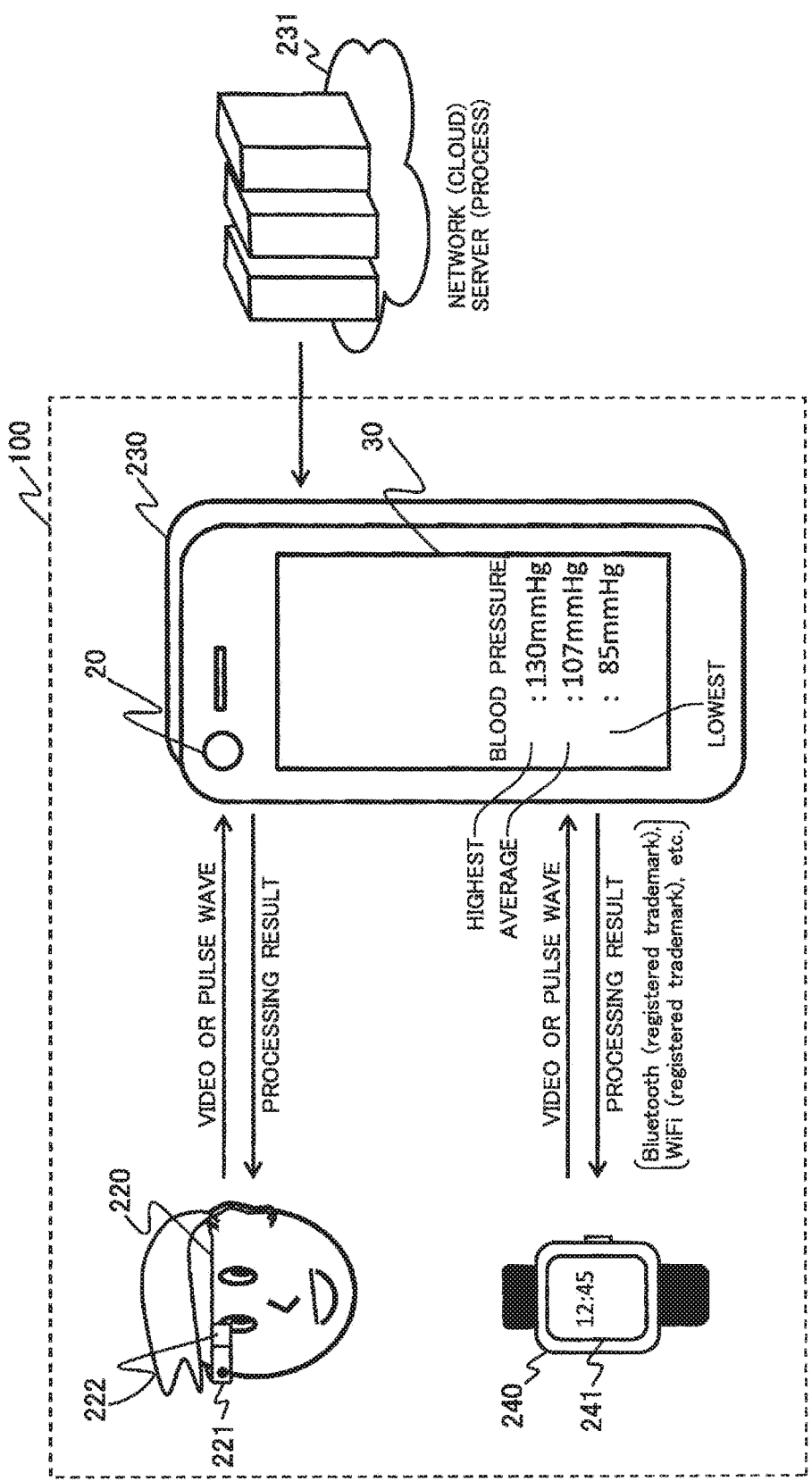
FIG. 6 shows the blood pressure information output apparatus 100 according to Embodiment 6.

FIG. 6 shows the blood pressure information output apparatus 100 according to Embodiment 6. The blood pressure information output apparatus 100 according to Embodiment 6 is different from the implementation example in FIG. 5 in that the smartphone 230 does not function as a local server, but functions as a relay unit in network communication processing. The smartphone 230 comprises a video transmitting unit, and transmits a video or pulse waveform information to a network server 231 (cloud server).

The network server 231 estimates real-time blood pressure information based on the received video or pulse waveform information. The smartphone 230 comprises a blood pressure information receiving unit, and receives the blood pressure information estimated by the network server 231.

The smartphone 230 transmits the blood pressure information in real time to the wristwatch 240 through a wireless network such as BlueTooth (registered trademark) or Wi-Fi (registered trademark). The wristwatch 240 displays the blood pressure information in real time on the clock display 241 on which time is displayed. Note that the destination of transmission from the smartphone 230 is not limited to the wristwatch 240, but may be the HMD 220.

Embodiment 7

Figure 7:
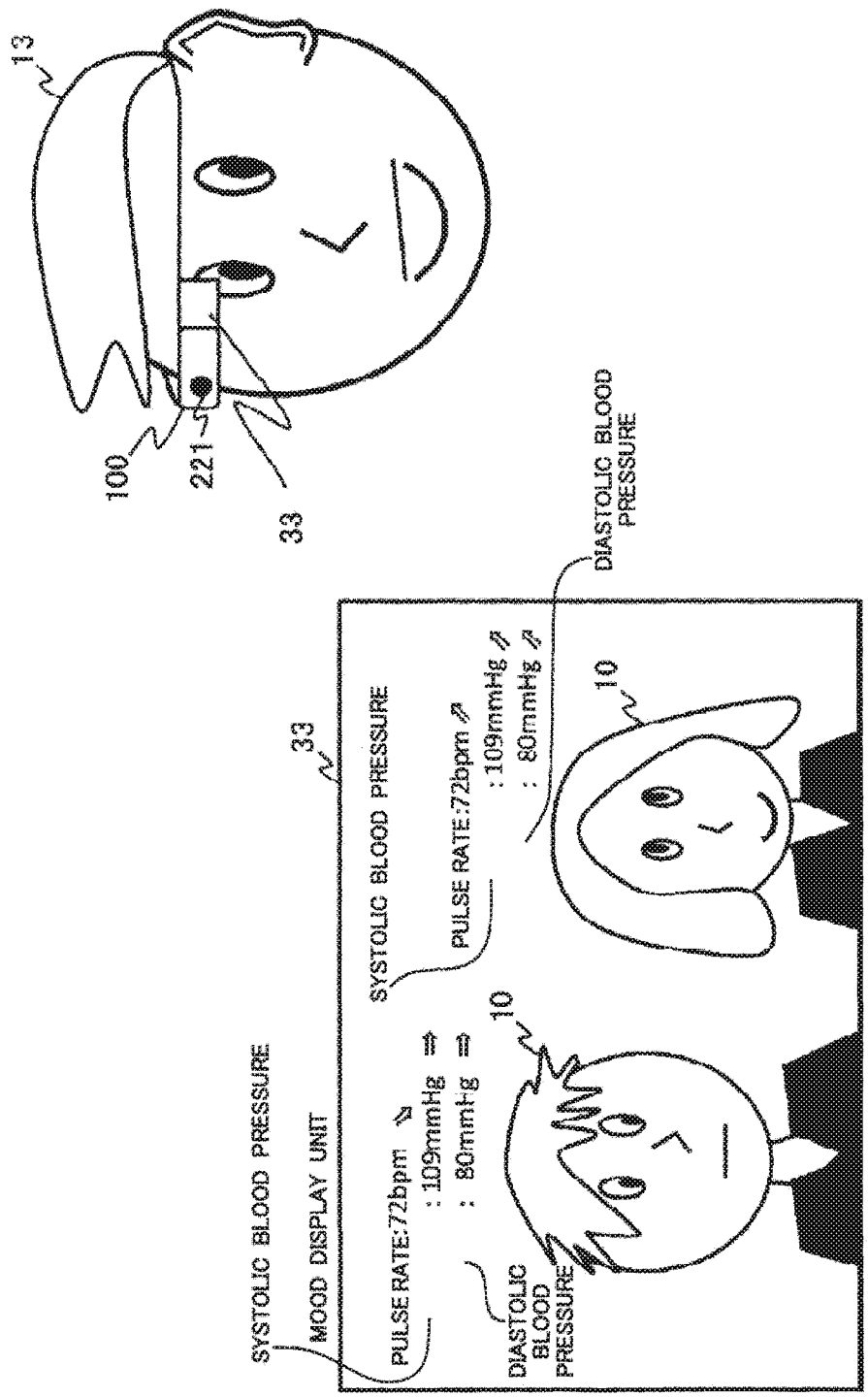
FIG. 7 shows the blood pressure information output apparatus 100 according to Embodiment 7.

FIG. 7 shows the blood pressure information output apparatus 100 according to Embodiment 7. The blood pressure information output apparatus 100 according to the present example is implemented in a HMD. The blood pressure information output apparatus 100 comprises the HMD camera 221 and a mood display unit 33. The blood pressure information output apparatus 100 according to the present example functions as a mood monitor that detects and displays a mood of the living body 10 in front of it.

The HMD camera 221 functions as the video input unit 20, and captures a video of the living body 10 in front of a user 13. The blood pressure information output apparatus 100 estimates blood pressure information based on the video captured by the HMD camera 221. The mood display unit 33 displays the estimated blood pressure information.

The blood pressure information output apparatus 100 according to the present example acquires, through the HMD camera 221, a video of the living body 10 in front of the HMD camera 221, and estimates a pulse rate HR and blood pressure BP of the living body 10 in front of it, and tendency of changes (increase or decrease) in them. For example, when a plurality of living bodies 10 is included in a video, the blood pressure information output apparatus 100 estimates blood pressure information of the plurality of living bodies 10.

For example, the mood display unit 33 indicates that the pulse rate HR of a living body 10 on the left is 72 bpm and is decreasing, his/her systolic blood pressure SBP is 109 mmHg and has remained unchanged, and his/her diastolic blood pressure DBP is 80 mmHg and has remained unchanged. Also, the mood display unit 33 displays that the pulse rate HR of a living body 10 on the right is 72 bpm and is increasing, his/her systolic blood pressure SBP is 109 mmHg and is increasing, and his/her diastolic blood pressure DBP is 80 mmHg and is increasing. Thereby, the user 13 can know the mood of a conversation with the living body 10 in front of him/her.

Embodiment 8

Figure 8:
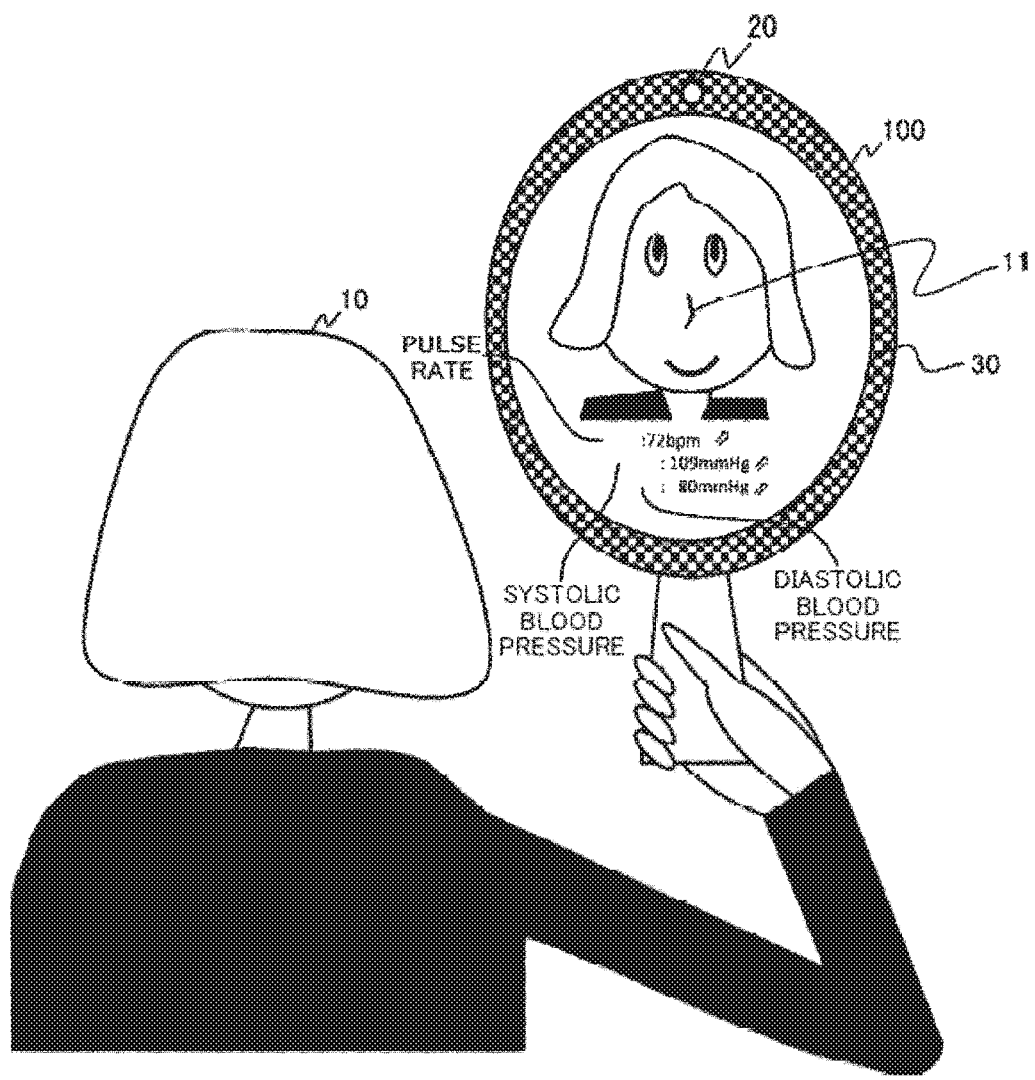
FIG. 8 shows the blood pressure information output apparatus 100 according to Embodiment 8.

FIG. 8 shows the blood pressure information output apparatus 100 according to Embodiment 8. The blood pressure information output apparatus 100 is implemented in a hand mirror. The blood pressure information output apparatus 100 comprises the video input unit 20 and the blood pressure information output unit 30.

The video input unit 20 captures a video of the nose 11 of the living body 10 by a camera or the like, and outputs the captured video to the blood pressure information output unit 30. The blood pressure information output unit 30 outputs real-time blood pressure information on the mirror based on the input video. The blood pressure information output apparatus 100 according to the present example estimates a pulse rate HR, systolic blood pressure SBP, diastolic blood pressure DBP of the living body 10 who is using the hand mirror, and tendency of changes (increase or decrease) in them, and displays blood pressure information on the mirror.

Embodiment 9

FIG. 9 shows the blood pressure information output apparatus 100 according to Embodiment 9. The blood pressure information output apparatus 100 is configured with the video input unit 20 that is provided to a bed, and the smartphone 230. The blood pressure information output apparatus 100 acquires, from the camera 25 provided to the bed, a video of the living body 10 who is lying on the bed. The blood pressure information output apparatus 100 transmits the acquired video to the smartphone 230 of the user 13 wirelessly. The blood pressure information output apparatus 100 according to the present example operates as a health monitor that manages health of the living body 10 or the like.

The smartphone 230 estimates real-time blood pressure information based on the acquired video. For example, the smartphone 230 displays, in real time, a pulse rate HR or blood pressure information of the living body 10 (baby, elderly, sick person or the like) who is lying on the bed. When a pulse rate HR or blood pressure BP is abnormal, the blood pressure information output apparatus 100 transmits information indicating the abnormality to electronic equipment (smartphone 230) of the user 13 (guardian, caregiver, doctor, nurse or the like) automatically.

Embodiment 10

Figure 10:
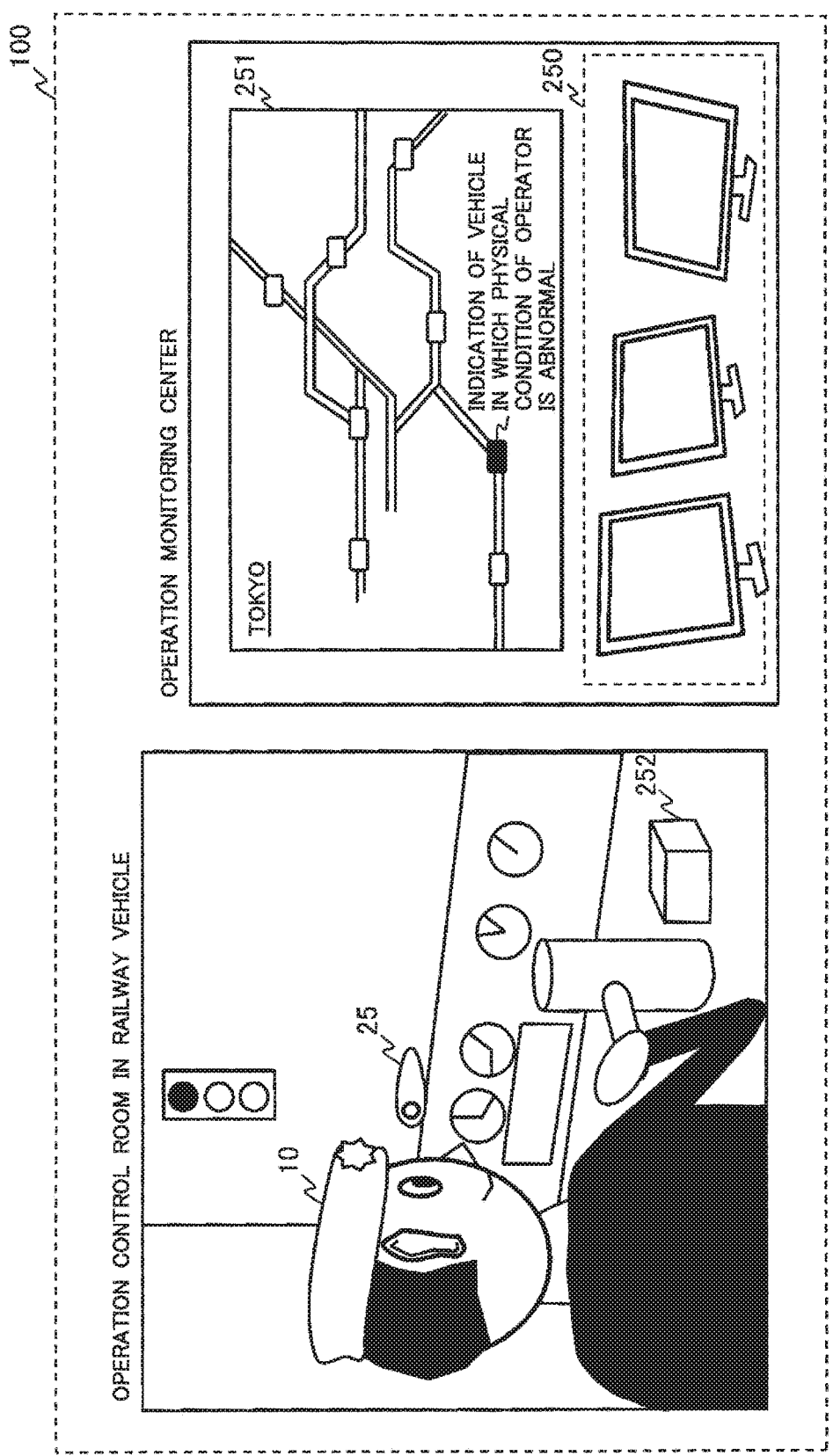
FIG. 10 shows the blood pressure information output apparatus 100 according to Embodiment 10.

FIG. 10 shows the blood pressure information output apparatus 100 according to Embodiment 10. The blood pressure information output apparatus 100 according to the present example functions as an operator monitoring system. The blood pressure information output apparatus 100 is configured with the camera 25 and an alarm output unit 252 that are provided to an operation control room in a railway vehicle, and an operation monitoring computer 250 and an operation monitoring display 251 at an operation monitoring center. The camera 25 according to the present example functions as an operation control room camera. Also, the operation monitoring computer 250 and the operation monitoring display 251 function as a physical condition information output computer.

The camera 25 acquires a video of an operator who is the living body 10, and transmits the video to the operation monitoring computer 250. The operation monitoring computer 250 estimates real-time blood pressure information of the operator based on the video received from the camera 25. When a pulse rate HR, blood pressure BP or the like of the operator who is the living body 10 is abnormal, the operation monitoring computer 250 displays, on the operation monitoring display 251, information about the vehicle in which the physical condition of the living body 10 is abnormal.

When the pulse rate HR, blood pressure BP or the like of the operator is abnormal, the computer at the operation monitoring center transmits, to the alarm output unit 252, information indicating that the physical condition of the living body 10 is abnormal. When the abnormality has been notified, the alarm output unit 252 issues an alarm by sound or light. Note that the blood pressure information output apparatus 100 according to the present example can be applied not only to trains, but to automobiles, airplanes, ships or the like similarly.

Embodiment 11

Figure 11:
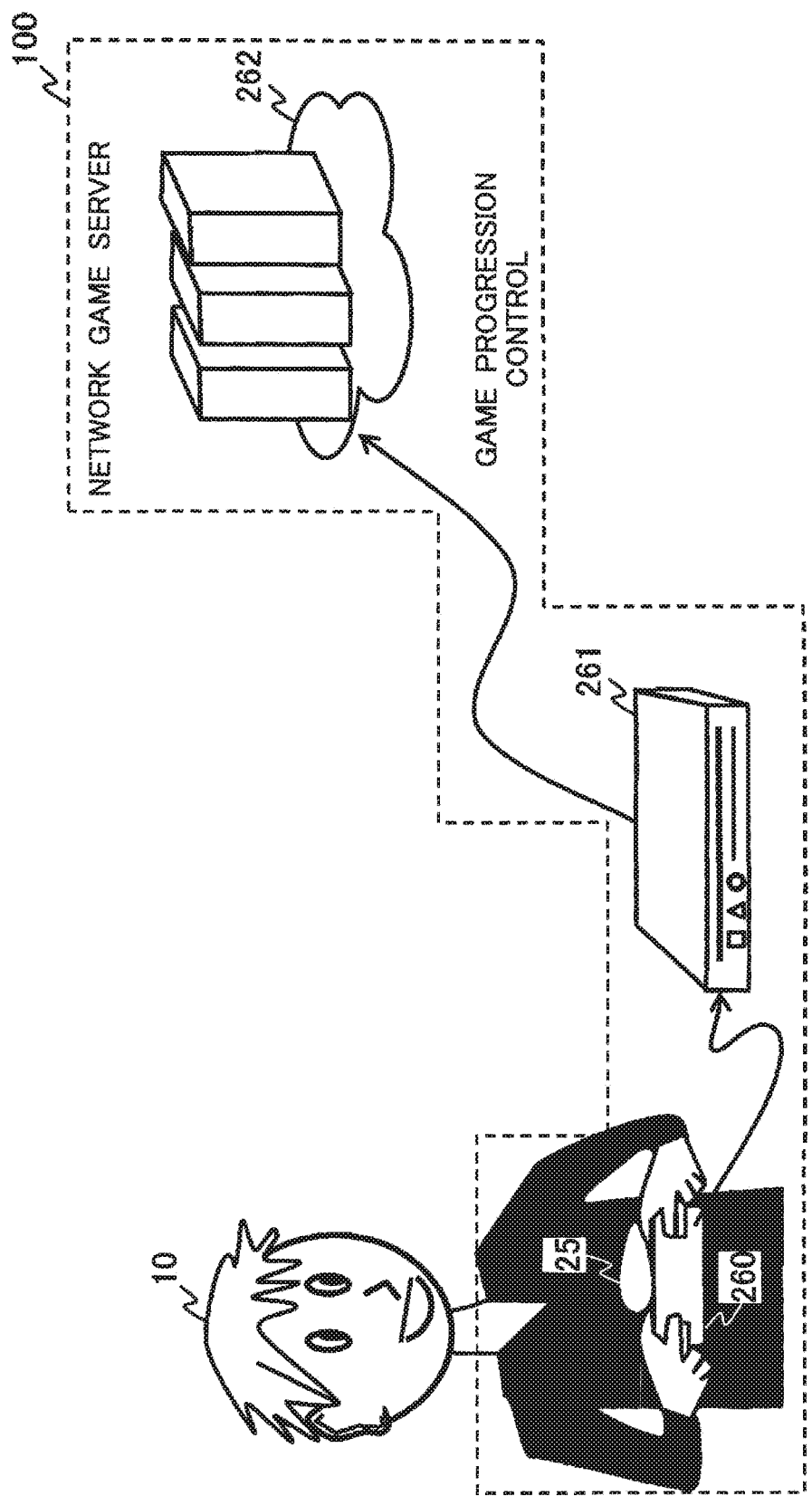
FIG. 11 shows the blood pressure information output apparatus 100 according to Embodiment 11.

FIG. 11 shows the blood pressure information output apparatus 100 according to Embodiment 11. The blood pressure information output apparatus 100 functions as a player monitor system that monitors the health state of a game player. The blood pressure information output apparatus 100 estimates the state of the game player who is the living body 10 from changes in a pulse rate HR or blood pressure BP, and controls the progression of a game interactively (bi-directionally). The blood pressure information output apparatus 100 is configured with the camera 25, a game controller 260, a game console main body 261 and a network game server 262.

The camera 25 acquires a video of the living body 10. The game controller 260 outputs information about operation on the game console main body 261 by the living body 10, and outputs the video obtained from the camera 25. The game console main body 261 estimates real-time blood pressure information based on video information output by the game controller 260.

The network game server 262 estimates an excited state or a mood of the living body 10 based on the blood pressure information estimated by the game console main body 261. The network game server 262 controls the speed of progression of the game processed by the game console main body 261 according to the estimated excited state or mood. In other words, the network game server 262 instructs the game console main body 261 to speed up or slow down the speed of progression of the game.

Embodiment 12

Figure 12:
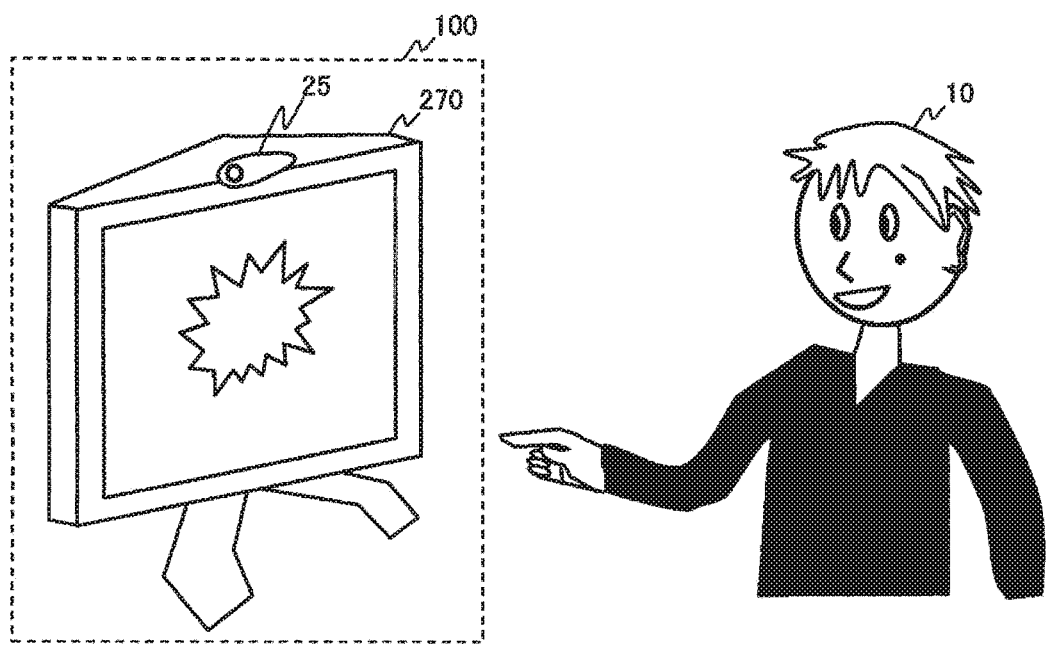
FIG. 12 shows the blood pressure information output apparatus 100 according to Embodiment 12.

FIG. 12 shows the blood pressure information output apparatus 100 according to Embodiment 12

The blood pressure information output apparatus 100 functions as a viewer monitoring system. The blood pressure information output apparatus 100 comprises the camera 25 and a television 270. The blood pressure information output apparatus 100 according to the present example functions as a contents display control television that controls display of contents based on a video acquired by the camera 25.

The camera 25 is provided to the television 270, and acquires a video of a viewer who is the living body 10. For example, the camera 25 is attached to an upper portion of the television 270. Also, the camera 25 may be provided within the television 270.

The television 270 estimates real-time blood pressure information based on the video of the living body 10 acquired by the camera 25. The television 270 detects photosensitive epilepsy and performs health management based on the estimated blood pressure information. For example, the television 270 shuts down automatically upon detection of photosensitive epilepsy based on the blood pressure information of the living body 10. Also, the television 270 may shut down automatically upon reception of contents that may cause photosensitive epilepsy to the living body 10.

The blood pressure information output apparatus 100 according to Embodiments 1 to 12 can estimate blood pressure information from a video of a single region of the living body 10 without contacting it. For this reason, the blood pressure information output apparatus 100 allows the video input unit 20 to be installed freely at any location. A user of the blood pressure information output apparatus 100 can monitor, in real time, blood pressure information of the living body 10 or the like with natural operation.

Figure 13:
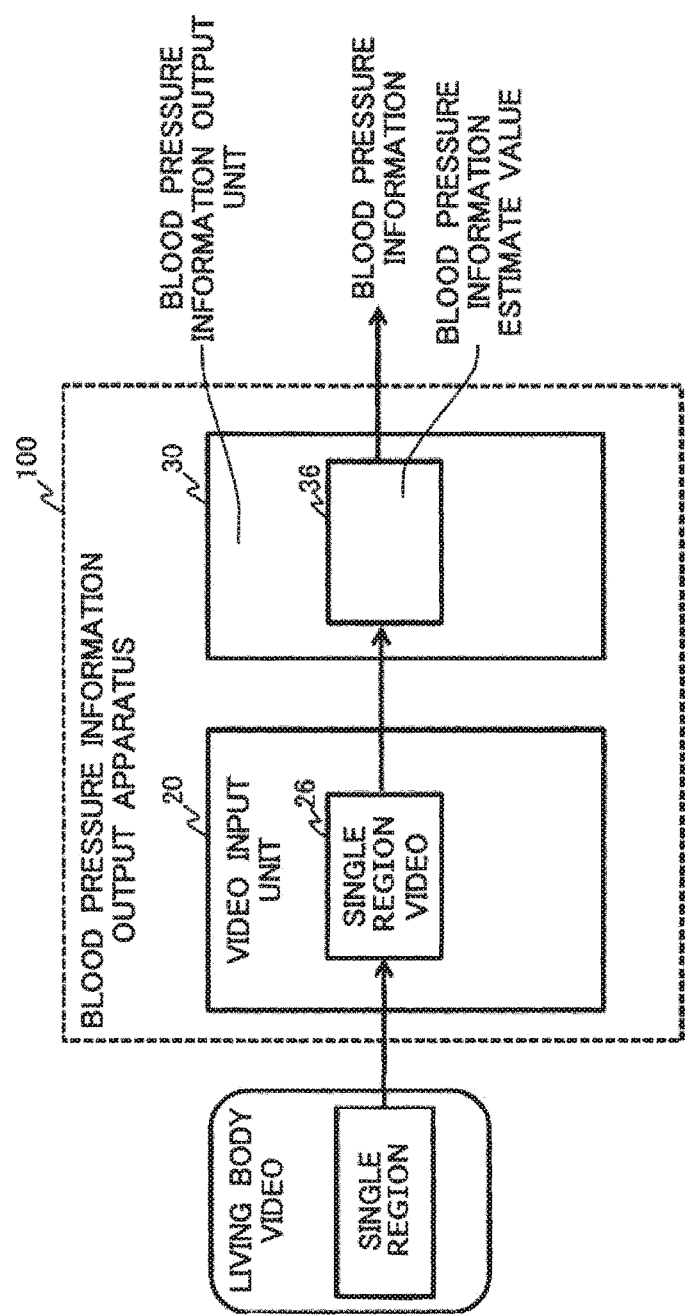
FIG. 13 shows one example of the configuration of the blood pressure information output apparatus 100.

FIG. 13 shows one example of the configuration of the blood pressure information output apparatus 100. The blood pressure information output apparatus 100 comprises the video input unit 20 and the blood pressure information output unit 30. The blood pressure information output apparatus 100 estimates and outputs blood pressure BP from an input video of a single region of the living body 10. Note that the configuration of the blood pressure information output apparatus 100 according to the present example can be utilized in any of Embodiments 1 to 12.

The video input unit 20 receives an input of a single region video 26 which is the video of the single region of the living body 10. The video input unit 20 outputs the single region video 26 to the blood pressure information output unit 30.

The blood pressure information output unit 30 estimates blood pressure information of the living body 10 based on the single region video 26. For example, the blood pressure information output unit 30 calculates a blood pressure information estimate value 36 from the single region video 26. The blood pressure information output unit 30 outputs the calculated blood pressure information estimate value 36 as blood pressure information.

Figure 14:
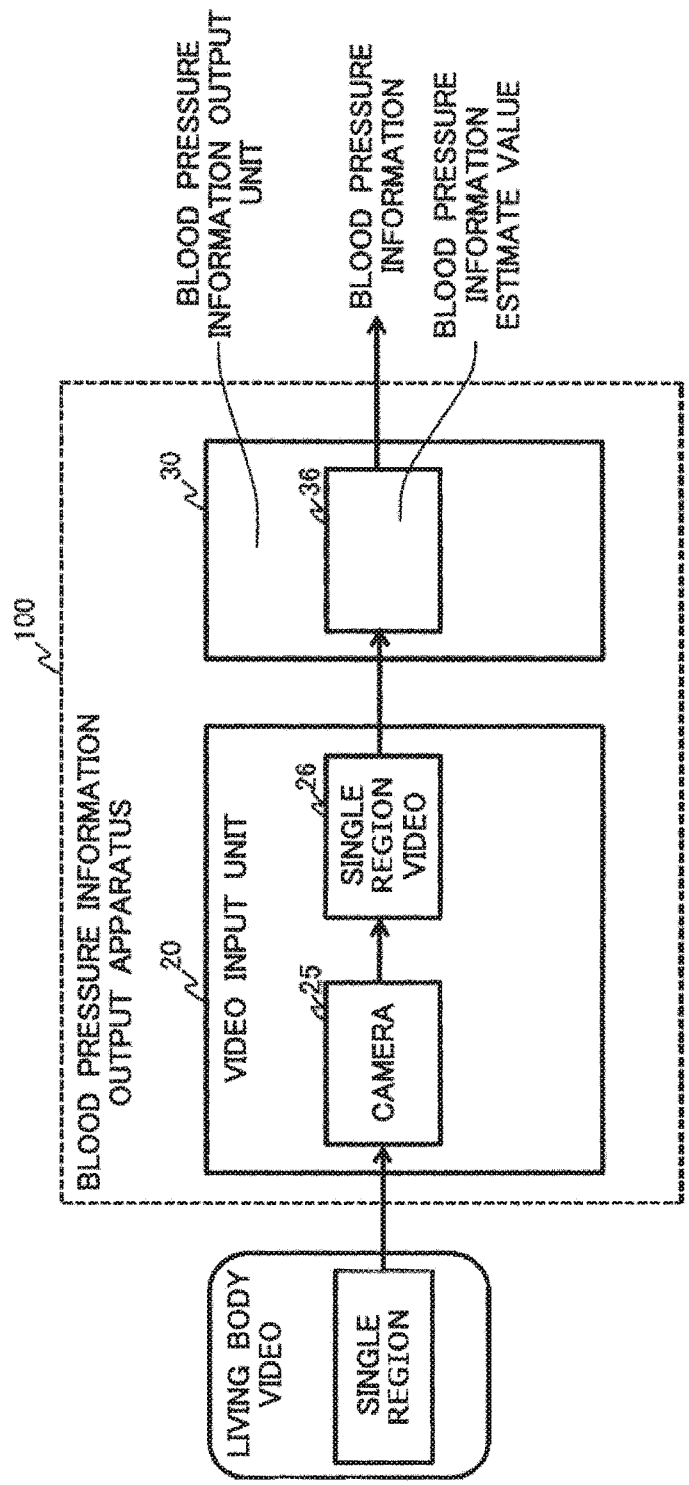
FIG. 14 shows one example of the configuration of the blood pressure information output apparatus 100.

FIG. 14 shows one example of the configuration of the blood pressure information output apparatus 100. The blood pressure information output apparatus 100 according to the present example is different from the implementation example in FIG. 13 in that the video input unit 20 comprises the camera 25. The video input unit 20 acquires a video of a single region of the living body 10 by the camera 25.

The camera 25 captures a video of a single region of the living body 10. The camera 25 comprises a CCD sensor, a CMOS sensor or the like as an image sensor. The camera 25 outputs the captured video of the single region to the blood pressure information output unit 30.

Figure 15:
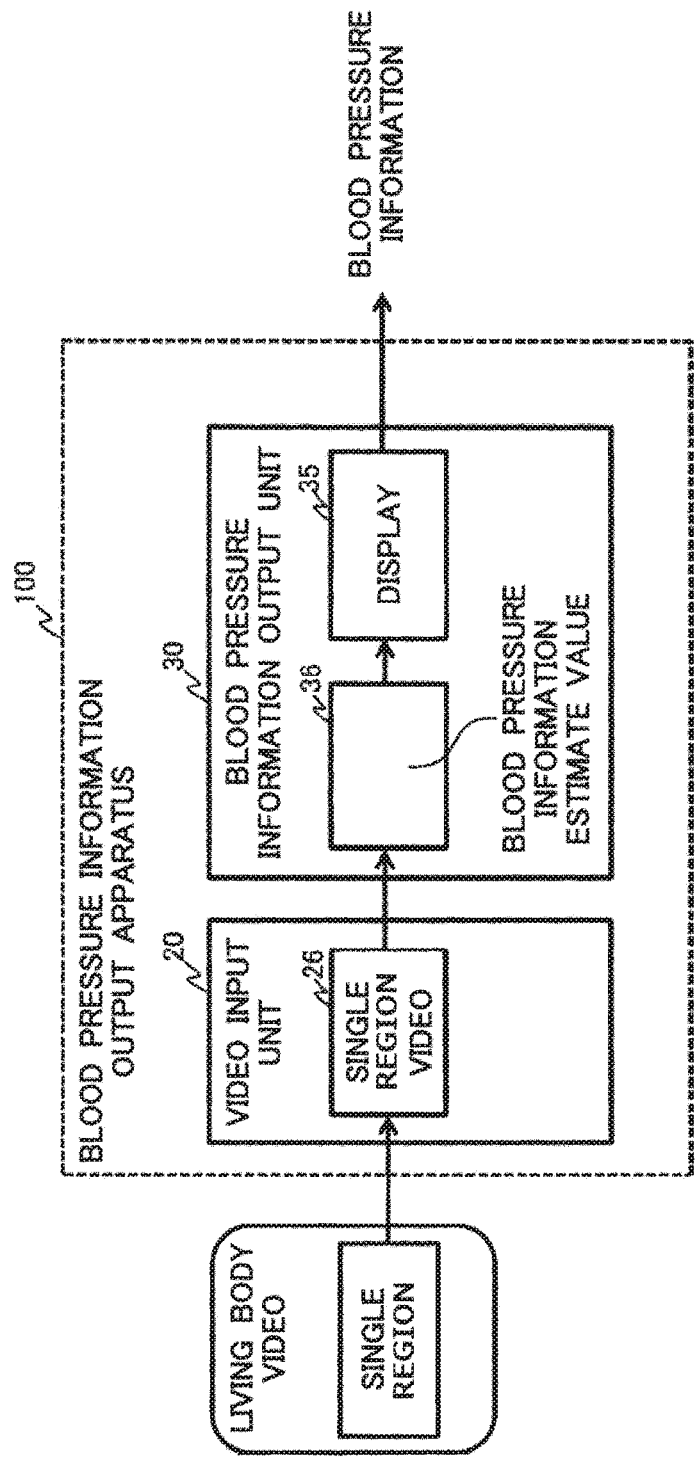
FIG. 15 shows one example of the configuration of the blood pressure information output apparatus 100.

FIG. 15 shows one example of the configuration of the blood pressure information output apparatus 100. The blood pressure information output apparatus 100 according to the present example is different from the implementation example in FIG. 13 in that the blood pressure information output unit 30 comprises a display 35.

The display 35 displays blood pressure information based on the blood pressure information estimate value 36. The display 35 may display all the pieces of information of the blood pressure information obtained from the blood pressure information estimate value 36, or may display a part of the information of the blood pressure information.

For example, the blood pressure information output unit 30 comprises a speaker instead of the display 35, and outputs blood pressure information as audio signals. Also, the blood pressure information output unit 30 transmits, to electronic equipment such as a PC or a database at a medical institution such as a hospital instead of the display 35, blood pressure information by wireless or wired communication.

Figure 16:
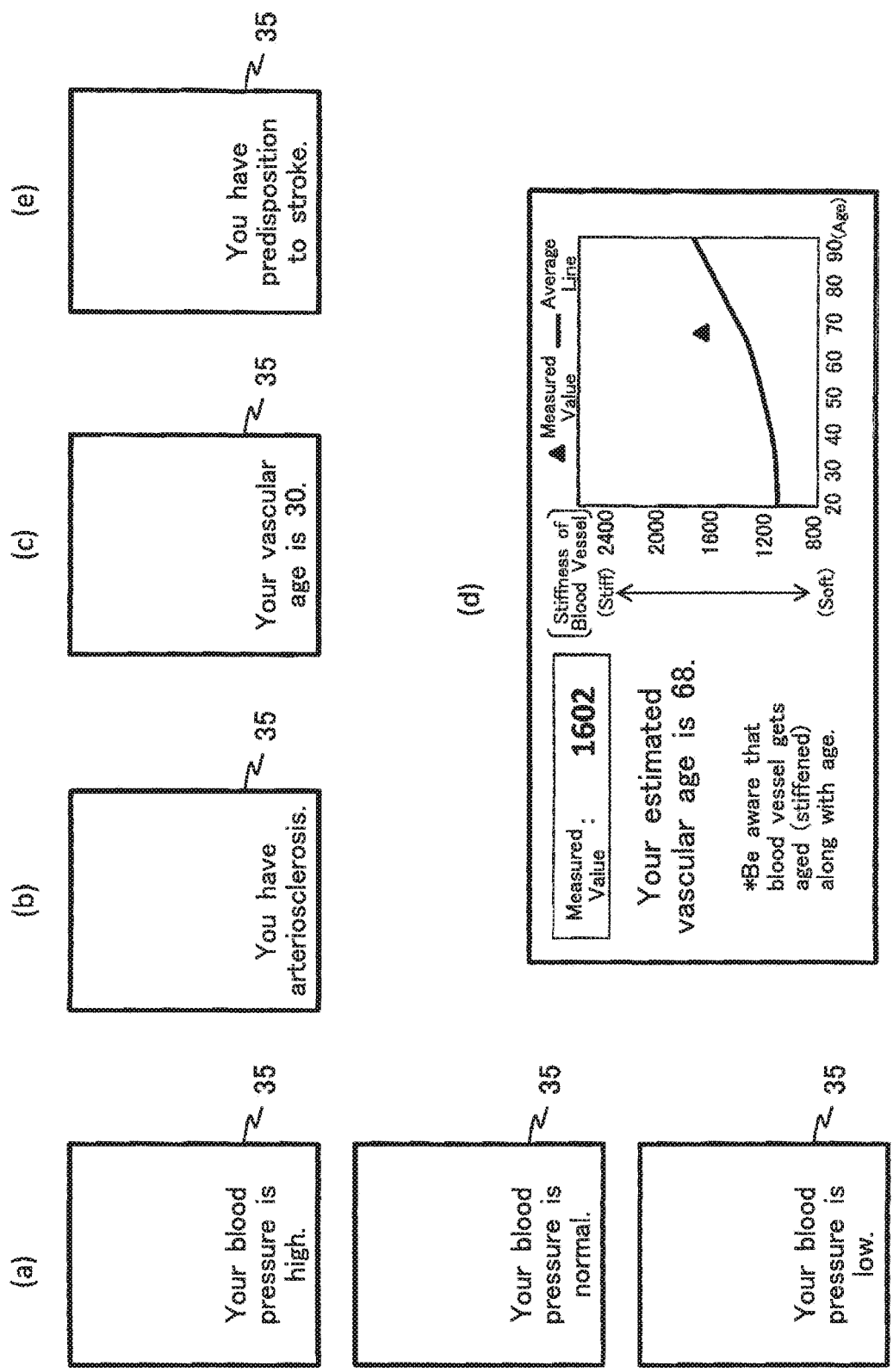
FIG. 16 shows one example of the display form of the display 35.

FIG. 16 shows one example of the display form of the display 35. The display form of the display 35 shown in FIG. 16 can be utilized in any of Embodiments 1 to 12.

(a) of FIG. 16 shows an example in which not a blood pressure itself of the living body 10, but a blood pressure state indicating whether blood pressure BP of the living body 10 is a high blood pressure, a normal blood pressure, a low blood pressure or the like is displayed. (b) of FIG. 16 shows an example in which whether arteriosclerosis is observed is displayed based on calculated pulse wave propagation information or estimated blood pressure BP. (c) of FIG. 16 shows an example in which a result of estimating a vascular age is displayed based on calculated pulse wave propagation information or estimated blood pressure BP. In other words, (b) and (c) of FIG. 16 show blood vessel states.

In addition to display of absolute evaluation shown in (a) to (c) of FIG. 16, the display 35 may display relative evaluation obtained by comparison with an average value of each individual. Also, the blood pressure information output apparatus 100 may be provided with a storage unit therein, and blood pressure information estimated in the past may be memorized in the storage unit. In this case, the blood pressure information output apparatus 100 may output, on the display 35, past blood pressure information and current blood pressure information together.

(d) of FIG. 16 shows the stiffness of blood vessels, a vascular age, advice to a user, and a graph indicating a relationship between the stiffness of blood vessels and a vascular age. The solid line indicates an average value line showing the average stiffness of blood vessels at each age. The user can know from the graph whether his/her stiffness is above or below the average value line. Other than this, for example, information such as "Your blood pressure measured at this time is higher than usual," "Your blood pressure measured at this time is lower than usual," or "Your blood pressure measured at this time is the same as usual" may be displayed.

(e) of FIG. 16 shows an example in which the display 35 displays whether the living body 10 has a predisposition to stroke. Judgement about whether the living body 10 has a predisposition to stroke can be made by examining blood pressure at a steady-state, and variation in blood pressure after exercise with a very low load. The user can know from the display on the display 35 whether he/she has a predisposition to stroke.

Figure 17:
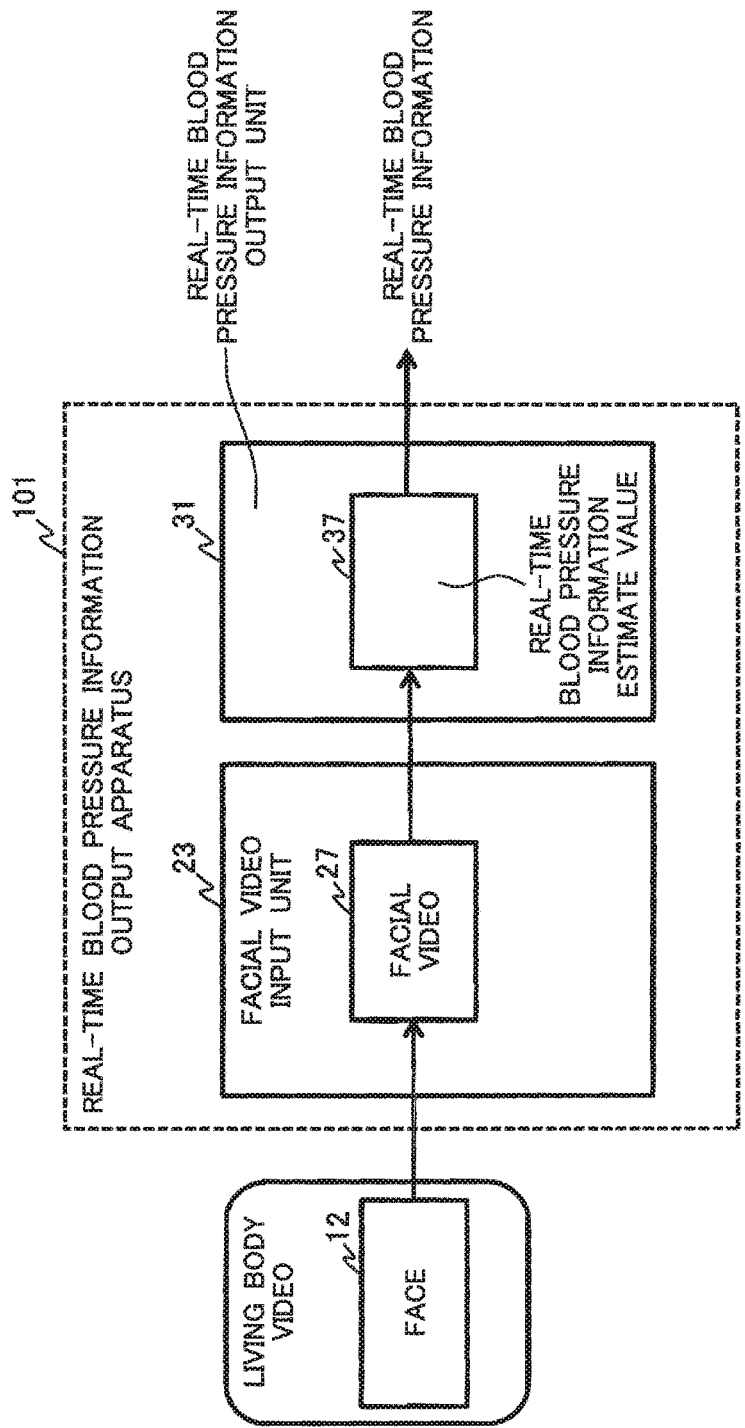
FIG. 17 shows one example of the configuration of a real-time blood pressure information output apparatus 101.

FIG. 17 shows one example of the configuration of a real-time blood pressure information output apparatus 101. The real-time blood pressure information output apparatus 101 is one example of the blood pressure information output apparatus 100 in a case where real-time blood pressure information is output from a facial video 27 of the living body 10, in particular. The real-time blood pressure information output apparatus 101 comprises a facial video input unit 23 and a real-time blood pressure information output unit 31.

The real-time blood pressure information output apparatus 101 estimates blood pressure BP from the input facial video 27 of the living body 10 and outputs it. Note that the configuration of the real-time blood pressure information output apparatus 101 according to the present example can be utilized in any of Embodiments 1 to 12.

The facial video input unit 23 receives an input of a video of the face 12 of the living body 10 as the facial video 27. For example, the facial video 27 is a video of the nose 11 of the living body 10. The facial video input unit 23 outputs the input facial video 27 to the real-time blood pressure information output unit 31 in a real-time format.

The real-time blood pressure information output unit 31 calculates a real-time blood pressure information estimate value 37 of the living body 10 based on the input facial video 27. For example, the real-time blood pressure information output unit 31 outputs the real-time blood pressure information estimate value 37 as real-time blood pressure information. The real-time blood pressure information output apparatus 101 according to the present example acquires information of the face 12 of the living body 10, which information changes from moment to moment, and outputs real-time blood pressure information from the real-time blood pressure information output unit 31.

Figure 18:
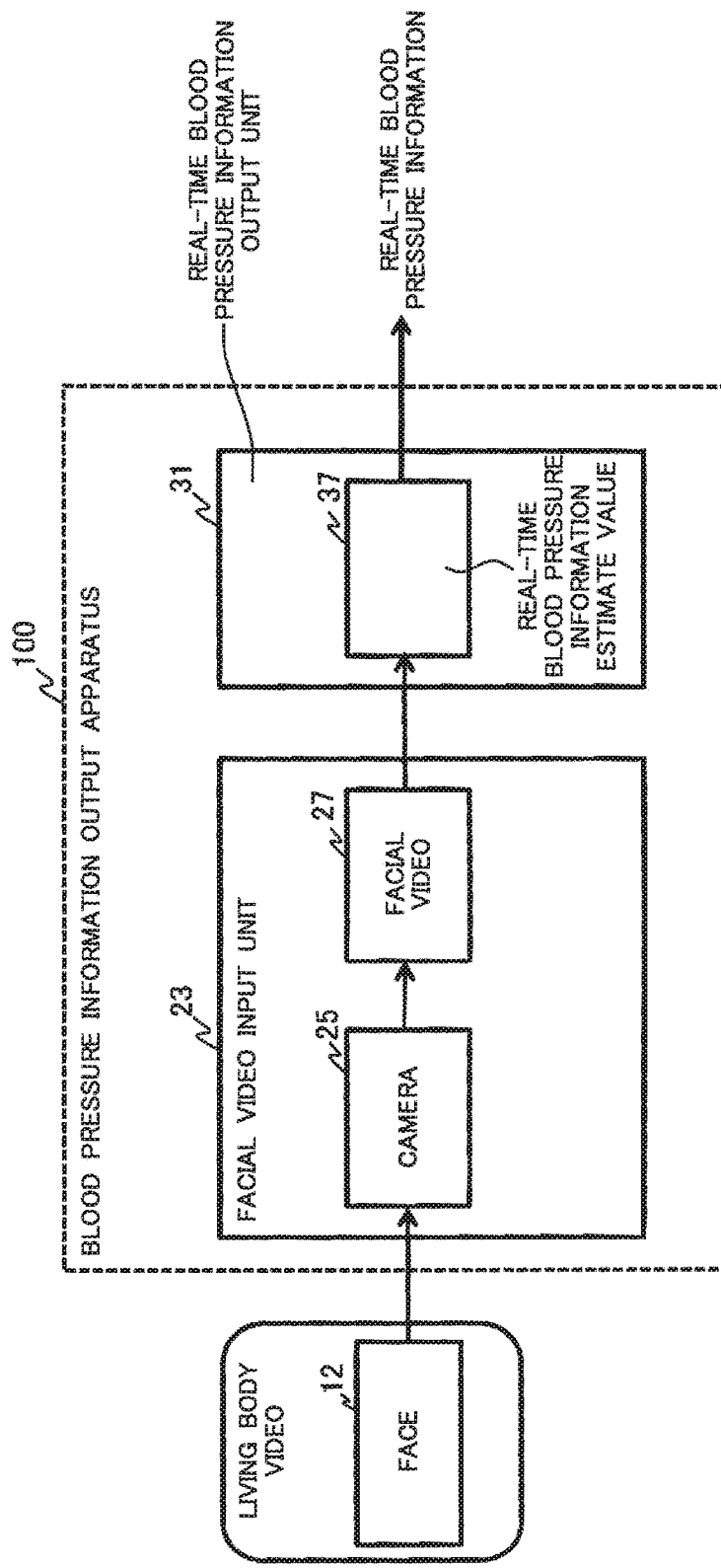
FIG. 18 shows one example of the configuration of the real-time blood pressure information output apparatus 101.

FIG. 18 shows one example of the configuration of the real-time blood pressure information output apparatus 101. The real-time blood pressure information output apparatus 101 according to the present example is different from the implementation example in FIG. 17 in that the facial video input unit 23 comprises the camera 25. The facial video input unit 23 acquires a video of the face 12 of the living body 10 by the camera 25. The configuration of the camera 25 is the same as the configuration of the camera 25 in FIG. 14, and the camera 25 outputs the acquired facial video 27 to the real-time blood pressure information output unit 31.

Figure 19:
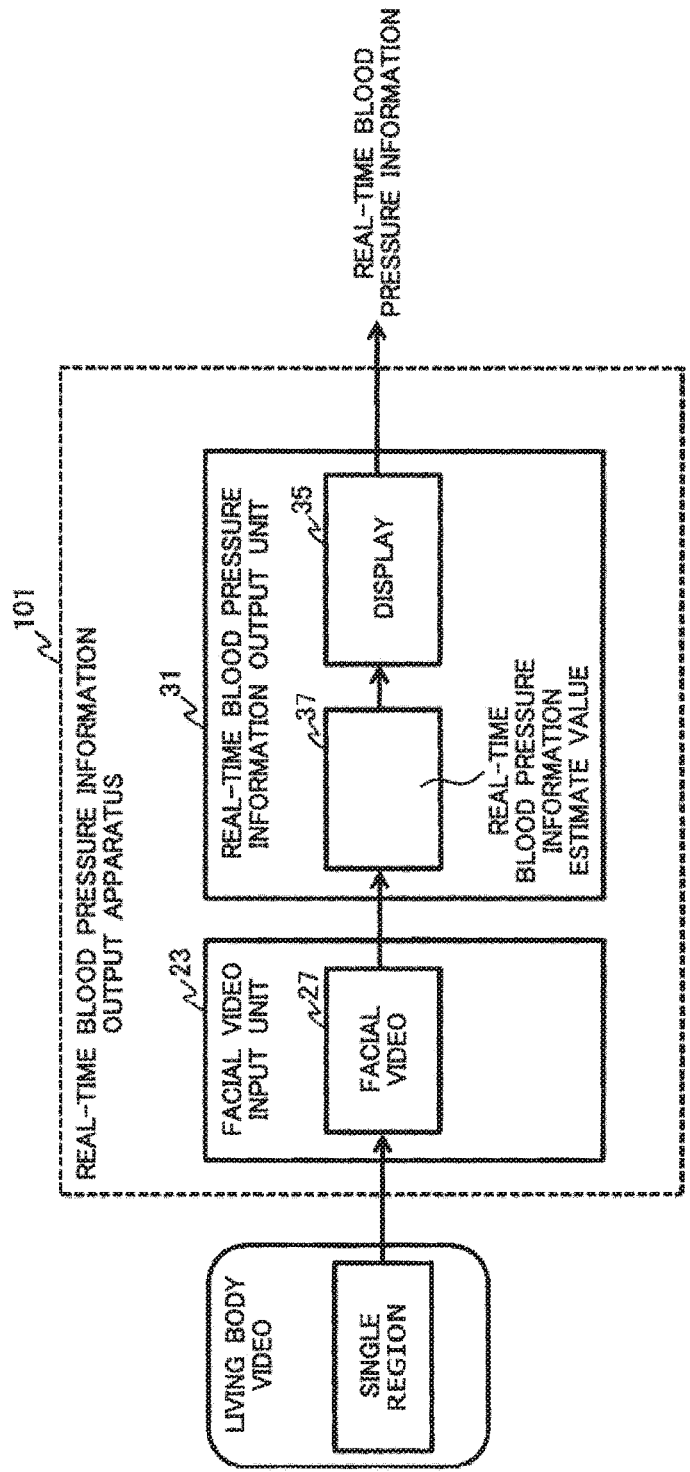
FIG. 19 shows one example of the configuration of the real-time blood pressure information output apparatus 101.

FIG. 19 shows one example of the configuration of the real-time blood pressure information output apparatus 101. The real-time blood pressure information output apparatus 101 according to the present example is different from the implementation example in FIG. 17 in that the real-time blood pressure information output unit 31 comprises the display 35. The display 35 has the configuration which is the same as that of the display 35 in FIG. 15, and displays real-time blood pressure information based on the facial video 27 in the real-time blood pressure information output unit 31. The display form of the display 35 may be the same as those in (a) to (e) of FIG. 16.

For example, the real-time blood pressure information output unit 31 comprises a speaker instead of the display 35, and outputs real-time blood pressure information as audio signals. Also, the real-time blood pressure information output unit 31 transmits, to electronic equipment such as a PC or a database at a medical institution such as a hospital instead of the display 35, blood pressure information by wireless or wired communication.

Figure 20:
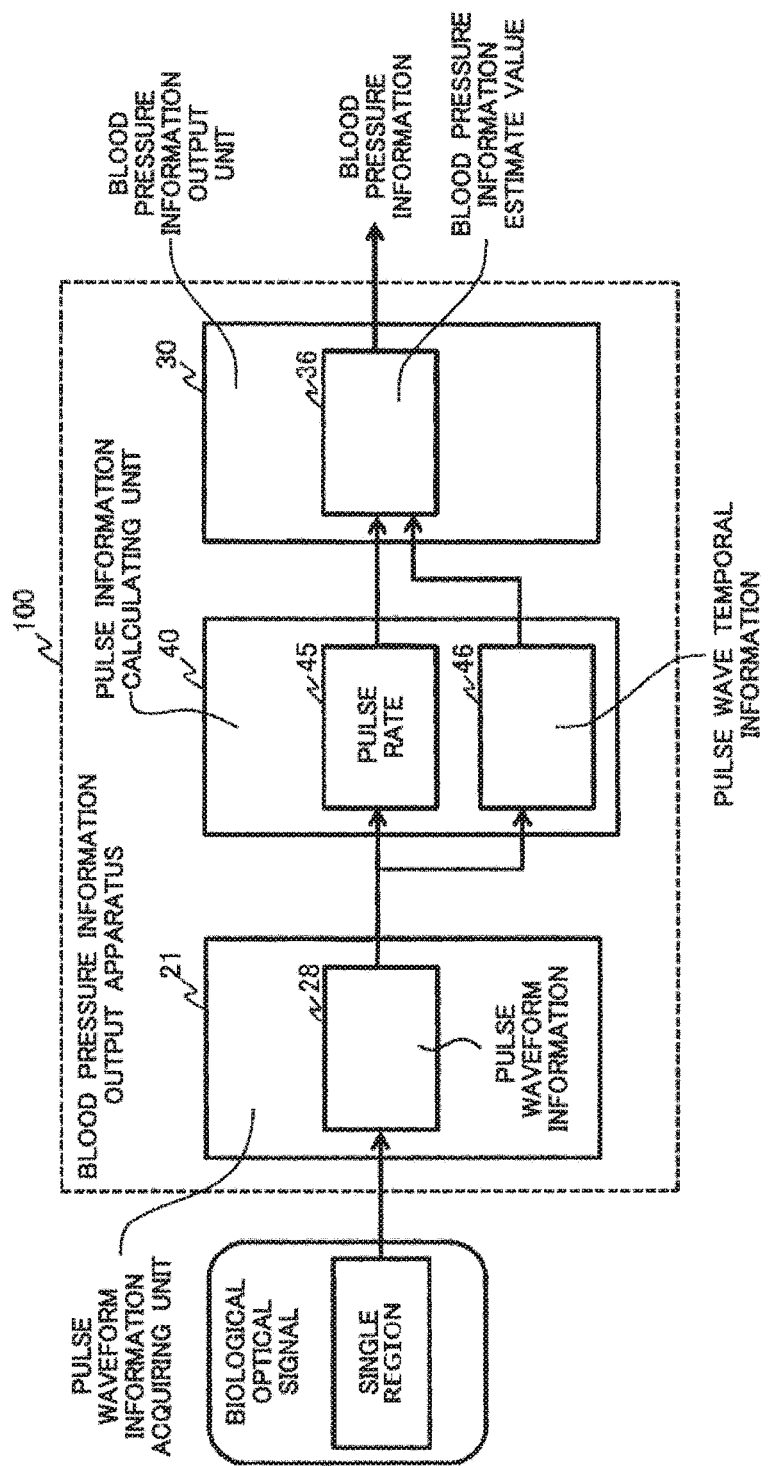
FIG. 20 shows one example of the configuration of the blood pressure information output apparatus 100.

FIG. 20 shows one example of the configuration of the blood pressure information output apparatus 100. The blood pressure information output apparatus 100 comprises the pulse waveform information acquiring unit 21, a pulse information calculating unit 40 and the blood pressure information output unit 30.

The pulse waveform information acquiring unit 21 optically acquires pulse waveform information 28 from optical signals from a single region of the living body 10. For example, the pulse waveform information acquiring unit 21 is a photoelectric plethysmogram wave meter that acquires pulse waveform information by detecting, with a photodiode (PD), transmitted light or reflected light of light output by a light-emitting diode (LED).

The pulse information calculating unit 40 calculates pulse information from the extracted pulse waveform information 28. Specifically, the pulse information calculating unit 40 calculates a pulse rate 45 by frequency analysis on the pulse waveform information 28. Also, the pulse information calculating unit 40 calculates pulse wave temporal information 46 of the living body 10 based on the extracted pulse waveform information 28 of a single region. The pulse wave temporal information 46 is, for example, rising time TR or falling time TF of a pulse wave or the like.

The frequency analysis may be a Fourier analysis such as fast Fourier transform (FFT) or discrete Fourier transform (DFT), or a wavelet analysis such as Haar transform or Daubechies transform. By using frequency analysis, the pulse information calculating unit 40 can obtain the stable and average pulse rate 45 in a short time without performing averaging operation or the like in a long time domain. Also, the pulse information calculating unit 40 may calculate temporal information of a pulse wave of the living body 10 based further on the stable pulse rate 45.

The blood pressure information output unit 30 calculates the blood pressure information estimate value 36 based on the pulse rate 45 and the pulse wave temporal information 46. The blood pressure information output unit 30 outputs the calculated blood pressure information estimate value 36 as blood pressure information.

Figure 21:
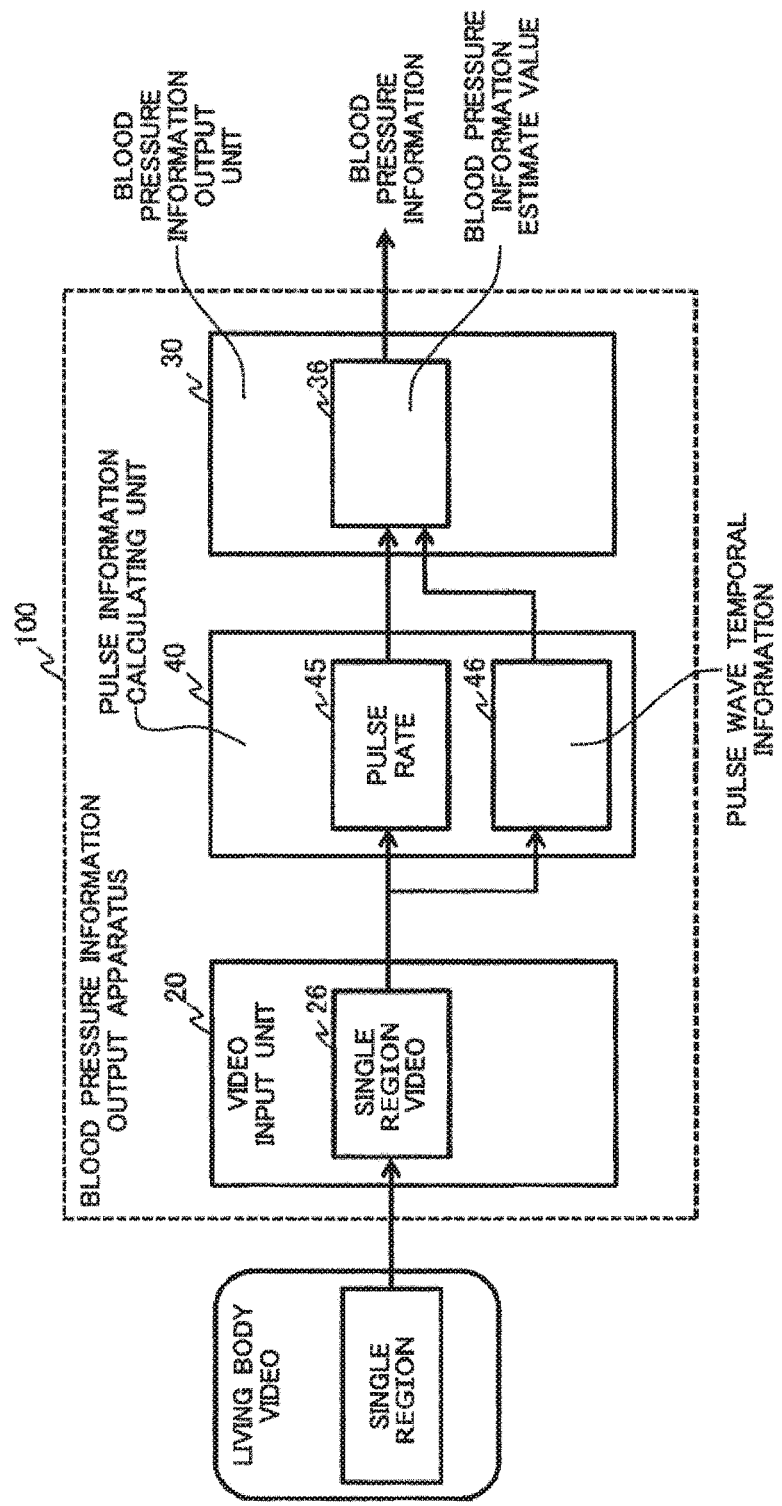
FIG. 21 shows one example of the configuration of the blood pressure information output apparatus 100.

FIG. 21 shows one example of the configuration of the blood pressure information output apparatus 100. The blood pressure information output apparatus 100 comprises the video input unit 20, the pulse information calculating unit 40 and the blood pressure information output unit 30. The blood pressure information output apparatus 100 according to the present example is different from the implementation example in FIG. 20 in that it comprises the video input unit 20 that acquires a video of the living body 10.

The video input unit 20 acquires the single region video 26 of the living body 10. Here, acquisition of the single region video 26 can be realized by well-known image recognition techniques. For example, the video input unit 20 acquires a video of the living body 10 by the camera 25.

The pulse information calculating unit 40 calculates pulse information from the acquired single region video 26. Specifically, the pulse information calculating unit 40 calculates the pulse rate 45 by frequency analysis on the single region video 26. Also, the pulse information calculating unit 40 calculates the pulse wave temporal information 46 of the living body 10 based on the extracted single region video 26. The frequency analysis according to the present example may be similar to frequency analysis in a case where the pulse information calculating unit 40 receives an input of the pulse waveform information 28 in the implementation example of FIG. 20.

Figure 22:
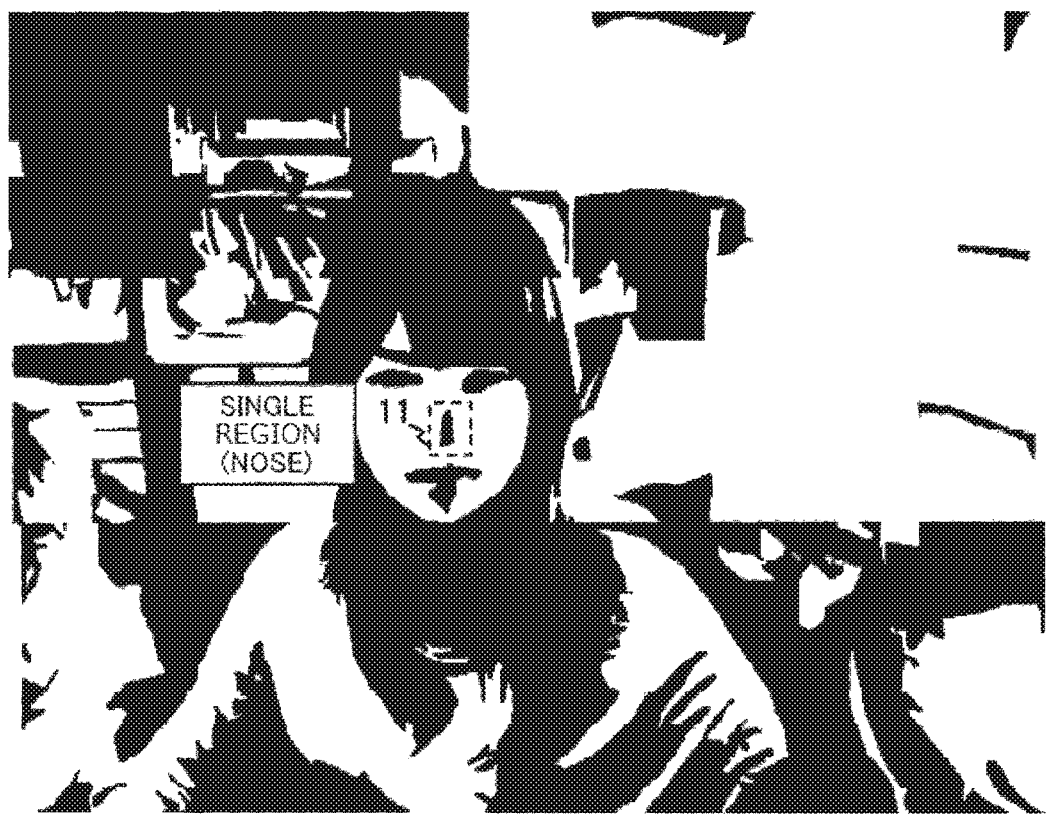
FIG. 22 shows a state of extracting a video of a living body 10.

FIG. 22 shows a state of extracting a video of the living body 10. For example, the single region video 26 is a video of the nose 11 of the living body 10. The video input unit 20 identifies, by an image recognition technique, a region including a video of the nose 11 from within a captured video. Also, the video input unit 20 extracts a video of the nose 11 from the identified region.

Figure 23:
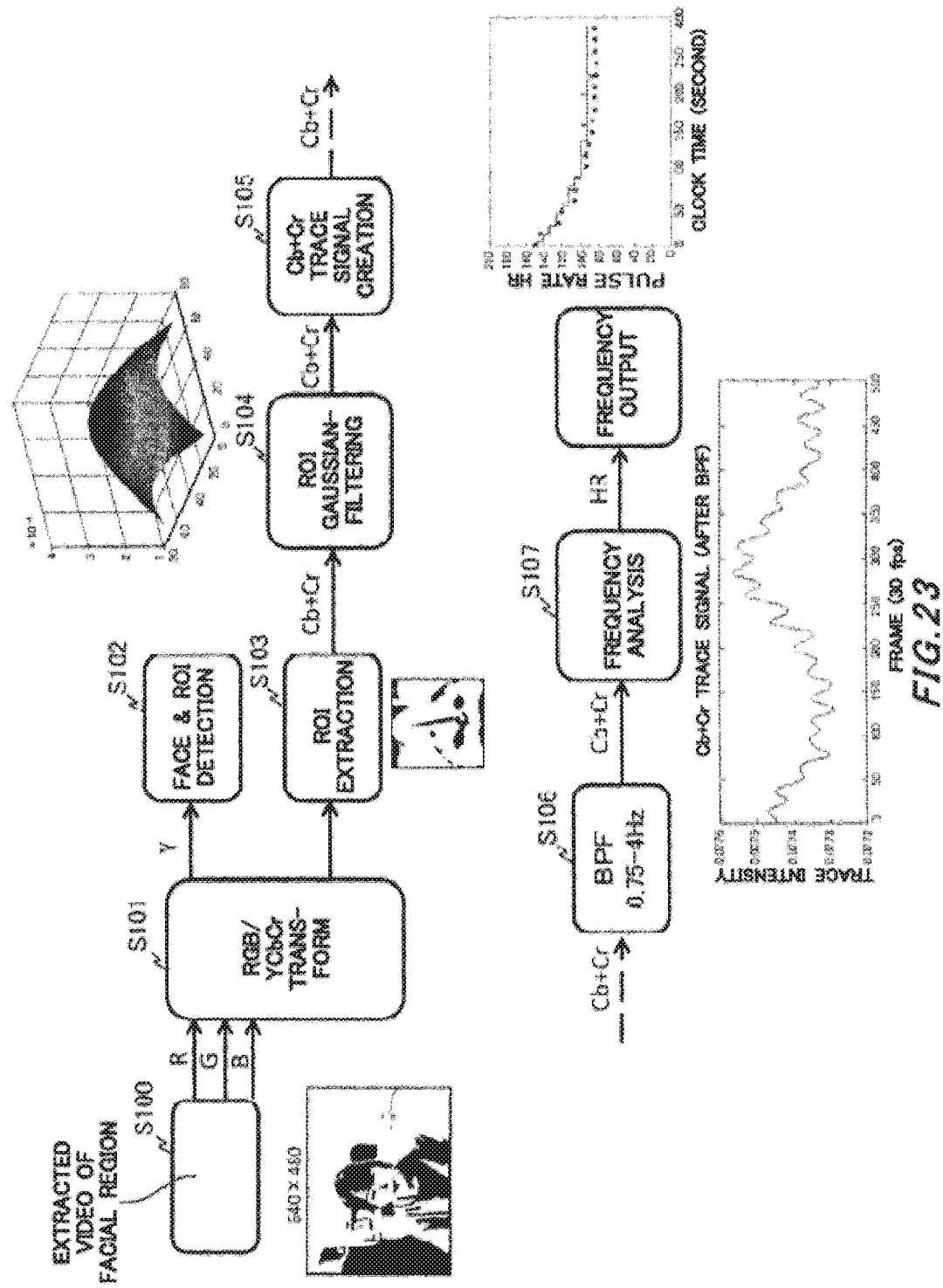
FIG. 23 shows one example of a pulse rate detection algorithm.

FIG. 23 shows one example of a pulse rate detection algorithm. By using the algorithm according to the present example, a pulse rate HR can be detected from a video of the living body 10. Stable extraction of a pulse wave waveform is a fundamental technique necessary for estimating blood pressure BP. For example, the blood pressure information output apparatus 100 can detect a pulse wave having a high S/N ratio by selecting, as a region of interest ROI, a nose region where capillaries concentrate.

At Step S100, the blood pressure information output apparatus 100 acquires a video of a measurement subject. Thereafter, the blood pressure information output apparatus 100 extracts an RGB signal from the acquired measurement subject video. In one example, the measurement subject video has 640×480 pixels.

At Step S101, the blood pressure information output apparatus 100 transforms the extracted RGB signal into a YCbCr signal. Here, Y is a luminance signal, and Cb and Cr are color-difference signals.

At Step S102, the blood pressure information output apparatus 100 detects a facial region and the region of interest ROI from the luminance signal Y. The region of interest ROI is identified based on the luminance signal Y. Here, the region of interest ROI is not limited to the nose region as long as it is a region where blood vessels concentrate to the degree that allows detection of changes in color-difference signals including pulse waveform information.

At Step S103, the blood pressure information output apparatus 100 extracts the region of interest ROI identified at Step S102. Also, the blood pressure information output apparatus 100 acquires a Cb+Cr signal in the extracted region of interest ROI.

At Step S104, the blood pressure information output apparatus 100 performs the Gaussian filtering on the region of interest ROI based on the acquired Cb+Cr signal. The Gaussian filtering is processing in which peripheral parts of the region of interest ROI are subdued by increasing the intensity of the center part of the region of interest ROI.

For example, when the region of interest ROI is a 50×50-pixel region, peripheral parts of the region of interest ROI have signals from regions other than the region of interest ROI mixed therein due to motion of the living body 10. The Gaussian filtering filters less reliable signals from the periphery of the region of interest ROI.

At Step S105, a Cb+Cr trace signal in which a value of any clock time is plotted is created based on a signal having been subjected to filtering. By using the Cb+Cr trace signal, it is possible to reduce an operation amount, and extract a pulse wave waveform stably. For example, the Cb+Cr trace signal is a value obtained by totaling Cb+Cr of each pixel over the entire region of interest ROI. Alternatively, the Cb+Cr trace signal may be the average of Cb+Cr signals of respective pixels. Thereby, a single value of the Cb+Cr trace signals can be obtained for the region of interest ROI.

At Step S106, wavelength regions other than the wavelength region of 0.75 Hz to 4 Hz are removed by a band-pass filter BPF.

Because the pulse rate HR of a general living body 10 corresponds to a range of 0.75 Hz to 4 Hz (pulse rate 45 to 240), noises other than the band of a pulse can be removed.

At Step S107, frequency analysis on the Cb+Cr trace signal is conducted. The Cb+Cr trace signal from which noises have been removed at Step 106 includes a low frequency signal that corresponds to an external environment or motion of the living body 10 and a high frequency signal that corresponds to a pulse rate HR. The blood pressure information output apparatus 100 removes an unnecessary signal by frequency analysis, and detects a pulse rate HR.

Figure 24:
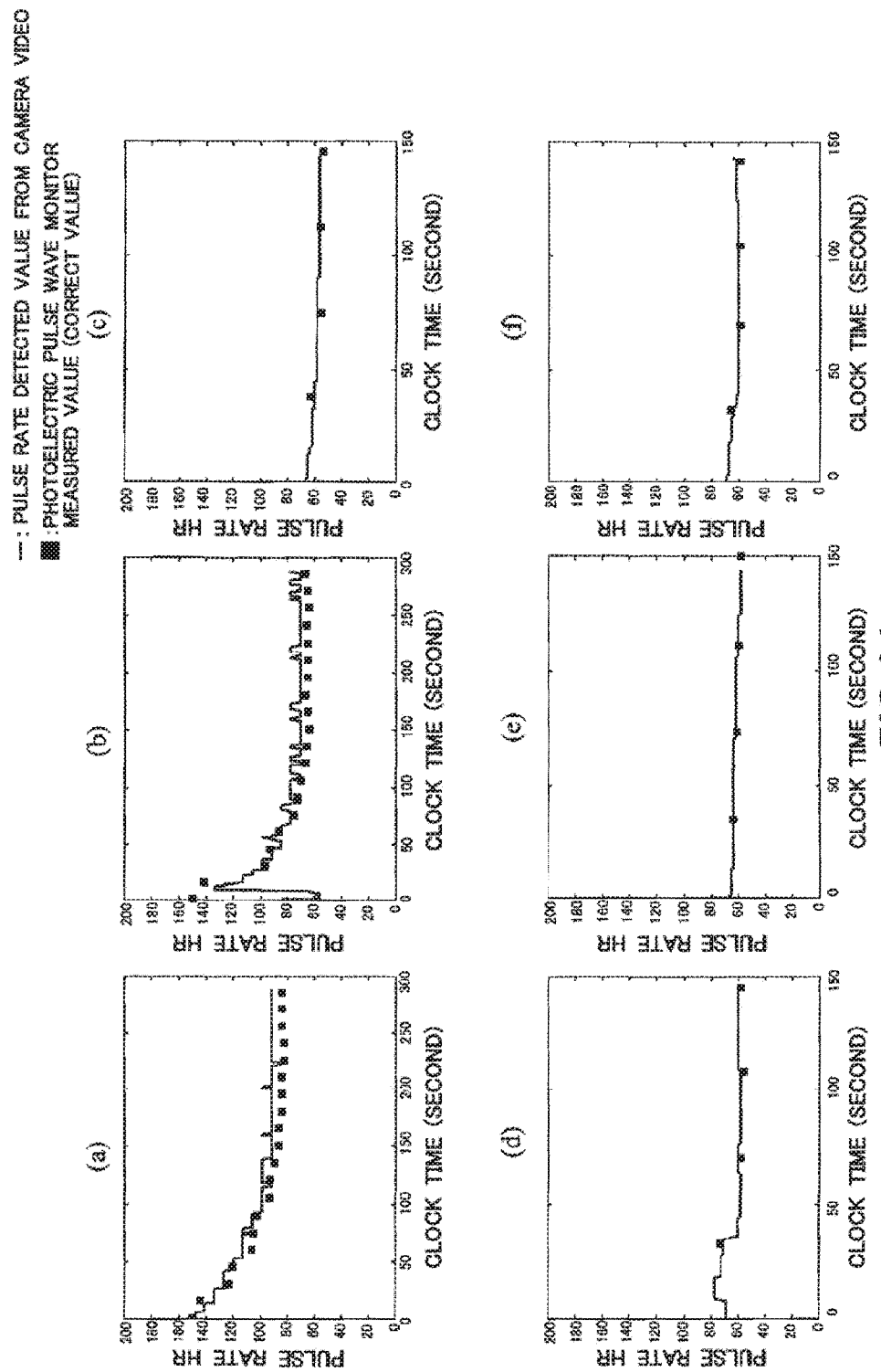
FIG. 24 shows detection results of a pulse rate HR.

FIG. 24 shows detection results of a pulse rate HR. Each graph indicates changes in a pulse rate HR (vertical axis) relative to a clock time [second] (horizontal axis). The solid lines indicate pulse rate detected values from camera videos, and the plots indicate photoelectric pulse wave monitor measured values (correct values). The graphs shown in FIG. 24 have different pulse rates HR at the clock time of 0 second. For example, in (a) and (b) of FIG. 24, pulse rates HR at the clock time of 0 second are raised due to exercising before the start of measurement. (c) to (f) of FIG. 24 show pulse rates HR of the almost normal state at the starting point of measurement.

In a period after the start of measurement, pulse rates HR are measured until they settle at normal values after stopping exercising. In the pulse detection method according to the present embodiment, changes in pulse rates HR over time are apprehend with small errors in comparison to measurement results of a photoelectric pulse wave monitor. In other words, pulse rates HR are detected accurately even from camera videos.

Figure 25:
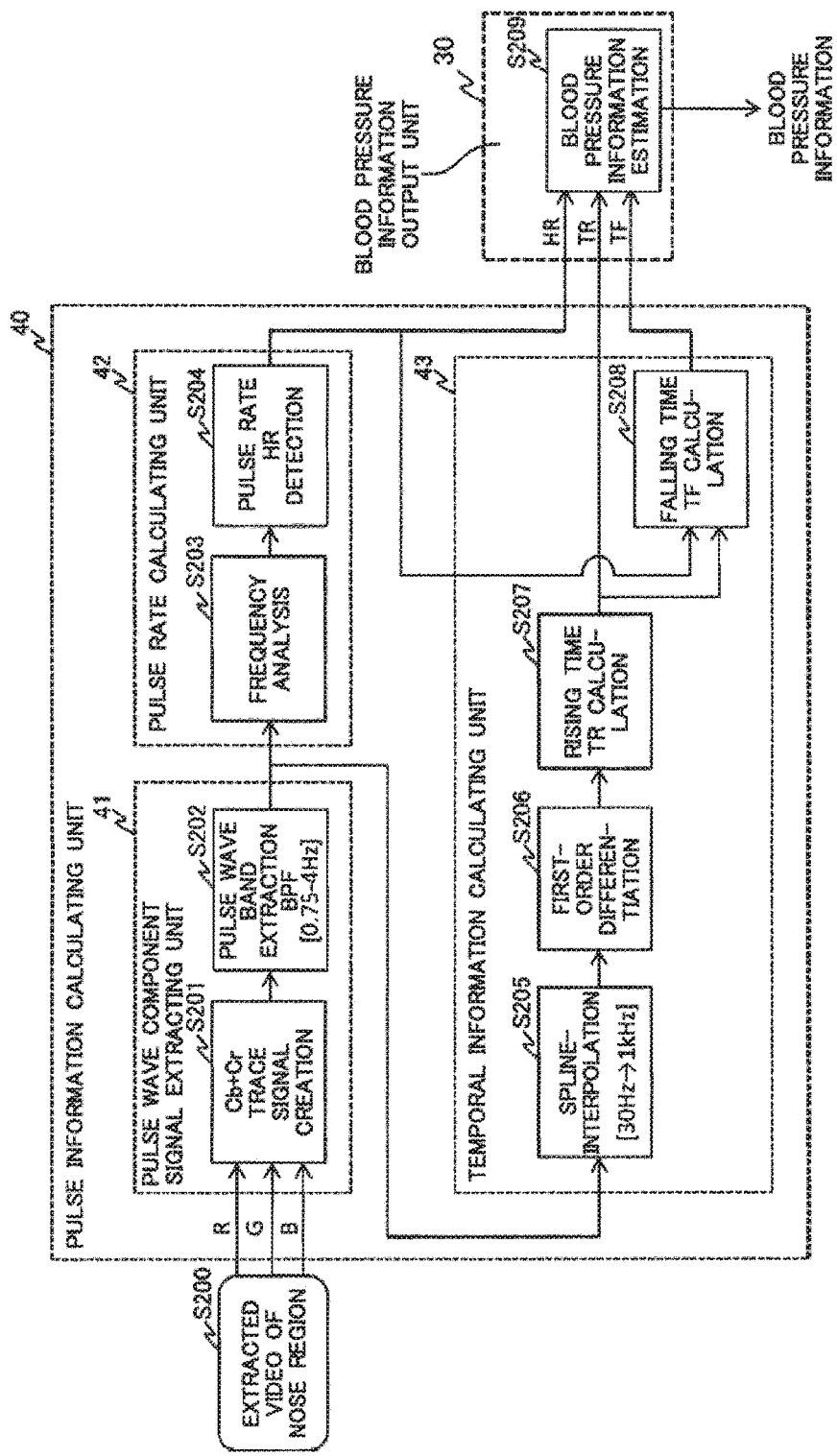
FIG. 25 shows one example of an algorithm of calculating pulse wave temporal information 46.

FIG. 25 shows one example of an algorithm of calculating the pulse wave temporal information 46. The pulse information calculating unit 40 according to the present example comprises a pulse wave component signal extracting unit 41, a pulse rate calculating unit 42 and a temporal information calculating unit 43. The pulse information calculating unit 40 calculates a pulse rate HR, rising time TR of a pulse wave and falling time TF of the pulse wave based on an RGB signal of a video extracted from a nose region of the living body 10.

At Step S200, the video input unit 20 extracts a region of the nose 11 from a video of the living body 10. The video input unit 20 extracts an RGB signal from the acquired extracted video of the nose 11 region.

At Step S201, the pulse wave component signal extracting unit 41 transforms the extracted RGB signal into a YCbCr signal consisting of a luminance component and a color difference component to generate a Cb+Cr trace signal. By generating the Cb+Cr trace signal, the amplitude of a pulse wave component becomes large.

At Step S202, the pulse wave component signal extracting unit 41 inputs the Cb+Cr signal to a band-pass filter BPF to extract a pulse wave component signal. For example, the band-pass filter BPF allows the band corresponding to the frequency of a pulse wave (0.75 Hz to 4 Hz) to pass.

At Step S203, the pulse rate calculating unit 42 conducts frequency analysis on the extracted pulse wave component signal to calculate a pulse rate HR. For example, the frequency analysis is a Fourier analysis such as FFT or DFT, or a wavelet analysis such as Haar transform or Daubechies transform. The pulse rate HR is derived by obtaining the average frequency component of a predetermined number of points by the frequency analysis, and detecting a peak corresponding to the pulse rate HR (Step S204).

At Step S205, the temporal information calculating unit 43 spline-interpolates the pulse wave component signal extracted from a camera video (30 Hz), and transforms the pulse wave component signal into continuous data at 1 kHz. In other words, spline interpolation raises the sampling rate from 30 Hz to 1 kHz (interpolation). Spline interpolation raises the accuracy of differential operation, and makes errors small. Note that the interpolation method is not limited to spline interpolation, but may be Lagrange interpolation or linear interpolation; however, spline interpolation is preferable because it requires a small operation amount, and provides good accuracy.

At Step S206, the temporal information calculating unit 43 calculates the rising time TR of a pulse wave by performing an operation of first-order differentiation on the spline-interpolated pulse wave component signal. Specifically, the temporal information calculating unit 43 calculates the rising time TR of the pulse wave by measuring a length of time from zero-crossing with a positive slope to zero-crossing with a negative slope (Step S207).

At Step S208, the temporal information calculating unit 43 calculates the falling time TF based on the rising time TR and the pulse rate HR calculated by the pulse rate calculating unit 42. The temporal information calculating unit 43 calculates the falling time TF of the pulse wave by obtaining the cycle of the pulse wave from the reciprocal of the pulse rate HR, and subtracting the rising time TR from the cycle of the pulse wave. Note that the falling time TF of the pulse wave is derived also by measuring a length of time from zero-crossing of the first-order differentiation signals of the pulse wave component signals with a negative slope to zero-crossing with a positive slope. Also, the pulse rate HR may be obtained as the reciprocal of the cycle calculated in the time domain, without transformation of the pulse wave component signals into the frequency region by frequency analysis. In other words, the pulse rate HR is obtained by measuring a length of time from zero-crossing of the first-order differentiation signals with a positive slope or a negative slope to zero-crossing with a positive slope or a negative slope.

The method of calculating the pulse rate HR by using frequency analysis according to the present example can prevent erroneous calculation of the pulse rate HR even when the slope of the pulse wave becomes zero multiple times within one cycle. Also, the rising time TR and falling time TF are calculated accurately by combining frequency analysis and first-order differentiation.

At Step S209, the blood pressure information output unit 30 estimates blood pressure information based on the pulse rate HR, the rising time TR and the falling time TF. The blood pressure information output unit 30 outputs an estimate value of the blood pressure information as blood pressure information.

Figure 26:
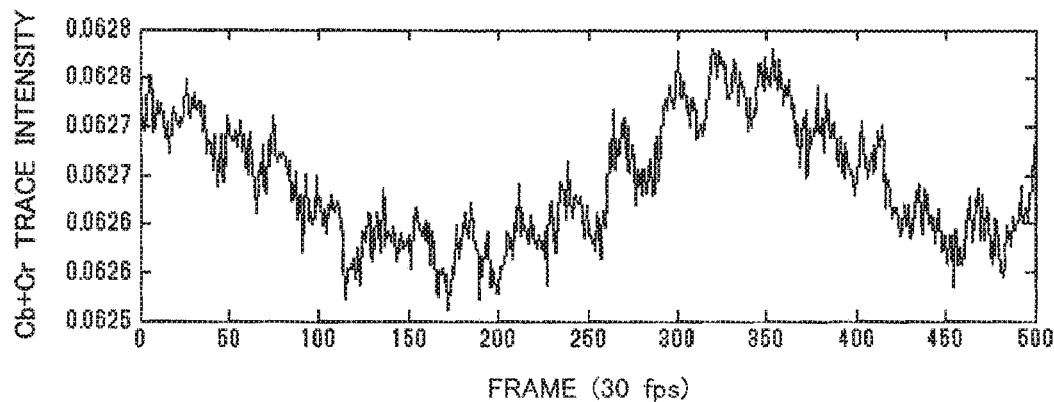
FIG. 26 shows a waveform of pulse wave component signals obtained at Step S201.

FIG. 26 shows a waveform of pulse wave component signals obtained at the Cb+Cr trace signal generating step (Step S201). Specifically, a waveform of pulse wave component signals of a nose region acquired by the video input unit 20 is shown. The horizontal axis shows the number of frames, and the vertical axis shows the trace intensity of a Cb+Cr signal. Each frame is updated 30 times per second (30 fps).

Figure 27:
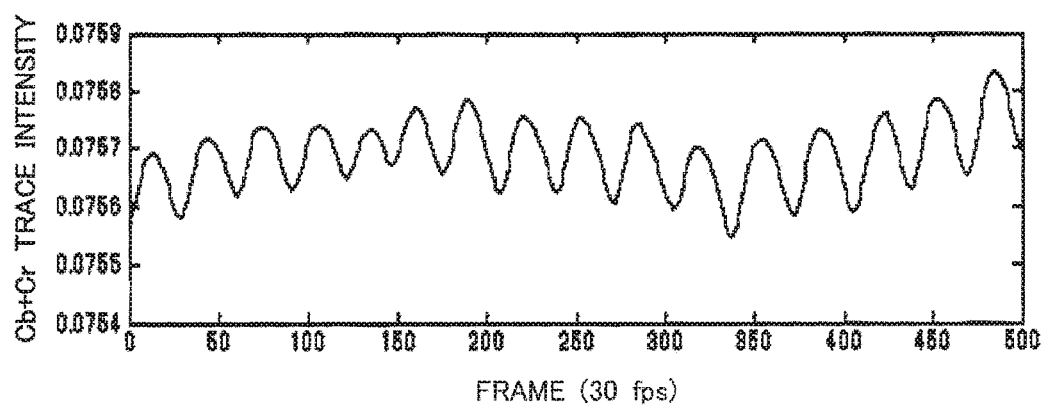
FIG. 27 shows a waveform of pulse wave component signals obtained at Step S202.

FIG. 27 shows a waveform of pulse wave component signals obtained at the pulse wave band extracting step (Step S202). Because the Cb+Cr signal according to the present example has passed the band-pass filter BPF, noises are reduced as compared with the Cb+Cr signal in FIG. 26. In other words, unnecessary bands other than the pulse wave band are removed from the trace signal generated at Step S201. The horizontal axis indicates the number of frames, and the vertical axis indicates the trace intensity of a Cb+Cr signal. Each frame is updated 30 times per second (30 fps).

Figure 28:
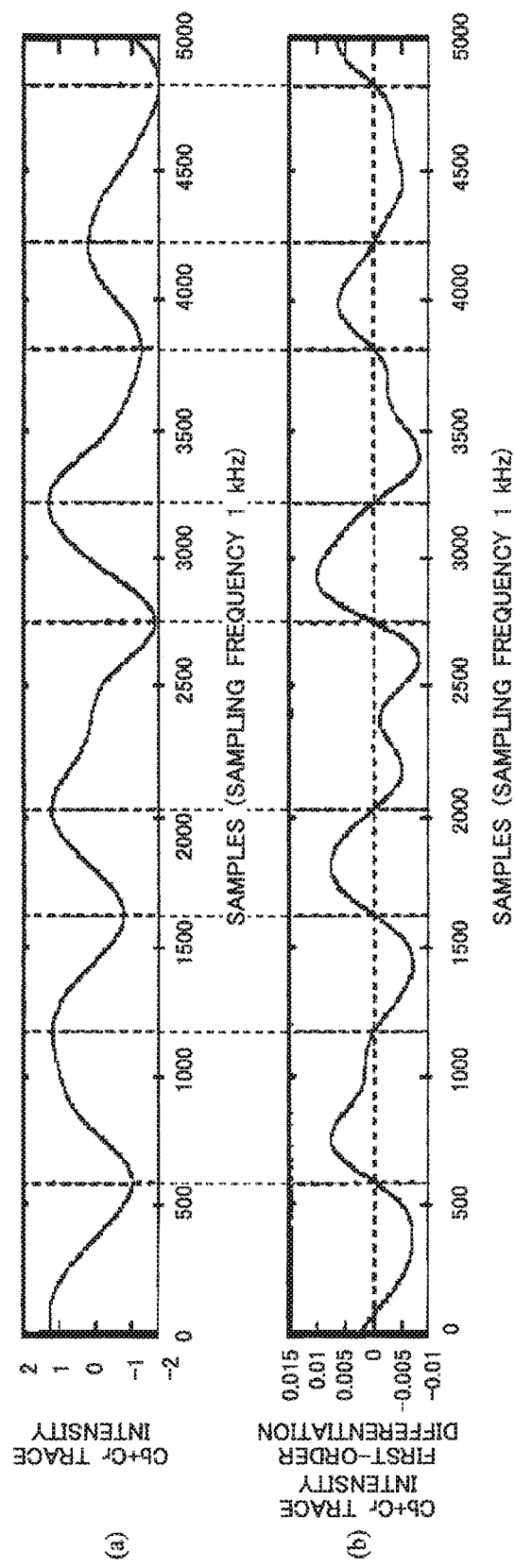
FIG. 28 shows comparison between a waveform of Cb+Cr trace intensity and a waveform obtained by first-order differentiation thereof.

FIG. 28 shows comparison between a waveform of Cb+Cr trace intensity and a waveform obtained by first-order differentiation thereof. The horizontal axis indicates samples (sampling frequency: 1 kHz), and the vertical axis indicates the intensity of a Cb+Cr trace signal.

(a) of FIG. 28 indicates an output waveform of the Cb+Cr trace signal intensity, after spline interpolation, of the nose region obtained at Step S205. (b) of FIG. 28 indicates a waveform obtained by first-order differentiation of the Cb+Cr trace signal obtained at Step S206. Samples at which slopes become zero in (a) of FIG. 28 correspond to zero-crossing of a waveform obtained by first-order differentiation of the intensity of the Cb+Cr trace signal in (b) of FIG. 28.

Figure 29:
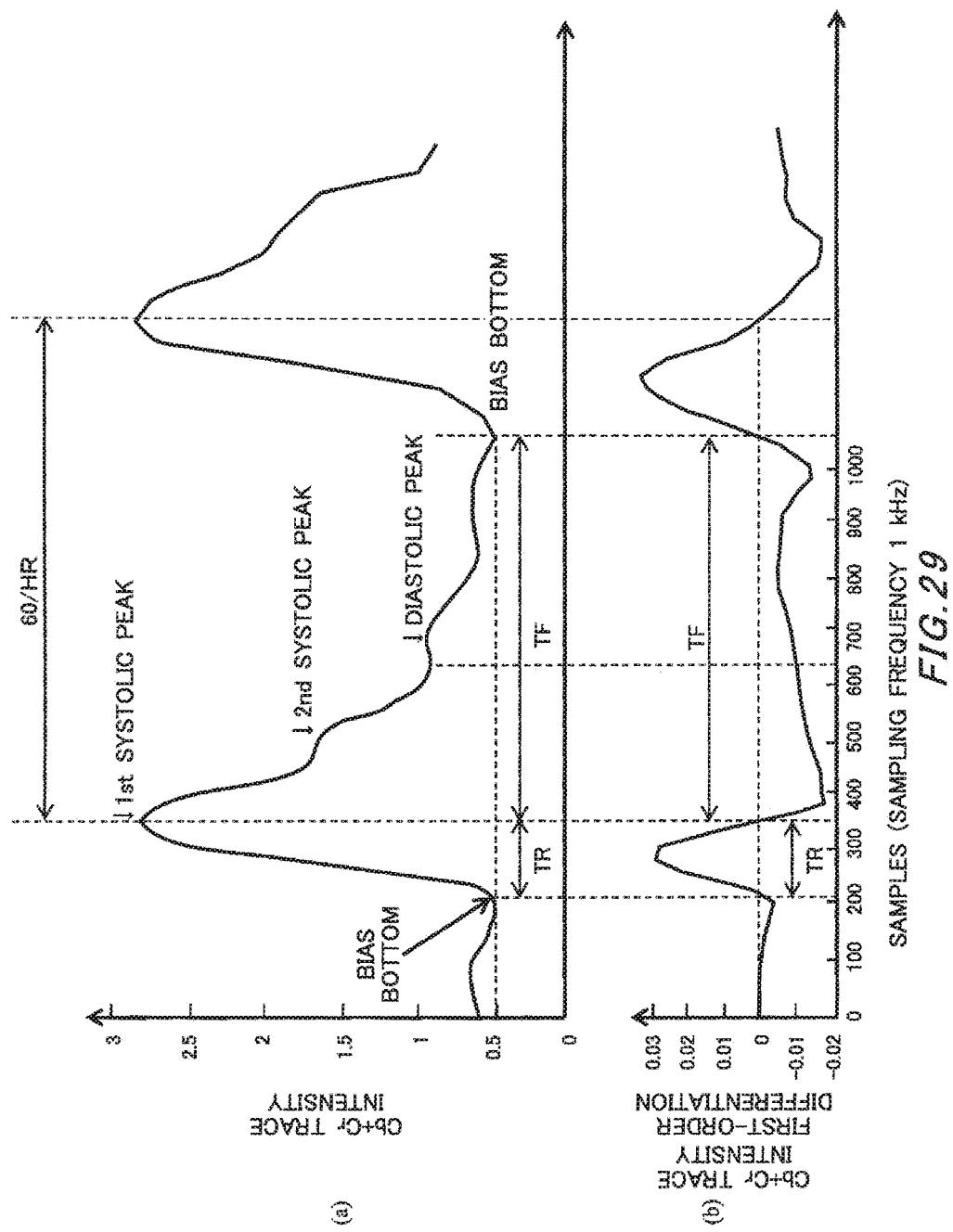
FIG. 29 shows expanded views of an output waveform after spline interpolation, and a waveform obtained by first-order differentiation thereof.

FIG. 29 shows expanded views of an output waveform after spline interpolation, and a signal waveform obtained by first-order differentiation thereof. The horizontal axis indicates samples (sampling frequency: 1 kHz). (a) of FIG. 29 indicates an output waveform of the Cb+Cr trace intensity, after spline interpolation, of the nose region obtained at Step S205. (b) of FIG. 29 indicates a waveform obtained by first-order differentiation of the Cb+Cr trace intensity obtained at Step S206. The Cb+Cr trace first-order differentiation intensity shows zero-crossing at the bottom and peak clock times of pulse wave component signals from the nose 11 region.

The pulse wave rising time TR is a length of time that is correlated with the systolic blood pressure SBP and is from the bias bottom (Bias Bottom) to the top (1st Systolic Peak) in one cycle. The pulse wave falling time TF is a length of time that is correlated with the diastolic blood pressure DBP and is from the top until the pulse wave goes down again to the bias bottom. Note that the sum (TR+RF) of the pulse wave rising time TR and falling time TF is expressed as 60/PR by using the pulse rate HR.

(Blood Pressure Estimation Method 1)

Figure 30:
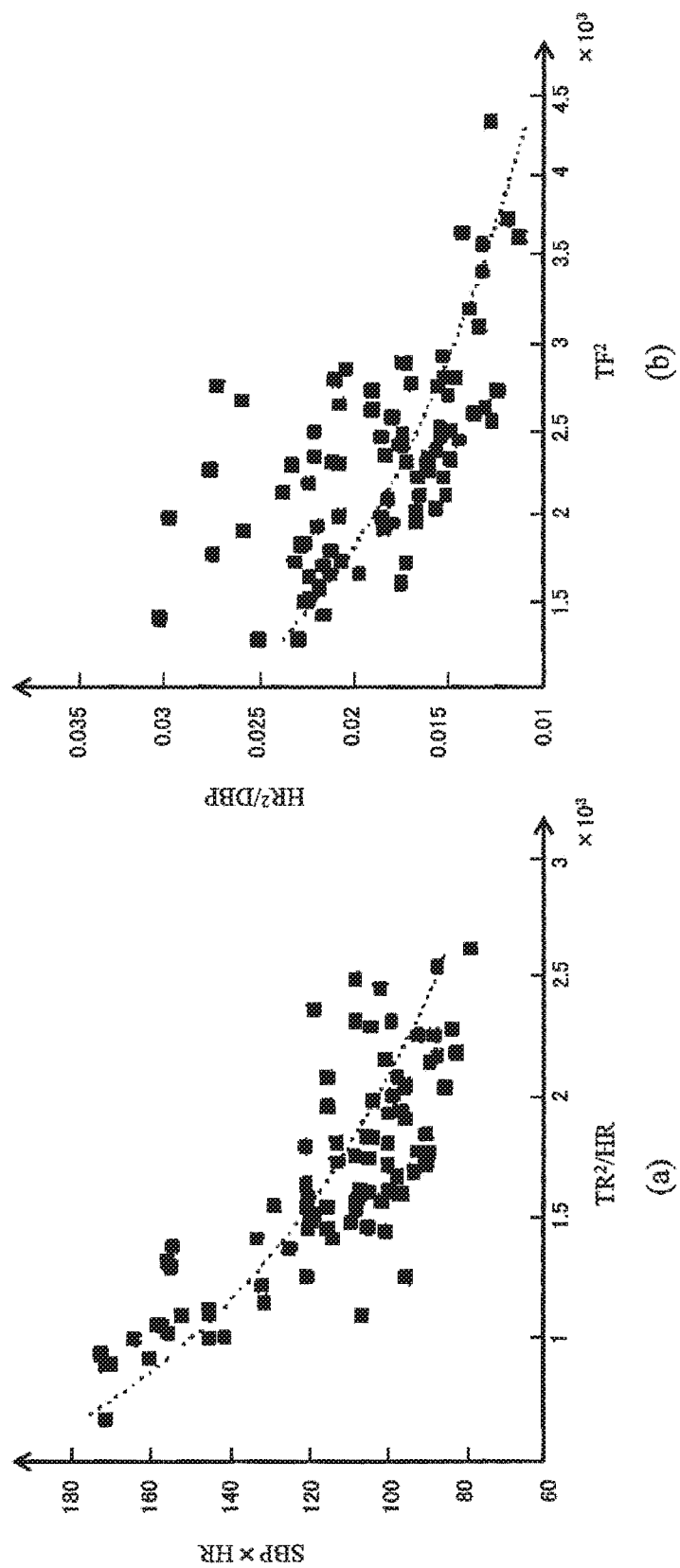
FIG. 30 shows a correlation between blood pressure BP and temporal information TR, TF.

FIG. 30 shows a correlation between the blood pressure BP and the temporal information TR, TF. (a) of FIG. 30 shows a correlation between the systolic blood pressure SBP and the rising time TR. The systolic blood pressure SBP is highly correlated with the square of the rising time TR. Also, (b) of FIG. 30 shows a correlation between the diastolic blood pressure DBP and the falling time TF. The diastolic blood pressure DBP is highly correlated with the square of the falling time TF. A relational expression between the systolic blood pressure SBP and the rising time TR, and a relational expression between the diastolic blood pressure DBP and the falling time TF are explained below.

Assuming that the area of a nose region of the living body 10 extracted as a video is S [m$^2$], the depth of a single blood vessel which is assumingly formed by capillaries of the nose region is D(t) [m], the mass of blood per unit volume is m [kg/m$^3$], the constant of proportionality about hemoglobin concentration is k, and the pulse wave intensity is I(t), the pulse wave intensity I(t) can be expressed by the following equation.

$$I(t) = kmSD(t) \qquad (1) \text{ [Equation 1]}$$

When the force is F, and the motion amount is p (provided that when the mass is M and the speed is v, p=Mv), the following Newton's equation of motion holds.

$$F = dp/dt = Mv \qquad (2) \text{ [Equation 2]}$$

The following equation can be obtained by assigning Equation 1 to Equation 2.

[Equation 3]

$$F = \frac{d}{dt}\left\{mSD(t)\frac{d}{dt}D(t)\right\} \qquad (3)$$

Based on Equation 3, the pressure P of blood vessels can be expressed by the following equation.

[Equation 4]

$$P = \frac{F}{S} \qquad (4)$$
$$= \frac{d}{dt}\left\{mD(t)\frac{d}{dt}D(t)\right\}$$

The following equation can be obtained by assigning Equation 1 to Equation 4.

[Equation 5]

$$P = \frac{1}{k^2 m s^2}\frac{d}{dt}\left\{I(t)\frac{d}{dt}I(t)\right\} \qquad (5)$$

Here, because the systolic blood pressure SBP is an average pressure at which blood compresses blood vessels over time in which the blood vessel expands and the pulse wave intensity rises from the bottom to the top, the systolic blood pressure SBP is derived as follows.

[Equation 6]

$$SBP = \frac{1}{TR} \int_0^{TR} P\, dt \qquad (6)$$
$$= \frac{1}{TR} \frac{1}{k^2 mS^2} \int_0^{TR} \frac{d}{dt}\left\{ I(t) \frac{d}{dt} I(t) \right\} dt$$
$$= \frac{1}{TR} \frac{1}{k^2 ms^2} \left[ I(t) \frac{d}{dt} I(t) \right]_0^{TR}$$

Here, assuming that $I(TR) = I_{peak1}$ (the top value of the pulse wave intensity: 1st Systolic Peak) and $dI(TR)/dt$ is approximated by using the average rate of change $I_{peak1}/TR$, Equation 6 turns into:

[Equation 7]

$$SBP = \frac{1}{k^2 ms^2} \frac{I_{peak1}^2}{TR^2} + \text{Const} \qquad (7)$$

It can be known from Equation 7 that the systolic blood pressure SBP is highly correlated with the square of the rising time TR.

Furthermore, assuming that $I_{peak1}$ is proportional to the pulse rate HR, and replacing all the constants of proportionality related to Equation 7 with a single constant of proportionality K1, the following equation is obtained.

[Equation 8]

$$SBP = K1 \frac{HR^2}{TR^2} + \text{Const} \qquad (8)$$

Transforming Equation 8 into a logarithmic approximation format, the following equation is obtained.

[Equation 9]

$$SBP \times HR = a \log_{10}\left(\frac{TR^2}{HR}\right) + b \qquad (9)$$

Note that the dashed line in (a) of FIG. 30 is a graph of Equation 9 after assigning predetermined values to a and b, and it can be known it is a curve conforming to each measurement plot.

The diastolic blood pressure DBP is an average pressure at which blood compresses blood vessels over time in which the blood vessel contracts and the pulse wave intensity goes down from the top to the bottom. The relational expression of the diastolic blood pressure DBP is derived in a similar manner to that for the systolic blood pressure SBP.

[Equation 10]

$$DBP = \frac{1}{TF} \int_{TR}^{TR+TF} P\, dt \qquad (10)$$
$$= \frac{1}{TF} \frac{1}{k^2 mS^2} \int_{TR}^{TR+TF} \frac{d}{dt}\left\{ I(t) \frac{d}{dt} I(t) \right\} dt$$
$$= \frac{1}{TF} \frac{1}{k^2 ms^2} \left[ I(t) \frac{d}{dt} I(t) \right]_{TR}^{TR+TF}$$

Here, approximating $dI(TF)/dt$ by using the average rate of change $-I_{peak1}/TF$, Equation 10 turns into:

[Equation 11]

$$DBP = \frac{1}{k^2 ms^2} \frac{I_{peak1}^2}{TF^2} + \text{Const} \qquad (11)$$

It can be known from Equation 11 that the diastolic blood pressure is highly correlated with the square of the falling time TF.

Furthermore, assuming that $I_{peak1}$ is proportional to the pulse rate HR, and replacing all the constants of proportionality related to Equation 11 with a single constant of proportionality K2, the following equation is obtained.

[Equation 12]

$$DBP = K2 \frac{HR^2}{TF^2} + \text{Const} \qquad (12)$$

Transforming Equation 12 into a logarithmic scale format, the following equation is obtained.

[Equation 13]

$$\frac{HR^2}{DBP} = c \log_{10}(TF^2) + d \qquad (13)$$

Note that the dashed line in (b) of FIG. 30 is a graph of Equation 13 after assigning predetermined values to c and d, and it can be known it is a curve conforming to each measurement plot. Equation 9 and Equation 13 are logarithmically approximated. But a method of approximation may be any method, and equations may be selected according to a method of approximation.

Figure 31:
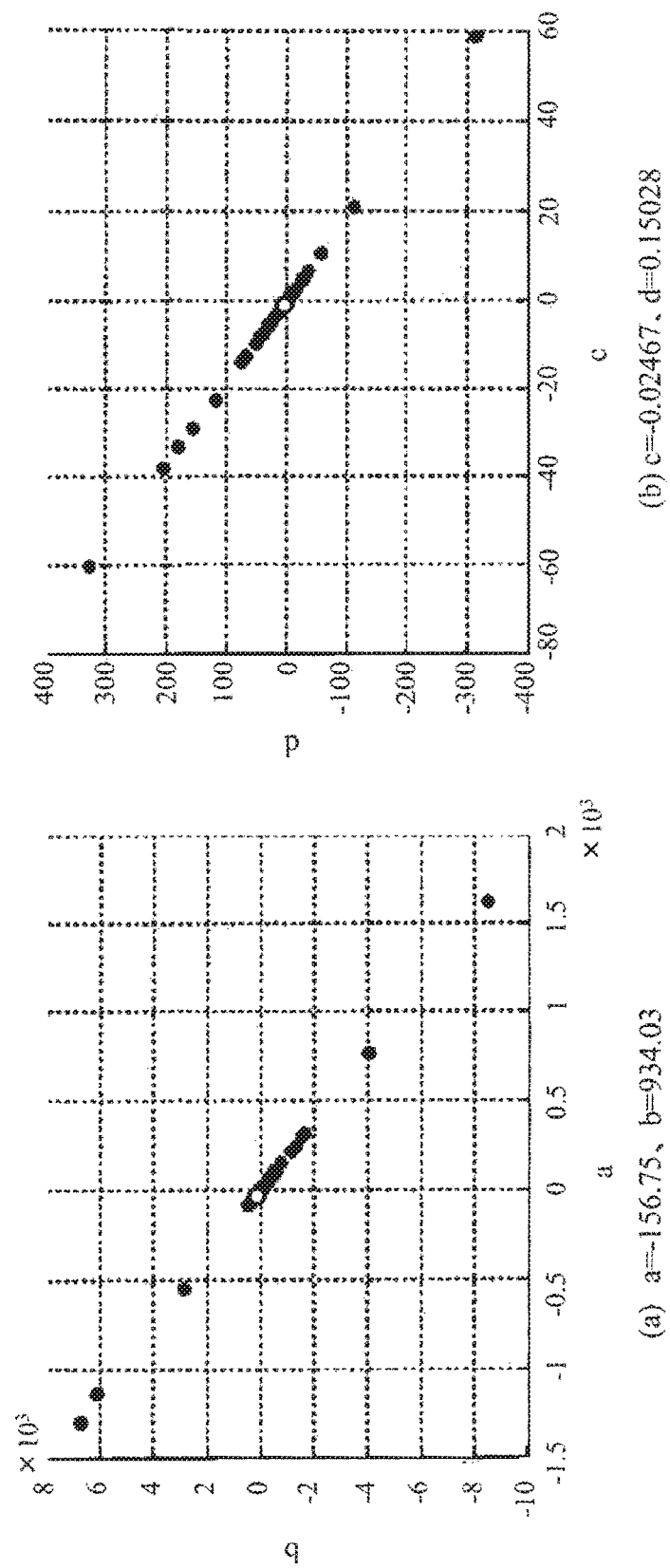
FIG. 31 is a figure for explaining an algorithm of calculating parameters a to d.

FIG. 31 is a figure for explaining an algorithm of calculating parameters (a, b, c, d) of Equation 9 and Equation 13. The blood pressure information output unit 30 records, in advance and in synchronization with each other, a video of a nose region and true blood pressure BP (correct blood pressure) measured by a sphygmomanometer. The blood pressure information output unit 30 can obtain a combination group of temporal information TR, TF of a pulse wave, a pulse rate HR calculated from a video of the nose 11 region, and blood pressures SBP, DBP. The blood pressure information output unit 30 solves a plurality of simultaneous equations based on the combination group of temporal information TR, TF of a pulse wave, a pulse rate HR, and blood pressure BP to calculate parameters (a, b, c, d).

In the present example, the temporal information TR, TF and the pulse rate HR are calculated from the recorded camera video and are combined with the correct values of SBP, DBP to calculate parameters (a, b, c, d) for each two pairs of data. Also, respective average values are calculated from the calculated parameters (a, b, c, d).

The parameters (a, b, c, d) calculated in the present example are as follows:

$a = -156.75$ $b = 934.03$ $c = -0.02467$ $d = 0.15028$

The blood pressure information output unit 30 can calculate, from the acquired video, the temporal information TR, TF and the pulse rate HR to estimate the blood pressure BP. In other words, once the temporal information TR, TF and the pulse rate HR are calculated, the blood pressure information output unit 30 can estimate the blood pressures SBP, DBP based on the pre-calculated parameters (a, b, c, d), Equation 9 and Equation 13.

Note that the parameters (a, b, c, d) may be determined by the least-squares method. Also, the blood pressure information output unit 30 may solve a simultaneous equation, from among a plurality of simultaneous equations, for each number of the parameters (a, b, c, d), and handle the center of gravity or central value of the respective solved parameters (a, b, c, d) as the respective parameters (a, b, c, d).

The parameters (a, b, c, d) have a dispersed but unitary distribution. Also, the blood pressure information output unit 30 may figure out the sex, age or the like from a facial image to select the parameters (a, b, c, d) according to the sex, age or the like. Thereby, the accuracy of estimating blood pressure improves.

(Blood Pressure Estimation Method 2)

Figure 32:
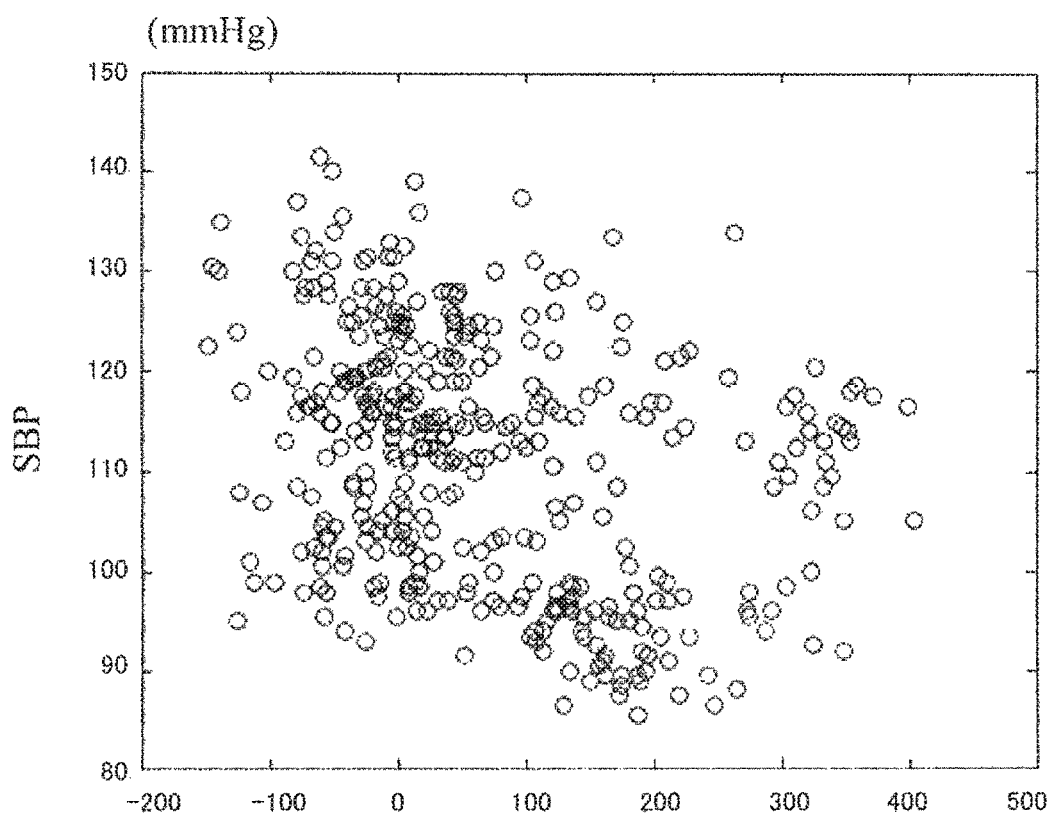
FIG. 32 shows one example of a method of estimating systolic blood pressure SBP.

FIG. 32 shows one example of a method of estimating the systolic blood pressure SBP. $TR^2/HR$ and HR are used as feature amounts in an equation of estimating the systolic blood pressure SBP according to the present example. The vertical axis indicates the systolic blood pressure SBP [mmHg] and the horizontal axis indicates:

$$-157 \log_{10}\left(\frac{TR^2}{HR}\right) + 934\frac{1}{HR}$$

The systolic blood pressure SBP has a correlation with an estimation equation in which the pulse rate HR and the rising time TR are used.

Figure 33:
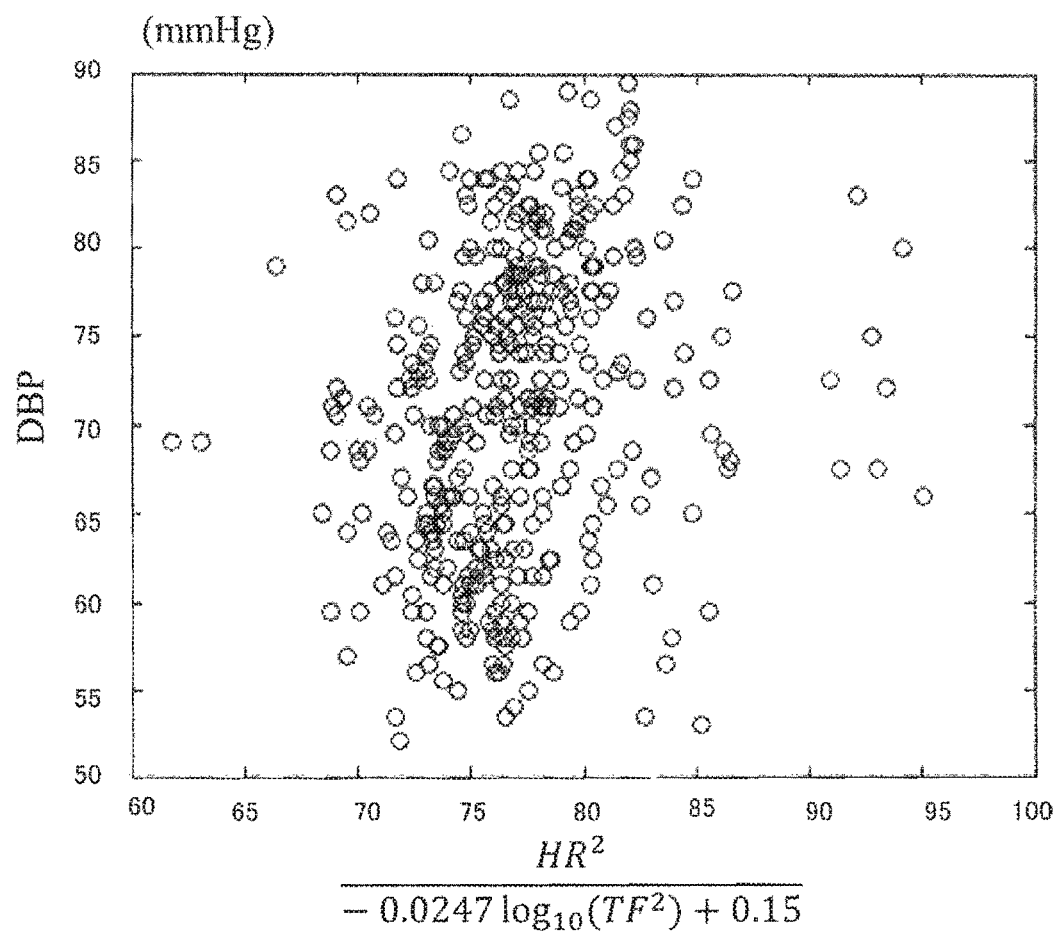
FIG. 33 shows one example of a method of estimating diastolic blood pressure DBP.

FIG. 33 shows one example of a method of estimating the diastolic blood pressure DBP. $HR^2$ and $TF^2$ are used as pulse wave feature amounts in an equation of estimating the diastolic blood pressure DBP according to the present example. The vertical axis indicates the diastolic blood pressure DBP [mmHg], and the horizontal axis indicates:

$$\frac{HR^2}{-0.0247 \log_{10}(TF)^2 + 0.15}$$

The diastolic blood pressure DBP has a correlation with an estimation equation in which the pulse rate HR and the falling time TF are used.

(Blood Pressure Estimation Method 3)

Figure 34:
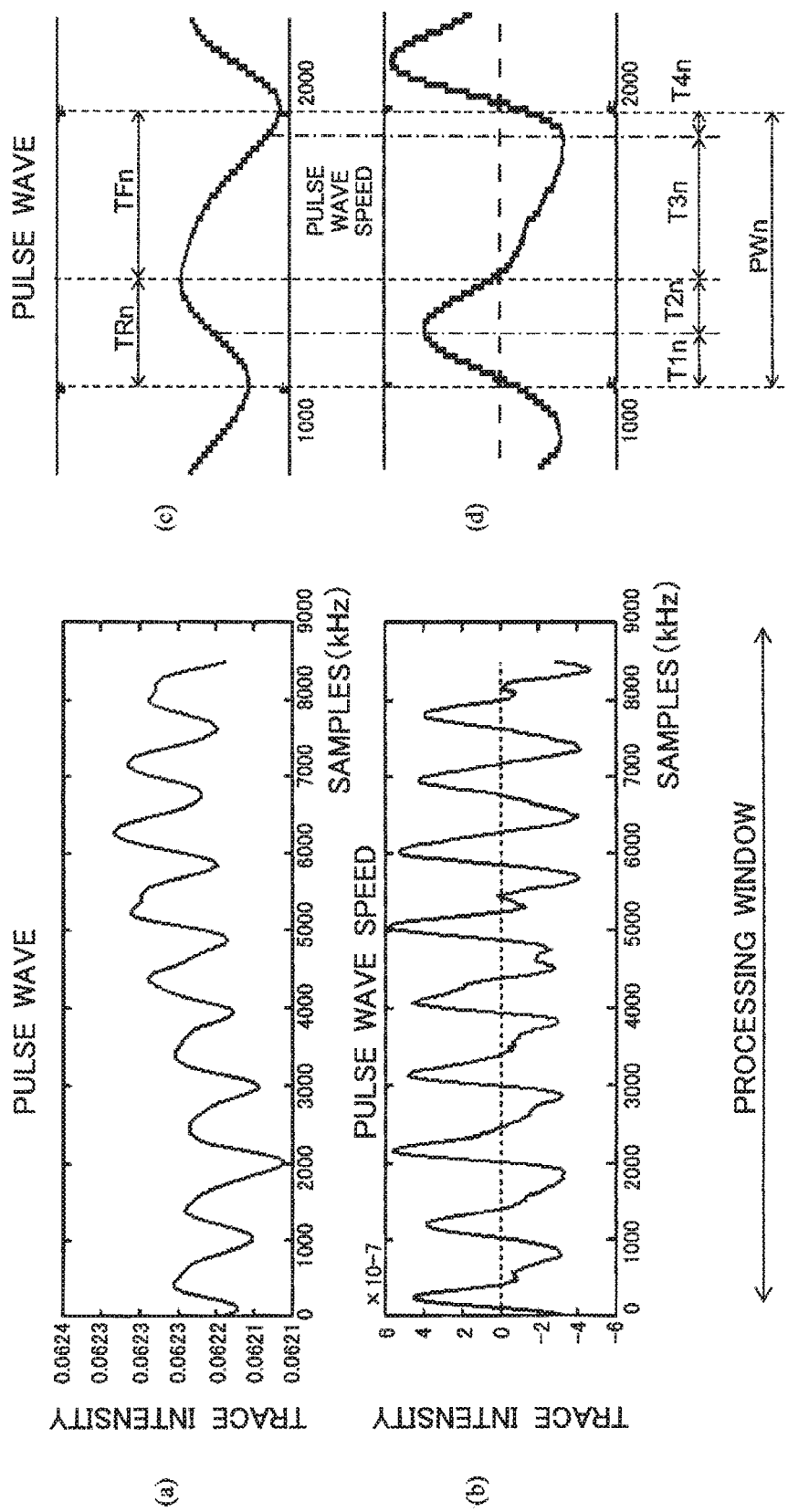
FIG. 34 shows one example of a method of setting an independent feature amount in the time domain.

FIG. 34 shows one example of a method of setting a pulse wave feature amount in the time domain. (a) and (b) of FIG. 34 indicate pulse wave and pulse wave speed, respectively. Also, (c) and (d) of FIG. 34 are expanded views of pulse wave and pulse wave speed around the portion corresponding to the number of samples of 1000 to 2000. In the present example, the pulse wave at the number of samples 1000 to 2000 are handled as an n-th pulse wave in a processing window.

Pulse wave feature amounts in the time domain are, for example, PWn, TRn, TFn, T1$n$, T2$n$, T3$n$ and T4$n$ in the figure. Pulse wave feature amounts in the time domain are less likely to be influenced by an imaging environment of a camera as compared with pulse wave feature amounts in the amplitude domain. For this reason, when acquiring pulse waveform information optically from the living body 10, the pulse waveform information preferably includes pulse wave feature amounts in the time domain.

PWn, TRn and TFn are feature amounts of an n-th pulse wave in the processing window. PWn indicates the pulse width of an n-th pulse wave. That is, PWn is a length of time in an n-th pulse wave between a rising zero-cross point of a pulse wave speed and a next rising zero-cross point. Note that the pulse widths of the pulse wave and pulse wave speed are equal to each other.

TRn indicates the rising time TR of an n-th pulse wave. That is, TRn is a length of time in an n-th pulse wave from a rising zero-cross point of a pulse wave speed to a next falling zero-cross point. Also, TFn indicates the falling time TF of an n-th pulse wave. That is, TFn is a length of time in an n-th pulse wave from a falling zero-cross point of a pulse wave speed to a next rising zero-cross point.

T1$n$ is a length of time from a rising zero-cross point of a pulse wave speed to a next top peak. Also, T2$n$ is a length of time from a top peak of a pulse wave speed to a next falling zero-cross point. T3$n$ is a length of time from a falling zero-cross point of a pulse wave speed to a next bottom peak. Also, T4$n$ is a length of time from a bottom peak of a pulse wave speed to a next rising zero-cross point. Note that the top peak and bottom peak of a pulse wave are where the pulse wave speed becomes 0.

In the blood pressure estimation method 3, pulse wave feature amounts PWn, TRn, TFn, T1$n$, T2$n$, T3$n$ and T4$n$ in the time domain are pulse wave feature amounts calculated respectively independently. In the present specification, to calculate pulse wave feature amounts independently means that two or more pulse wave feature amounts are calculated so that they do not become dependent on each other. That is, that pulse wave feature amounts are independent of each other means one pulse wave feature amount is not a function of another pulse wave feature amount. Note that pulse wave feature amounts that are independent of each other may be not only those that are completely independent of each other, but also those whose correlation with each other is low. For example, when T1$n$ and T4$n$ are used as pulse wave feature amounts, they are more independent as compared with a case where TRn and TFn are used as pulse wave feature amounts. On the other hand, the pulse rate HR, the rising time TR and the falling time TF have a relationship of TF=60/HR−TR Accordingly, when an estimation equation in which the pulse rate HR, and the rising time TR, the falling time TF or the like are dependent on each other are used in estimation of the systolic blood pressure SBP and diastolic blood pressure DBP, the systolic blood pressure SBP and the diastolic blood pressure DBP show mutually linked behaviors.

When mutually independent pulse wave feature amounts are used for estimation of the systolic blood pressure SBP and diastolic blood pressure DBP, preferably, one pulse wave feature amount is used for an equation of estimating the systolic blood pressure SBP, and another pulse wave feature amount is used for an equation of estimating the diastolic blood pressure DBP. Thereby, each of the systolic blood pressure SBP and the diastolic blood pressure DBP is never forcibly changed in a mutually linked manner, and can be estimated respectively independently.

Note that in addition to a viewpoint of independence, pulse wave feature amounts may be chosen from various viewpoints such as a viewpoint of estimation accuracy. In other words, pulse wave feature amounts may be varied as needed according to purposes of uses.

Figure 35:
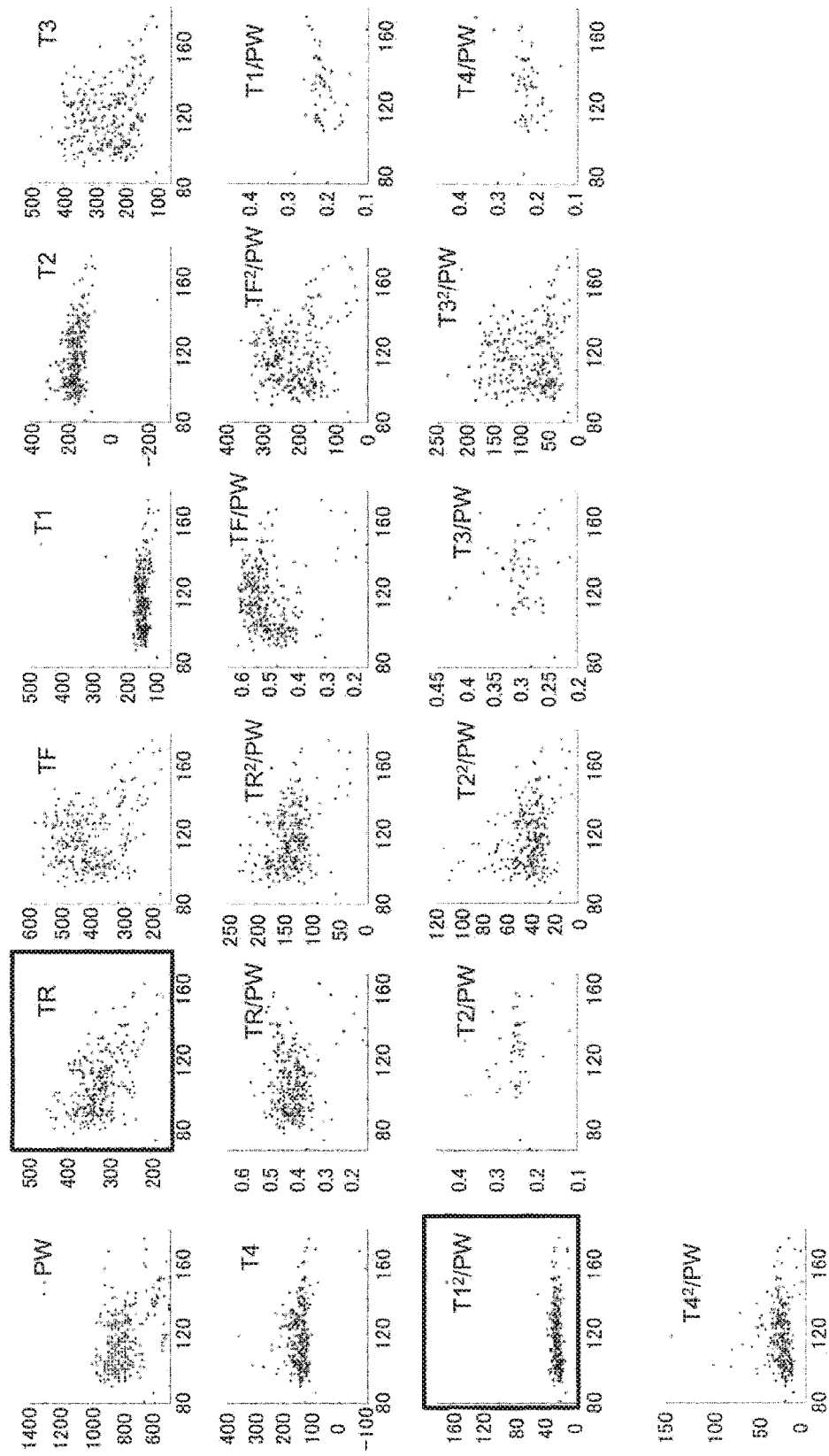
FIG. 35 is a figure for explaining a method of choosing a feature amount of systolic blood pressure SBP.

FIG. 35 is a figure for explaining a method of choosing a pulse wave feature amount of the systolic blood pressure SBP. On the basis of extracted pulse wave feature amounts (T1 to T4) in the time domain, variations of various pulse wave feature amounts were tested. Among them, pulse wave feature amounts that are highly correlated with the systolic blood pressure SBP were chosen.

In the present example, the horizontal axes indicate the systolic blood pressure SBP, and the vertical axes indicate PW, TR, TF, T1, T2, T3, T4, TR/PW, TR$^2$/PW, TF/PW, TF$^2$/PW, T1/PW, T1$^2$/PW, T2/PW, T2$^2$/PW, T3/PW, T3$^2$/PW, T4/PW and T4$^2$/PW, respectively. Comparison among the respective graphs shows that TR and T1$^2$/PW are most correlated with the systolic blood pressure SBP.

Figure 36:
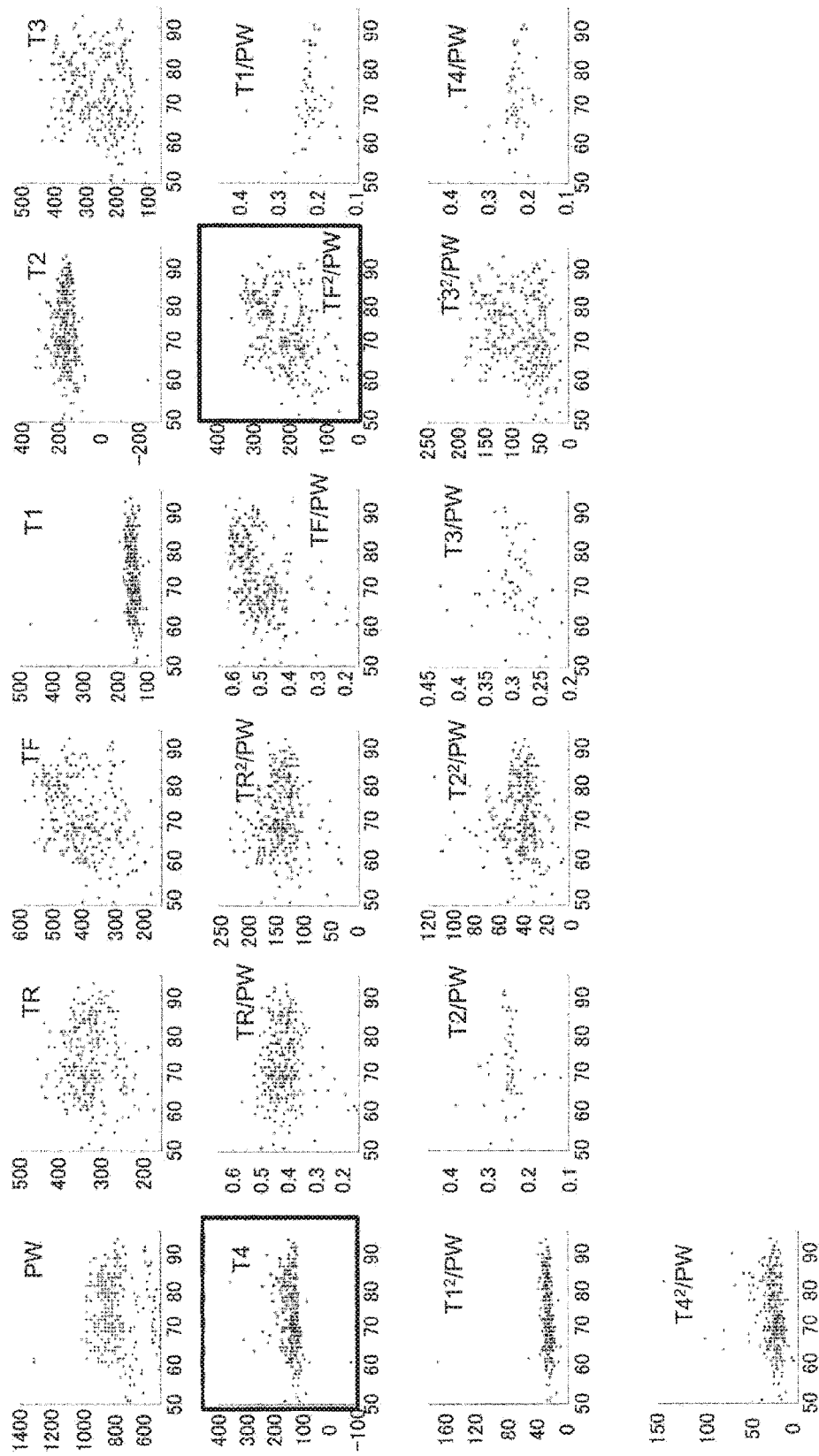
FIG. 36 is a figure for explaining a method of choosing a feature amount of diastolic blood pressure DBP.

FIG. 36 is a figure for explaining a method of choosing a pulse wave feature amount for the diastolic blood pressure DBP. In a similar manner to that for the systolic blood pressure SBP, on the basis of extracted pulse wave feature amounts (T1 to T4) in the time domain, variations of various pulse wave feature amounts were tested. Among them, pulse wave feature amounts that are highly correlated with the diastolic blood pressure DBP were chosen.

In the present example, the horizontal axes indicate the diastolic blood pressure DBP, and the vertical axes indicate PW, TR, TF, T1, T2, T3, T4, TR/PW, TR$^2$/PW, TF/PW, TF$^2$/PW, T1/PW, T1$^2$/PW, T2/PW, T2$^2$/PW, T3/PW, T3$^2$/PW, T4/PW and T4$^2$/PW, respectively. Comparison among the respective graphs shows that T4 and TF$^2$/PW are most correlated with the diastolic blood pressure DBP.

Figure 37:
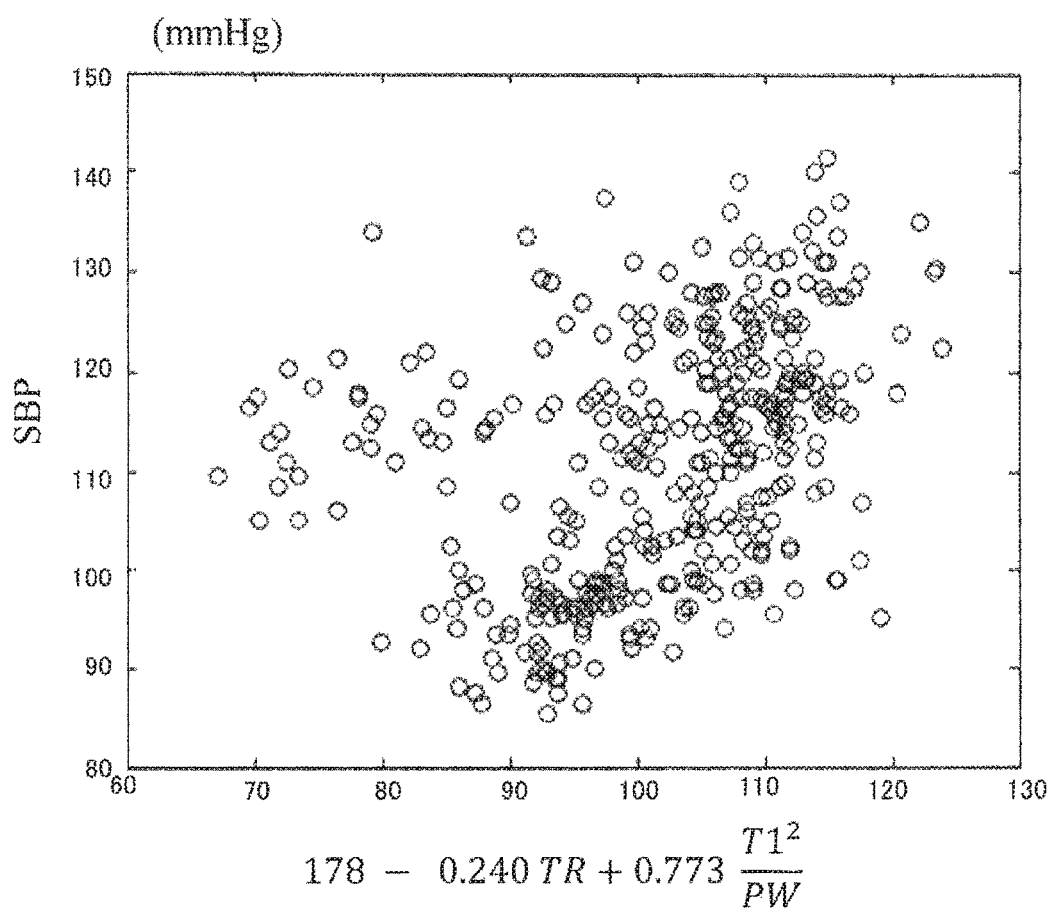
FIG. 37 shows an estimation equation using a pulse wave feature amount in the time domain.

FIG. 37 shows an equation of estimating the systolic blood pressure SBP using a pulse wave feature amount in the time domain. Based on the results of comparison in FIGS. 35, TR and T1$^2$/PW are used in the equation of estimating the systolic blood pressure SBP. The equation of estimating the systolic blood pressure SBP according to the present example is derived by multiple linear combination of selected pulse wave feature amounts.

That is, the equation of estimating the systolic blood pressure SBP is expressed as:

$$SBP = a + b \times TR + c \times \frac{T1^2}{PW}$$

Here, respective coefficient values a, b, c are calculated by a multiple regression analysis. The coefficient values according to the present example are a=177.6, b=−0.2405, and c=0.7729.

In FIG. 37, the vertical axis indicates the systolic blood pressure SBP [mmHg], and the horizontal axis indicates:

$$178 - 0.240\ TR + 0.773 \frac{T1^2}{PW}$$

In the estimation equation according to the present example, the accuracy of estimating the systolic blood pressure SBP is improved as compared with the case of FIG. 32.

Figure 38:
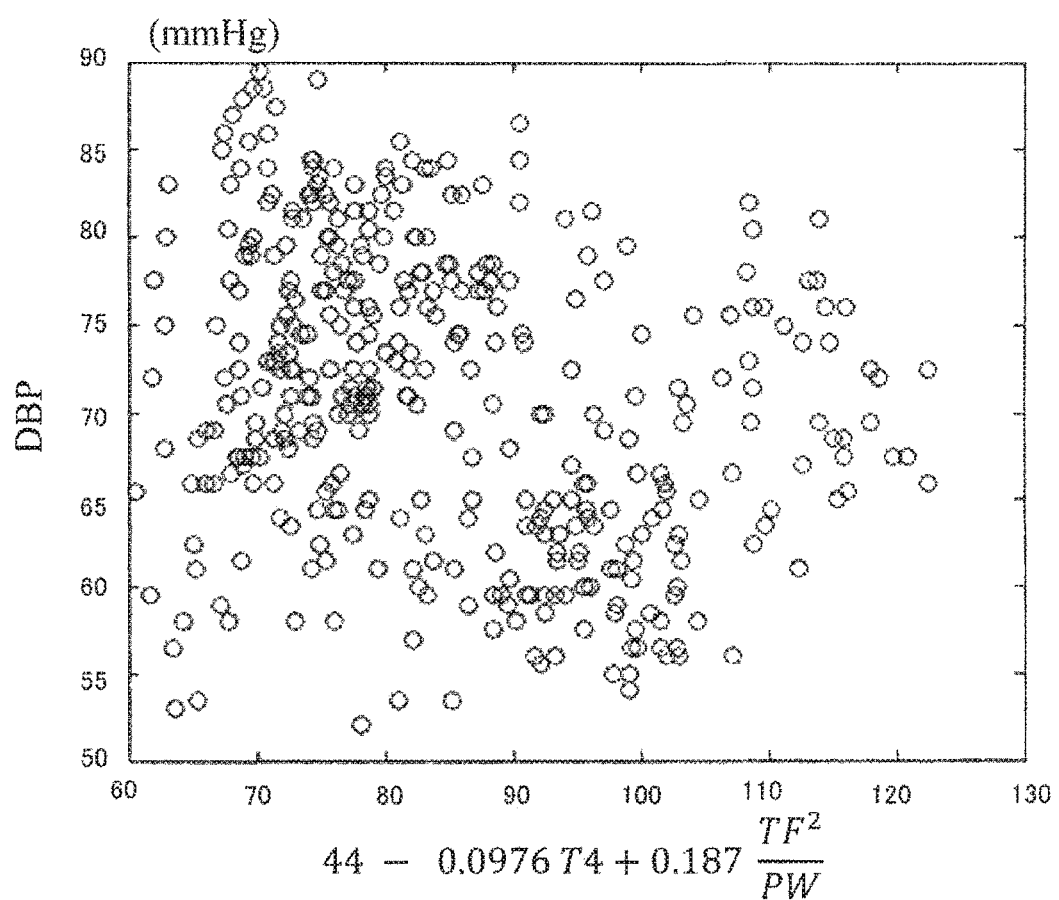
FIG. 38 shows an estimation equation using a pulse wave feature amount in the time domain.

FIG. 38 shows an equation of estimating the diastolic blood pressure DBP using a pulse wave feature amount in the time domain. Based on the results of comparison in FIG. 36, T4 and TF$^2$/PW are used in the equation of estimating the diastolic blood pressure DBP. The equation of estimating the diastolic blood pressure DBP according to the present example is derived by multiple linear combination of selected pulse wave feature amounts. That is, the equation of estimating the diastolic blood pressure DBP is expressed as follows.

$$DBP = d + e \times T4 + f \times \frac{TF^2}{PW}$$

Here, respective coefficient values d, e, f are calculated by a multiple regression analysis. The coefficient values according to the present example are d=44.07, e=−0.0796 and f=0.1867.

In FIG. 38, the vertical axis indicates the diastolic blood pressure DBP [mmHg], and the horizontal axis indicates:

$$44 - 0.0976\ T4 + 0.187 \frac{TF^2}{PW}$$

In the estimation equation according to the present example, the estimation accuracy of the diastolic blood pressure DBP is improved as compared with the case of FIG. 33.

Figure 39:
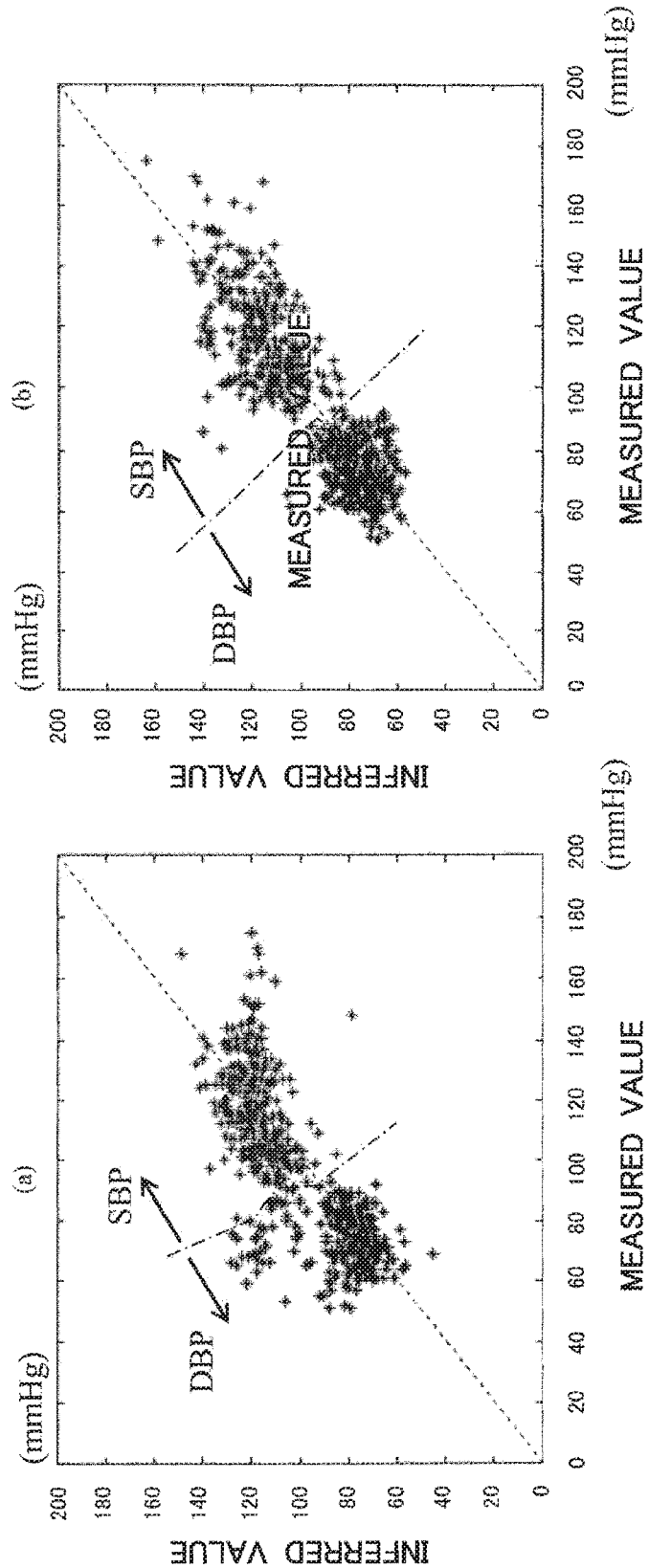
FIG. 39 shows a result of comparison between a blood pressure estimation method 2 and a blood pressure estimation method 3.

FIG. 39 shows a result of comparison between the blood pressure estimation method 2 and the blood pressure estimation method 3. (a) of FIG. 39 shows an estimation result obtained when the blood pressure estimation method 2 is used. (b) of FIG. 39 shows an estimation result obtained when the blood pressure estimation method 3 is used. In the present example, measurement about evaluation of the improvement in the accuracy of estimating blood pressure was performed multiple times on multiple people. The dashed lines indicate matches between inferred values and measured values. That is, the closer a plotted point is to a dashed line, the higher the accuracy of estimating blood pressure. Comparison between (a) and (b) of FIG. 39 shows that the systolic blood pressure SBP in a case where the blood pressure estimation method 3 was used was plotted conforming more to the dashed line as compared with that in a case where the blood pressure estimation method 2 was used. That is, the blood pressure estimation method 3 provides high accuracy of estimating the systolic blood pressure SBP.

The blood pressure estimation method 3 removed forcible and mutually linked changes in the systolic blood pressure SBP and the diastolic blood pressure DBP. To put it in another way, the pulse wave feature amount of the systolic blood pressure SBP and the pulse wave feature amount of the diastolic blood pressure DBP do not include the same pulse rate and rising time. Also, because the pulse rate HR which varies significantly is not used in estimation of the systolic blood pressure SBP and diastolic blood pressure DBP according to the present example, dependence on the pulse rate HR can be removed.

In the following, a method of improving the accuracy of estimating blood pressure by taking the elasticity of blood vessels into consideration is explained. For example, the elasticity of blood vessels is correlated with the curvature near the top peak $a_{PT}$ or the bottom peak $a_{PB}$ of a pulse wave waveform or a first- or higher-order differentiation pulse wave waveform. Therefore, estimation of blood pressure by taking the elasticity of blood vessels into consideration becomes possible by estimating the blood pressure based on a pulse wave feature amount equivalent to the curvature.

Figure 40:
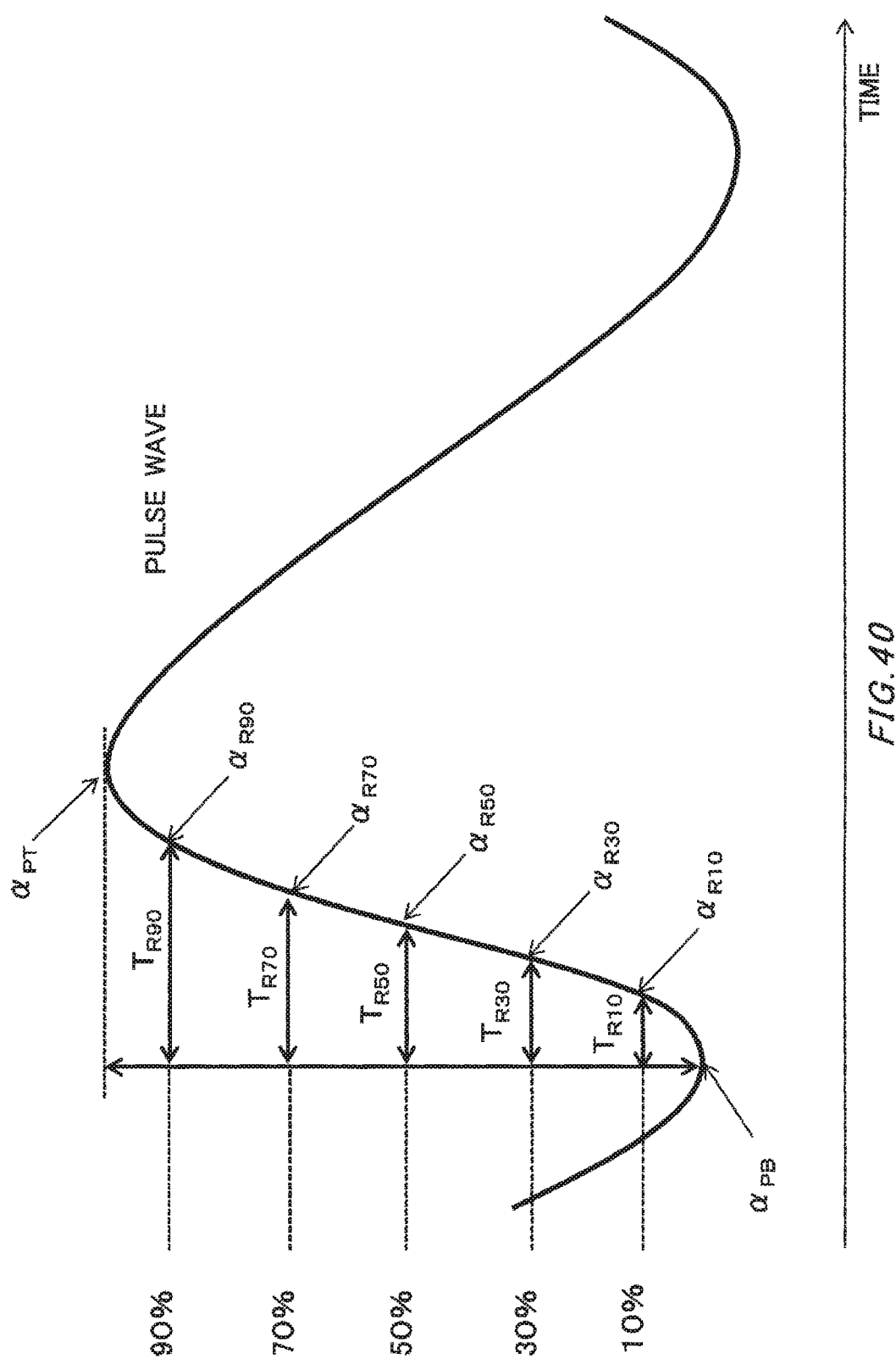
FIG. 40 shows an example of deriving curvature based on a top peak and a bottom peak.

FIG. 40 shows one example of a method of deriving the curvatures based on the top peak $\alpha_{PT}$ and the bottom peak $\alpha_{PB}$. Pulse wave feature points may be points that are between given two points among the top peaks αPT and the bottom peaks αPB and that correspond to points between segments of the amplitude, the time or the trajectory of a pulse wave. For example, when the amplitude between two points of adjacent top peak $\alpha_{PT}$ and bottom peak $\alpha_{PB}$ are segmented, points at 10%, 30%, 50%, 70% and 90% from the bottom peak $\alpha_{PB}$ are handled as the pulse wave feature points $\alpha_{R10}$, $\alpha_{R30}$, $\alpha_{R50}$, $\alpha_{R70}$, $\alpha_{R90}$, respectively.

Also, respective time $T_{R10}$, $T_{R30}$, $T_{R50}$, $T_{R70}$, $T_{R90}$ from the time of the bottom peak $\alpha_{PB1}$ to the pulse wave feature points $\alpha_{R10}$, $\alpha_{R30}$, $\alpha_{R50}$, $\alpha_{R70}$, $\alpha_{R90}$ may be handled as pulse wave feature amounts.

Figure 41:
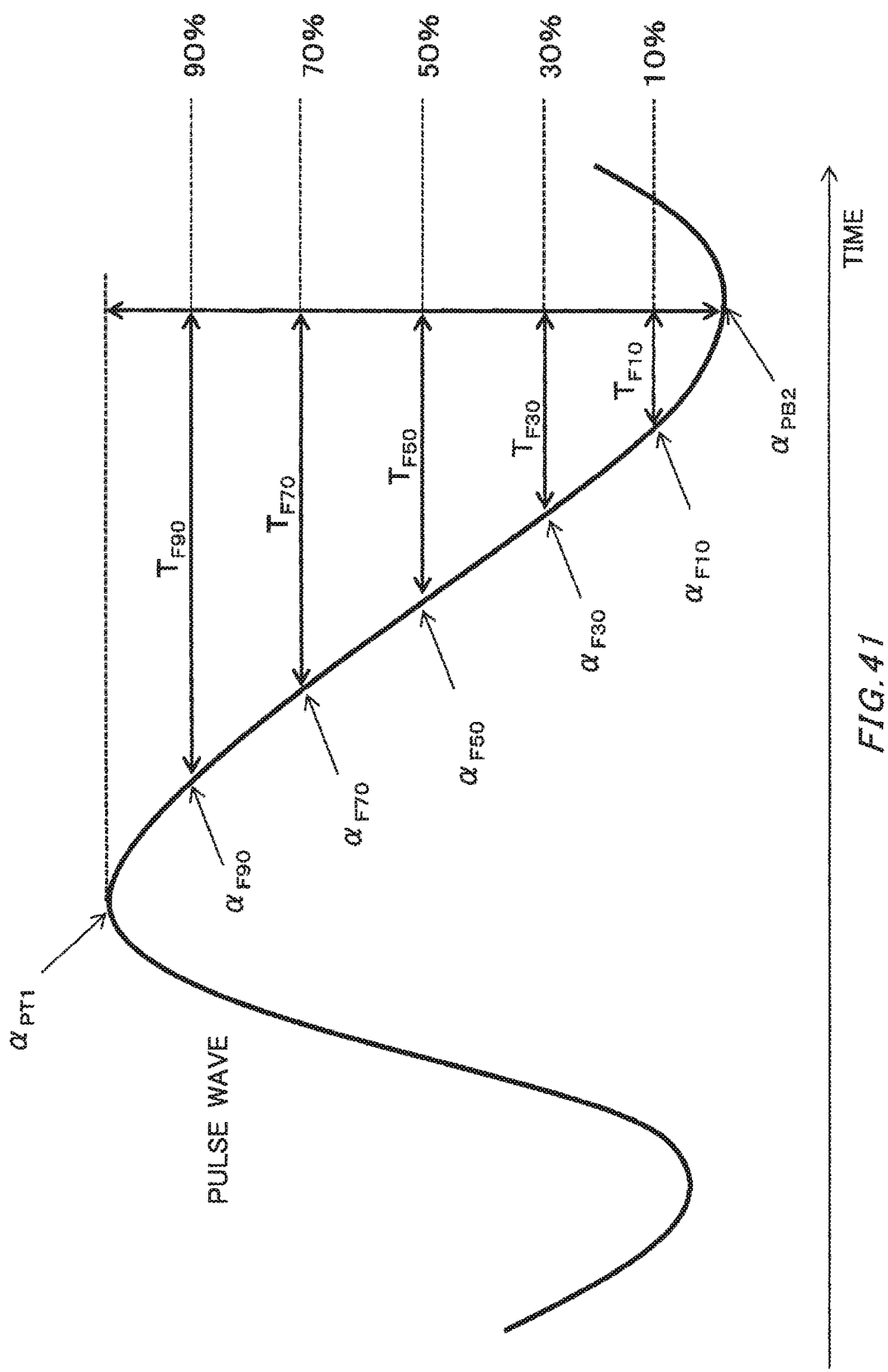
FIG. 41 shows an example of deriving curvature based on a top peak and a bottom peak.

FIG. 41 shows one example of a method of deriving the curvature based on the top peak $\alpha_{PT1}$ and the bottom peak $\alpha_{PB2}$. For example, the amplitude from the top peak $\alpha_{PT1}$ to the bottom peak $\alpha_{PB2}$ are segmented, and points of 10%, 30%, 50%, 70%, 90% are handles as pulse wave feature points $\alpha_{F10}$, $\alpha_{F30}$, $\alpha_{F50}$, $\alpha_{F70}$, $\alpha_{F90}$. Also, respective time $T_{F10}$, $T_{F30}$, $T_{F50}$, $T_{F70}$, $T_{F90}$ from the time of the bottom peak $\alpha_{PB2}$ to the pulse wave feature points $\alpha_{F10}$, $\alpha_{F30}$, $\alpha_{F50}$, $\alpha_{F70}$, $\alpha_{F90}$ may be handled as pulse wave feature amounts.

Although in the present example, a case where the curvature of a pulse wave is derived is explained, the curvature of a differential pulse wave may be derived in a similar manner to the case of a pulse wave. For example, the pulse wave feature amount is the top peak $\alpha_{1PT}$ and the bottom peak $\alpha_{1BT}$ of a first-order differentiation pulse wave, the top peak $\alpha_{2PT}$ and the bottom peak $\alpha_{2BT}$ of a second-order differentiation pulse wave or the like.

Figure 42:
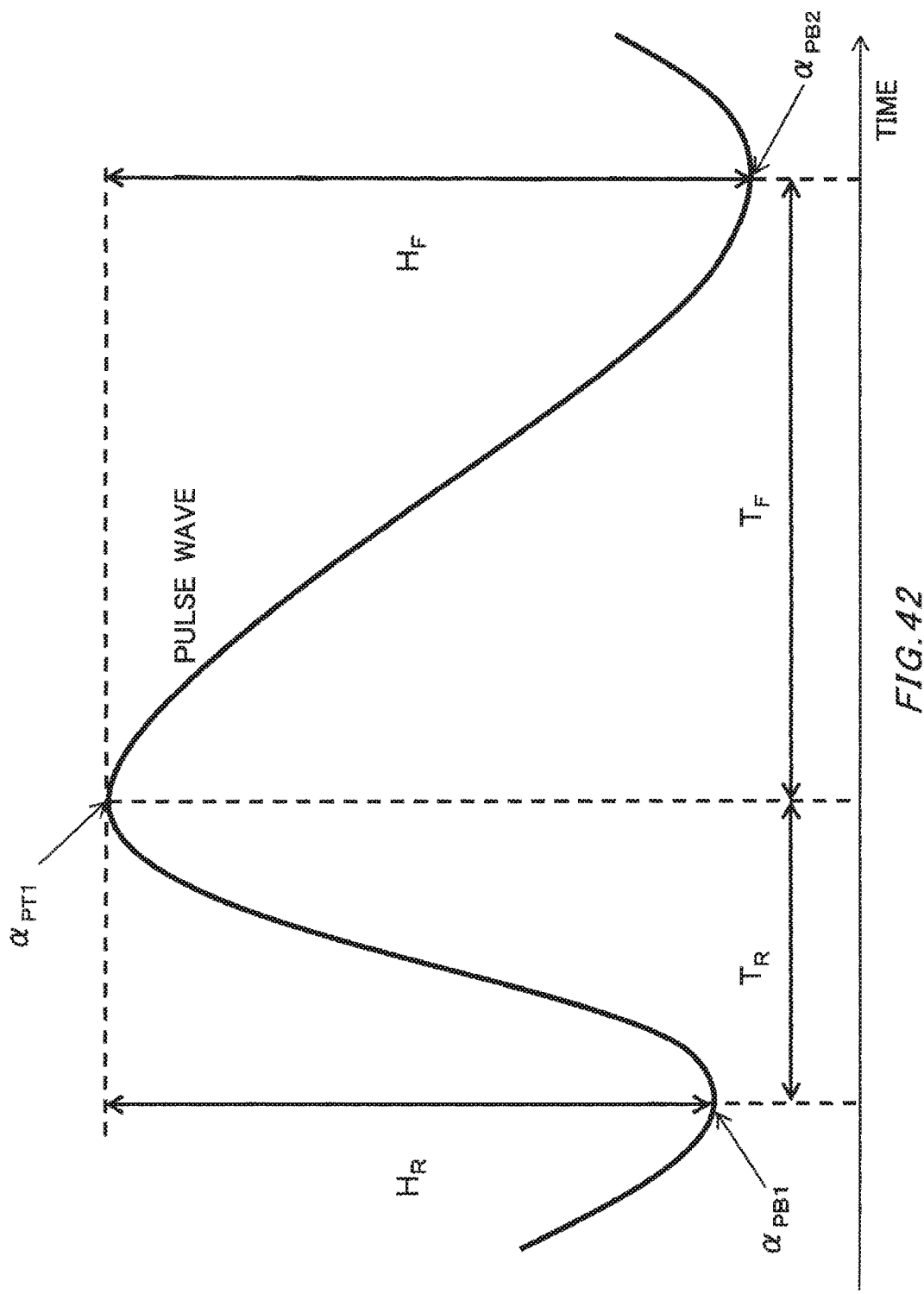
FIG. 42 shows one example of a method of calculating a pulse wave feature amount.

FIG. 42 shows one example of a method of setting a pulse wave feature amount. The pulse wave feature amount according to the present example is calculated based on at least one of the amplitude of the pulse wave feature point, the time interval of the pulse wave feature point, the frequency of the pulse wave, and the phase of the pulse wave. For example, the rising amplitude $H_R$ and the rising time $T_R$ from the bottom peak $\alpha_{PB1}$ of a pulse wave to the immediately following top peak $\alpha_{PT1}$ may be handled as the pulse wave feature amount. Also, the falling amplitude $H_F$ and the falling time $T_F$ from the top peak $\alpha_{PT1}$ of a pulse wave to the immediately following bottom peak $\alpha_{PB2}$ may be handled as the pulse wave feature amount.

Figure 43:
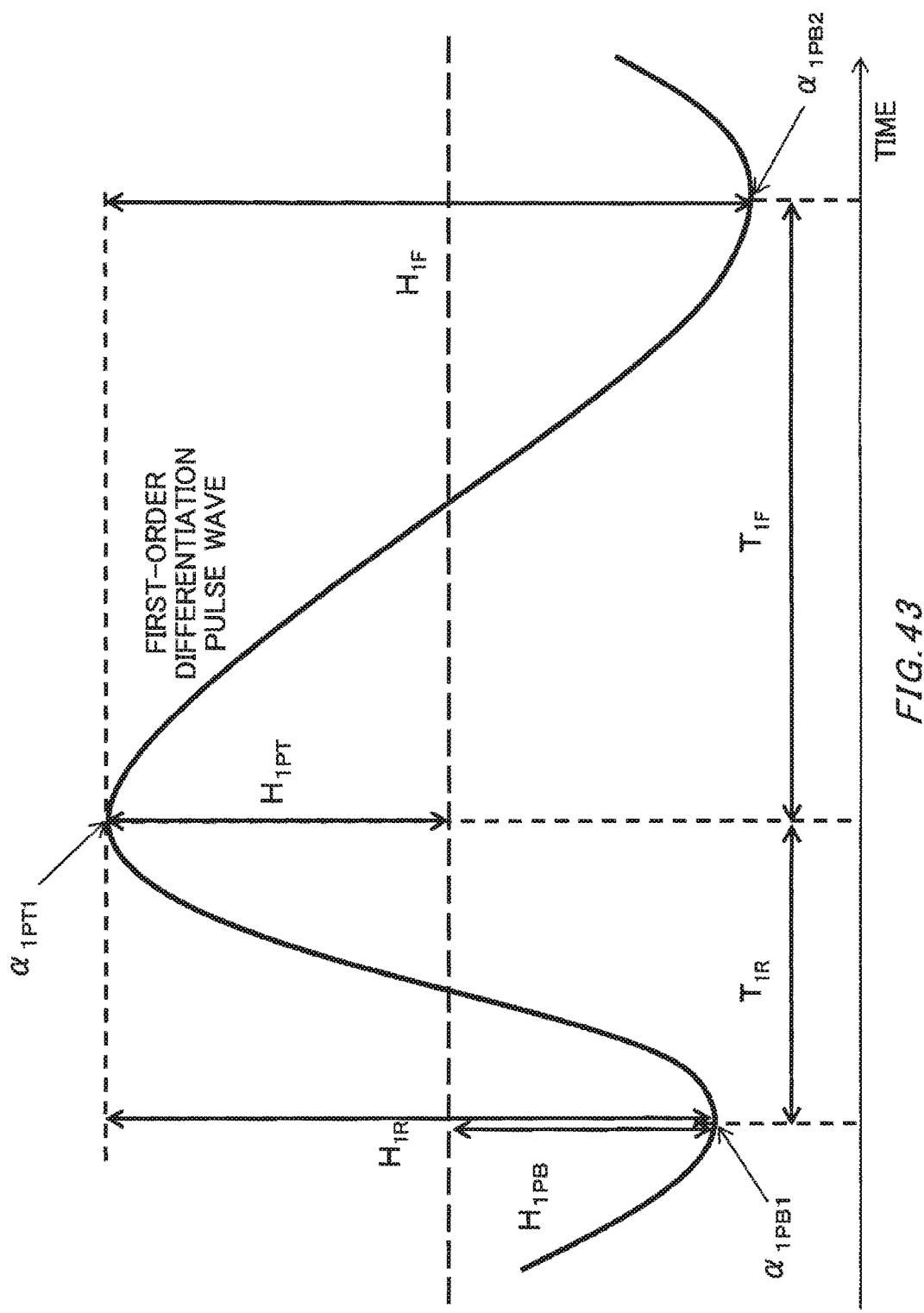
FIG. 43 shows one example of a method of calculating a feature amount by using a differential pulse wave.

FIG. 43 shows one example of a method of calculating a pulse wave feature amount by using a differential pulse wave. For example, the pulse wave feature amount is a rising amplitude $H_{1R}$ or rising time $T_{1R}$ from a bottom peak $\alpha_{1PB1}$ of a first-order differentiation pulse wave to the immediately following top peak $\alpha_{1PT1}$, a falling amplitude $H_{1F}$ or falling time $T_{1F}$ from a top peak $\alpha_{1PT1}$ of a pulse wave to the immediately following bottom peak $\alpha_{1PB2}$, a rising amplitude $H_{2R}$ or rising time $T_{2R}$ from a bottom peak $\alpha_{2PB1}$ of a second-order differentiation pulse wave to the immediately following top peak $\alpha_{2PT1}$, or a falling amplitude $H_{2F}$ or falling time $T_{2F}$ from a top peak $\alpha_{2PT1}$ of a pulse wave to the immediately following bottom peak $\alpha_{2PB2}$.

Note that a differential pulse wave obtained by differentiating a pulse wave of the living body 10 is a cyclic function similar to the pulse wave of the living body 10. Also, the amplitude of a differential pulse wave repeats upward and downward variation with 0 as a reference point. Therefore, the pulse wave feature amount of the first-order differentiation pulse wave may be the amplitude $H_{1PT}$ of the top peak $\alpha_{1PT}$ of the first-order differentiation pulse wave or the amplitude $H_{1PB}$ of the bottom peak $\alpha_{1PB}$ of the first-order differentiation pulse wave. Similarly, the pulse wave feature amount of the second-order differentiation pulse wave may be the amplitude $H_{2PT}$ of the top peak $\alpha_{2PT}$ of the second-order differentiation pulse wave or the amplitude $H_{2PB}$ of the bottom peak $\alpha_{2PB}$ of the second-order differentiation pulse wave.

Furthermore, the pulse wave feature amount may be a power of the pulse wave feature amount of a pulse wave of the living body 10, the pulse wave feature amount of a first-order differentiation pulse wave, the pulse wave feature amount of a second-order differentiation pulse wave, or the pulse wave feature amount of nth-order differentiation pulse wave. Also, the pulse wave feature amount may be the sum, remainder, product or ratio of a combination of at least one of the pulse wave feature amount of a pulse wave of the living body 10, the pulse wave feature amount of a first-order differentiation pulse wave, the pulse wave feature amount of a second-order differentiation pulse wave, and the pulse wave feature amount of an nth-order differentiation pulse wave.

The pulse wave feature amount may be calculated based on a pulse wave feature amount in a predetermined length of time or during a predetermined number of beats. More specifically, the pulse wave feature amount is the average, total, variance, covariance, standard deviation or median of pulse wave feature amounts in a predetermined length of time or during a predetermined number of beats. Also, when a median over ten seconds is handled as a pulse wave feature amount, a median may be computed again after every one second. As a result, because the pulse wave feature amount can be updated every one second, the blood pressure information can be estimated continuously.

Note that the pulse wave feature amount representing the curvature near the top peak $\alpha_{PT}$ of a pulse wave is preferably represented by (HR+HF)/$H_{2PB}$, $T_F$-$T_{F90}$, $T_F$-$T_{F70}$, $T_F$-$T_{F50}$, $T_F$-$T_{F30}$, $T_F$-$T_{F10}$, $T_R$+$T_F$-$T_{R90}$-$T_{F90}$, $T_R$+$T_F$-$T_{R70}$-$T_{F70}$, $T_R$+$T_F$-$T_{R50}$-$T_{F50}$, $T_R$+$T_F$-$T_{R30}$-$T_{F30}$, $T_R$+$T_F$-$T_{R10}$-$T_{F10}$. Also, the pulse wave feature amount representing the curvature near the bottom peak $\alpha_{PT}$ of a pulse wave is preferably represented by (HR+HF)/$H_{2PT}$, $T_{R10}$, $T_{R30}$, $T_{R50}$, $T_{R70}$, $T_{R90}$, $T_{R10}$+$T_{F10}$, $T_{R30}$+$T_{F30}$, $T_{R50}$+$T_{F50}$, $T_{R70}$+$T_{F70}$, $T_{R90}$+$T_{F90}$.

When the pulse wave feature amount representing the curvature near a peak of a pulse wave is used, the pulse wave feature amount may be a power of the pulse wave feature amount representing the curvature near the peak of the pulse wave. Also, the sum, remainder, product or ratio obtained by combining a plurality of pulse wave feature amounts from among pulse wave feature amounts representing the curvature near a peak of a pulse wave may be handled as a pulse wave feature amount. In particular, the ratio between a pulse wave feature amount representing the curvature near the top peak $a_{PT}$ of a pulse wave and a pulse wave feature amount representing the curvature near the bottom peak $ap_T$ of the pulse wave is preferable because they are highly correlated with the systolic blood pressure SBP and diastolic blood pressure DBP.

Figure 44:
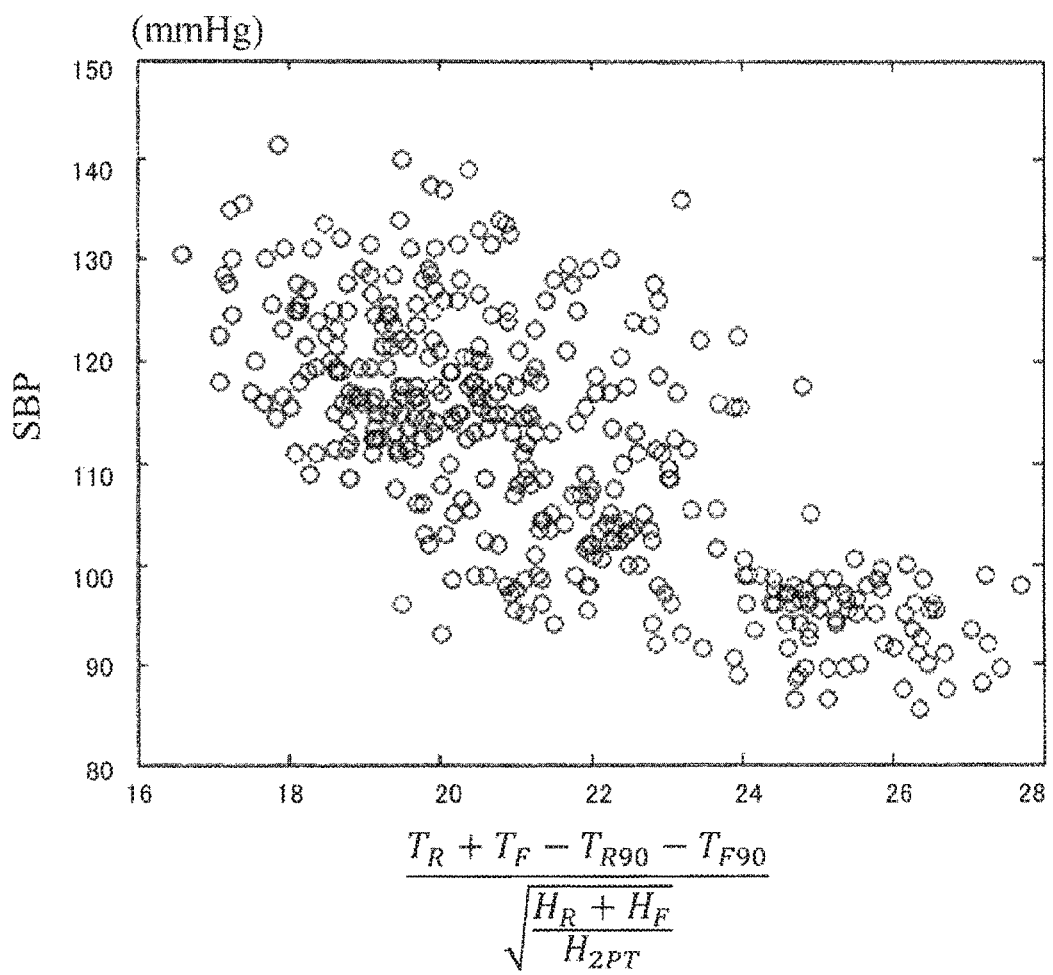
FIG. 44 shows one example of a correlation between a dimensionless pulse wave feature amount and systolic blood pressure SBP.

FIG. 44 shows one example of a correlation between a dimensionless pulse wave feature amount and systolic blood pressure SBP. The amplitude ratio is used as a dimensionless pulse wave feature amount in an equation of estimating the systolic blood pressure SBP according to the present example. The horizontal axis indicates a dimensionless pulse wave feature amount $(T_R+T_F-T_{R90}-T_{F90})/(H_R+H_F)/H_{2PT})^{1/2}$, and the vertical axis indicates the systolic blood pressure SBP [mmHg]. Here, assuming that the pulse wave feature amount is X, the systolic blood pressure SBP=aX+b. The coefficients a and b are any values.

The pulse wave feature amount according to the present example is a dimensionless pulse wave feature amount standardized by computing the ratio among pulse wave feature amounts. Therefore, the dimensionless pulse wave feature amount can reduce influence of the degree of pulse rates.

Figure 45:
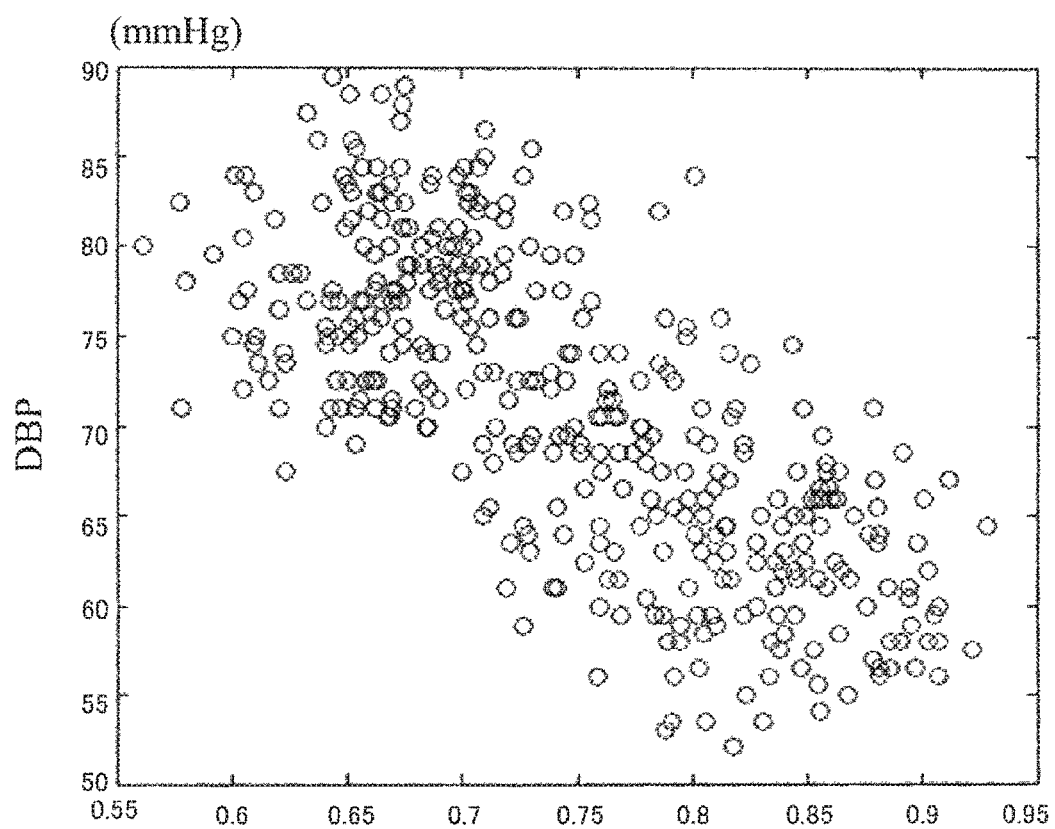
FIG. 45 shows one example of a correlation between a dimensionless pulse wave feature amount and diastolic blood pressure DBP.

FIG. 45 shows one example of a correlation between a dimensionless pulse wave feature amount and diastolic blood pressure DBP. The amplitude ratio is used as a dimensionless pulse wave feature amount in an equation of estimating the diastolic blood pressure DBP according to the present example. The horizontal axis indicates a dimensionless pulse wave feature amount $(T_F-T_{F90})/(T_{R10}+T_{F10})$, and the vertical axis indicates diastolic blood pressure DBP [mmHg]. Here, assuming that the pulse wave feature amount is X, the diastolic blood pressure DBP=cY+d. The coefficients c and d are any values.

The pulse wave feature amount according to the present example is a dimensionless pulse wave feature amount standardized by computing the ratio among pulse wave feature amounts. Therefore, estimation of blood pressure that is less influenced by the degree of pulse rates becomes possible by using dimensionless pulse wave feature amounts for equations of estimating the systolic blood pressure SBP and diastolic blood pressure DBP.

Figure 46:
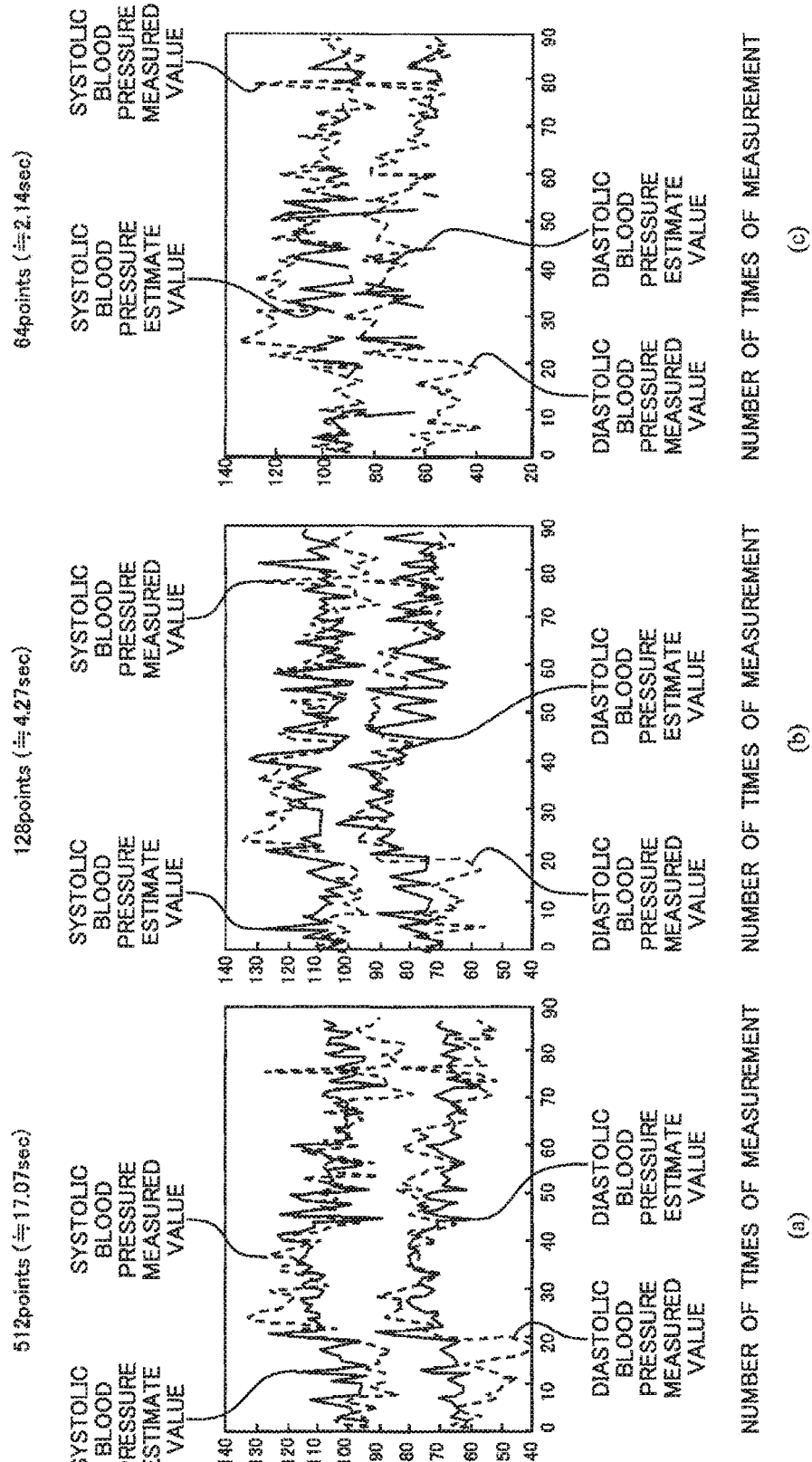
FIG. 46 shows a result of estimating systolic blood pressure SBP of the living body 10.

FIG. 46 shows a result of estimating systolic blood pressure SBP and diastolic blood pressure DBP of the living body 10. The horizontal axes indicates the numbers of times of measurement (times), and the vertical axes indicate the blood pressure BP [mmHg]. The solid lines indicate systolic blood pressure estimate values and diastolic blood pressure estimate values [mmHg] obtained from a camera video according to the present example, and the dashed lines indicate systolic blood pressure measured values and diastolic blood pressure measured values [mmHg] obtained from a sphygmomanometer. Here, correct values are the blood pressure BP measured by the sphygmomanometer.

(a) to (c) of FIG. 46 indicate cases where FFT, which is one of the discrete-time analyses, is used as frequency analysis by the pulse rate calculating unit 42. (a), (b) and (c) of FIG. 46 indicate cases where the numbers of points of pulse wave component signals input in the frequency analysis are 512 points (≈17.07 sec), 128 points (≈4.27 sec) and 64 points (≈2.14 sec), respectively. All of (a) to (c) of FIG. 46 show as good accuracy of estimating blood pressure as that obtained by using a cuff. In particular, as in (b) and (c) of FIG. 46, if the number of points is merely approximately 128, blood pressure information is output at a little less than five seconds after input of a video of a measurement subject, and thereafter, blood pressure information is continuously output by shifting the number of points while causing it to overlap preceding points. Thereby, blood pressure information is output in real time.

Because the blood pressure information output apparatus 100 is configured to optically extract the pulse waveform information to output the blood pressure information, the burden on the living body 10 is small. Also, because the blood pressure information output apparatus 100 does not require pressurization and depressurization by means of a cuff, blood pressure information can be acquired continuously. In particular, when extracting pulse waveform information of the living body 10 from a video, the blood pressure information output apparatus 100 can estimate blood pressure information without contacting and binding the living body 10.

Note that in the present example, the blood pressure information output apparatus 100 that outputs blood pressure information based on a video having RGB components is shown. However, a video to be input is not limited to a video having RGB components, but may be a grayscale video. For example, the blood pressure information output apparatus 100 extracts a shading component corresponding to a G component from a grayscale video from a near infrared camera. Thereby, blood pressure information can be output in a similar manner to that of the blood pressure information output apparatus 100 according to the present example. Furthermore, the blood pressure information output apparatus 100 may acquire pulse waveform information from a video from an array sensor with 2×2 pixels or 1×2 pixels.

(Estimation of Arteriosclerosis)

The blood pressure information output apparatus 100 can estimate arteriosclerosis based on a calculated blood pressure BP. Arteriosclerosis obliterans is characterized by thickened, hardened and narrowed vascular walls. Arteriosclerosis obliterans is an advanced state of arteriosclerosis affecting peripheral artery, and when blood vessels are highly exploited, it becomes difficult for pulse waves to be propagated, and the rising time TR and falling time TF of the pulse waves become short. That is, the rising time TR and falling time TF become shorter in blood vessels whose vascular wall has thickened, hardened and narrowed more, along with progression of arteriosclerosis. Therefore, estimation not only of the blood pressure BP, but also of arteriosclerosis can be performed simply based on the rising time TR and falling time TF.

(Estimation of Vascular Age)

Also, the blood pressure information output apparatus 100 figures out a corresponding age from statistical data on the stiffness of blood vessels, and displays an estimation result on arteriosclerosis as an estimated vascular age. Thereby, display of the blood pressure information output apparatus 100 becomes easier for a user to understand.

(Estimation of Predisposition to Stroke)

The blood pressure information output apparatus 100 can estimate a predisposition to stroke based on a calculated blood pressure BP. Stroke occurs due to variation in blood pressure. This occurs because of a perforator where a blood vessel that is directly connected to a thick blood vessel and is susceptible to the pressure of blood flow is clogged or torn due to variation in blood pressure. In other words, judgement about whether a person has a predisposition to stroke can be made by examining blood pressure at a steady-state, and variation in blood pressure after exercise with a very low load. For example, judgement about whether a person has a predisposition to stroke can be made based on whether the difference between a blood pressure value measured when having sat down and a blood pressure value measured after standing up once and then sitting down again is about 15 mmHg or larger. Therefore, the blood pressure information output apparatus 100 can measure, continuously and in real time, variation in blood pressure that is observed between at the time of a steady-state and at the time after low load exercise by non-contact and continuous blood pressure measurement so that judgement about a predisposition to stroke can be performed very simply.

Figure 47:
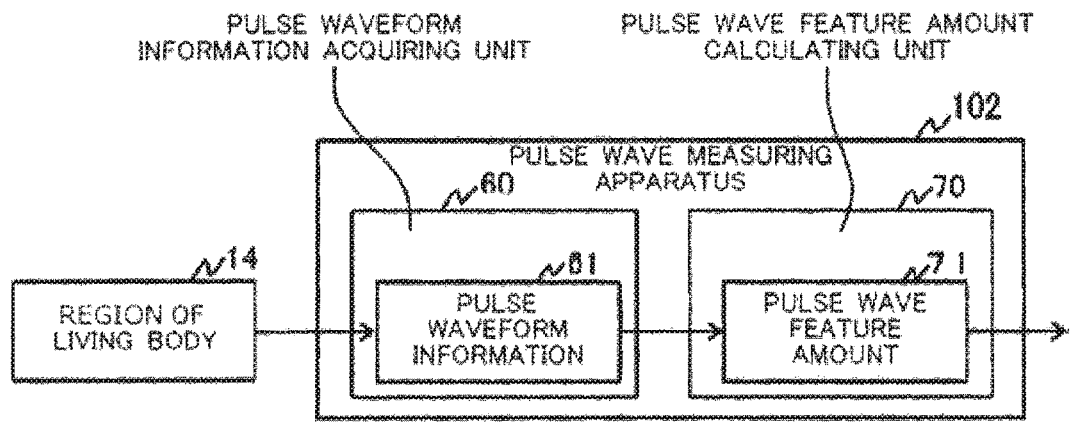
FIG. 47 shows one example of the configuration of a pulse wave measuring apparatus 102.

FIG. 47 shows one example of the configuration of the pulse wave measuring apparatus 102. The pulse wave measuring apparatus 102 measures a pulse wave of a living body based on a region 14 of the living body. The pulse wave measuring apparatus 102 comprises a pulse waveform information acquiring unit 60 and a pulse wave feature amount calculating unit 70.

The pulse waveform information acquiring unit 60 acquires pulse waveform information 61 from the region 14 of the living body. For example, the region 14 of the living body is any of a forearm portion, a wrist, an ankle, the face, an ear and the nose of the living body. Among them, the nose can realize a high S/N ratio because capillaries are concentrated there. The pulse waveform information 61 is preferably a pulse wave trace signal.

The pulse wave feature amount calculating unit 70 calculates a pulse wave feature amount 71 based on the pulse waveform information 61. The pulse wave feature amount 71 is a characteristic portion of the shape of a pulse wave which has been turned into a numerical value. Also, the pulse wave feature amount 71 may include information about the intensity and time of a pulse wave. For example, the pulse wave feature amount 71 is calculated based on at least one of a pulse wave, a speed pulse wave and an acceleration pulse wave acquired based on the pulse wave trace signal.

Figure 48:
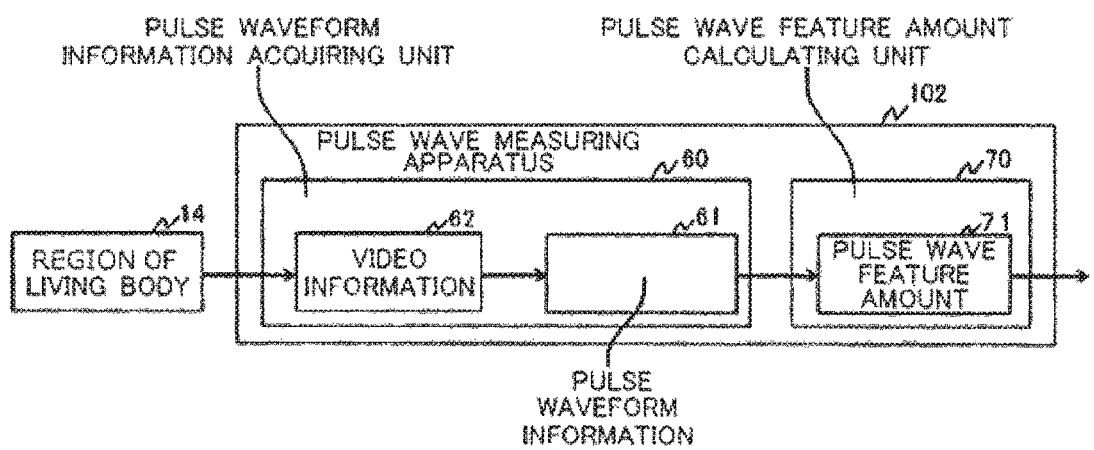
FIG. 48 shows one example of the configuration of the pulse wave measuring apparatus 102.

FIG. 48 shows one example of the configuration of the pulse wave measuring apparatus 102. The pulse waveform information 61 according to the present example is based on video information 62 acquired from the region 14 of the living body.

The pulse waveform information acquiring unit 60 acquires the video information 62 from the region 14 of the living body. The video information 62 is an image or a moving image that the pulse waveform information acquiring unit 60 optically captured from the region 14 of the living body. Because the pulse wave measuring apparatus 102 acquires the pulse waveform information 61 based on the video information 62, the burden on the living body is small.

Figure 49:
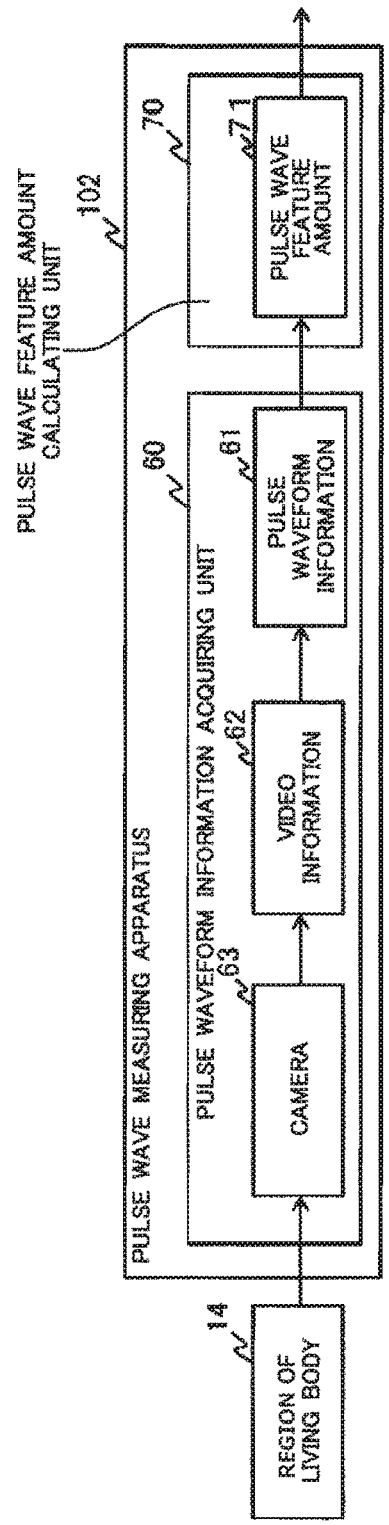
FIG. 49 shows one example of the configuration of the pulse wave measuring apparatus 102.

FIG. 49 shows one example of the configuration of the pulse wave measuring apparatus 102. The pulse waveform information acquiring unit 60 according to the present example is different from the pulse waveform information acquiring unit 60 in FIG. 47 in that it comprises a camera 63.

The camera 63 acquires the video information 62 from the region 14 of the living body. For example, the camera 63 has a CCD sensor or a CMOS sensor. Also, the camera 63 may be a camera for an information terminal. The camera for an information terminal is used by being built in or attached externally to a desktop PC, a laptop PC, a tablet PC, a mobile phone, a smartphone, a wristwatch-type terminal, a television or a game console. Note that the camera 63 may comprise a video information storage medium that retains the video information 62, and output the video information 62 acquired in the past.

Figure 50:
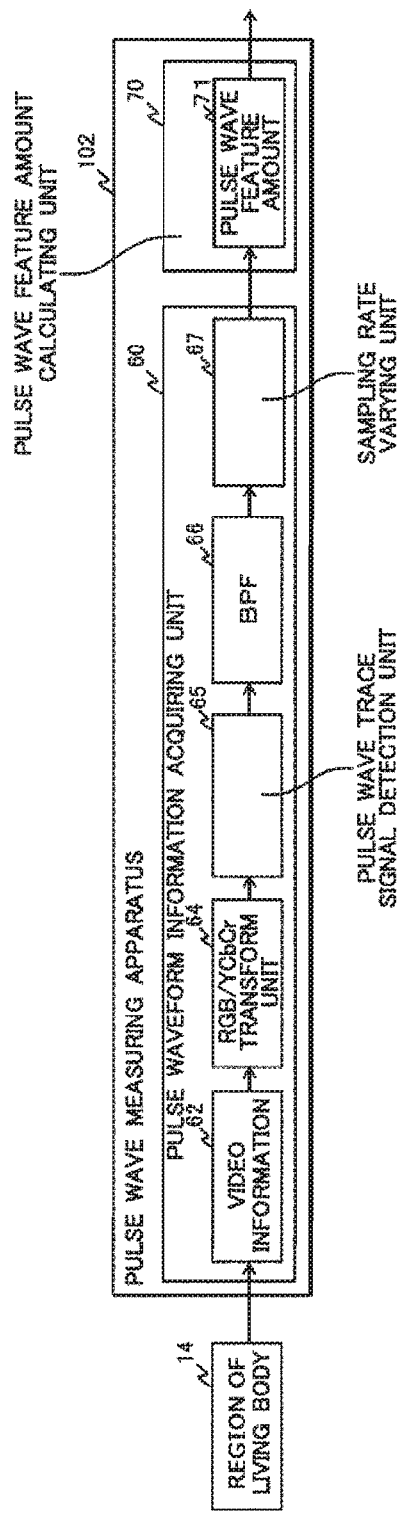
FIG. 50 shows one example of the configuration of the pulse wave measuring apparatus 102.

FIG. 50 shows one example of the configuration of the pulse wave measuring apparatus 102. The pulse waveform information acquiring unit 60 acquires video signals from the video information 62. The pulse waveform information acquiring unit 60 according to the present example comprises a RGB/YCbCr transform unit 64, a pulse wave trace signal detection unit 65, a BPF 66 and a sampling rate varying unit 67.

The RGB/YCbCr transform unit 64 transforms the video information 62 acquired from the region 14 of the living body into video signals. For example, the video signals are RGB signals, CMYK signals or YCbCr signals. Y corresponds to a luminance signal, and Cb and Cr correspond to color-difference signals. The RGB/YCbCr transform unit 64 may transform the video signals into any format. For example, the RGB/YCbCr transform unit 64 can transform RGB signals into YCbCr signals, and can perform inverse transform thereof.

Also, the RGB/YCbCr transform unit 64 may detect a facial region and a region of interest ROI based on, among the video signals, any one signal or a combination of a plurality of signals. For example, the region of interest ROI can be detected based only on a Y signal among YCbCr signals.

Furthermore, the RGB/YCbCr transform unit 64 can acquire a video pulse wave signal from the video signals. The video pulse wave signal is any one signal or a signal obtained by combining a plurality of signals from among the video signals. The video pulse wave signal is preferably a Cb+Cr signal which provides high signal stability. The Cb+Cr signal is a signal based on the sum of Cb and Cr from among the YCbCr signals. Note that the RGB/YCbCr transform unit 64 may Gaussian-filter the video pulse wave signal based on a video region.

The pulse wave trace signal detection unit 65 detects a pulse wave trace signal obtained by plotting a value of any clock time based on the video pulse wave signal. The operation amount can be reduced by detecting the pulse wave trace signal so that a pulse wave waveform can be extracted stably. For example, the pulse wave trace signal is a signal obtained by totaling video pulse wave signals of respective pixels over the entire video region. Also, the pulse wave trace signal may be the average of video pulse wave signals of respective pixels. In this case, the pulse wave trace signal becomes one value for each video region.

The BPF 66 filters the pulse wave trace signal. The BPF 66 removes regions other than a predetermined wavelength region. Thereby, the BPF 66 can remove noises in regions other than the wavelength region to be used in the pulse waveform information 61.

The sampling rate varying unit 67 varies the sampling rate of signals filtered by the BPF 66. For example, the sampling rate varying unit 67 interpolates pulse wave trace signals at 30 Hz acquired from the video information 62 to turn them into pulse wave trace signals at 1 kHz. The interpolation method may be spline interpolation, Lagrange interpolation, linear interpolation or the like. Among them, spline interpolation that provides high accuracy is preferable.

Figure 51:
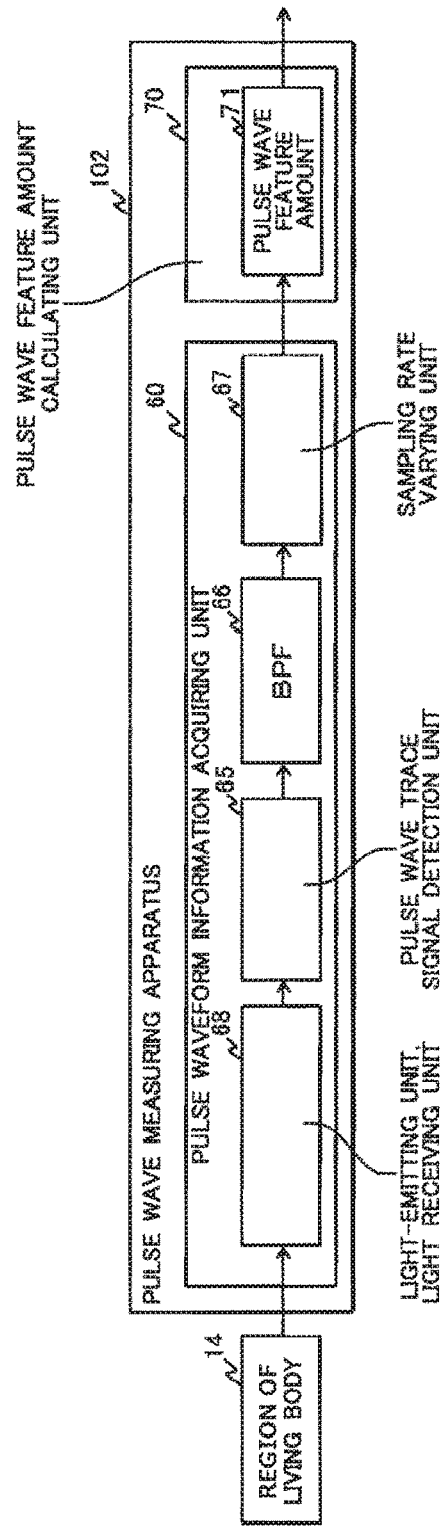
FIG. 51 shows one example of the configuration of the pulse wave measuring apparatus 102.

FIG. 51 shows one example of the configuration of the pulse wave measuring apparatus 102. The pulse waveform information acquiring unit 60 according to the present example comprises the pulse wave trace signal detection unit 65, the BPF 66, the sampling rate varying unit 67 and a light-emitting unit and a light receiving unit 68.

The light-emitting unit and the light receiving unit 68 comprises a light-emitting unit that irradiates the region 14 of the living body with light, and a light receiving unit that receives reflected light or transmitted light from the region 14 of the living body. For example, the light-emitting unit has a light-emitting diode (LED). The light-emitting unit is preferably a green LED because hemoglobin contained in blood of the region 14 of the living body has a characteristic of absorbing light in the green wavelength region. Also, the light receiving unit may have a photodiode (PD) or a phototransistor. The light receiving unit detects changes in the amount of light emitted by the light-emitting unit that results from changes in the blood flow of the living body.

Based on the amount of light detected by the light receiving unit, the pulse wave trace signal detection unit 65 can create a pulse wave trace signal in which values at predetermined clock times are plotted. The pulse waveform information acquiring unit 60 according to the present example can vary the filtering and/or sampling rate.

Figure 52:
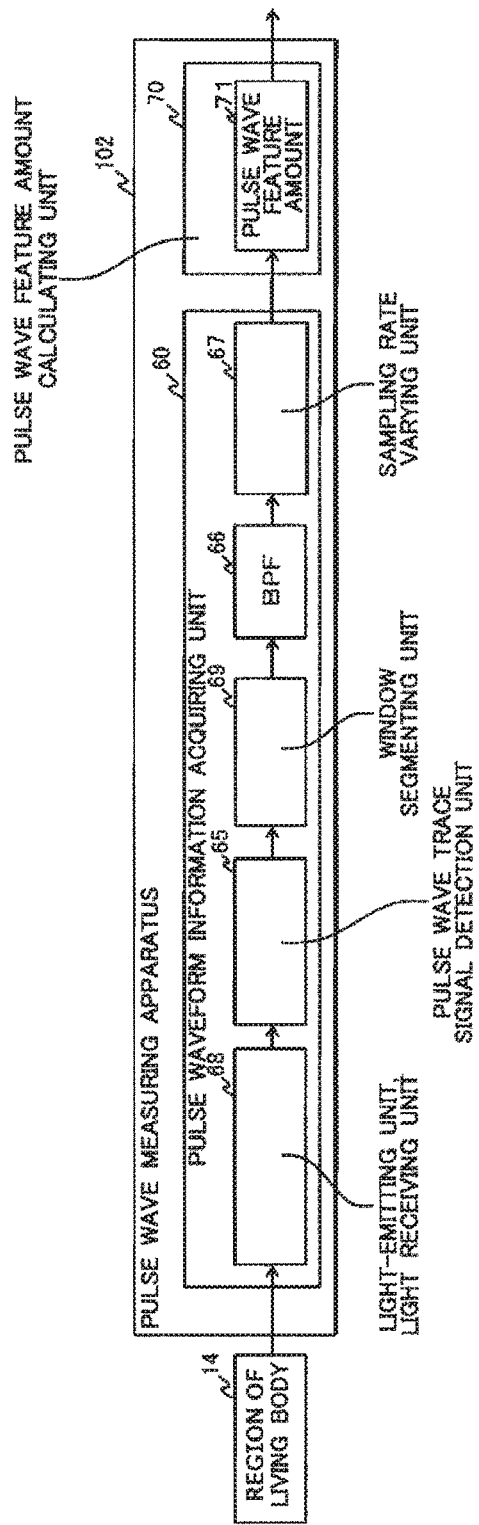
FIG. 52 shows one example of the configuration of the pulse wave measuring apparatus 102.

FIG. 52 shows one example of the configuration of the pulse wave measuring apparatus 102. The pulse waveform information acquiring unit 60 according to the present example is different from the configuration in FIG. 51 in that it further comprises a window segmenting unit 69.

The window segmenting unit 69 segments out a trace signal in a predetermined window size. The trace signal segmented out is called a window signal in the present specification. Also, the window size refers to a temporal width of the window signal. The window segmenting unit 69 segments out the window signal at predetermined intervals. The window segmenting unit 69 outputs the window signal segmented out to the BPF 66.

Figure 53:
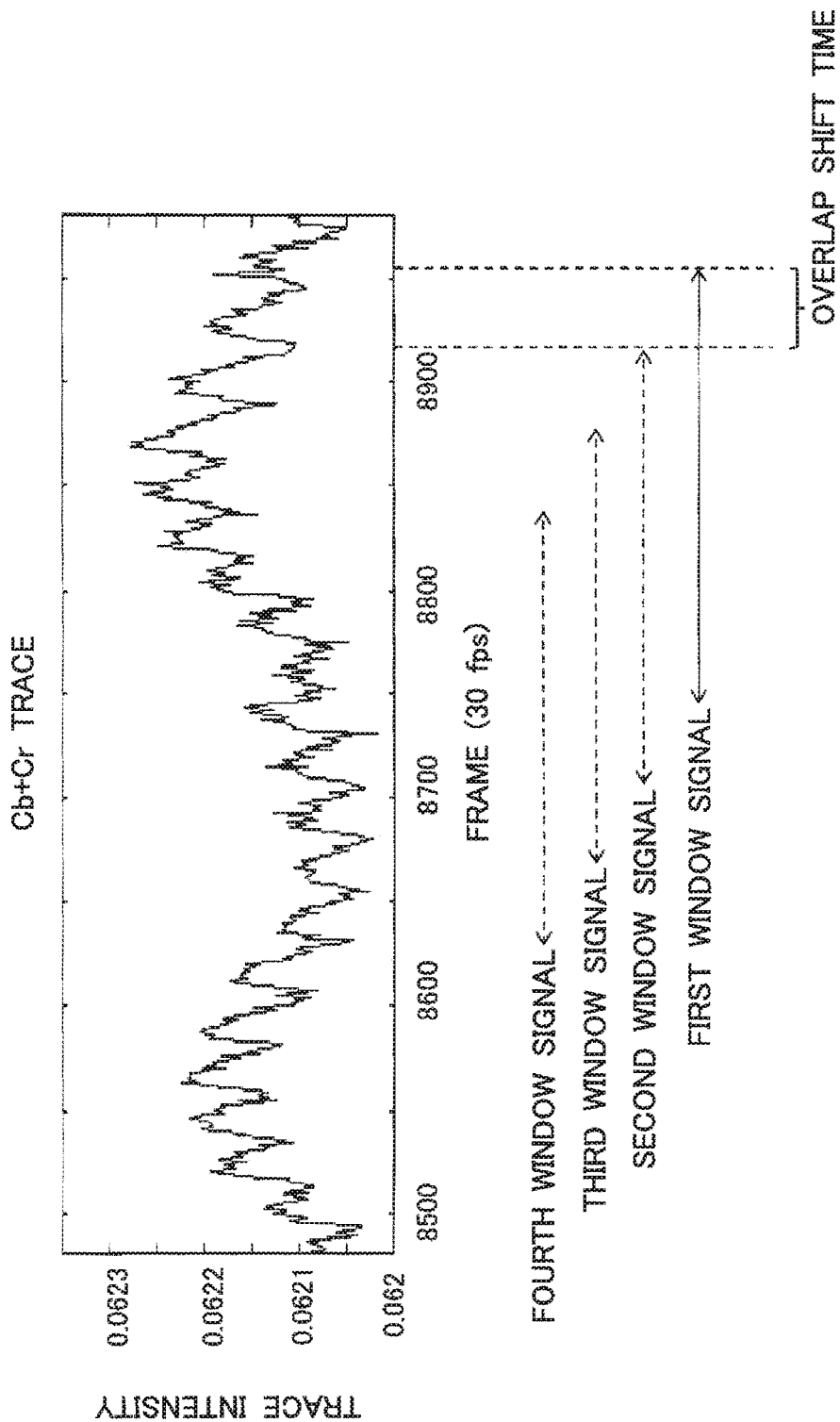
FIG. 53 shows one example of a method of segmenting out a window signal.

FIG. 53 shows one example of a method of segmenting out a window signal. The window segmenting unit 69 segments out, from the Cb+Cr trace signal, a plurality of window signals at predetermined time intervals so that they overlap. A first window signal is an immediately preceding window signal. Window signals adjacent to the first window signal are handled as second to fourth window signals, respectively. In the present specification, shifts between adjacent window signals are called overlap shift time.

The overlap shift time is equal to the cycle at which the pulse waveform information acquiring unit 60 calculates a pulse rate. That is, the pulse waveform information acquiring unit 60 calculates the pulse rate every shift amount of the overlap time. The overlap shift time according to the present example is equal to each other.

Figure 54:
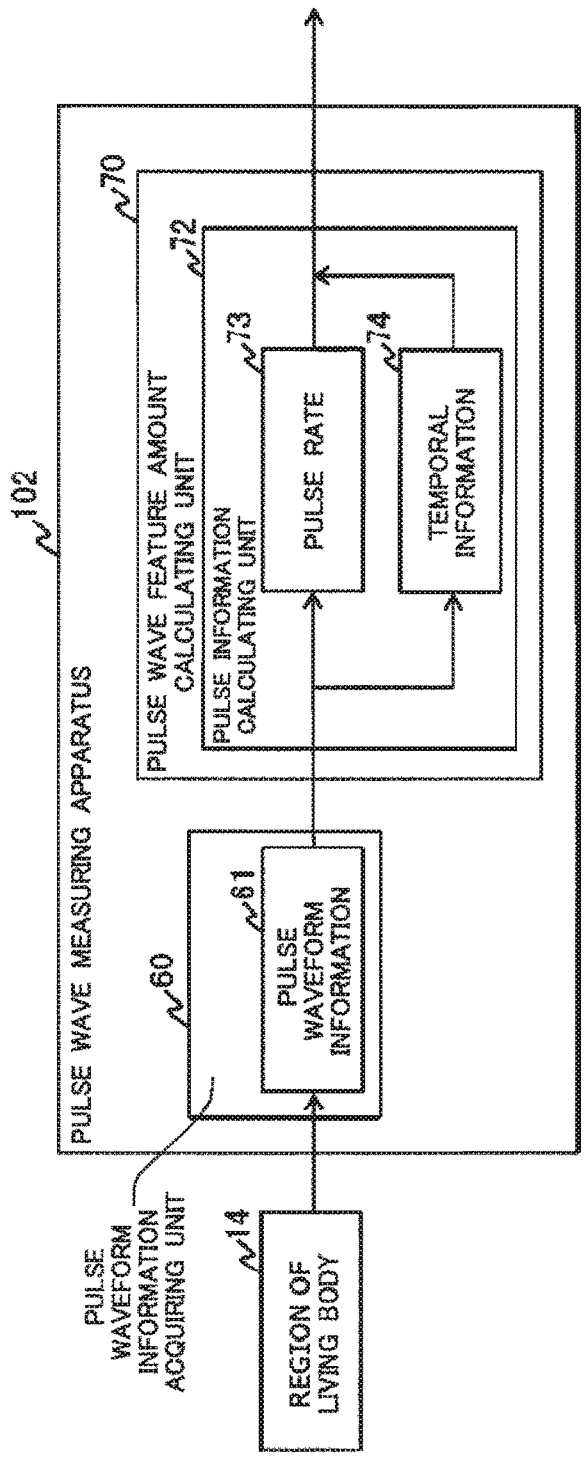
FIG. 54 shows one example of the configuration of the pulse wave measuring apparatus 102.

FIG. 54 shows one example of the configuration of the pulse wave measuring apparatus 102. The pulse wave feature amount calculating unit 70 according to the present example further comprises a pulse information calculating unit 72.

The pulse information calculating unit 72 calculates, based on the pulse waveform information 61, a pulse rate 73 of the living body and pulse wave temporal information 74 of the living body. The pulse information calculating unit 72 may calculate the pulse rate 73 and the temporal information 74 by using the algorithm of calculating the pulse wave temporal information 46 shown in FIG. 25.

The pulse rate 73 can be calculated based on time intervals of feature points in a pulse wave, or can be calculated by frequency analysis that provides high stability. For example, the frequency analysis is Fourier analysis or a wavelet analysis. Fourier analysis may be any of fast Fourier transform (FFT) and discrete Fourier transform (DFT). Also, the wavelet analysis may be any of Haar transform and Daubechies transform.

The temporal information 74 is information including at least one of the rising time of a pulse wave and the falling time of the pulse wave. The temporal information 74 may be calculated based on the pulse waveform information 61 and the pulse rate 73. Also, the temporal information 74 may include a feature amount in the time domain explained with reference to FIG. 40 to FIG. 43.

For example, when the temporal information 74 includes first time and second time that is different from the first time, the pulse information calculating unit 72 calculates independently each of the first time and the second time. In this case, the systolic blood pressure SBP may be estimated based on the pulse rate 73 output by the pulse information calculating unit 72 and the first time. Also, the diastolic blood pressure DBP may be estimated based on the pulse rate 73 output by the pulse information calculating unit 72 and the second time. In this manner, by independently obtaining feature amounts in the time domain to be used for estimating the systolic blood pressure SBP and the diastolic blood pressure DBP, an issue about forcible and mutually linked changes in the systolic blood pressure SBP and the diastolic blood pressure DBP can be solved.

Also, when the temporal information 74 includes rising time TR and falling time TF, the pulse information calculating unit 72 calculates independently each of the rising time TR and the falling time TF. In this case, the systolic blood pressure SBP may be estimated based on the pulse rate 73 output by the pulse information calculating unit 72 and the rising time TR. The diastolic blood pressure DBP may be estimated based on the pulse rate 73 output by the pulse information calculating unit 72 and the falling time TF.

Furthermore, the temporal information 74 may include a length of time between the rising zero-cross point and the top peak and a length of time between the bottom peak and the rising zero-cross point, in a first-order differentiation signal corresponding to one pulse in a pulse wave. Also, the pulse information calculating unit 72 calculates independently each of a length of time between the rising zero-cross point and the top peak and a length of time between the bottom peak and the rising zero-cross point, in a first-order differentiation signal corresponding to one pulse in a pulse wave. In this case, the systolic blood pressure SBP may be estimated based on the pulse rate 73 output by the pulse information calculating unit 72 and a length of time between the rising zero-cross point and the top peak in the first-order differentiation signal corresponding to the one pulse in the pulse wave. The diastolic blood pressure DBP may be estimated based on the pulse rate 73 output by the pulse information calculating unit 72 and a length of time between the bottom peak and the rising zero-cross point.

Figure 55:
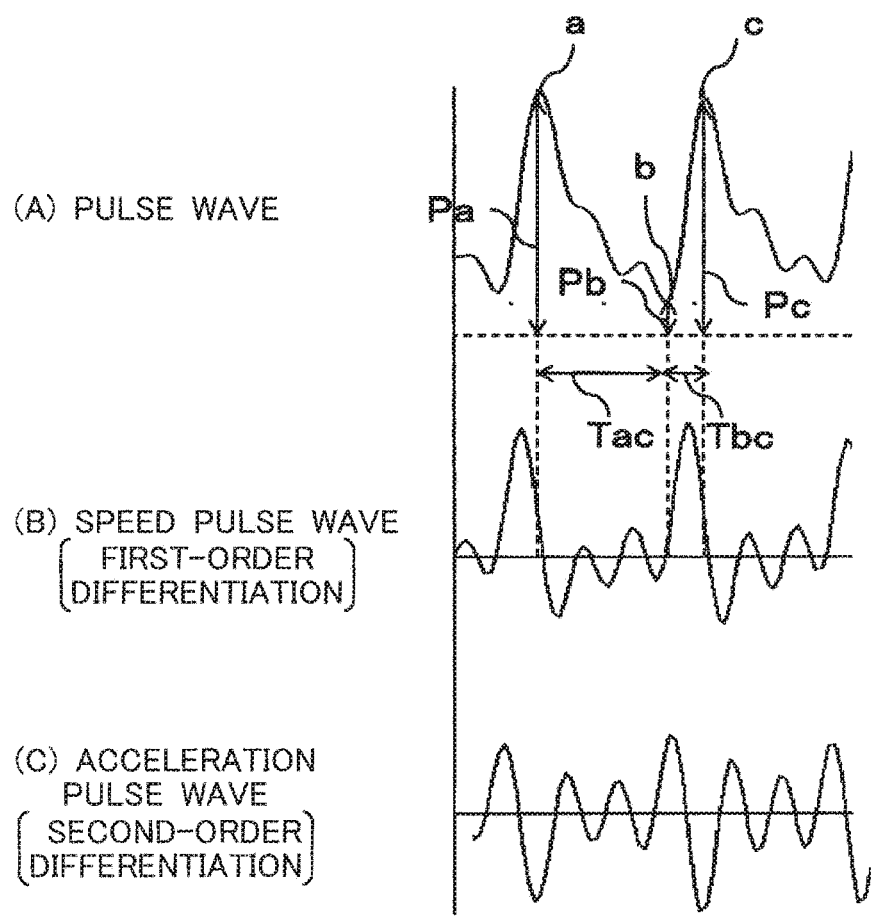
FIG. 55 shows one example of a method of calculating a pulse wave feature amount 71.

FIG. 55 shows one example of a method of calculating the pulse wave feature amount 71. (A) to (C) of FIG. 55 show a pulse wave, a speed pulse wave, and an acceleration pulse wave, respectively. The speed pulse wave and the acceleration pulse wave are obtained by first-order differentiation and second-order differentiation of the pulse wave, respectively.

The pulse wave feature amount 71 may be any single one of a pulse rate, the time interval of feature points of a pulse wave or the amplitude of feature points in a pulse wave, or may be a combination of a plurality of these. The number of the pulse wave feature amounts 71 calculated by the pulse wave feature amount calculating unit 70 is not limited. For example, the pulse wave feature amount calculating unit 70 acquires three feature points (a, b, c) of a pulse wave. The time intervals between a and b, and b and c are defined as Tab and Tbc, respectively, and the amplitudes of the point a, b, c are defined as Pa, Pb and Pc, respectively. In this case, the pulse wave feature amount 71 may be any one of Tab, Tbc, Pa, Pb and Pc, or a power of any of them. Also, the pulse wave feature amount 71 may be the sum, remainder, product or quotient of a combination of any two or more of Tab, Tbc, Pa, Pb and Pc. The pulse wave feature amount 71 is preferably any one of a pulse rate and the time interval of feature point of a pulse wave, or a combination of a plurality of them. A reason for this is because fluctuation in a pulse rate and the time interval of feature points of a pulse wave that may be caused by a measurement environment is small, and thus they provide high accuracy.

For example, a feature point of a pulse wave is at least one of the maximum or the minimum of each of a pulse wave, a speed pulse wave and an acceleration pulse wave, or the maximum point or the minimum point of each of a pulse wave, a speed pulse wave and an acceleration pulse wave in a predetermined section. Also, a feature point of a pulse wave may be a point where the amplitude of each of a pulse wave, a speed pulse wave and an acceleration pulse wave meets a predetermined condition. A feature point of a pulse wave may be a point of each of a pulse wave, a speed pulse wave and an acceleration pulse wave after elapse of a predetermined length of time from another feature point.

Note that the pulse wave feature amount 71 can be updated. Update may be done every predetermined number of beats or every predetermined length of time. When update is done every predetermined length of time, update is done preferably within 30 seconds, more preferably within 10 seconds, further preferably within five seconds, and most preferably within one second. On the other hand, when update is done every predetermined number of beats, update is done within 30 beats, more preferably within 10 beats, further preferably within five beats, and most preferably every beat. By making short the length of time at which update is done, rapid changes in a pulse wave can be reflected in an output. Also, by making short the length of time at which update is done, detailed variation in a pulse wave can be measured. Variation in the pulse wave feature amount due to update may be handled as the pulse wave feature amount 71. Also, the number of times when the pulse wave feature amount meets a predetermined condition may be handled as the pulse wave feature amount 71. The predetermined number of times may be the number of times in a predetermined length of time or a predetermined number of beats.

Figure 56:
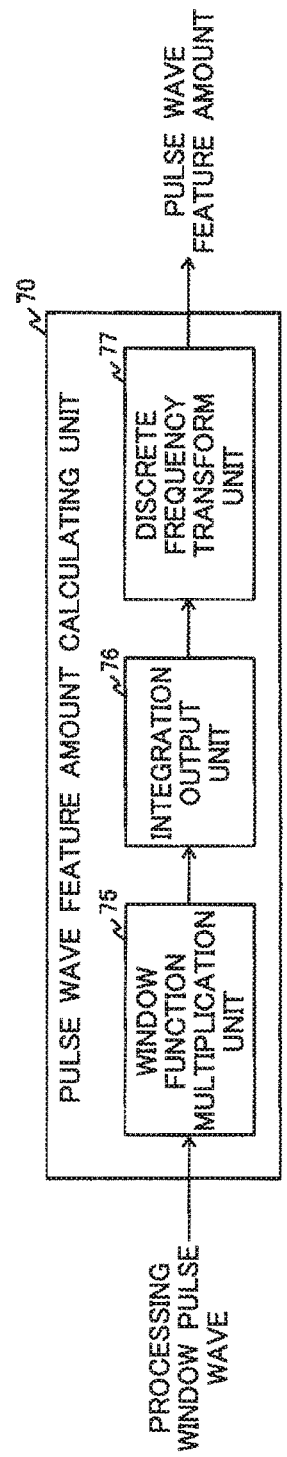
FIG. 56 shows one example of the configuration of a pulse wave feature amount calculating unit 70.

FIG. 56 shows one example of the configuration of the pulse wave feature amount calculating unit 70. The pulse wave feature amount calculating unit 70 comprises a window function multiplication unit 75, an integration output unit 76 and a discrete frequency transform unit 77. In the case explained below, the pulse wave feature amount calculating unit 70 according to the present example receives, as the pulse waveform information 61, an input of a processing window pulse wave segmented out in a predetermined window size.

The window function multiplication unit 75 multiplies the input processing window pulse wave with a predetermined window function. The window function may be any function that is generally used in signal processing, such as the Hanning window, the Kaiser-Bessel derived window, the Gaussian window, the Hamming window, the Tukey window or the Blackman window. The window function multiplication unit 75 outputs, as a window-processing pulse wave to the integration output unit 76, the processing window pulse wave which has been processed by being multiplied with the window function.

The integration output unit 76 generates an integration window signal formed by integrating the input window-processing pulse wave with sample data. The sample data may be integrated before, after or before and after the window signal multiplied with the window function.

For example, when the integration output unit 76 performs zero-extension on the window-processing pulse wave, the sample data is zero. By performing zero-extension on the window-processing pulse wave, the resolution of the window-processing pulse wave increases. The integration output unit 76 outputs the generated integration window signal to the discrete frequency transform unit 77.

The discrete frequency transform unit 77 performs discrete frequency transform on the integration window signal output by the integration output unit 76 to calculate a pulse wave feature amount. The discrete frequency transform unit 77 calculates a fast Fourier transform (FFT: Fast Fourier Transform) spectrum that is obtained by executing FFT on the integration window signal. For example, the discrete frequency transform unit 77 calculates a high-resolution pulse rate based on the FFT spectrum obtained from a high-resolution integration window signal.

Figure 57:
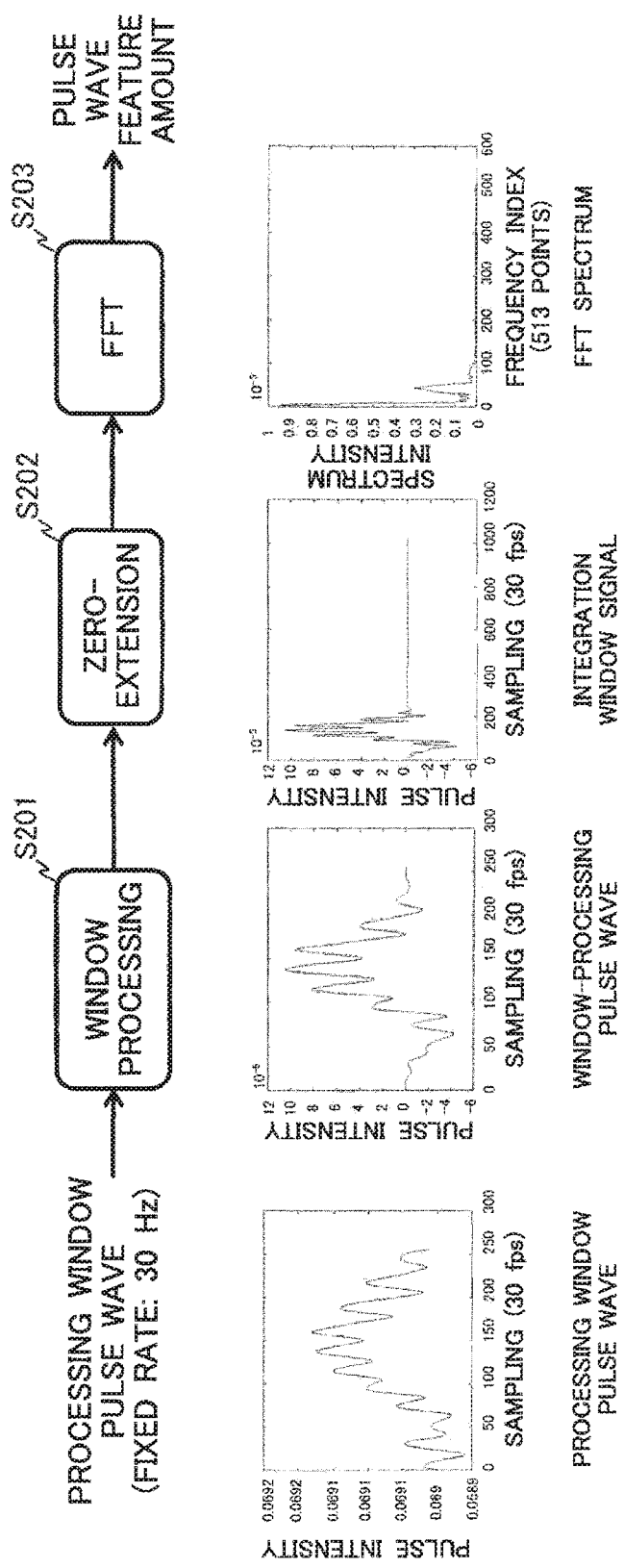
FIG. 57 shows one example of an algorithm of signal processing by a pulse rate calculating unit 20.

FIG. 57 shows one example of an algorithm of signal processing by the pulse wave feature amount calculating unit 70. The processing window pulse wave input to the pulse wave feature amount calculating unit 70 according to the present example is a highly reliable pulse wave from which unnecessary components are removed by the pulse waveform information acquiring unit 60. The pulse wave feature amount calculating unit 70 uses the processing window pulse wave segmented out to perform the processing of Steps S201 to 203 in order to calculate an accurate pulse rate.

At Step S201, the window function multiplication unit 75 executes, on the processing window pulse wave, window processing by using the Hanning window function or the Kaiser-Bessel derived window function. Thereby, temporal weighting becomes possible. Also, a window function may be selected so as to make the pulse intensities at both ends of the processing window pulse wave become equal.

At Step S202, the integration output unit 76 generates an integration window signal by integrating sample data at the end of the window-processing pulse wave. For example, the sample data is data which is the same as the pulse intensities at both ends of the processing window pulse wave having been multiplied with the window function. In this case, the sample data according to the present example is zero. Also, the size of the integration window signal is zero-extended so that it has a size of a power of two. By performing zero-extension, the resolution can be increased as compared with that before integration of the sample data.

At Step S203, the discrete frequency transform unit 77 executes FFT on the integration window signal, and calculates a FFT spectrum. The frequency resolution $\Delta f$ of FFT is determined by $\Delta f = fs/N$ based on the sample count N and the sampling rate fs. Accordingly, the larger the sample count N, the more improved the resolution $\Delta f$ is.

For example, when the frequency analysis by FFT is directly performed without zero-extension on a window signal with 128 points, the frequency resolution is 0.23 Hz. Because this corresponds to a pulse rate of 14 bpm, variation in pulse rates smaller than that cannot be detected. On the other hand, when 896 zero-signals are added to a window signal with the same 128 points, and the number of samples is increased to 1024, the frequency resolution becomes 0.029 Hz. This corresponds to a pulse rate of 1.7 bpm. The number of samples after zero-extension is not limited, but is preferably a power of two, and is more preferably 256, 512, 1024, 2048 or 4096.

As explained above, the pulse wave feature amount calculating unit 70 calculates an integration window signal from a processing window pulse wave at a sampling rate as low as 30 Hz. For this reason, when optically acquiring a pulse wave signal, pulse rate variation with a high resolution can be measured without up-sampling of the sampling frequency.

Figure 58:
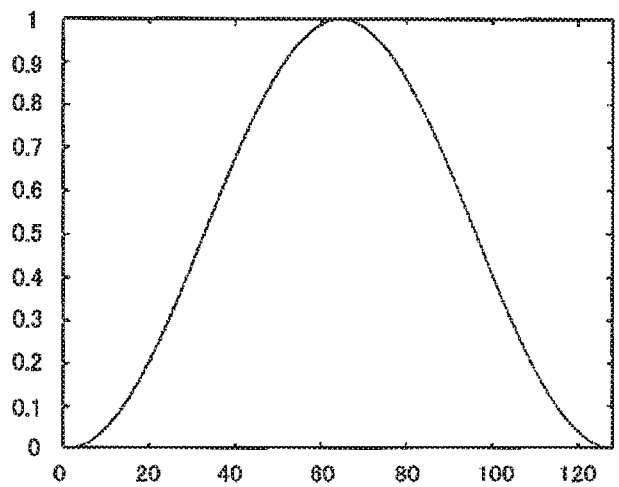
FIG. 58 shows one example of the Hanning window function.

FIG. 58 shows the Hanning window function. The Hanning window function is one example of a window function for FFT. The Hanning window function is a window function that make both ends of a frame zero. Also, the Hanning window function w(n) is expressed by the following Equation 14.

[Equation 14]

$$w(n) = 0.5\left(1 - \cos\left(2\pi\frac{n}{N}\right)\right), \ 0 \le n \le N$$

Here, n indicates a sampling element, and N indicates the number of samples.

The Hanning window function is a function that places weight at the window central time (around a portion corresponding to the number of frames of 64). For this reason, a pulse rate is to be measured with a pulse wave around the window central time as the center. For example, at the frame rate at 30 Hz, when pulse rate measurement is performed by FFT with the window size of 128 samples, pulse rate measurement is performed with the pulse wave about four seconds before as the center in the Hanning window. That is, there may be response time due to a temporal difference between the time of pulse rate measurement and the central time.

Figure 59:
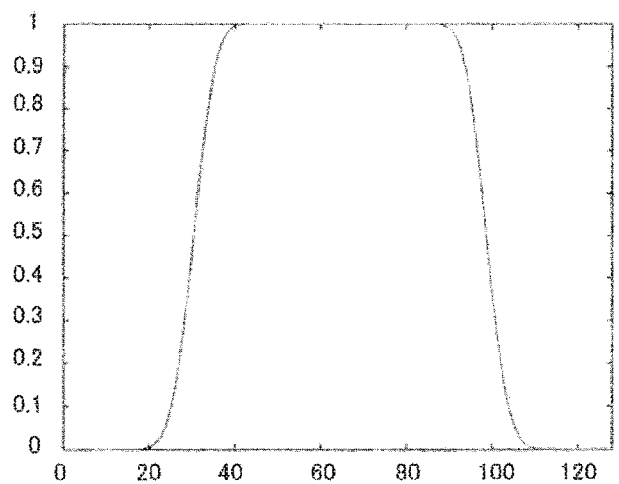
FIG. 59 shows one example of the Kaiser-Bessel derived window function.

FIG. 59 shows one example of the Kaiser-Bessel derived (KBD) window function. The KBD window function is a window function that makes both ends of a frame zero in a similar manner to that of the Hanning window function.

The KBD window function $d_k$ is expressed by the following Equation 15 in terms of a Kaiser window $w_k$.

Equation 15

$$d_k = \begin{cases} \sqrt{\dfrac{\sum_{j=0}^{k} w_j}{\sum_{j=0}^{n} w_j}} & \text{if } 0 \le k < n \\ \sqrt{\dfrac{\sum_{j=0}^{2n-1-k} w_j}{\sum_{j=0}^{n} w_j}} & \text{if } n \le k < 2n \\ 0 & \text{if } k \le 0, 2n \le k \end{cases}$$

Equation 15 defines a window of length $2n$. Here, $d_k$ satisfies the following Princen-Bradley condition for the modified discrete cosine transform (MDCT). That is, $d_k$ is expressed as $d_k^2 + d_{k+n}^2 = 1$ when $w_{n-k} = w_k$. Also, the KBD window satisfies symmetricity $d_k = d_{2n-1-k}$ which is another MDCT condition.

The KBD window function places more weight around portions corresponding to the number of frames of 40 to 90. On the other hand, the Hanning window function concentrates weight around a portion corresponding to the number of frames of 64. Therefore, the KBD window function places more weight on a pulse wave close to a newer extracted sample as compared with the Hanning window function. For this reason, because the KBD window is likely to reflect a value of a pulse wave closer to a newer extracted sample, the response of breathing state estimation can be improved.

Figure 60:
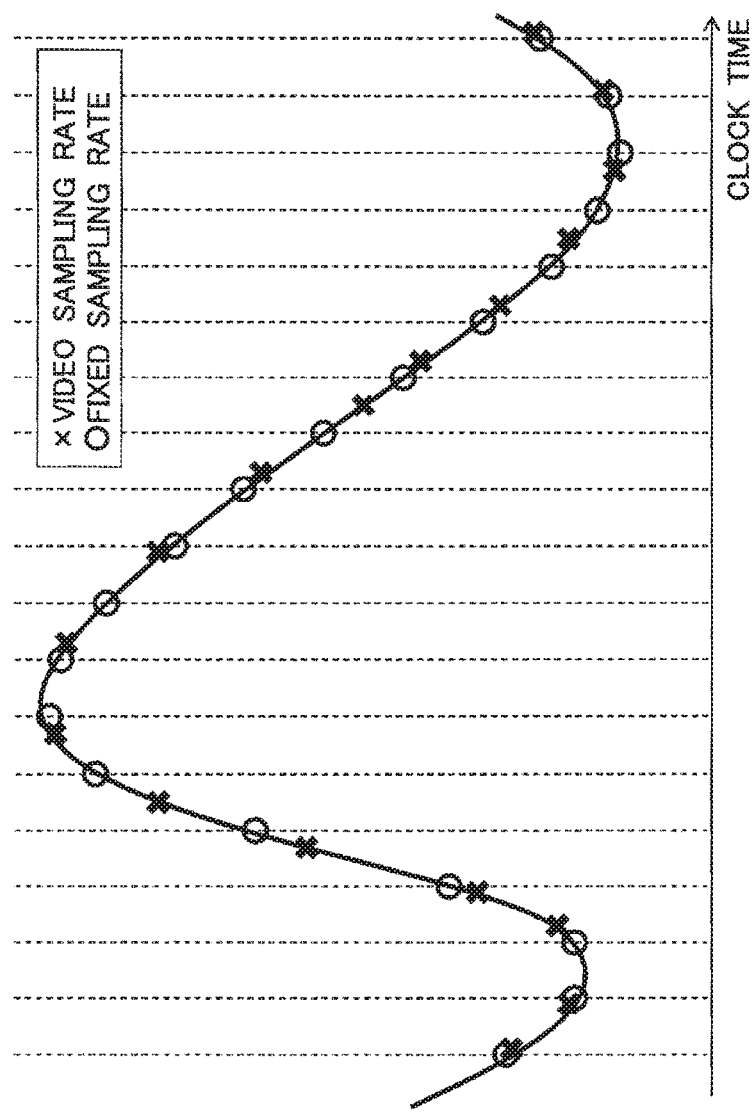
FIG. 60 shows one example of fixed resampling using illumination.

FIG. 60 shows one example of fixed resampling using illumination. The pulse waveform information acquiring unit 60 can enhance the accuracy of detecting a pulse wave by performing fixed resampling on an acquired video. In FIG. 60, the marks O correspond to a fixed sampling rate, and the marks x correspond to video sampling rate.

The fixed sampling rate refers to an ideal frequency for the pulse waveform information acquiring unit 60 to acquire videos. For example, the pulse waveform information acquiring unit 60 acquires a video at the fixed sampling rate of 30 Hz.

The video sampling rate refers to an actual sampling rate at which the pulse waveform information acquiring unit 60 acquires a video. For example, when the pulse waveform information acquiring unit 60 is equipped on a mobile terminal such as a smartphone, fluctuation occurs in the video sampling rate. For this reason, discrepancies are generated between the video sampling rate and the fixed sampling rate. Also, when fluctuation is generated in the video sampling rate, accurate time at which pulse rates were acquired cannot be known.

On the other hand, light generated by illumination driven by an AC power supply operates accurately at a constant luminance frequency, although such a luminance frequency is not sensed by human eyes. Also, a video acquired by the pulse waveform information acquiring unit 60 includes information necessary for calculating the phase of illumination. The phase of illumination can be calculated from the intensity of reflected light of illumination within a predetermined region. The predetermined region may be a partial region of an object included in a video. The predetermined region preferably does not move. Also, the pulse waveform information acquiring unit 60 may capture not reflected light of illumination, but light of illumination directly. For example, the pulse waveform information acquiring unit 60 calculates in advance the maximum intensity and minimum intensity of reflected light in a predetermined region. Thereby, the pulse waveform information acquiring unit 60 can measure the intensity of reflected light within a predetermined region, and calculate the phase of the illumination from the video. That is, when a video sampling rate is different from the target phase, the phase of the video can be corrected based on the phase of the illumination. In this manner, the pulse waveform information acquiring unit 60 can improve the accuracy of estimating breathing information by correcting fluctuation in the video sampling rate with the use of the luminance frequency of the illumination. To put it in another way, the pulse waveform information acquiring unit 60 can use, as a reference clock, illumination that has been taken into an image.

With such a method, the blood pressure information output apparatus 100 may correct fluctuation in the sampling rate of a video at Step S105 in FIG. 23 or at Step S201 in FIG. 25. The variation in the sampling rate can be corrected to a fixed sampling rate by spline interpolation based on timestamps (clock time information) acquired in association with a video of a measurement subject. Note that the interpolation method is not limited to the spline interpolation, but may be the Lagrange interpolation or the linear interpolation. But the spline interpolation is preferable because it takes a small operation amount and provides good accuracy.

Figure 61:
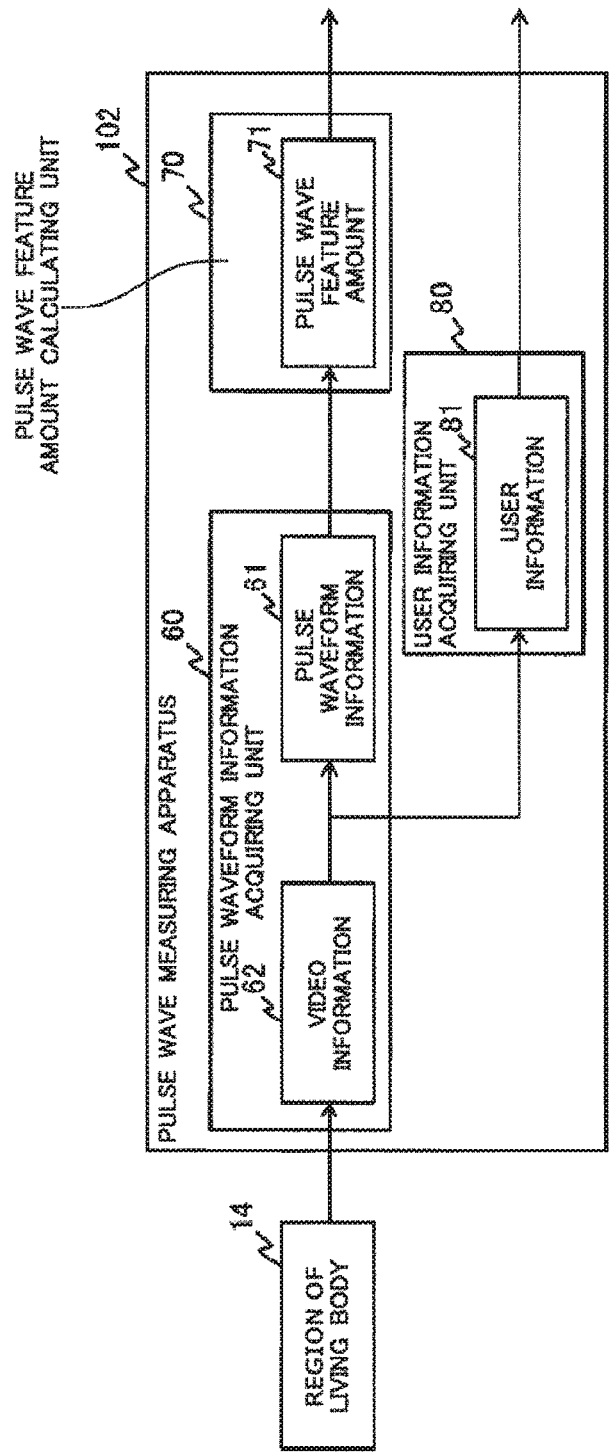
FIG. 61 shows one example of the configuration of the pulse wave measuring apparatus 102.

FIG. 61 shows one example of the configuration of the pulse wave measuring apparatus 102. The pulse wave measuring apparatus 102 according to the present example further comprises a user information acquiring unit 80.

The user information acquiring unit 80 identifies a user based on the video information 62. The user information acquiring unit 80 acquires user information 81 of the identified user. The user information acquiring unit 80 can identify a user by extracting, from the video information 62, a feature of the face of a measurement subject. A relative position or size of a part of a face, the shape of an eye, nose, cheekbone or jaw may be utilized as a feature in identification of a user. The user information acquiring unit 80 compares the video information 62 of a pre-registered existing user and the acquired video information 62 to identify a user who has a matching feature. When not having been able to identify a user, the user information acquiring unit 80 registers the user as a new user. The user information 81 includes identification information, confirmation information and peripheral information. For example, the identification information includes a name, an ID and a fixed phrase. The confirmation information includes a schedule, an informative matter and a memorandum. The peripheral information includes measurement history information and information about another user.

For example, when a plurality of users uses an apparatus at a medical institution, home, school or workplace, measurement results are recorded and managed for respective users. In this case, information such as names or IDs identifying individuals needs not be input separately. Only with the user information 81, the room-entrance clock time, room-exit clock time, duration of stay and outing time of users can be managed.

Figure 62:
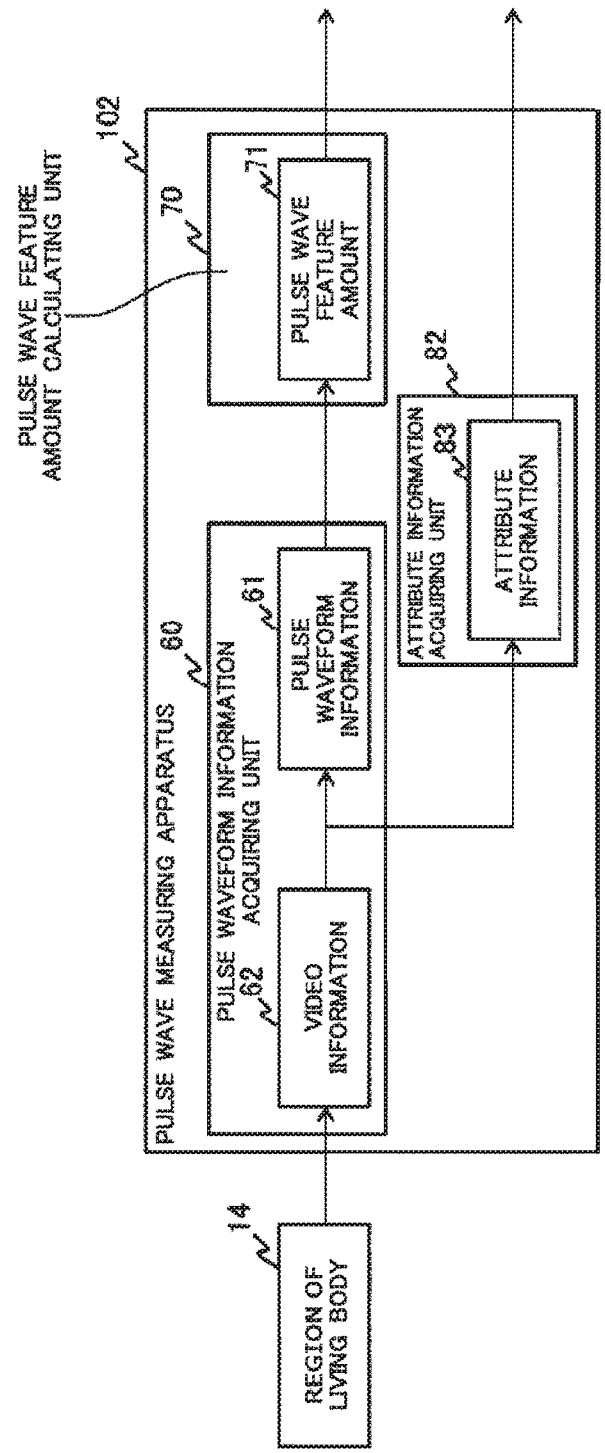
FIG. 62 shows one example of the configuration of the pulse wave measuring apparatus 102.

FIG. 62 shows one example of the configuration of the pulse wave measuring apparatus 102. The pulse wave measuring apparatus 102 according to the present example is different from the example in FIG. 61 in that it comprises an attribute information acquiring unit 82 instead of the user information acquiring unit 80.

The attribute information acquiring unit 82 estimates attribute information 83 based on the video information 62. The attribute information acquiring unit 82 can identify an attribute by extracting, from the video information 62, a feature of the face of a measurement subject.

A relative position or size of a part of a face, the shape of an eye, nose, cheekbone or jaw may be utilized as a feature in identification of an attribute. The attribute information acquiring unit 82 compares a pre-registered model for each attribute and the acquired attribute information 83 to identify an attribute that has a matching feature. For example, the attribute information 83 includes at least one of a sex, an age, a generation, a blood type, a birthplace, a nationality, a mother tongue, a race and a build.

Figure 63:
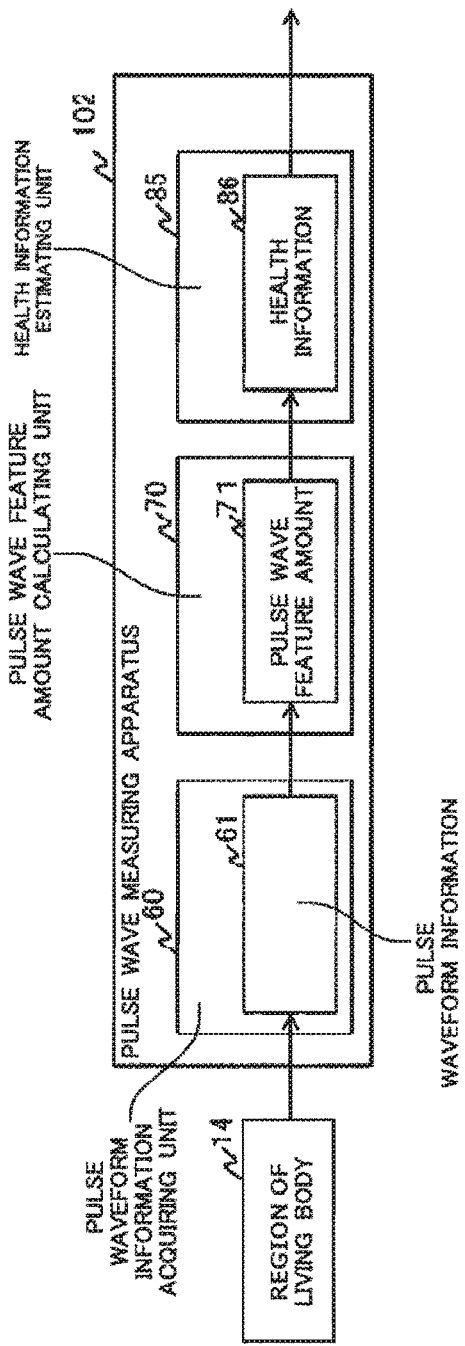
FIG. 63 shows one example of the configuration of the pulse wave measuring apparatus 102.

FIG. 63 shows one example of the configuration of the pulse wave measuring apparatus 102. The pulse wave measuring apparatus 102 according to the present example is different from the example in FIG. 47 in that it further comprises a health information estimating unit 85.

The health information estimating unit 85 estimates health information 86 based on the pulse wave feature amount 71. For example, assuming that the pulse wave feature amount 71 is a, the health information 86 can estimated by using a preset function f(a). However, when there is a plurality of the pulse wave feature amounts 71, a can be expressed as a matrix including a plurality of elements.

For example, the health information estimating unit 85 estimates the health information 86 indicating whether or not a person is in a relaxed state. When a pulse rate calculated by frequency analysis is handled as the pulse wave feature amount 71, the health information 86 indicates a person is as much in a mentally relaxed state as the pulse rate is lower. Also, when time Tbc from a minimum b of a pulse wave to the immediately following maximum c is handled as the pulse wave feature amount 71, when Tbc is larger, the health information 86 indicates that a person has a tendency of hypertension.

The health information 86 may include at least one of pulse-related information, blood pressure-related information, breathing-related information, mental state-related information and recommendation information. The blood pressure-related information is any of blood pressure information, blood flow information, vascular information, blood information, function information and circulatory organ information. For example, the blood pressure information is any of the highest (systolic) blood pressure, the lowest (diastolic) blood pressure, the average blood pressure and a pulse pressure. The blood pressure information may be expressed in the unit of mmHg. The blood pressure information may be stepwise evaluation such as three-step evaluation of high blood pressure, normal blood pressure and low blood pressure.

For example, the blood flow information is a blood flow rate or a blood flow amount. Also, the vascular information is a blood vessel diameter, a vascular wall thickness, an arteriosclerosis level, a Young's modulus or a vascular age. The blood information may be a blood oxygenation level, a blood composition, a hemoglobin concentration or a blood viscosity. The pulse-related information may be a pulse rate, pulse wave propagation time or a pulse wave propagation speed. The pulse rate may be expressed in the unit of bpm or Hz. The mental state-related information may be the degree of tension, a stress level, an arousal level, the degree of concentration or an emotion. The recommendation information may be about drugs, medical institutions, supplements, exercise schedules, sleeping methods, fitness clubs, foods and drinks, restaurants, dishes, books, music, videos, Internet sites, health advice or health risks.

Figure 64:
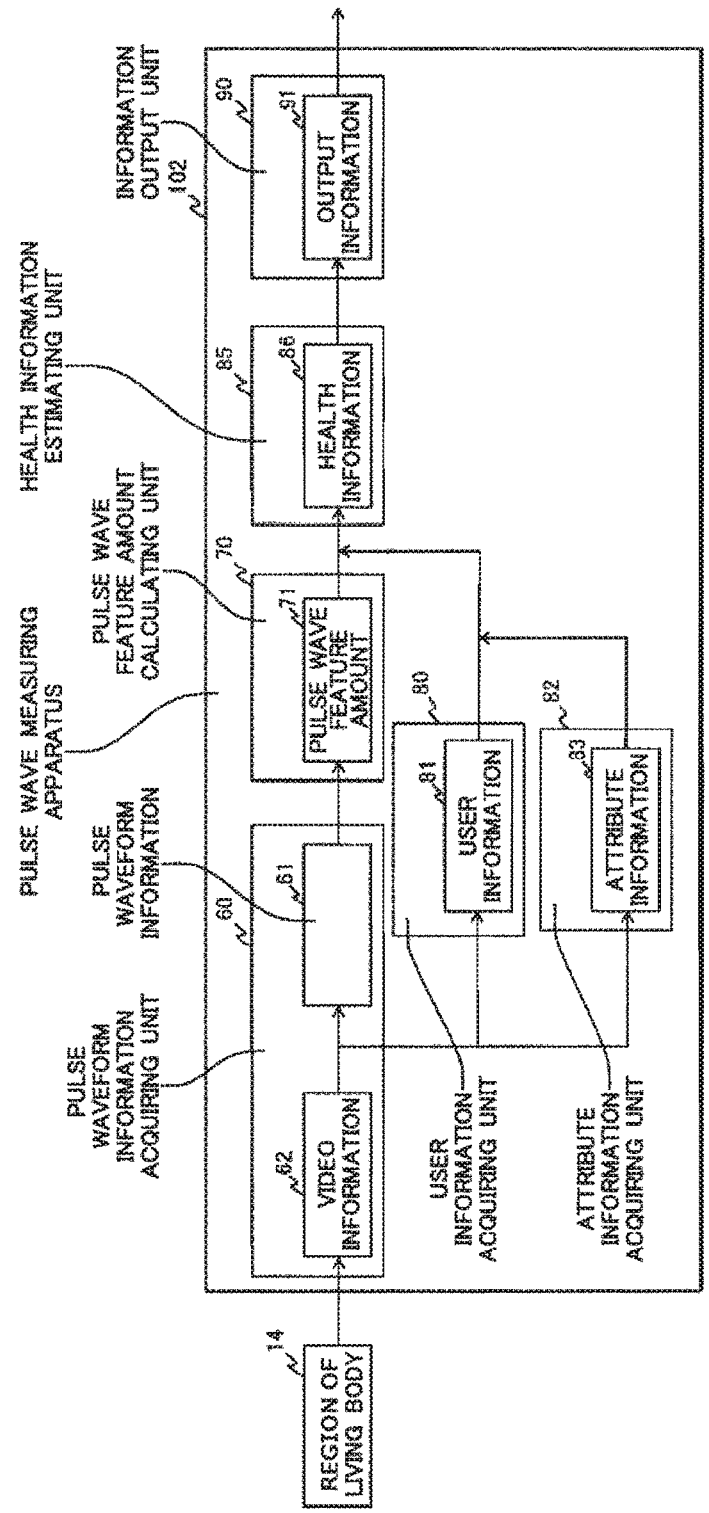
FIG. 64 shows one example of the configuration of the pulse wave measuring apparatus 102.

FIG. 64 shows one example of the configuration of the pulse wave measuring apparatus 102. The pulse wave measuring apparatus 102 according to the present example comprises the pulse waveform information acquiring unit 60, the pulse wave feature amount calculating unit 70, the user information acquiring unit 80, the attribute information acquiring unit 82, the health information estimating unit 85 and an information output unit 90.

The health information estimating unit 85 estimates the health information 86 based on the user information 81 in addition to the pulse wave feature amount 71. For example, assuming that the pulse wave feature amount 71 and the user information 81 are a and b, respectively, the health information 86 can be estimated by using a preset function f(a,b). Note that when there are pluralities of the pulse wave feature amounts 71 and pieces of the user information 81, respectively, a and b can be expressed as matrices each including a plurality of elements.

Also, the health information estimating unit 85 may compare the user information 81 and a measurement history of a user to estimate the health information 86. Because the health information estimating unit 85 reflects the user information 81 to estimate the health information 86, the accuracy of estimating the health information 86 improves. Also, the health information estimating unit 85 can enhance the estimation accuracy by correcting the health information 86 for each user.

The health information estimating unit 85 may estimate the health information 86 based on the attribute information 83 in addition to the pulse wave feature amount 71. For example, assuming that the pulse wave feature amount 71 and the attribute information 83 are a and c, respectively, the health information 86 can be estimated by using a function f(a,c). Note that when there are pluralities of the pulse wave feature amounts 71 and pieces of the attribute information 83, respectively, a and c can be expressed by matrices each including a plurality of elements. In this case, the health information estimating unit 85 can refer to a statistical measurement result for each attribute. That is, the health information estimating unit 85 can estimate the health information 86 based on a statistical measurement result.

Because the health information estimating unit 85 reflects the attribute information 83 to estimate the health information 86, the accuracy of estimating the health information 86 improves. Also, the health information estimating unit 85 can enhance the estimation accuracy by correcting the health information 86 for each attribute. Note that the health information estimating unit 85 may be configured to include the information output unit 90.

The health information estimating unit 85 can calculate a correlation between the estimated health information 86 and the statistical health information 86 of a specific attribute. Furthermore, the health information estimating unit 85 may estimate the health information 86 based on any or both of environment information and the user information 81 in addition to the pulse wave feature amount 71 and the attribute information 83.

The information output unit 90 outputs output information 91 based on the health information 86 estimated by the health information estimating unit 85. For example, the information output unit 90 comprises any one or more of a lamp, a display and a speaker. The lamp may indicate the output information 91 by means of optical intensity or optical wavelength. The display may indicate the output information 91 by combining one or more of characters and images. The characters are for example any of numbers, alphabetical characters, Greek characters, Arabic alphabets, Japanese hiraganas, Japanese katakanas and Japanese kanjis. The images may be for example graphs, still images or moving images. The still images are for example illustrations or images of faces obtained by editing/processing the video information 62. The moving images are for example image videos that indicate variation in a pulse wave, an estimate value, blood vessels or a blood flow. The speaker may output the output information 91 as audio. The information output unit 90 may output the output information 91 as pressure, current or shape. The information output unit 90 may transmit the output information 91 to peripheral equipment or a database connected by a wireless or wired network.

Also, the information output unit 90 may operate/control peripheral equipment based on the output information 91. The peripheral equipment is for example health equipment, medical equipment, a vehicle or another apparatus. The health equipment is for example a running machine, an exercise bike, a pressure band or a massage chair. The medical equipment is for example a defibrillator, a dialysis apparatus, a drip infusion apparatus, a blood transfusion apparatus, a blood collecting apparatus or an artificial respirator. The vehicle is for example a rocket, an airplane, a train, a bus, a passenger car, playground equipment or a bicycle. The other apparatus may be an air conditioner, a heating appliance, a cooling appliance, a dryer, a humidifier, a dehumidifier, a ventilation fan, lighting equipment, an acoustic apparatus, a mobile music player, a cooking appliance, a desktop PC, a laptop PC, a tablet PC, a mobile phone, a smartphone, a wristwatch-type terminal, a television, a game console or a door.

Figure 65:
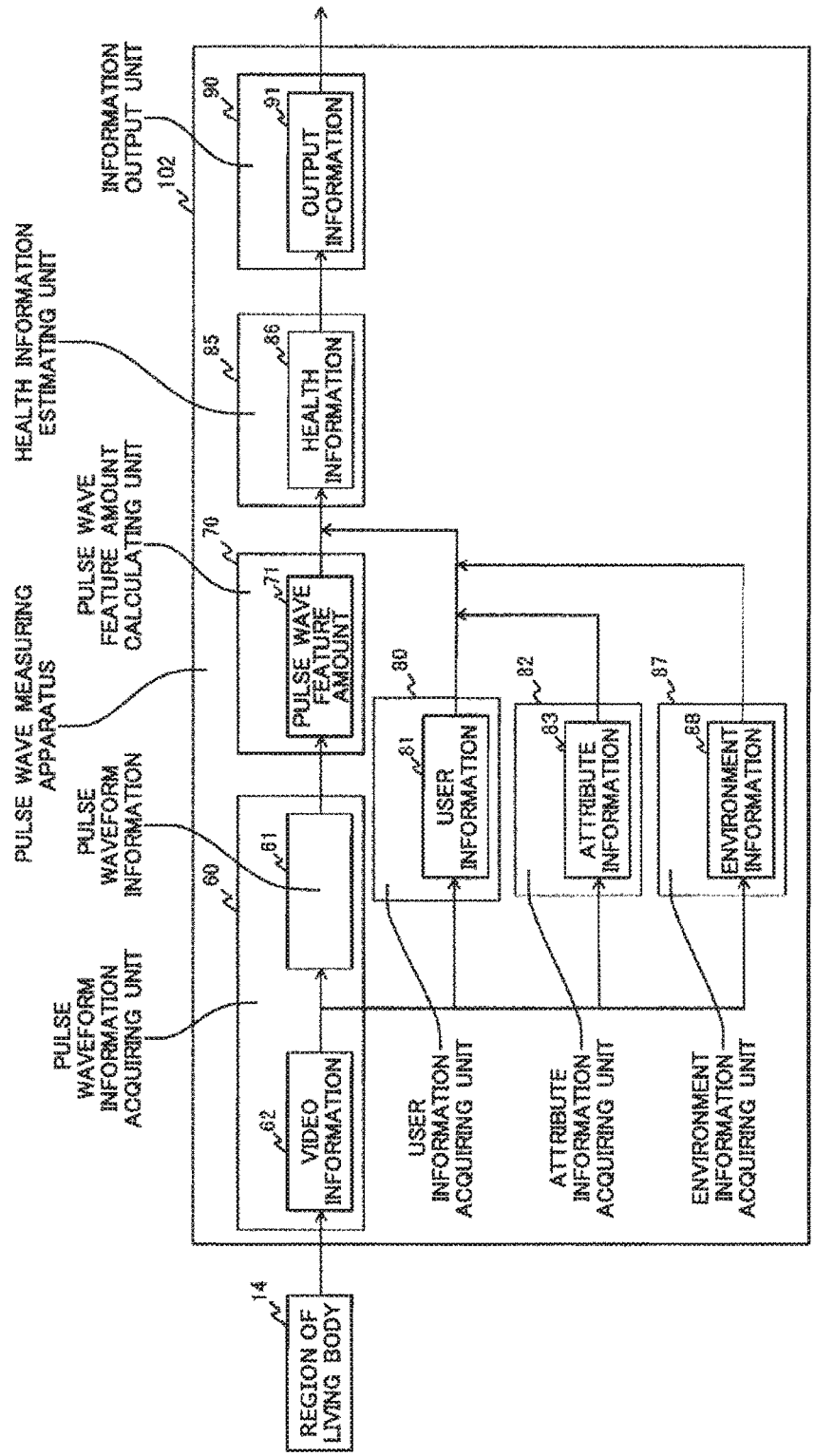
FIG. 65 shows one example of the configuration of the pulse wave measuring apparatus 102.

FIG. 65 shows one example of the configuration of the pulse wave measuring apparatus 102. The pulse wave measuring apparatus 102 according to the present example further comprises an environment information acquiring unit 87 in addition to the configuration of the pulse wave measuring apparatus 102 in FIG. 64.

The environment information acquiring unit 87 acquires environment information 88 from the video information 62.

The environment information 88 is for example the date on which measurement was performed, the clock time at which measurement was performed, a location at which measurement was performed, air temperature, humidity or a barometric pressure. The pulse wave measuring apparatus 102 according to the present example estimates the health information 86 based on the environment information 88, in addition to the pulse wave feature amount 71. Also, the health information 86 may be estimated based on at least one of the user information 81, the attribute information 83 and the environment information 88, in addition to the pulse wave feature amount 71.

The health information 86 can be estimated by using a function. For example, assuming that the pulse wave feature amount 71 and the environment information 88 are a and d, respectively, the health information 86 can be estimated by using a function $f(a,d)$. Note that when there are pluralities of the pulse wave feature amounts 71 and pieces of the environment information 88, respectively, a and d can be expressed as matrices each including a plurality of elements.

Also, the pulse wave measuring apparatus 102 may estimate the health information 86 based on at least one of the user information 81, the attribute information 83 and the environment information 88, in addition to the pulse wave feature amount 71. For example, assuming that the pulse wave feature amount 71, the user information 81, the attribute information 83 and the environment information 88 are a, b, c and d, respectively, the health information 86 can be estimated by using a predetermined function $f(a,b,c,d)$.

Figure 66:
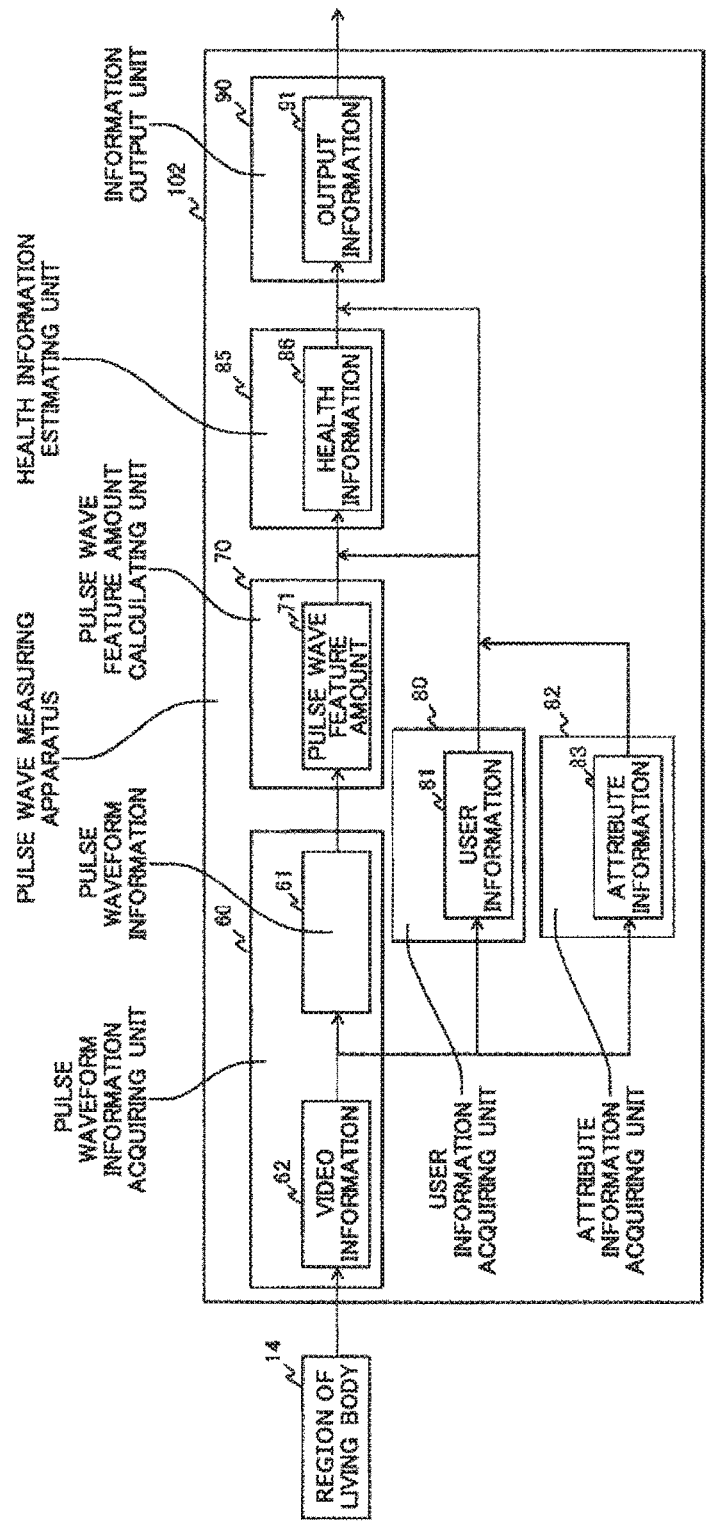
FIG. 66 shows one example of the configuration of the pulse wave measuring apparatus 102.

FIG. 66 shows one example of the configuration of the pulse wave measuring apparatus 102. The information output unit 90 according to the present example outputs information based on at least one information among the video information 62, the pulse waveform information 61, the user information 81 and the attribute information 83, in addition to the health information 86. Note that, by comprising the environment information acquiring unit 87, the pulse wave measuring apparatus 102 may output the output information 91 based on the environment information 88.

Figure 67:
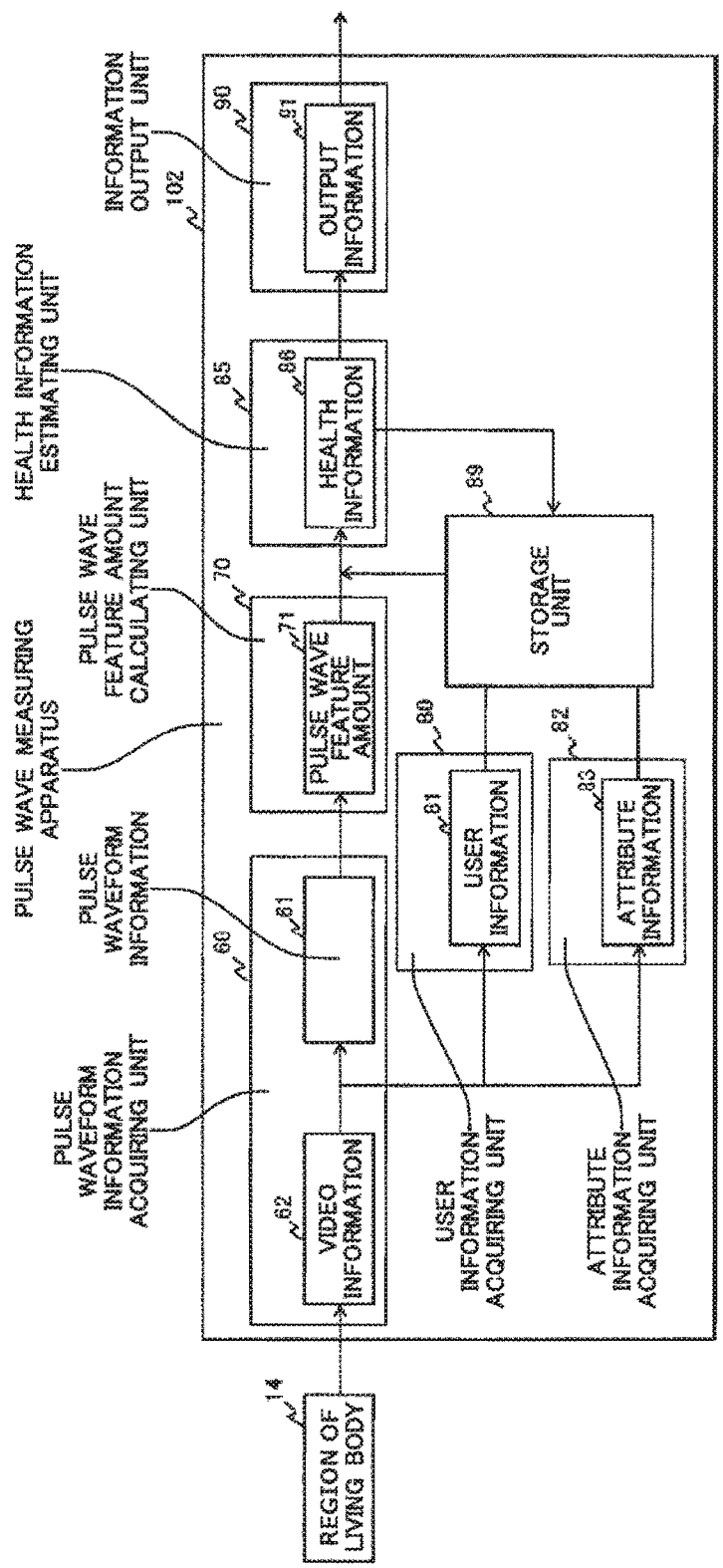
FIG. 67 shows one example of the configuration of the pulse wave measuring apparatus 102.

FIG. 67 shows one example of the configuration of the pulse wave measuring apparatus 102. The pulse wave measuring apparatus 102 according to the present example comprises a storage unit 89.

The storage unit 89 memorizes the user information 81 and the attribute information 83. Also, the storage unit 89 may memorize the past health information 86. In the present example, the user information 81 and the attribute information 83 in combination are called personal identification information. The storage unit 89 transmits the memorized personal identification information to the health information estimating unit 85 when the personal identification information and personal identification information acquired by the user information acquiring unit 80 and the attribute information acquiring unit 82 match. On the other hand, the storage unit 89 does not transmit the personal identification information memorized in the storage unit 89 to the health information estimating unit 85 when the personal identification information and personal identification information acquired by the user information acquiring unit 80 and the attribute information acquiring unit 82 do not match. That is, the pulse wave measuring apparatus 102 estimates the health information 86 only when personal identification information matches personal identification information memorized in advance.

The pulse wave measuring apparatus 102 disclosed in the present specification may be clothing or an accessory worn by a living body. The accessory is for example a finger ring, a collar, a necklace, a hair ornament, a pierced earring, an earing, an earplug, an earphone, a headphone, eye glasses, goggles, an eye mask, a wrist band, a misanga, a wristwatch, a mask, a hat, a glove, a helmet, a shoe or a sandal. Also, the pulse wave measuring apparatus 102 may be a seal or a patch to be applied onto the skin of a living body.

Embodiment 13

Figure 68:
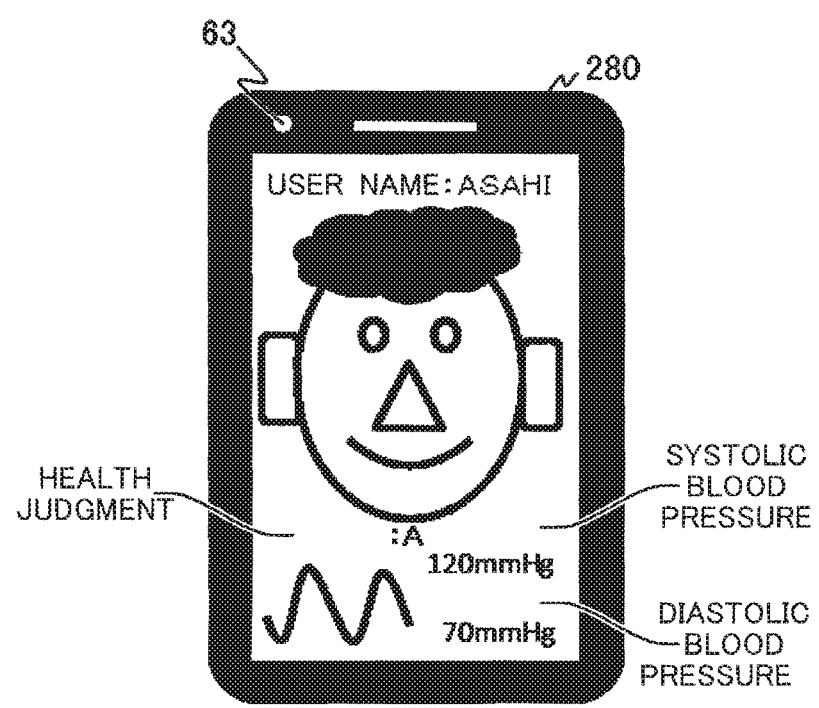
FIG. 68 shows one example of the pulse wave measuring apparatus 102 according to Embodiment 13.

FIG. 68 shows one example of the pulse wave measuring apparatus 102 according to Embodiment 13. The pulse wave measuring apparatus 102 according to the present example is implemented on a mobile information terminal 280, and acquires the user information 81. The pulse wave measuring apparatus 102 receives an input of the video information 62 at 30 fps acquired by the camera 63 provided to the mobile information terminal 280. The mobile information terminal 280 according to the present example displays, based on the input video information 62, a user name, a health judgment result, a systolic blood pressure, a diastolic blood pressure and a pulse wave. In this manner, a user can refer to a judgment result of the health information 86 simply.

Figure 69:
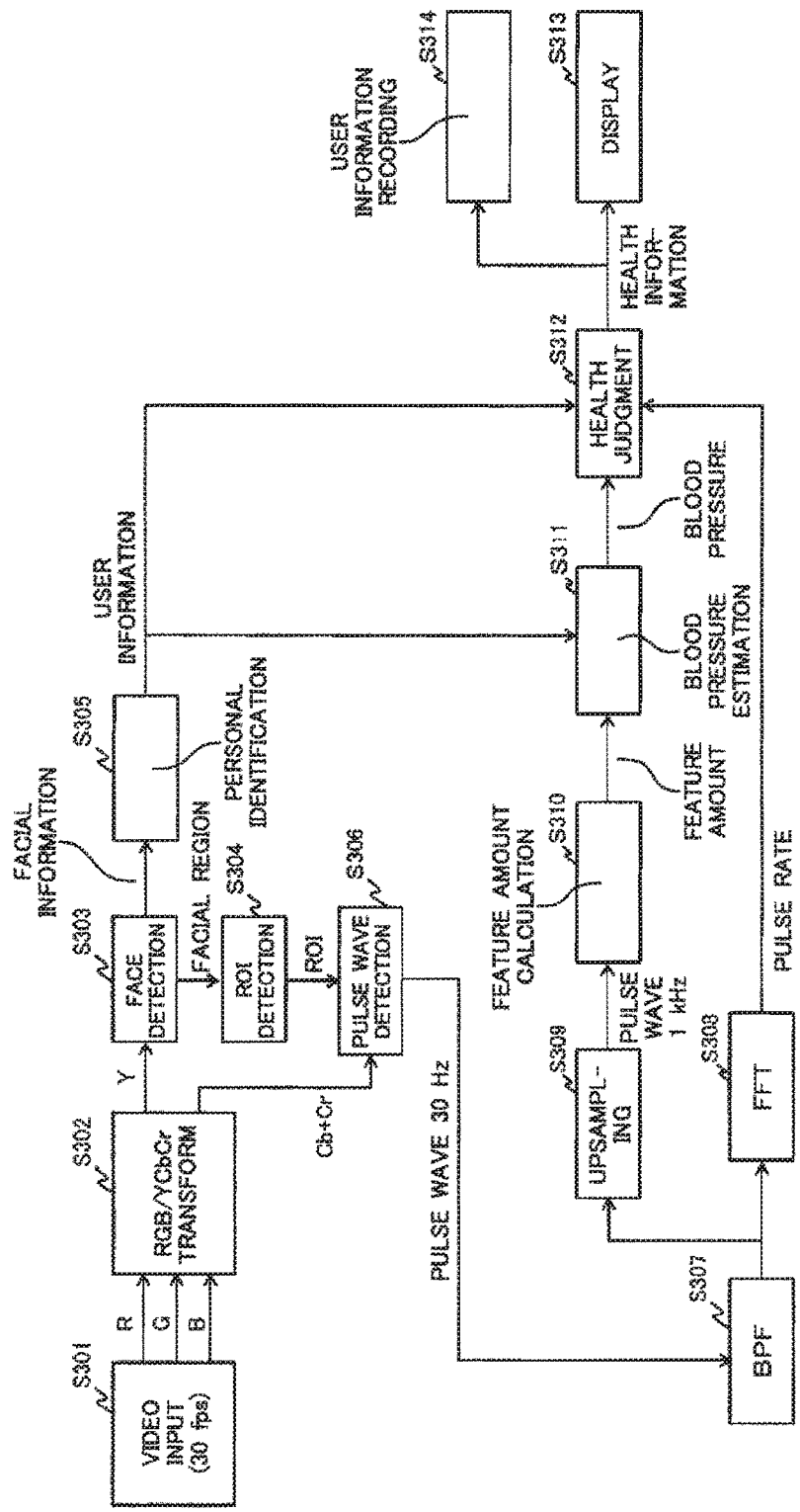
FIG. 69 shows one example of signal processing by the pulse wave measuring apparatus 102.

FIG. 69 shows one example of signal processing by the pulse wave measuring apparatus 102 according to Embodiment 13. The pulse wave measuring apparatus 102 according to the present example executes Step S301 to Step S314.

At Step S301, the camera 63 acquires the video information 62 at 30 fps. At Step S302, RGB signals of the video information 62 acquired at Step S301 are transformed into a Y signal and a Cb+Cr signal. At Step S303, a facial region is detected based on the transformed Y signal. Also, at Step S304, a region of interest ROI is identified in the detected facial region.

At Step S305, a feature of a face is extracted from an image of the facial region to identify an individual, and the user information 81 is acquired. At Step S306, a pulse wave trace signal at 30 Hz is created based on the Cb+Cr signal of the region of interest ROI. At Step S307, the pulse wave trace signal is made to pass a band-pass filter BPF, and then at Step S308, the frequency analysis is performed by the fast Fourier transform (FFT) to calculate a pulse rate.

On the other hand, at Step S309, the pulse wave trace signal that has been made to pass the band-pass filter BPF is subjected to spline interpolation to be up-sampled to a pulse wave at 1 kHz. At Step S310, a pulse wave feature amount is calculated from the up-sampled 1 kHz pulse wave. At Step S311, the blood pressure information is estimated based on the pulse wave feature amount 71 and the user information 81.

At Step S312, the health information of a user is judged based on the blood pressure information, the user information 81 and the pulse rate. Because at Step S312, corrections can be made according to comparison with past measurement data of a measurement subject based on the user information 81, the accuracy of estimating the blood pressure information improves.

At Step S313, a user name, pulse waveform information, blood pressure information and health information are displayed on a display. On the other hand, at Step S314, health information of a user is recorded as the user information 81. Thereby, the pulse wave measuring apparatus 102 can manage health of each user simply.

Embodiment 14

Figure 70:
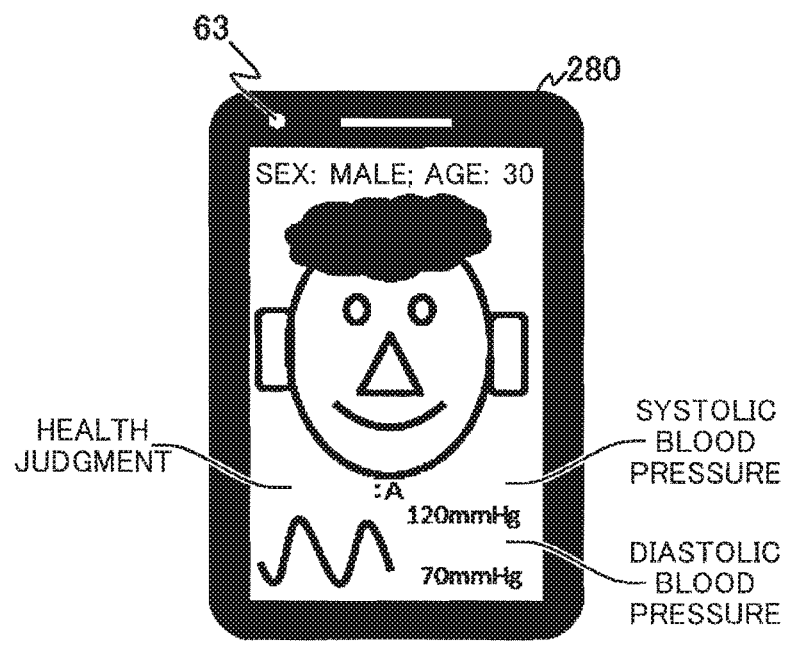
FIG. 70 shows one example of the pulse wave measuring apparatus 102 according to Embodiment 14.

FIG. 70 shows one example of the pulse wave measuring apparatus 102 according to Embodiment 14. The pulse wave measuring apparatus 102 according to the present example is implemented on the mobile information terminal 280 which is one example of mobile devices, and acquires the attribute information 83. The pulse wave measuring apparatus 102 receives an input of the video information 62 at 30 fps acquired by the camera 63 provided to the mobile information terminal 280. The mobile information terminal 280 according to the present example displays, based on the input video information 62, the attribute information 83 such as sex or age, a health judgment result, a systolic blood pressure, a diastolic blood pressure and a pulse wave. In this manner, a user can refer to a judgment result of the health information 86 simply.

Figure 71:
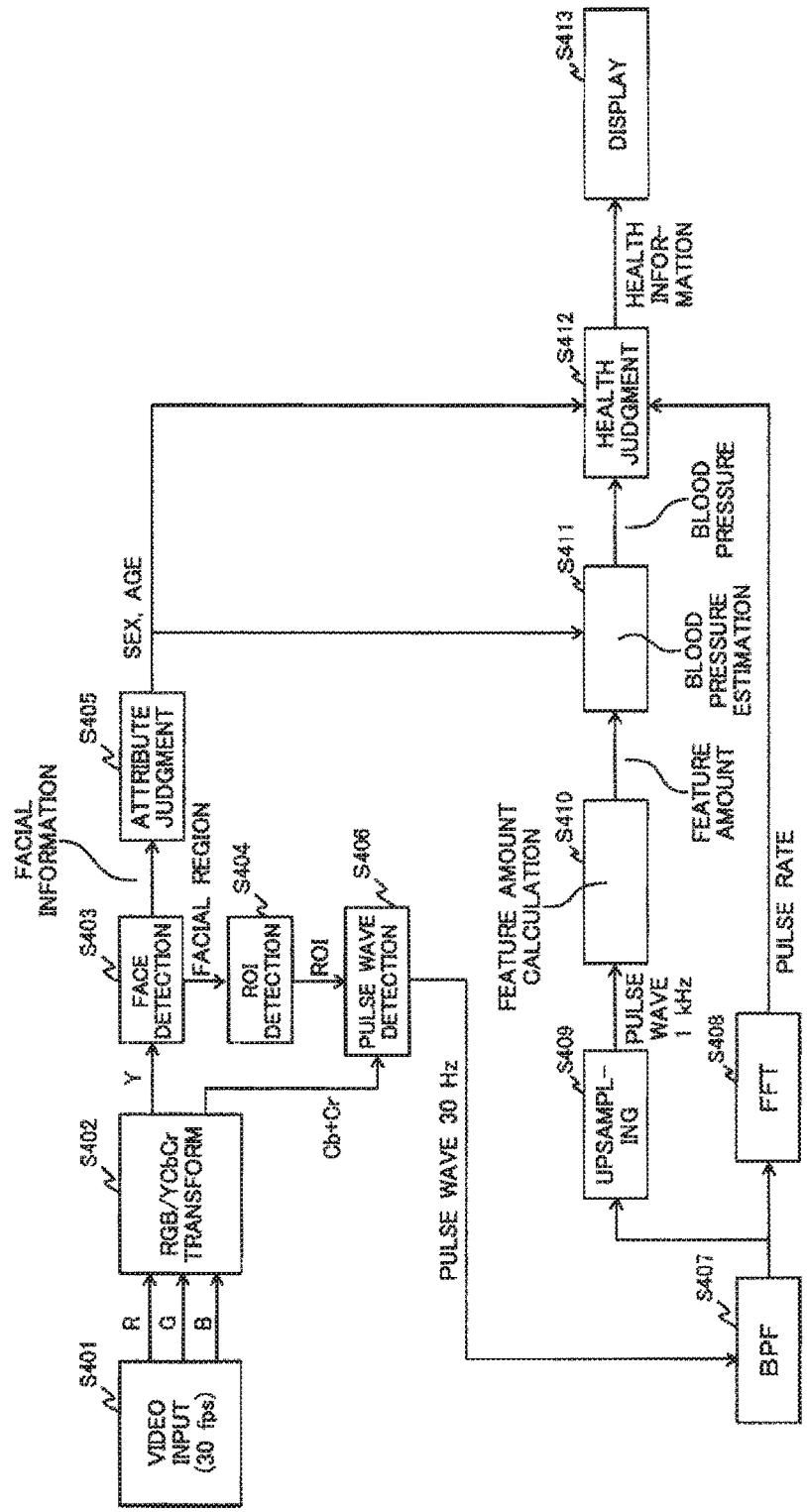
FIG. 71 shows one example of signal processing by the pulse wave measuring apparatus 102.

FIG. 71 shows one example of signal processing by the pulse wave measuring apparatus 102 according to Embodiment 14. The pulse wave measuring apparatus 102 according to the present example executes Step S401 to Step S413.

Step S401 to Step S413 are basically executed in a flow similar to that of Step S301 to Step S313. In the present example, mainly, differences from Step S301 to Step S313 are explained.

Step S401 to Step S404 correspond to Step S301 to Step S304. At Step S405, a feature of a face is extracted from an image in a facial region detected at Step S403 to judge an attribute. That is, at Step S405, the attribute information 83 is acquired.

Also, Step S406 to Step S410 correspond to Step S306 to Step S310. At Step S411, the blood pressure information is estimated based on the pulse wave feature amount 71 and the attribute information 83. Based on the attribute information 83, the pulse wave measuring apparatus 102 according to the present example can make corrections determined for each attribute. For this reason, the accuracy of estimating the blood pressure information is high. At Step S412, the health information 86 of a measurement subject is judged based on the blood pressure information, the attribute information 83 and the pulse rate. At Step S413, the attribute information 83, the pulse waveform information 61, the blood pressure information and the health information 86 are displayed on the display. Thereby, the pulse wave measuring apparatus 102 can manage health for each attribute simply.

Figure 72:
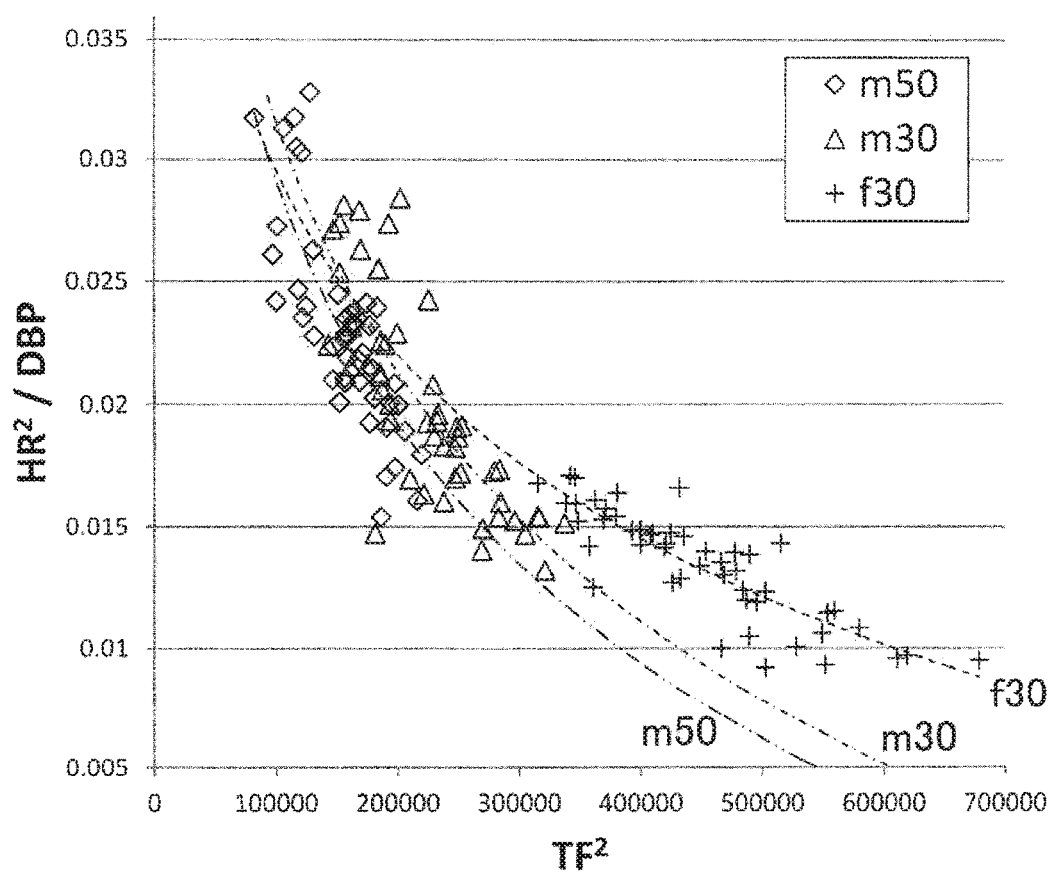
FIG. 72 shows a method of estimating the age of a measurement subject.

FIG. 72 shows a method of estimating diastolic blood pressure information based on the age of a measurement subject. m50 indicates a male in his fifties, m30 indicates a male in his thirties, and f30 indicates a female in her thirties. Each curve is a logarithmic approximation of each plot. The vertical axis indicates the ratio between the square of a pulse frequency HR (Hz) and diastolic blood pressure DBP [mmHg], and the horizontal axis indicates the square of the falling time DF (msec). An equation of estimating the diastolic blood pressure DBP can be derived from the plots. For example, because the approximation curves are different for each age, an equation of estimating the diastolic blood pressure DBP may be switched based on the age of a measurement subject. Similarly, the equation of estimating the diastolic blood pressure DBP may be switched based on the sex of a measurement subject. In this manner, by switching the equation of estimating the diastolic blood pressure DBP for each measurement subject, the accuracy of estimating the diastolic blood pressure DBP of the pulse wave measuring apparatus 102 improves.

Figure 73:
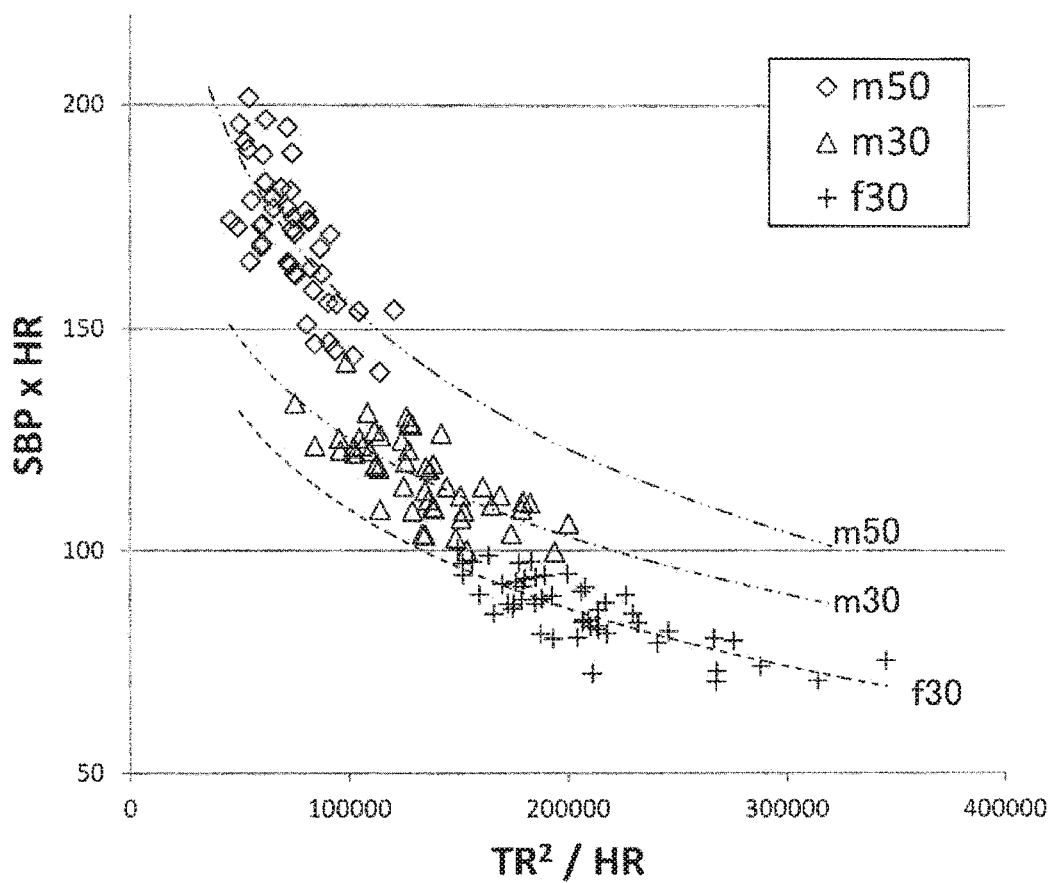
FIG. 73 shows a method of estimating the age of a measurement subject.

FIG. 73 shows a method of estimating systolic blood pressure information based on the age of a measurement subject. m50 indicates a male in his fifties, m30 indicates a male in his thirties, and f30 indicates a female in her thirties. Each curve in the figure is a logarithmic approximation of each plot. The vertical axis indicates the product of the pulse rate HR (Hz) and the systolic blood pressure SBP [mmHg], and the horizontal axis indicates the ratio between the square of the rising time TR (msec) and the pulse rate HR (Hz). An equation of estimating the systolic blood pressure SBP can be derived from the plots. For example, because the approximation curves are different for each age, the equation of estimating the systolic blood pressure may be switched based on the age of a measurement subject. Similarly, the estimation equation may be switched based on the sex of a measurement subject. In this manner, by switching the equation of estimating the systolic blood pressure SBP for each measurement subject, the accuracy of estimating the systolic blood pressure SBP of the pulse wave measuring apparatus 102 improves.

Embodiment 15

Figure 74:
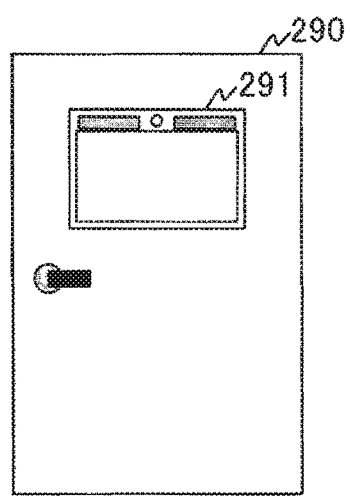
FIG. 74 shows one example of the pulse wave measuring apparatus 102 according to Embodiment 15.

FIG. 74 shows one example of the pulse wave measuring apparatus 102 according to Embodiment 15. The pulse wave measuring apparatus 102 according to the present example is implemented on a door 290. In a similar manner to that of the mobile information terminal 280 according to Embodiment 13, the door 290 can estimate blood pressure information, and display it on the display 291. Furthermore, by registering the user information 81 of users who are allowed to pass through the door 290 in advance, authentication of living bodies can be performed based on the user information 81. Also, the door 290 may record unlocking of a door lock and entering and leaving times of users.

Figure 75:
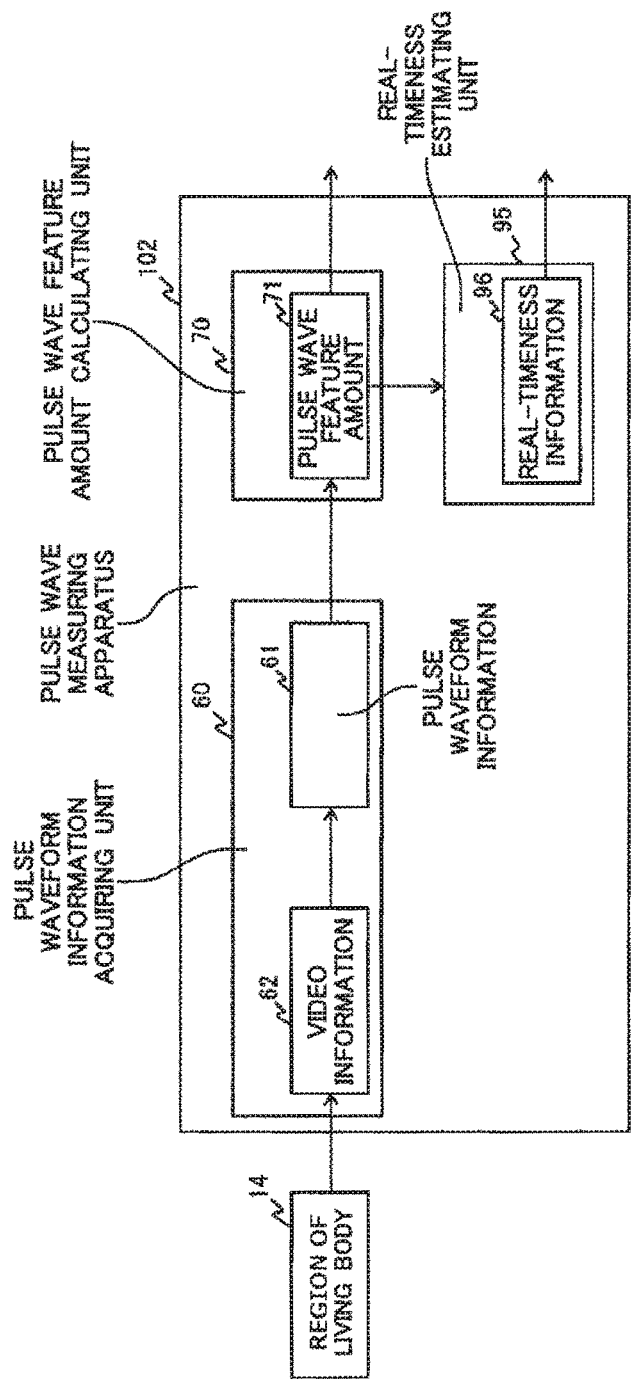
FIG. 75 shows one example of the configuration of the pulse wave measuring apparatus 102.

FIG. 75 shows one example of the configuration of the pulse wave measuring apparatus 102. The pulse wave measuring apparatus 102 according to the present example comprises a real-timeness estimating unit 95, in addition to the pulse waveform information acquiring unit 60 and the pulse wave feature amount calculating unit 70. The pulse wave measuring apparatus 102 can be utilized as a living body authentication system or a personal identification information acquiring unit that acquires personal identification information of a living body.

The real-timeness estimating unit 95 estimates real-timeness information 96 based on the pulse wave feature amount 71. For example, the real-timeness estimating unit 95 estimates that an imaged subject is a living body when the pulse wave feature amount 71 is within a predetermined range. Also, the real-timeness estimating unit 95 estimates that an imaged subject is not a living body when the pulse wave feature amount 71 is not within a predetermined range. Note that the real-timeness estimating unit 95 may estimate the real-timeness information 96 of a living body based on the health information 86, instead of the video information 62.

The real-timeness information 96 indicates whether or not the video information 62 acquired by the pulse waveform information acquiring unit 60 is not about a photograph or an image of a living body, but it has acquired information about the region 14 of a real living body. That is, the real-timeness information 96 is used as living body authentication information, viability information or activity information.

The pulse wave measuring apparatus 102 according to the present example performs living body authentication based on the real-timeness information 96. The pulse wave measuring apparatus 102 can construct a highly secure and convenient system by performing object recognition of a non-imaged object based on the calculated pulse wave feature amount 71 or the like. For example, the pulse wave measuring apparatus 102 that performs image authentication with the use of a camera is utilized for unlocking a door by identifying an individual, for unlocking an operation lock of a mobile device, for authenticating an account holder at an ATM or the like or for other uses. The pulse wave measuring apparatus 102 can remove necessity for forcing a user to blink, move his/her body in a direction of a screen display, or to do other operation which places a load on the user. Also, because the pulse wave measuring apparatus 102 according to the present example does not require input of a personal identification number or the like, authentication of the real-timeness information 96 can be completed without taking much time.

Embodiment 16

Figure 76:
FIG. 76 shows one example of the pulse wave measuring apparatus 102 according to Embodiment 16.

FIG. 76 shows one example of the pulse wave measuring apparatus 102 according to Embodiment 16. The pulse wave measuring apparatus 102 according to the present example is implemented on an intercom 295. In a similar manner to that in a case of Embodiment 13, the pulse wave measuring apparatus 102 can estimate blood pressure information and record unlocking of a door lock and entering and leaving times based on the user information 81. For example, the intercom 295 automatically unlocks a lock when the user information 81 of a measurement subject is pre-registered, and the lock is unlocked manually when the user information 81 of a measurement subject is not pre-registered.

Embodiment 17

Figure 77:
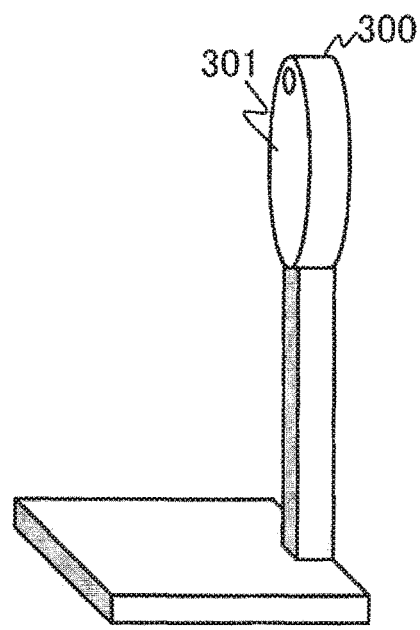
FIG. 77 shows one example of the pulse wave measuring apparatus 102 according to Embodiment 17.

FIG. 77 shows one example of the pulse wave measuring apparatus 102 according to Embodiment 17. The pulse wave measuring apparatus 102 according to the present example is implemented on a body composition meter 300. In a similar manner to that in the case of Embodiment 13, the pulse wave measuring apparatus 102 can estimate the blood pressure information, and display it on the display 301. The pulse wave measuring apparatus 102 may estimate the comprehensive health information 86 based on, in addition to the blood pressure information, a body weight and a body fat percentage measured simultaneously. The estimated health information 86 is displayed on the display 301.

Embodiment 18

Figure 78:
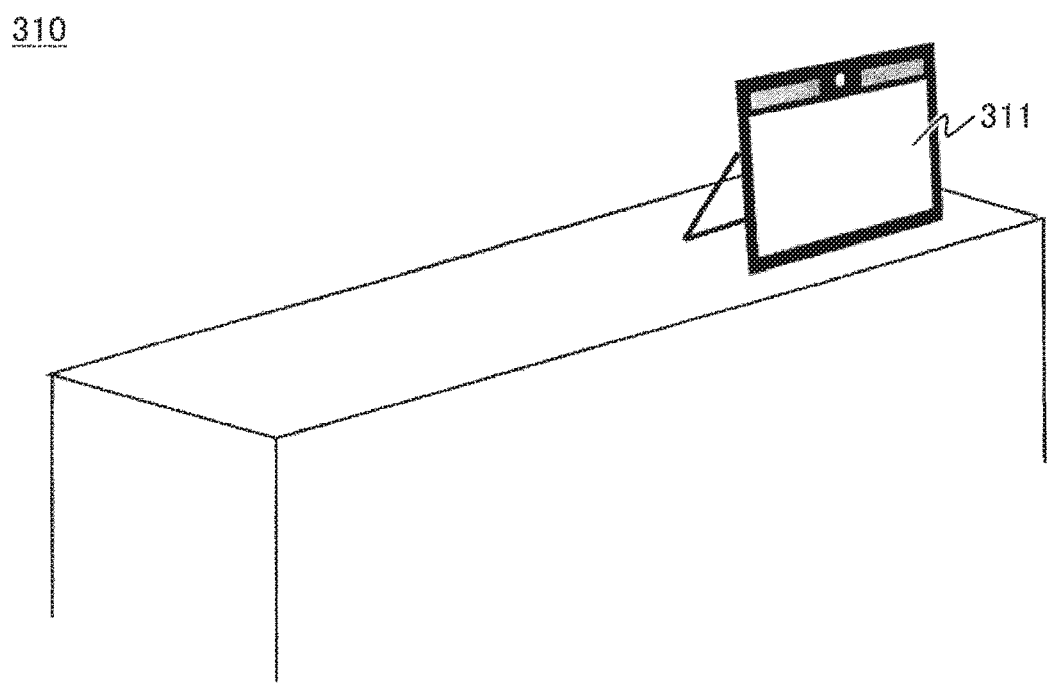
FIG. 78 shows one example of the pulse wave measuring apparatus 102 according to Embodiment 18.

FIG. 78 shows one example of the pulse wave measuring apparatus 102 according to Embodiment 18. The pulse wave measuring apparatus 102 according to the present example is implemented on a customer service counter 310. In a similar manner to that in the case of Embodiment 14, the pulse wave measuring apparatus 102 can estimate the blood pressure information, and display it on the display 311. Also, the pulse wave measuring apparatus 102 judges recommendation information about goods suitable for a customer based on the blood pressure information and the attribute information 83. The pulse wave measuring apparatus 102 proposes goods to a customer by displaying the judged recommendation information on the display 311. In this manner, the pulse wave measuring apparatus 102 can propose goods optimum for a customer simply by capturing the customer with the camera 63. Note that when a customer is a member, the recommendation information may be judged based further on the user information 81.

Embodiment 19

Figure 79:
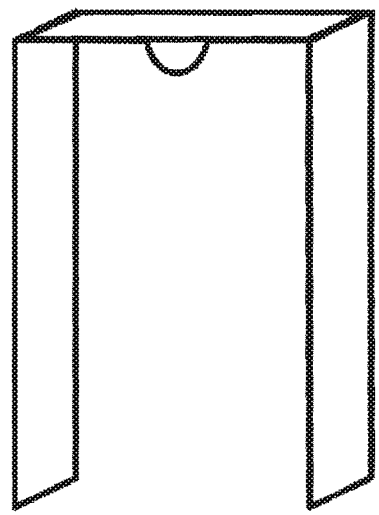
FIG. 79 shows one example of the pulse wave measuring apparatus 102 according to Embodiment 19.

FIG. 79 shows one example of the pulse wave measuring apparatus 102 according to Embodiment 19. The pulse wave measuring apparatus 102 according to the present example is implemented on an entrance gate 320. In a similar manner to that in Embodiment 14, the pulse wave measuring apparatus 102 can judge the health information 86 based on the video information 62 acquired with the camera 63. The pulse wave measuring apparatus 102 controls opening and closing of the entrance gate 320 based on the health information 86 to limit entrance.

Embodiment 20

Figure 80:
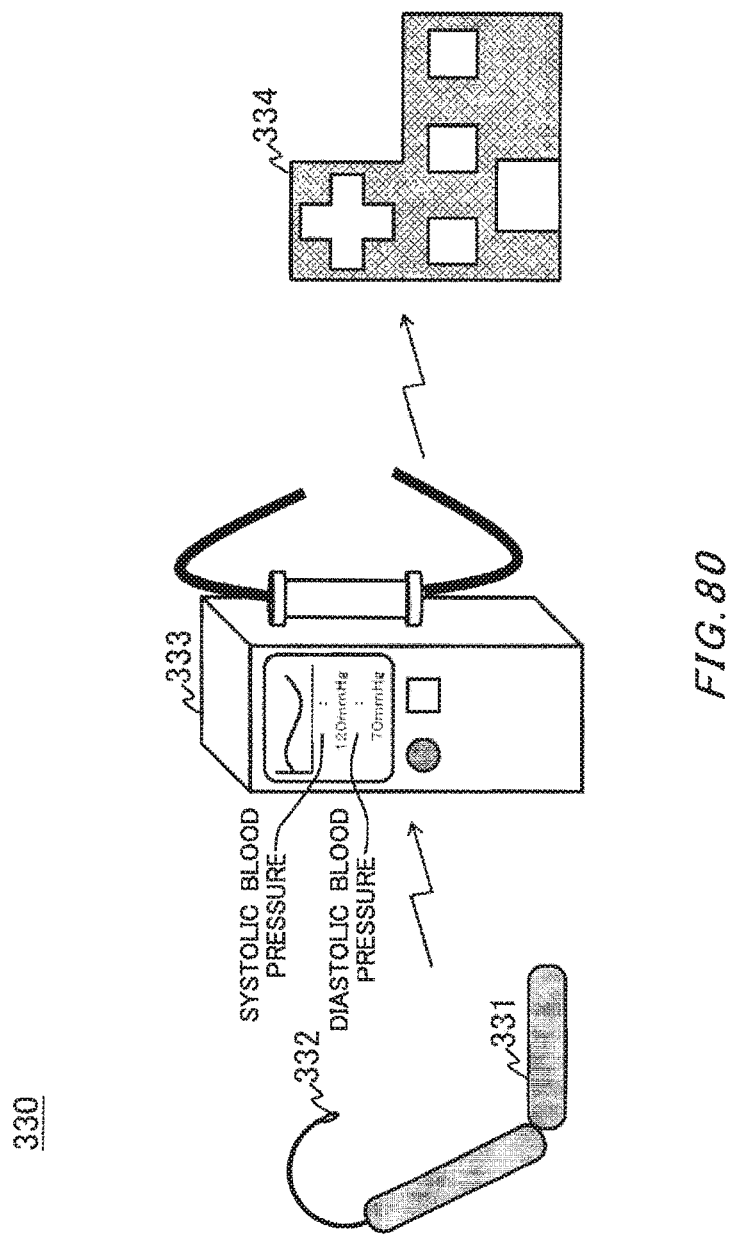
FIG. 80 shows one example of the pulse wave measuring apparatus 102 according to Embodiment 20.

FIG. 80 shows one example of the pulse wave measuring apparatus 102 according to Embodiment 20. The pulse wave measuring apparatus 102 according to the present example is provided to a dialysis system 330.

A recliner 331 on which a patient undergoing dialysis sits comprises a camera 332 that acquires video information at 30 fps. The video information at 30 fps is transmitted to a dialysis apparatus main body 333 by BlueTooth (registered trademark) or the like. Note that communication between the recliner 331 and the dialysis apparatus main body 333 may be wired or wireless communication, and may be performed through a known system.

The dialysis apparatus main body 333 calculates the health information 86 based on the video information acquired by the camera 332. Also, the dialysis apparatus main body 333 controls a dialysis flow rate in real-time based on the calculated health information 86. The calculated health information 86 may be displayed on a display.

Figure 81:
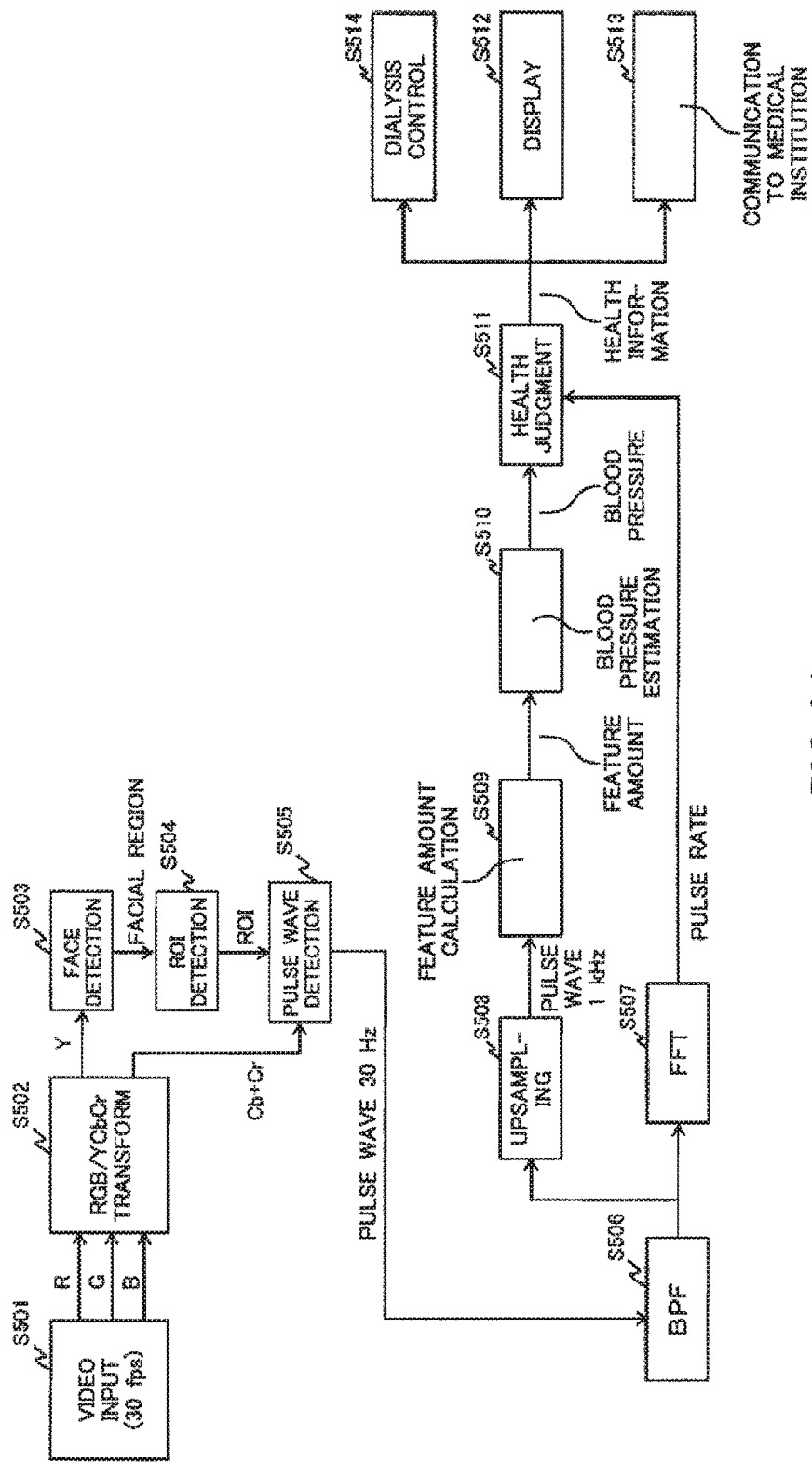
FIG. 81 shows one example of signal processing by the pulse wave measuring apparatus 102.

FIG. 81 shows one example of signal processing by the pulse wave measuring apparatus 102 according to Embodiment 20. The pulse wave measuring apparatus 102 according to the present example executes Step S501 to Step S515.

Step S501 to Step S511 are basically similar to Step S301 to Step S412 and Step S401 to Step S412. However, the pulse wave measuring apparatus 102 according to the present example does not execute the personal identification at Step S305 and the attribute judgment at Step S405. For this reason, at Step S510, the blood pressure information is estimated based only on the pulse wave feature amount 71. Also, at Step S511, the health information 86 of a patient undergoing dialysis is judged based on the blood pressure information and the pulse rate.

At Step S512, a graph indicating pulse rates, blood pressure information, and transition of the blood pressure information is displayed on a display. At Step S513, the blood pressure information is transmitted to the medical institution 334 which is connected by a network. Thereby, the blood pressure information of a patient undergoing dialysis can be informed to a remotely-located medical worker. The medical institution 334 may be connected to a data management system.

At Step S514, the dialysis apparatus is controlled based on the blood pressure information. For example, the blood pressure of a patient may drop rapidly during dialysis. However, a blood pressure measuring apparatus with a cuff places a burden on a patient due to compression of blood vessels, and cannot monitor variation in blood pressure continuously. The dialysis system 330 according to the present example does not compress blood vessels during dialysis, and is non-invasive, so the burden on a patient is small. For this reason, the pulse wave measuring apparatus 102 according to the present example can monitor variation in blood pressure of a patient continuously. Thereby, the dialysis system 330 according to the present example can control a dialysis flow rate in real-time so as to reduce a load on a patient undergoing dialysis.

The dialysis system 330 according to the present example may transmit the health information 86 or an alarm to a data management system at the medical institution 334 when the health information 86 is not within a predetermined range. On the other hand, when the health information 86 is within a predetermined range, the health information 86 or an alarm may not be transmitted to the data management system at the medical institution 334. The data management system at the medical institution 334 outputs the alarm upon receiving the health information 86 or the alarm. Note that in the present embodiment, the dialysis system 330 is shown as an example. However, the pulse wave measuring apparatus 102 may monitor variation in blood pressure of a patient non-invasively and continuously similarly in a defibrillator, a drip infusion apparatus, a blood transfusion apparatus, a blood collecting apparatus and an artificial respirator.

Embodiment 21

Figure 82:
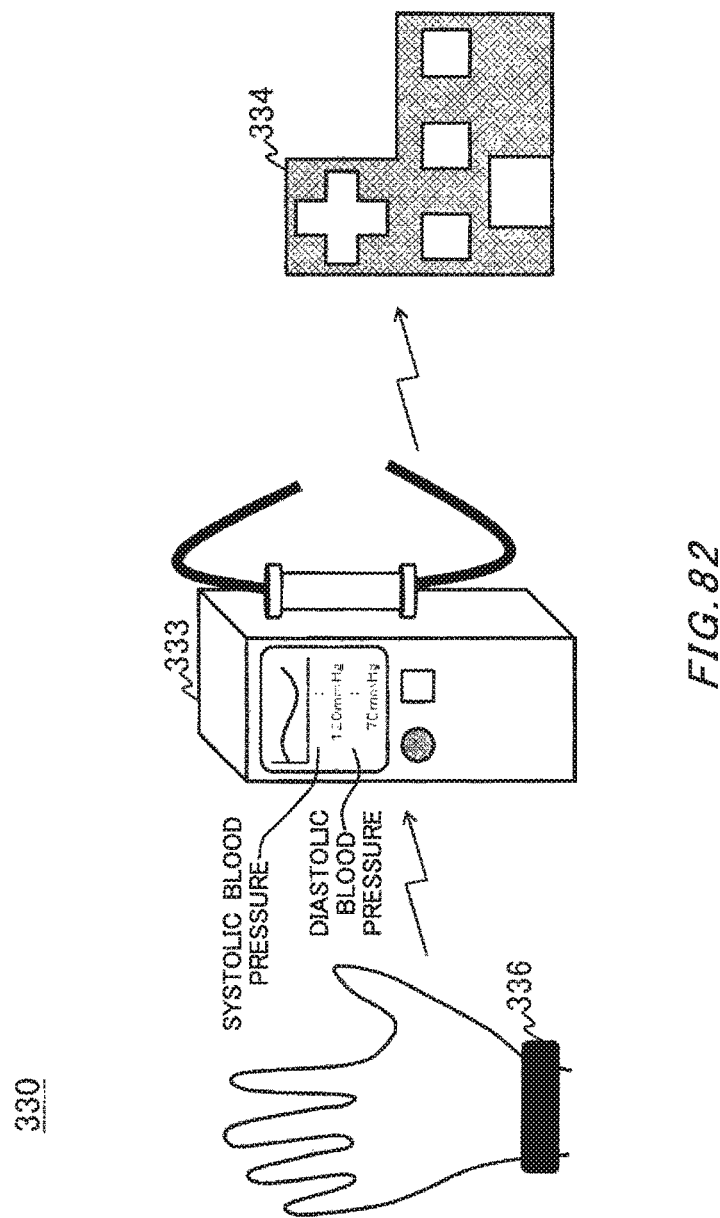
FIG. 82 shows one example of the pulse wave measuring apparatus 102 according to Embodiment 21.

FIG. 82 shows one example of the pulse wave measuring apparatus 102 according to Embodiment 21. The pulse wave measuring apparatus 102 according to the present example is provided to the dialysis system 330. A pulse wave trace signal at 30 Hz acquired by the light-emitting unit and the light receiving unit provided to a wrist band 336 worn on a wrist of the patient undergoing dialysis is transmitted, by BlueTooth (registered trademark), and input to the dialysis apparatus main body 333. The dialysis apparatus main body 333 and the medical institution 334 may function in a similar manner to those in Embodiment 20.

Figure 83:
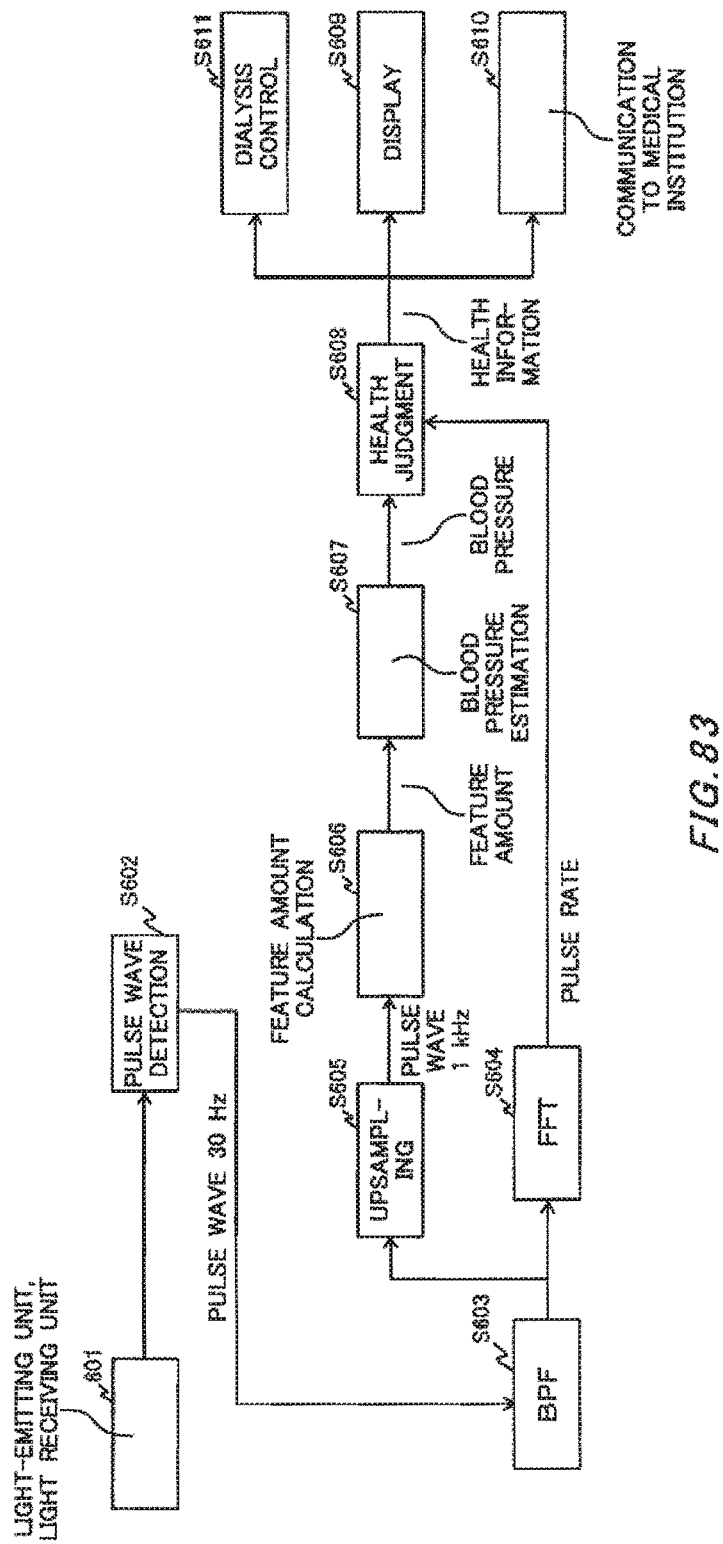
FIG. 83 shows one example of signal processing by the pulse wave measuring apparatus 102.

FIG. 83 shows one example of signal processing by the pulse wave measuring apparatus 102 according to Embodiment 21. The pulse wave measuring apparatus 102 according to the present example executes Step S601 to Step S611.

At Step S601, light emitted by the light-emitting unit provided to the wrist band 336 is received by the light receiving unit. Thereby, the wrist band 336 can detect a pulse wave at 30 Hz (Step S602). In Step S603 to Step S611, steps that are basically similar to Step S506 to Step S514 are executed. The dialysis system 330 according to the present example can monitor transitions in the blood pressure of a patient undergoing dialysis at any time with a simple configuration of wrapping the wrist band 336 around a wrist of the patient undergoing dialysis.

Embodiment 22

Figure 84:
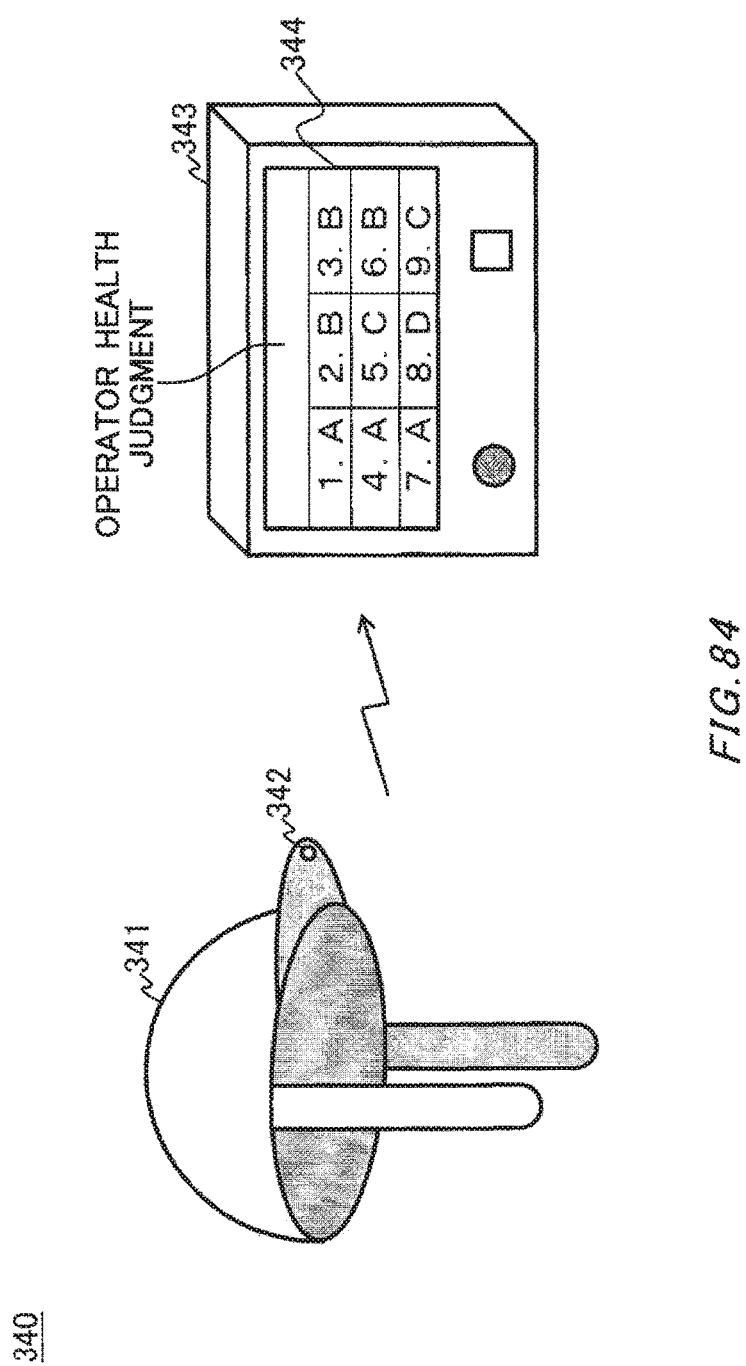
FIG. 84 shows one example of the pulse wave measuring apparatus 102 according to Embodiment 22.

FIG. 84 shows one example of the pulse wave measuring apparatus 102 according to Embodiment 22. The pulse wave measuring apparatus 102 according to the present example is provided to an operator management system 340. The operator management system 340 is configured with a helmet 341 and a management computer 343. The operator management system 340 manages health information of a worker at a construction site or the like.

Video information at 30 fps acquired by a camera 342 provided to the helmet 341 worn by a measurement subject is transmitted to the management computer 343 by BlueTooth (registered trademark). The management computer 343 judges the health information 86 of the measurement subject by using the video information 62. The judged health information 86 is displayed on a display 344. Note that when a plurality of measurement subjects are respectively wearing the helmets 341, the management computer 343 may display, on the display 344 collectively, the health information 86 of the plurality of measurement subjects.

Embodiment 23

Figure 85:
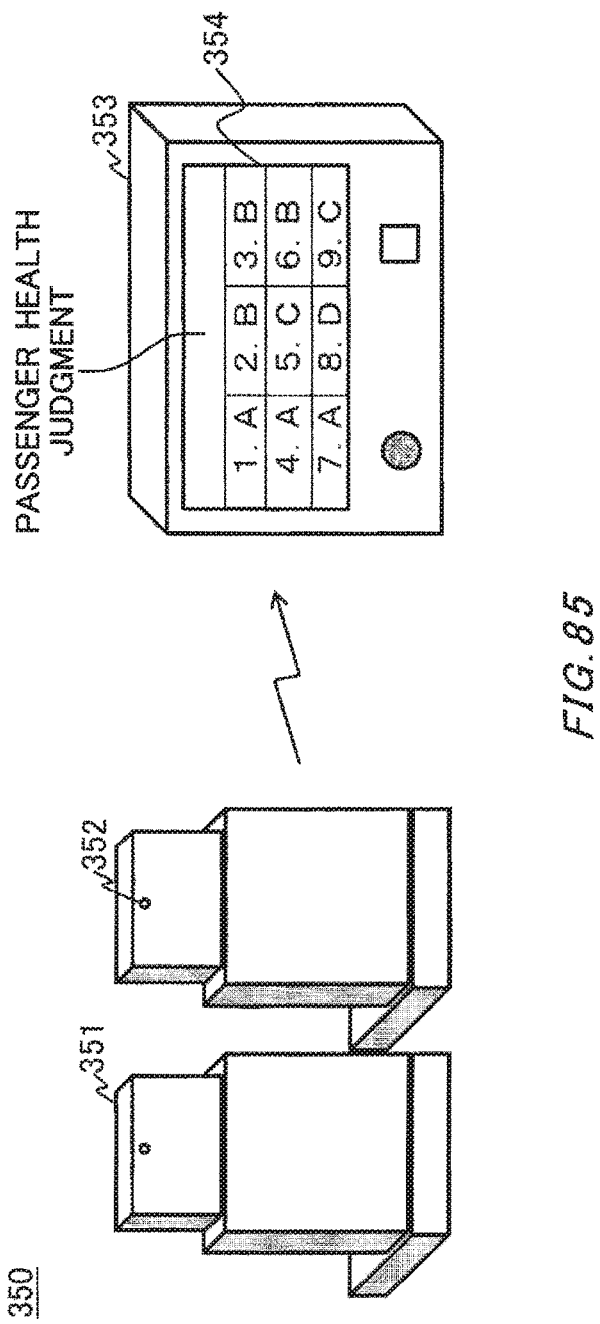
FIG. 85 shows one example of the pulse wave measuring apparatus 102 according to Embodiment 23.

FIG. 85 shows one example of the pulse wave measuring apparatus 102 according to Embodiment 23. The pulse wave measuring apparatus 102 according to the present example is provided to a passenger management system 350. The passenger management system 350 comprises a seat 351 and a management computer 353.

Video information at 30 fps acquired by a camera 352 provided to a head rest of the seat 351 in front of a measurement subject is transmitted and input to the management computer 353 by BlueTooth (registered trademark). The management computer 353 judges the health information 86 of the measurement subject by using the video information 62. The judged health information 86 is displayed on a display 354. Note that when a plurality of measurement subjects are respectively seated on the seats 351, the management computer 353 may display, on the display 354 collectively, the health information 86 of the plurality of measurement subjects.

Embodiment 24

Figure 86:
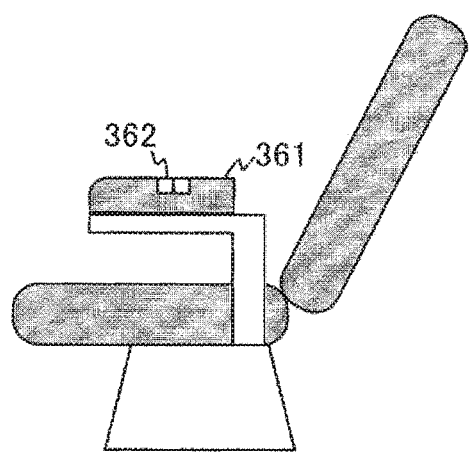
FIG. 86 shows one example of the pulse wave measuring apparatus 102 according to Embodiment 24.

FIG. 86 shows one example of the pulse wave measuring apparatus 102 according to Embodiment 24. The pulse wave measuring apparatus 102 according to the present example is implemented on a massage chair 360.

The massage chair 360 comprises an arm rest 361 having a light-emitting unit and a light receiving unit 362. The light-emitting unit and the light receiving unit 362 acquire a pulse wave trace signal from a skin surface of a forearm of a measurement subject. The massage chair 360 judges the health information 86 by using the pulse wave trace signal. The massage chair 360 can adjust the load of massage based on the health information 86. Although an example of the massage chair 360 is shown here, by providing the pulse wave measuring apparatus 102 according to the present invention to a reclining bed, for example, its reclining angle can be manipulated based on the health information 86.

As explained above, the pulse wave measuring apparatus 102 estimates highly accurately a blood pressure by a non-invasive method which does not compress blood vessels of a living body. For this reason, by implementing the pulse wave measuring apparatus 102 on various tools, apparatuses and the like utilized by humans, pulse waves of humans can be measured in a natural form.

Figure 87:
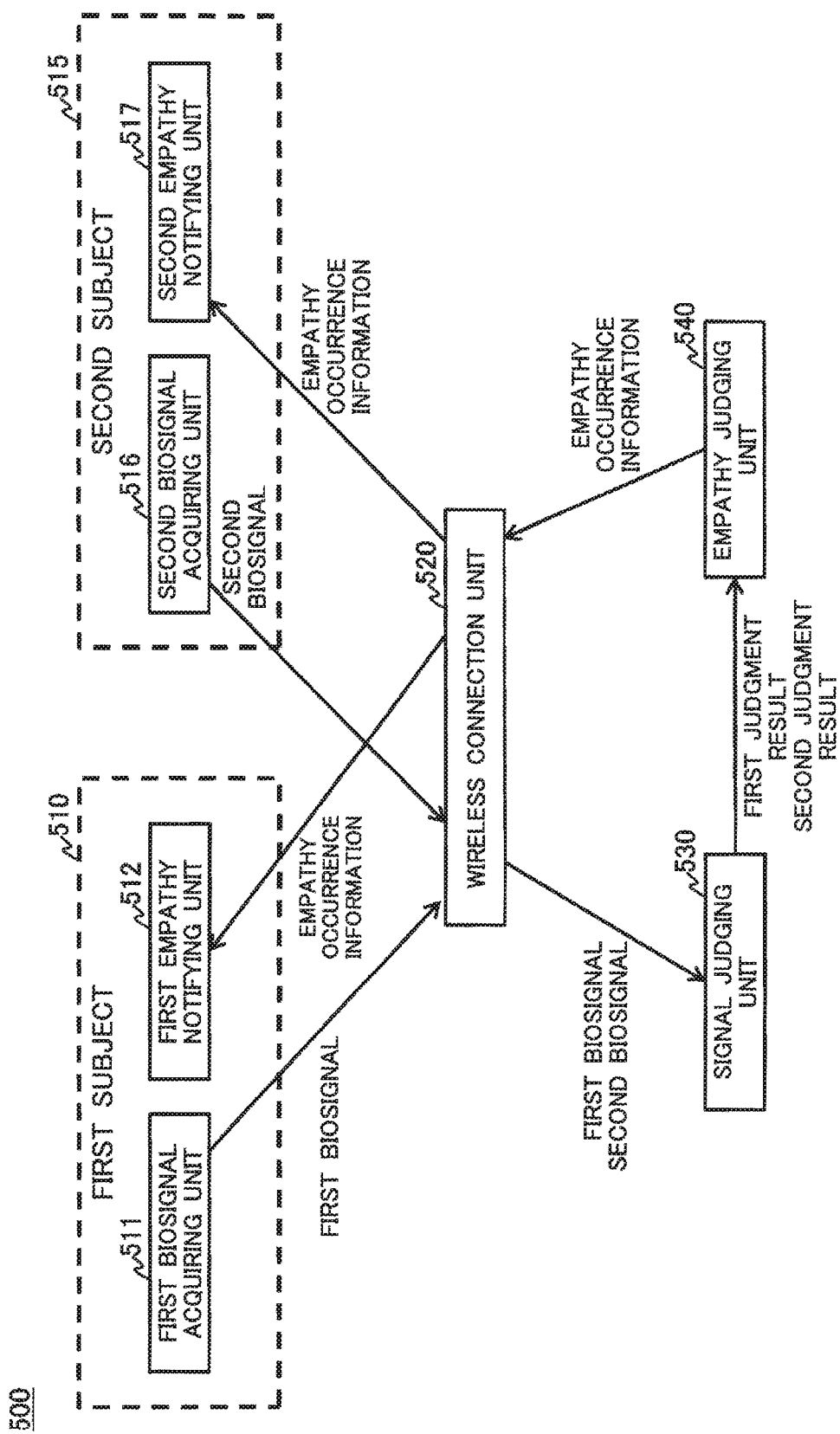
FIG. 87 shows one example of the configuration of an empathy detection system 500.

FIG. 87 shows one example of the configuration of an empathy detection system 500. The empathy detection system 500 according to the present example comprises a first biometric sensor 510, a second biometric sensor 515, a wireless connection unit 520, a signal judging unit 530 and an empathy judging unit 540. Each of the biometric sensors is worn by each of two or more subjects. In the present example, the first biometric sensor 510 is worn by a first subject, and the second biometric sensor 515 is worn by a second subject. The signal judging unit 530 and the empathy judging unit 540 may be installed in a server linked by a network with a first biosignal acquiring unit 511 and a second biosignal acquiring unit 516.

The empathy detection system 500 causes the first biometric sensor 510 and the second biometric sensor 515 to cooperate with each other, and judges whether or not each biometric sensor has output a significant signal simultaneously or in a certain length of time. Thereby, the empathy detection system 500 detects empathy among a plurality of subjects.

The first biometric sensor 510 comprises a first biosignal acquiring unit 511 and a first empathy notifying unit 512. The first biosignal acquiring unit 511 acquires a first biosignal from a region 14 of a living body. For example, the first biosignal is the pulse waveform information 61 of the first subject. The pulse waveform information 61 may be acquired from the video information 62 or acquired by measurement of skin conductivity.

The second biometric sensor 515 comprises a second biosignal acquiring unit 516 and a second empathy notifying unit 517. The second biosignal acquiring unit 516 acquires a second biosignal from a region 14 of a living body. For example, the second biosignal is the pulse waveform information 61 of the second subject. Although the second biosignal according to the present example is measured by a measurement method similar to that for the first biosignal, it may be measured by a measurement method different from that for the first biosignal.

The wireless connection unit 520 performs wireless communication of a signal between the first biometric sensor 510 and the second biometric sensor 515. Also, the wireless connection unit 520 is connected to the first biosignal acquiring unit 511 and the second biosignal acquiring unit 516. The wireless connection unit 520 receives an input of the first biosignal acquired by the first biosignal acquiring unit 511 and the second biosignal acquired by the second biosignal acquiring unit 516. The wireless connection unit 520 transmits the first biosignal and the second biosignal to the signal judging unit 530.

The signal judging unit 530 judges whether or not the first biosignal and the second biosignal are significant signals, and obtains a first judgment result and a second judgment result. For example, a significant signal refers to a signal which is not caused by a noise. Also, a significant signal refers to a signal that is generated by a change in the emotion of a subject. The signal judging unit 530 transmits the first judgment result and the second judgment result to the empathy judging unit 540.

Based on the first judgment result and the second judgment result, the empathy judging unit 540 judges whether or not empathy has occurred between the first subject and the second subject. Specifically, by judging whether or not two or more of the first judgment result and the second judgment result have occurred within a predetermined period, the empathy judging unit 540 judges whether or not empathy has occurred. For example, that two or more have occurred in a predetermined period means that a significant signal occurs from the second biosignal acquiring unit 516 while a significant signal keeps occurring from the first biosignal acquiring unit 511. The empathy judging unit 540 transmits the judged empathy occurrence information to the wireless connection unit 520. The wireless connection unit 520 transmits the empathy occurrence information to the first empathy notifying unit 512 and the second empathy notifying unit 517.

The first empathy notifying unit 512 transmits the empathy occurrence information to the first subject, and the second empathy notifying unit 517 notifies the second subject about the empathy occurrence information. For example, the empathy detection system 500 determines that empathy of subjects has not occurred when any of the biometric sensors of the first biometric sensor 510 and the second biometric sensor 515 sensed a insignificant signal. Also, the empathy detection system 500 detects empathy among a plurality of subjects when significant signals of a plurality of subjects are sensed simultaneously. When a plurality of subjects are wearing biometric sensors, empathy of all the subjects may be notified, or only empathy of subjects who felt empathy may be notified.

Figure 88:
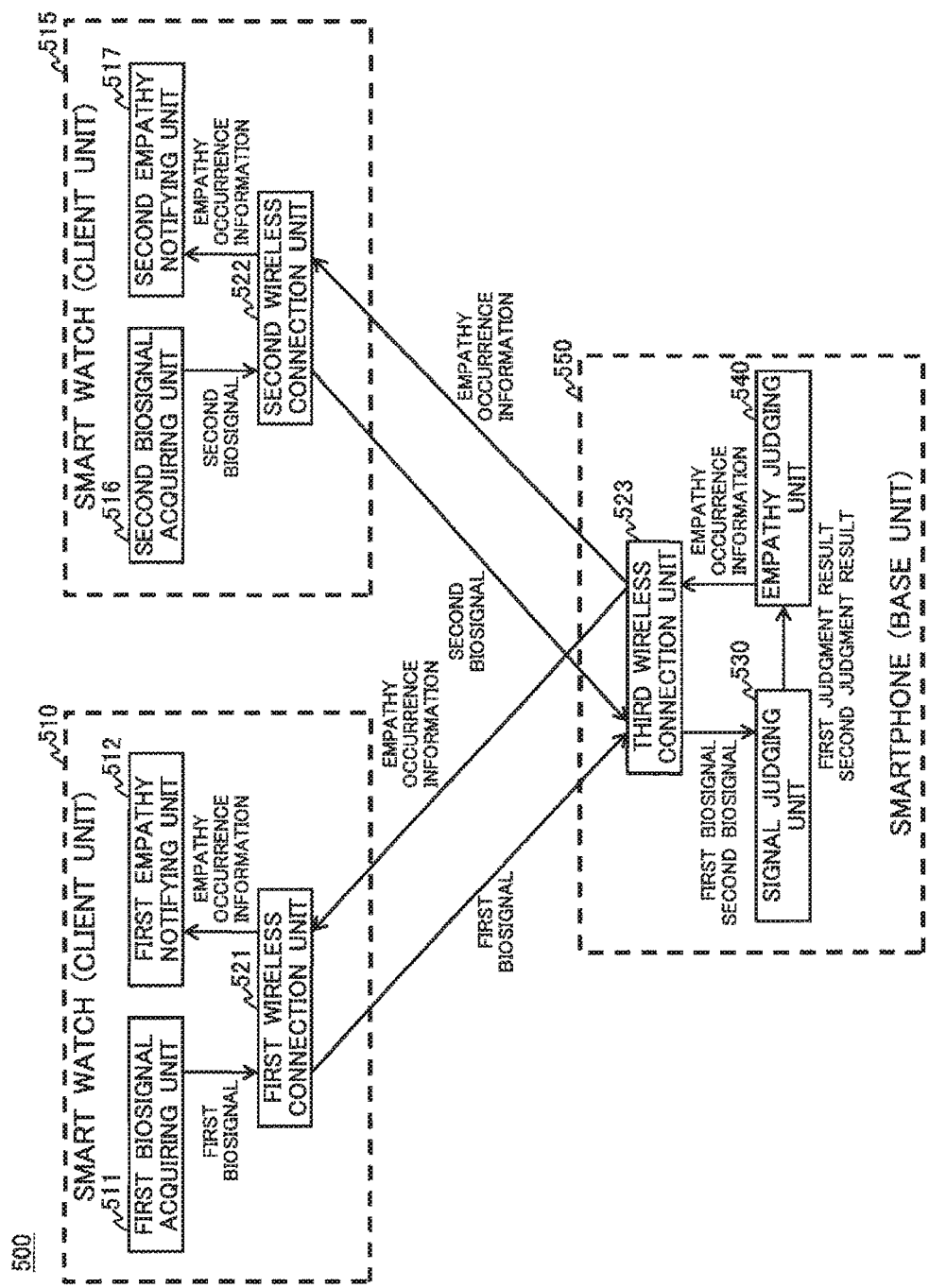
FIG. 88 shows one example of the configuration of the empathy detection system 500.

FIG. 88 shows one example of the configuration of the empathy detection system 500. The empathy detection system 500 according to the present example comprises the first biometric sensor 510, the second biometric sensor 515 and a sensor with analysis functions 550. For example, the first biometric sensor 510 and the second biometric sensor 515 are smart watches (client units) and the sensor with analysis functions 550 is a smartphone (base unit). The respective smart watches and smartphone comprise wireless connection units. Also, the same configuration as that of the empathy detection system 500 shown in FIG. 87 operates in a similar manner to that in the example of FIG. 87.

The first biometric sensor 510 comprises the first biosignal acquiring unit 511, the first empathy notifying unit 512 and the first wireless connection unit 521. The first wireless connection unit 521 transmits, to the sensor with analysis functions 550, a first biosignal acquired by the first biosignal acquiring unit 511. The first wireless connection unit 521 according to the present example performs communication by Bluetooth (registered trademark), but may perform Internet communication by Wi-Fi (registered trademark).

The second biometric sensor 515 comprises the second biosignal acquiring unit 516, the second empathy notifying unit 517 and the second wireless connection unit 522. The second wireless connection unit 522 transmits, to the sensor with analysis functions 550, a second biosignal acquired by the second biosignal acquiring unit 516. The second wireless connection unit 522 according to the present example performs communication by Bluetooth (registered trademark), but may perform Internet communication by Wi-Fi (registered trademark).

The sensor with analysis functions 550 comprises a third wireless connection unit 523, the signal judging unit 530 and the empathy judging unit 540. The third wireless connection unit 523 receives the first biosignal and the second biosignal, and transmits them to the signal judging unit 530. Also, the third wireless connection unit 523 receives the empathy occurrence information judged by the empathy judging unit 540, and transmits it to the first wireless connection unit 521 and the second wireless connection unit 522.

Because the first biometric sensor 510 and the second biometric sensor 515 according to the present example respectively comprise the wireless connection units, the smartphones and the smart watch can communicate with each other. For this reason, the empathy detection system 500 according to the present example can be used for a wide range of applications.

Figure 89:
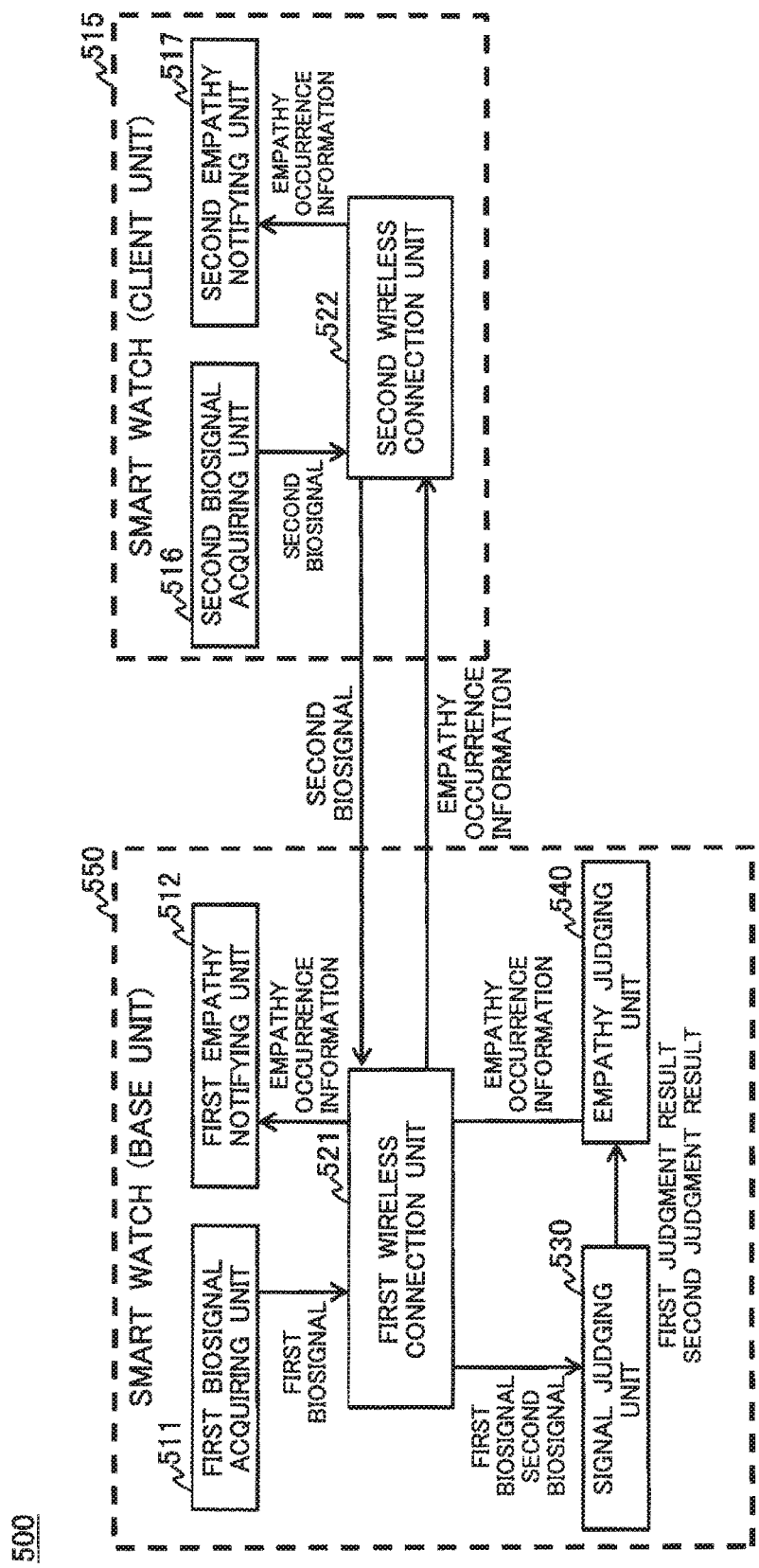
FIG. 89 shows one example of the configuration of the empathy detection system 500.

FIG. 89 shows one example of the configuration of the empathy detection system 500. The empathy detection system 500 according to the present example is configured with the sensor with analysis functions 550 and the second biometric sensor 515. The sensor with analysis functions 550 is a base unit of a smart watch, and the second biometric sensor 515 is a smart watch client unit.

The sensor with analysis functions 550 comprises the first biosignal acquiring unit 511, the first empathy notifying unit 512, the first wireless connection unit 521, the signal judging unit 530 and the empathy judging unit 540. Thereby, the sensor with analysis functions 550 can execute all of acquisition of a biosignal, judgement, empathy judgement and empathy notification. The configuration shown in the example of FIG. 87 operates in a similar manner to that in FIG. 87.

The sensor with analysis functions 550 according to the present example is implemented on a smart watch. For this reason, the empathy detection system 500 according to the present example can notify empathy information to a user only with a smart watch without using a smartphone.

Figure 90:
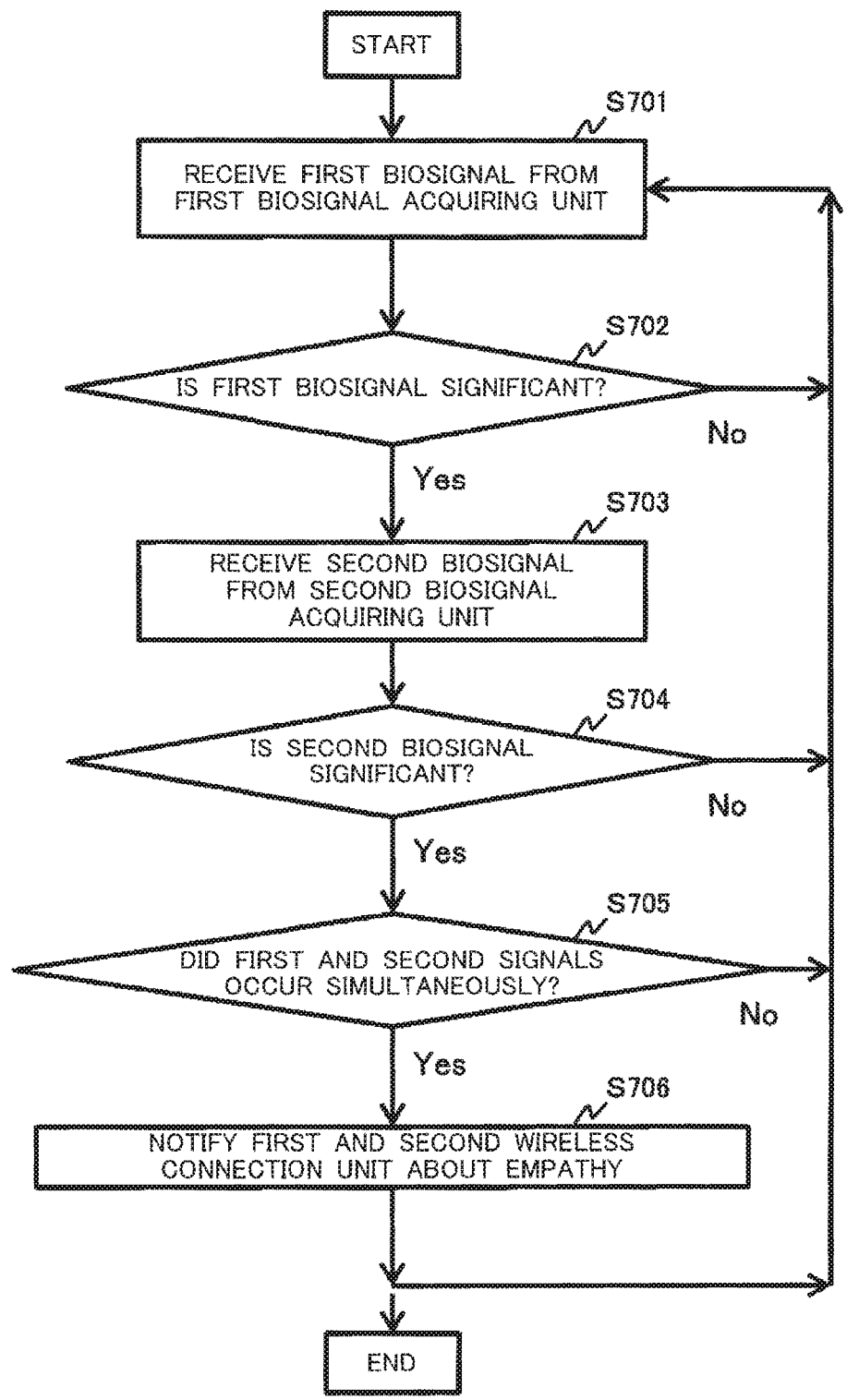
FIG. 90 shows one example of operation of the empathy detection system 500.

FIG. 90 shows one example of operation of the empathy detection system 500. The empathy judging unit 540 judges empathy by executing Step S701 to Step S706.

At Step S701, the signal judging unit 530 receives the first biosignal acquired by the first biosignal acquiring unit 511. At Step S702, the signal judging unit 530 judges whether or not the first biosignal is a significant signal. When the signal judging unit 530 judges that the first biosignal is a significant signal, the process proceeds to Step S703. On the other hand, when the signal judging unit 530 judges that the first biosignal is not a significant signal, the process returns to Step S701.

At Step S703, the signal judging unit 530 receives the second biosignal of the second biosignal acquiring unit 516. At Step S704, the signal judging unit 530 judges whether or not the second biosignal is a significant signal. When the signal judging unit 530 judges that the second biosignal is a significant signal, the process proceeds to Step S705. On the other hand, when the signal judging unit 530 judges that the second biosignal is not a significant signal, the process returns to Step S701.

At Step S705, the empathy judging unit 540 judges whether or not the first biosignal and the second biosignal have occurred simultaneously. When the empathy judging unit 540 has judged that occurrence of the first biosignal and occurrence of the second biosignal are simultaneous, the process proceeds to Step S706. On the other hand, when the empathy judging unit 540 has judged that occurrence of the first biosignal and occurrence of the second biosignal are not simultaneous, the process returns to Step S701. At Step S706, the first wireless connection unit 521 and the second wireless connection unit 522 are notified about the empathy occurrence information. Basically, after Step S706 is ended, the process returns to Step S701, and Step S701 to Step S706 are repeated. However, when it became unnecessary to cause the empathy detection system 500 to operate, the process may be ended at any timing.

Figure 91:
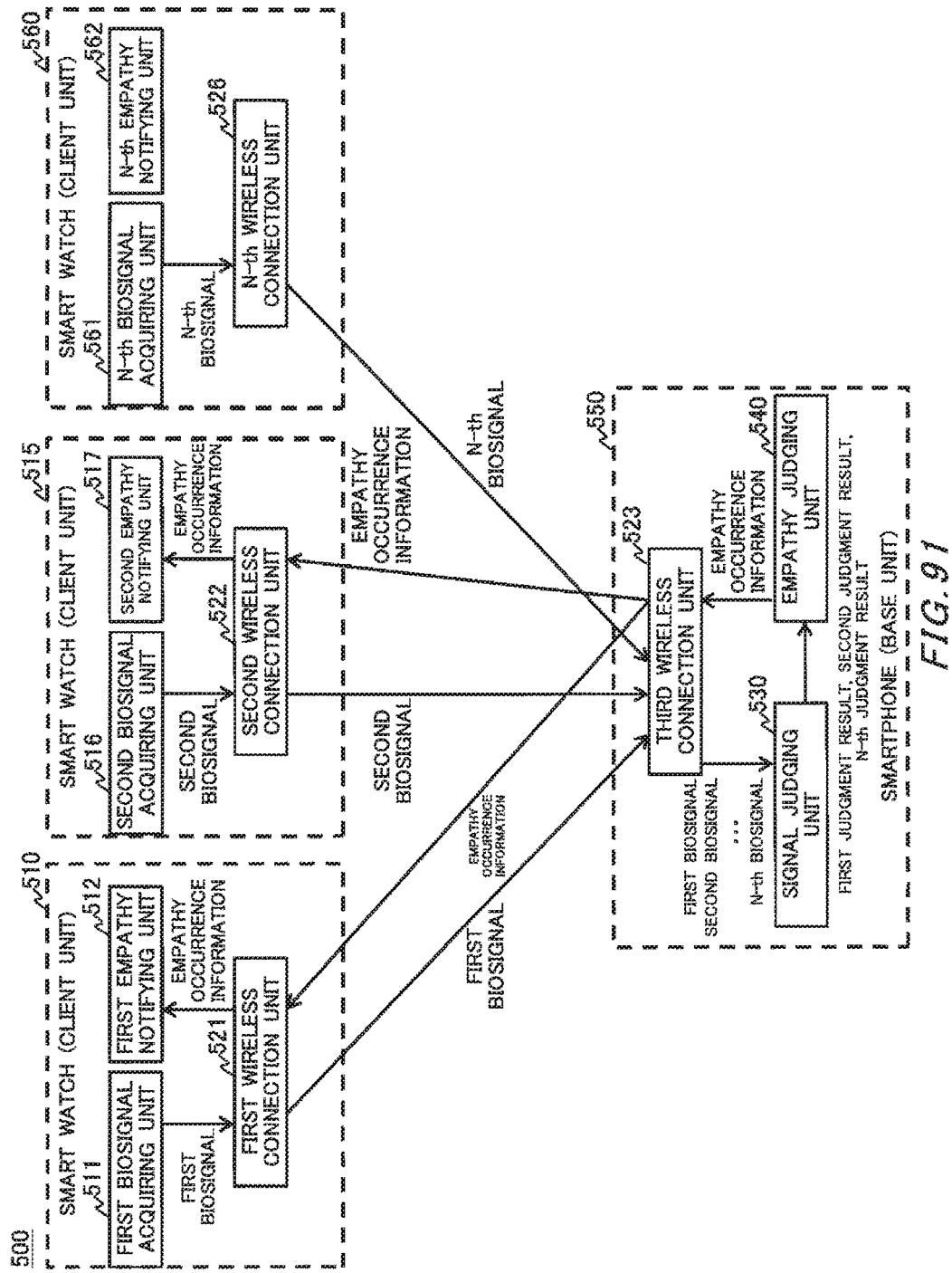
FIG. 91 shows one example of the configuration of the empathy detection system 500.

FIG. 91 shows one example of the configuration of the empathy detection system 500. The empathy detection system 500 according to the present example further comprises an N-th biometric sensor 560, in addition to the configuration shown in FIG. 88.

The N-th biometric sensor 560 comprises an N-th biosignal acquiring unit 561, an N-th empathy notifying unit 562 and an N-th wireless connection unit 526 The N-th biosignal acquiring unit 561 acquires an N-th biosignal. The N-th wireless connection unit 526 transmits the N-th biosignal to the third wireless connection unit 523.

The third wireless connection unit 523 transmits the first to N-th biosignals to the signal judging unit 530. The signal judging unit 530 transmits, to the empathy judging unit 540, the first to N-th judgment results obtained by judging whether or not the first to N-th biosignals are significant. The empathy judging unit 540 judges presence and absence of empathy based on the first to N-th judgment results and generates empathy occurrence information.

For example, when the first subject wearing the first biometric sensor 510 and the second subject wearing the second biometric sensor 515 are feeling empathy, and the N-th subject wearing the N-th biometric sensor 560 is not feeling empathy, the third wireless connection unit 523 transmits empathy occurrence information to the first wireless connection unit 521 and the second wireless connection unit 522, and on the contrary, does not transmit empathy occurrence information to the N-th wireless connection unit 526. In this manner, because the empathy detection system 500 according to the present example can notify only subjects who are feeling empathy about empathy occurrence information, it can let people who are feeling empathy know the empathy occurrence information without letting subjects who are not feeling empathy know it. Note that the empathy judging unit 540 may be provided to each of the first biometric sensor 510, the second biometric sensor 515 and the N-th biometric sensor 560.

Figure 92:
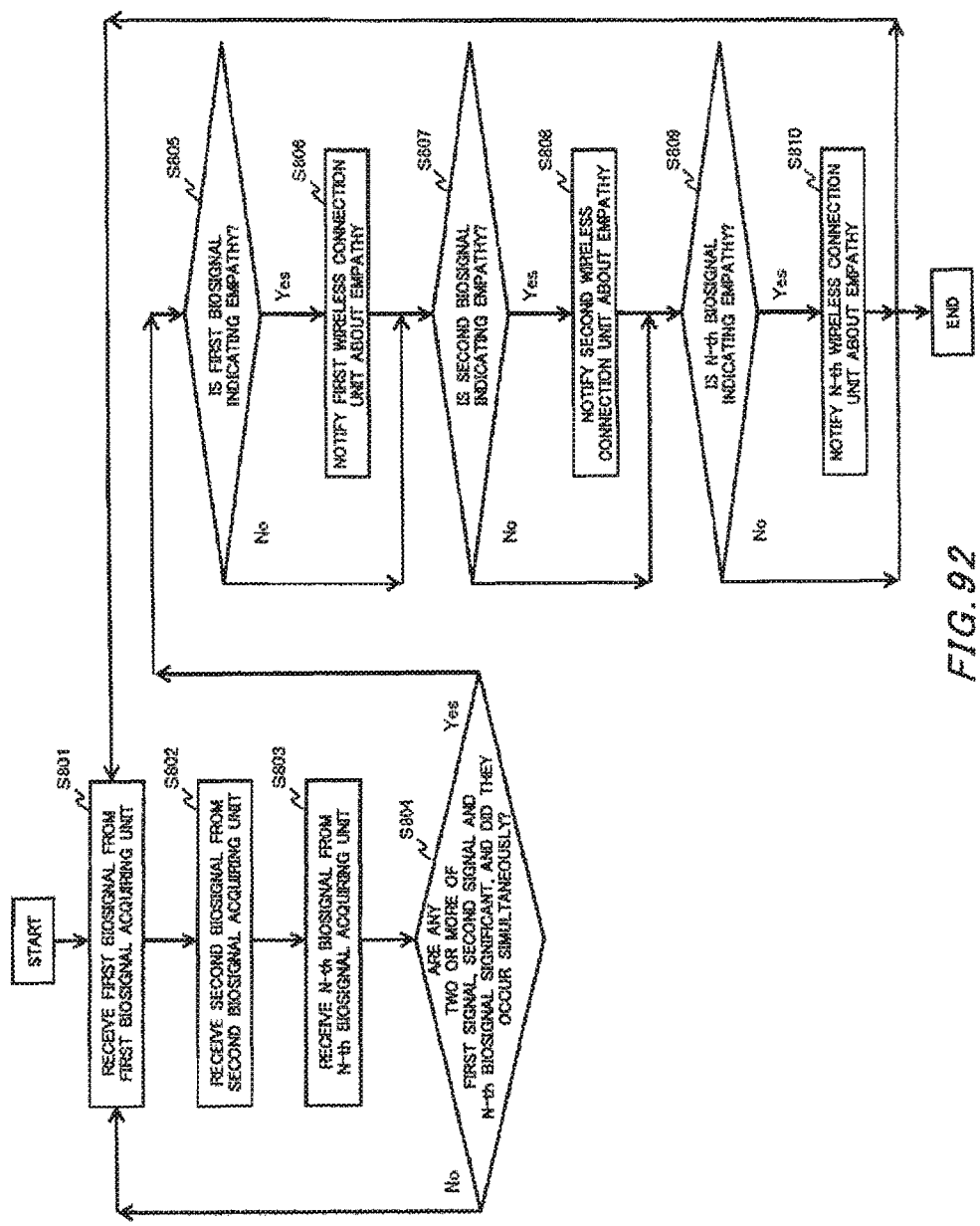
FIG. 92 shows one example of operation of the empathy detection system 500.

FIG. 92 shows one example of operation of the empathy detection system 500. The empathy detection system 500 executes Step S801 to Step S810.

At Step S801 the third wireless connection unit 523 receives a first biosignal from the first biosignal acquiring unit 511. At Step S802, the third wireless connection unit 523 receives a second biosignal from the second biosignal acquiring unit 516. At Step S803, the third wireless connection unit 523 receives an N-th biosignal from the N-th biosignal acquiring unit 561.

At Step S804, the signal judging unit 530 judges a significant signal among the first to the N-th signals, and calculates first to N-th judgment results. Also, the empathy judging unit 540 judges whether or not there are two or more signals which are significant and have occurred simultaneously based on the first to N-th judgment results.

At Step S805, the empathy judging unit 540 judges whether or not the first biosignal is a signal indicating empathy. When the first biosignal is a signal indicating empathy, the process proceeds to Step S806. On the other hand, when the first biosignal is not a signal indicating empathy, the process proceeds to Step S807. At Step S806, the third wireless connection unit 523 notifies the first wireless connection unit 521 about empathy occurrence information.

At Step S807, the empathy judging unit 540 judges whether or not the second biosignal is a signal indicating empathy. When the second biosignal is a signal indicating empathy, the process proceeds to Step S808. On the other hand, when the second biosignal is not a signal indicating empathy, the process proceeds to Step S809. At Step S808, the third wireless connection unit 523 notifies the second wireless connection unit 522 about empathy occurrence information.

At Step S809, the empathy judging unit 540 judges whether or not the N-th biosignal is a signal indicating empathy. When the N-th biosignal is a signal indicating empathy, the process proceeds to Step S810. On the other hand, when the N-th biosignal is not a signal indicating empathy, the process returns to Step S801. At Step S810, the third wireless connection unit 523 notifies the N-th wireless connection unit 526 about empathy occurrence information. Basically, after Step S810 is ended, the process returns to Step S801, and Step S801 to Step S810 are repeated. However, when it became unnecessary to cause the empathy detection system 500 to operate, the process may be ended at any timing.

Figure 93:
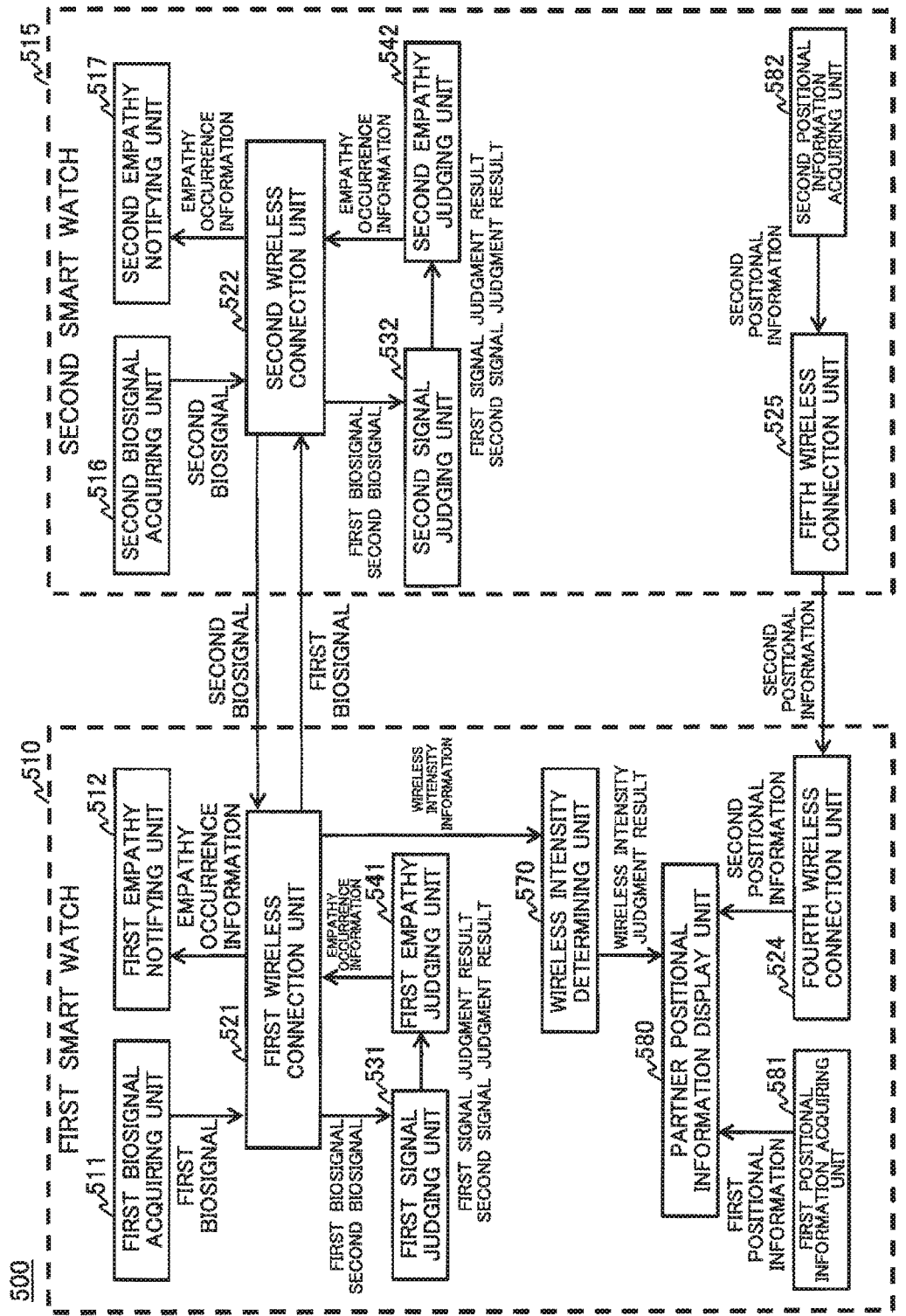
FIG. 93 shows one example of the configuration of the empathy detection system 500.

FIG. 93 shows one example of the configuration of the empathy detection system 500. The empathy detection system 500 according to the present example comprises the first biometric sensor 510 and the second biometric sensor 515. The first biometric sensor 510 is implemented in a first smart watch, and the second biometric sensor 515 is implemented in a second smart watch.

The first biometric sensor 510 comprises a wireless intensity determining unit 570, a partner positional information display unit 580, a first positional information acquiring unit 581 and a fourth wireless connection unit 524, in addition to the first biosignal acquiring unit 511, the first empathy notifying unit 512, the first wireless connection unit 521, the first signal judging unit 531 and the first empathy judging unit 541. On the other hand, the second biometric sensor 515 comprises a fifth wireless connection unit 525 and a second positional information acquiring unit 582, in addition to the second biosignal acquiring unit 516, the second empathy notifying unit 517, the second wireless connection unit 522, the second signal judging unit 532 and the second empathy judging unit 542.

The wireless intensity determining unit 570 receives an input of wireless intensity information from the first wireless connection unit 521. For example, the wireless intensity information is information indicating whether or not the first biosignal acquiring unit 511 and the second biosignal acquiring unit 516 are connected wirelessly. Also, the wireless intensity information indicates whether or not the intensity of wireless signals between the first wireless connection unit 521 and the second wireless connection unit 522 is at a predetermined threshold or higher. The wireless intensity determining unit 570 calculates a wireless intensity judgment result based on the wireless intensity information. The wireless intensity determining unit 570 according to the present example is provided only to the first biometric sensor 510, but the wireless intensity determining unit 570 may be provided also to the second biometric sensor 515.

The partner positional information display unit 580 determines whether or not to display partner positional information according to the wireless intensity judgment result. More specifically, the partner positional information display unit 580 does not display partner positional information when the wireless intensity judgment result is within a predetermined range. On the other hand, the partner positional information display unit 580 displays partner positional information when the wireless intensity judgment result is not within a predetermined range.

When displaying the partner positional information, the partner positional information display unit 580 displays the distance and direction from the first biometric sensor 510 to the second biometric sensor 515 based on the positional information of the first biometric sensor 510 and the second biometric sensor 515. Also, the partner positional information may be the distance and direction from the first biosignal acquiring unit 511 to the second biosignal acquiring unit 516. The distance may include a barometric pressure difference, and the direction may be a point of the compass or an upward, downward, forward, backward, leftward or rightward direction.

The first positional information acquiring unit 581 acquires first positional information indicating the positional information of the first biometric sensor 510. For example, the first positional information is at least one of information obtained by using a global positioning system, information obtained by using a wireless base station, and information obtained by using a barometric pressure sensor.

The fourth wireless connection unit 524 receives, from the second biometric sensor 515, second positional information indicating the positional information of the second biometric sensor 515. The fourth wireless connection unit 524 transmits the second positional information to the partner positional information display unit 580. The fourth wireless connection unit 524 according to the present example performs Internet communication by Wi-Fi (registered trademark), but may perform communication by Bluetooth (registered trademark).

The second positional information acquiring unit 582 acquires the second positional information. For example, the second positional information is information about the second biometric sensor 515, which is at least one of information obtained by using a global positioning system, information obtained by using a wireless base station and information obtained by using a barometric pressure sensor.

Figure 94:
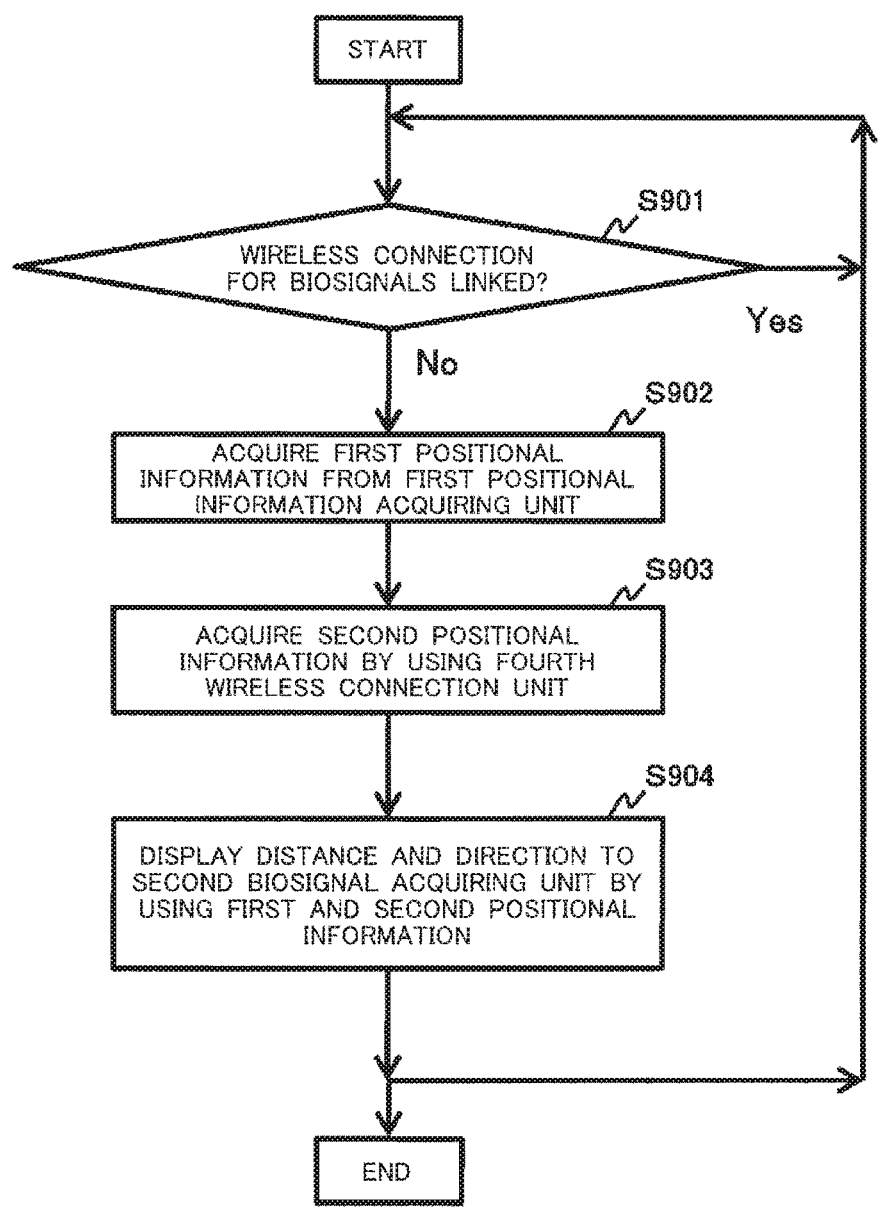
FIG. 94 shows one example of operation of the empathy detection system 500.

FIG. 94 shows one example of operation of the empathy detection system 500. The empathy detection system 500 according to the present example executes Step S901 to Step S904. By executing Step S901 to Step S904, positional information is displayed on the partner positional information display unit 580 when the first biometric sensor 510 and the second biometric sensor 515 are not linked. Thereby, users of the first biometric sensor 510 and the second biometric sensor 515 can approach a position where their biometric sensors can be linked.

At Step S901, the wireless intensity determining unit 570 judges whether or not the first wireless connection unit 521 and the second wireless connection unit 522 are linked. When the first wireless connection unit 521 and the second wireless connection unit 522 are linked, the process does not proceed to Step S902. The wireless intensity determining unit 570 starts execution of Step S901 again after elapse of a predetermined period. On the other hand, when the first wireless connection unit 521 and the second wireless connection unit 522 are not linked, the process proceeds to Step S902.

At Step S902, the partner positional information display unit 580 acquires the first positional information from the first positional information acquiring unit 581. At Step S903, the second positional information is acquired from the fifth wireless connection unit 525 by using the fourth wireless connection unit 524. At Step S904, the partner positional information display unit 580 displays the distance and the direction from the first biosignal acquiring unit 511 to the second biosignal acquiring unit 516 based on the first positional information and the second positional information.

Note that basically, after Step S904 is ended, the process returns to Step S901, and Step S901 to Step S904 are repeated. However, when it became unnecessary to cause the empathy detection system 500 to operate, when it became unnecessary for the wireless intensity determining unit 570 to judge the wireless intensity, or in any other certain cases, the process may be ended at any timing.

Figure 95:
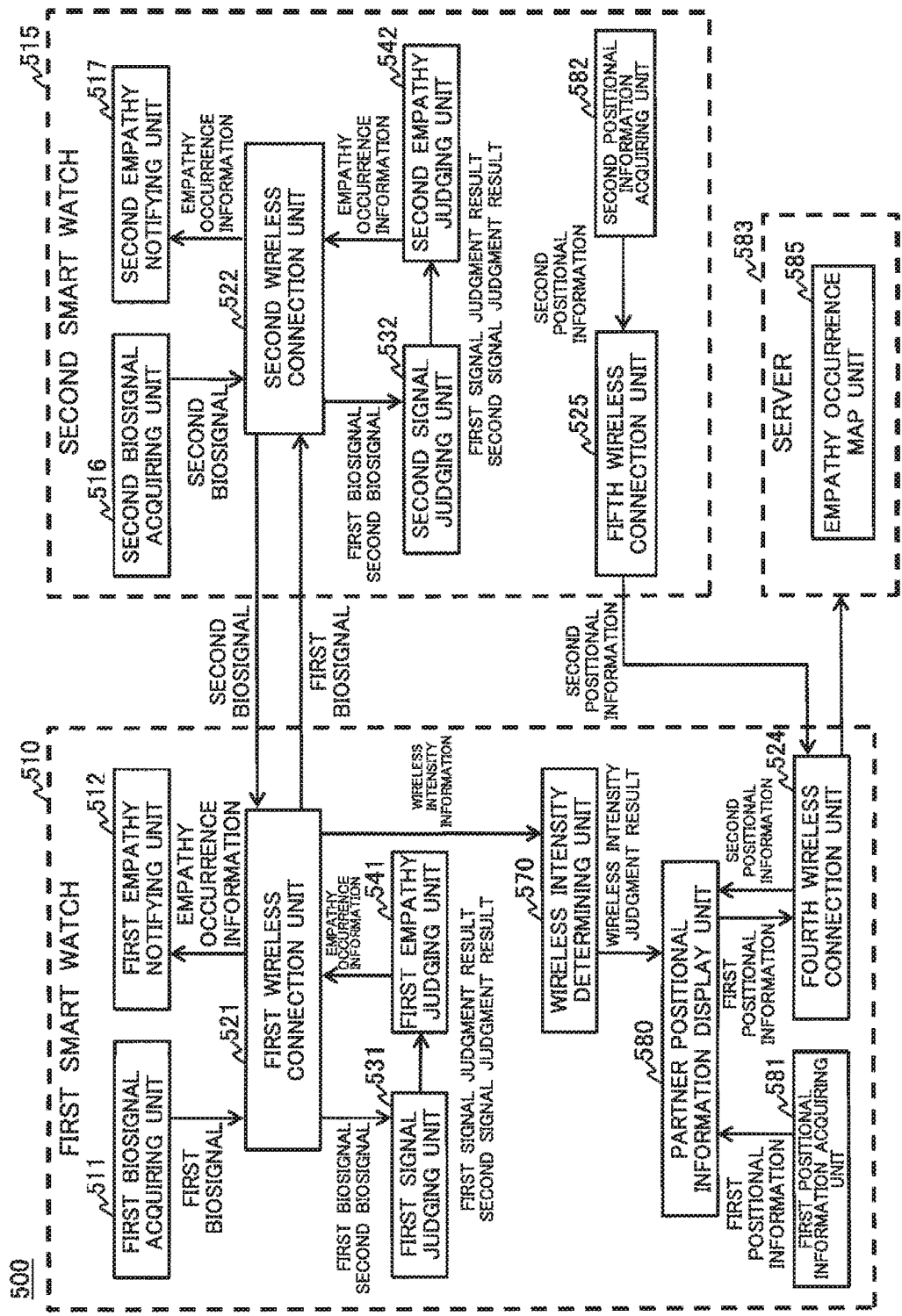
FIG. 95 shows one example of the configuration of the empathy detection system 500.

FIG. 95 shows one example of the configuration of the empathy detection system 500. The empathy occurrence map unit 585 according to the present example further comprises an empathy occurrence map unit 585 provided to a server 583, in addition to the first biometric sensor 510 and the second biometric sensor 515. The server 583 is linked with the fourth wireless connection unit 524 by a network.

The empathy occurrence map unit 585 plots, on a map and by using the acquired positional information, a geographical point at which empathy has occurred. The map on which the geographical point is plotted may be a facility plan view, in addition to a general map. When plotting, on a map, geographical points at which empathy has occurred, the empathy occurrence map unit 585 can classify the geographical points based on user information.

Figure 96:
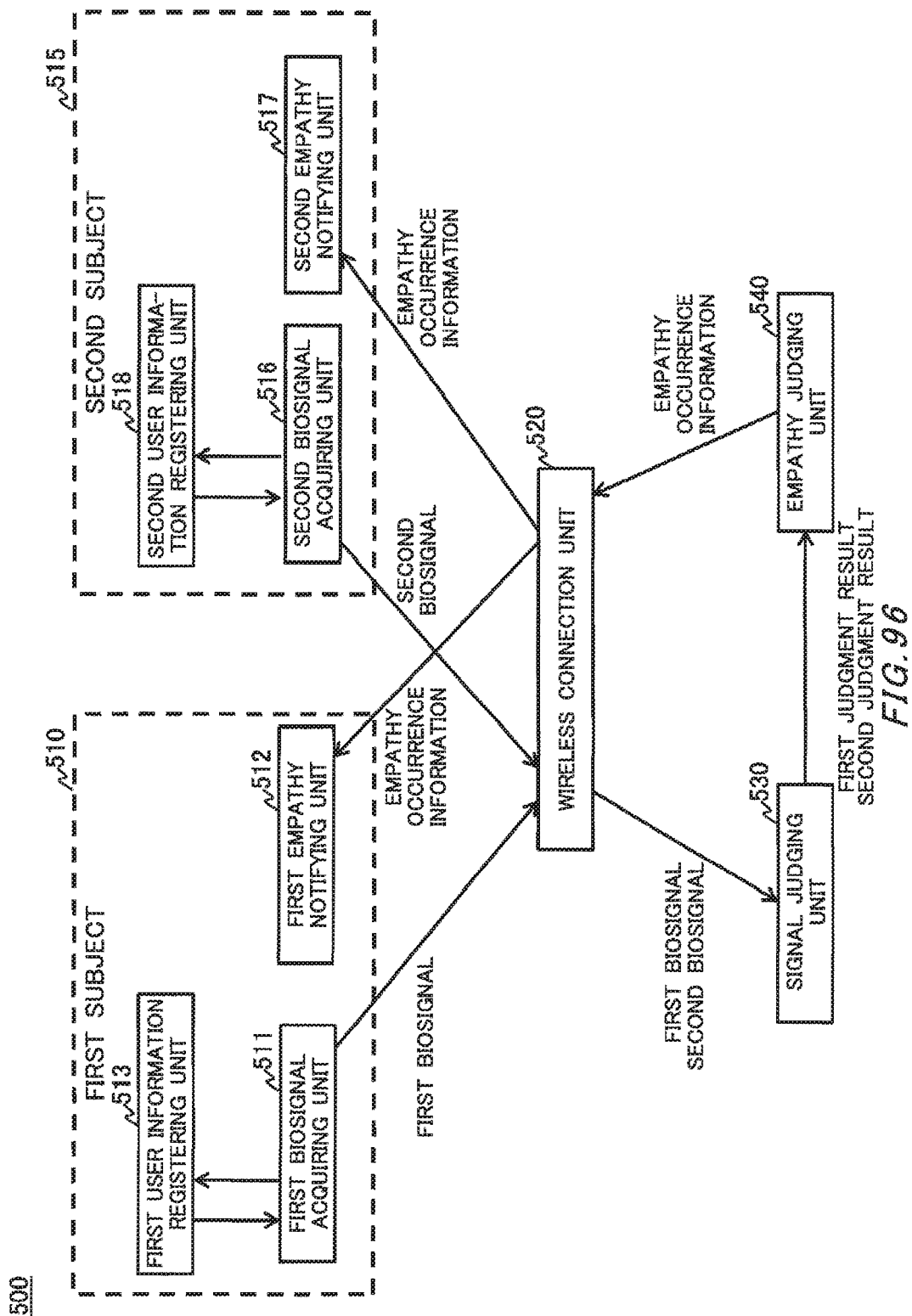
FIG. 96 shows one example of the configuration of the empathy detection system 500.

FIG. 96 shows one example of the configuration of the empathy detection system 500. The first biometric sensor 510 and the second biometric sensor 515 according to the present example comprise the first user information registering unit 513 and the second user information registering unit 518, respectively.

The first user information registering unit 513 pre-registers user information 81 of a user of the first biometric sensor 510. By registering the user information 81 in the first user information registering unit 513, the accuracy of signal judgement and empathy judgement improves. Also, the first user information registering unit 513 may register the user information 81 of a user of the second biometric sensor 515 with whom a pair is formed.

The empathy detection system 500 may classify occurrence of empathy based on the user information 81. Thereby, tendency about the user information 81 that users who feel empathy together have can be known. For example, the user information 81 includes at least one of age, generation, sex, race, nationality and mother tongue.

Figure 97:
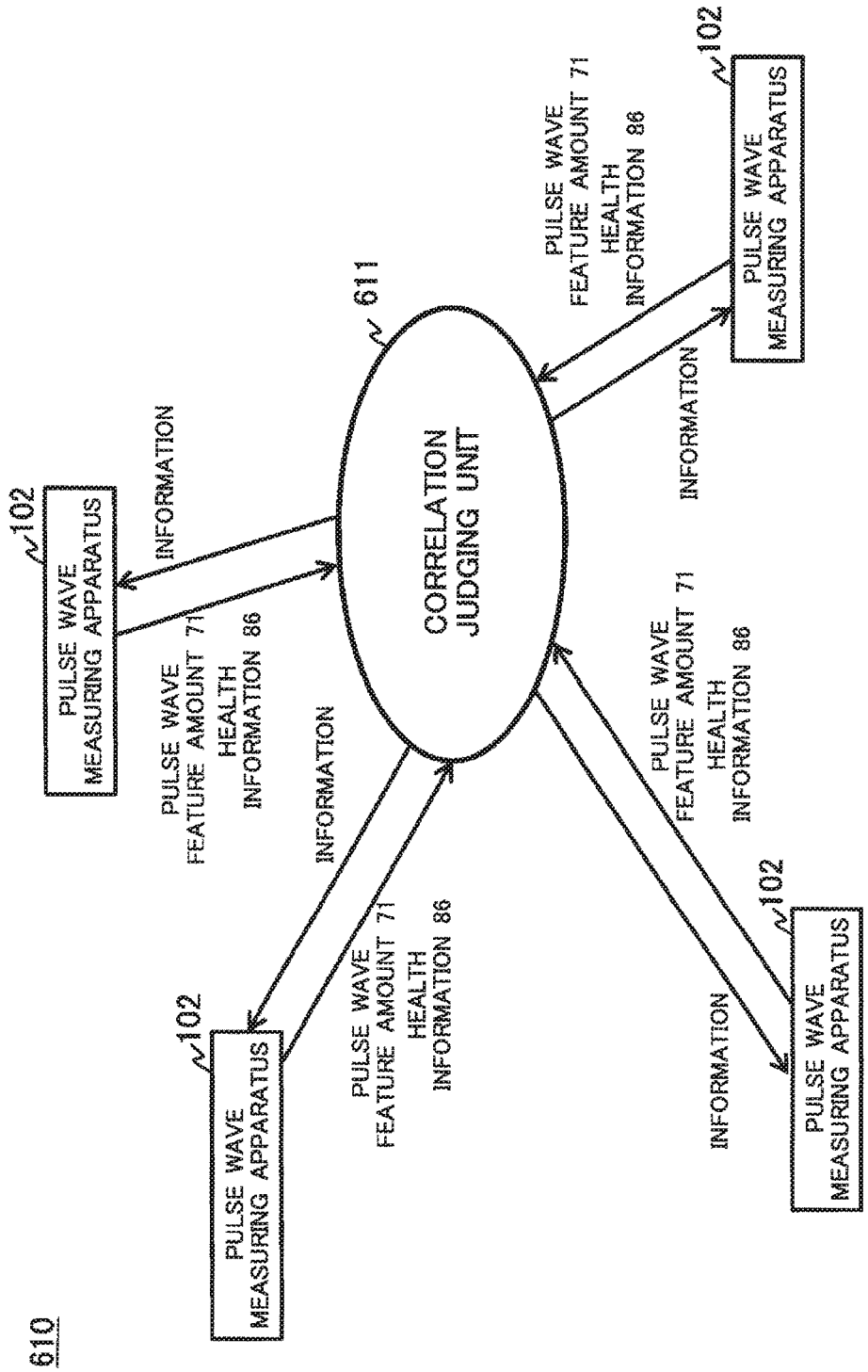
FIG. 97 shows one example of the configuration of a biological information communication system 610.

FIG. 97 shows one example of the configuration of a biological information communication system 610. The biological information communication system 610 is configured with a plurality of the pulse wave measuring apparatuses 102 and a correlation judging unit 611.

The biological information communication system 610 is used for users of the pulse wave measuring apparatuses 102 who are highly correlated to communicate with each other. Thereby, communication among users who get along well with each other can be enhanced.

The correlation judging unit 611 judges respective correlations of a plurality of the pulse wave feature amounts 71 or the health information 86 calculated by the plurality of pulse wave measuring apparatuses 102. When there is a correlation which is among judged respective correlations and is higher than a predetermined value, the correlation judging unit 611 transmits information indicating that the correlation is higher than the predetermined value to the pulse wave measuring apparatus 102 that calculates a corresponding pulse wave feature amount among the plurality of pulse wave feature amounts 71.

At least one of the pulse wave measuring apparatuses 102 may have configuration comprising the correlation judging unit 611. In such a case, the pulse wave measuring apparatus 102 provided with the correlation judging unit 611 judges correlations of the pulse wave feature amounts 71 calculated by the other pulse wave measuring apparatuses 102. Then, when a correlation is higher than a predetermined value, the pulse wave measuring apparatus 102 provided with the correlation judging unit 611 may output information indicating that the correlation is higher than the predetermined value.

Figure 98:
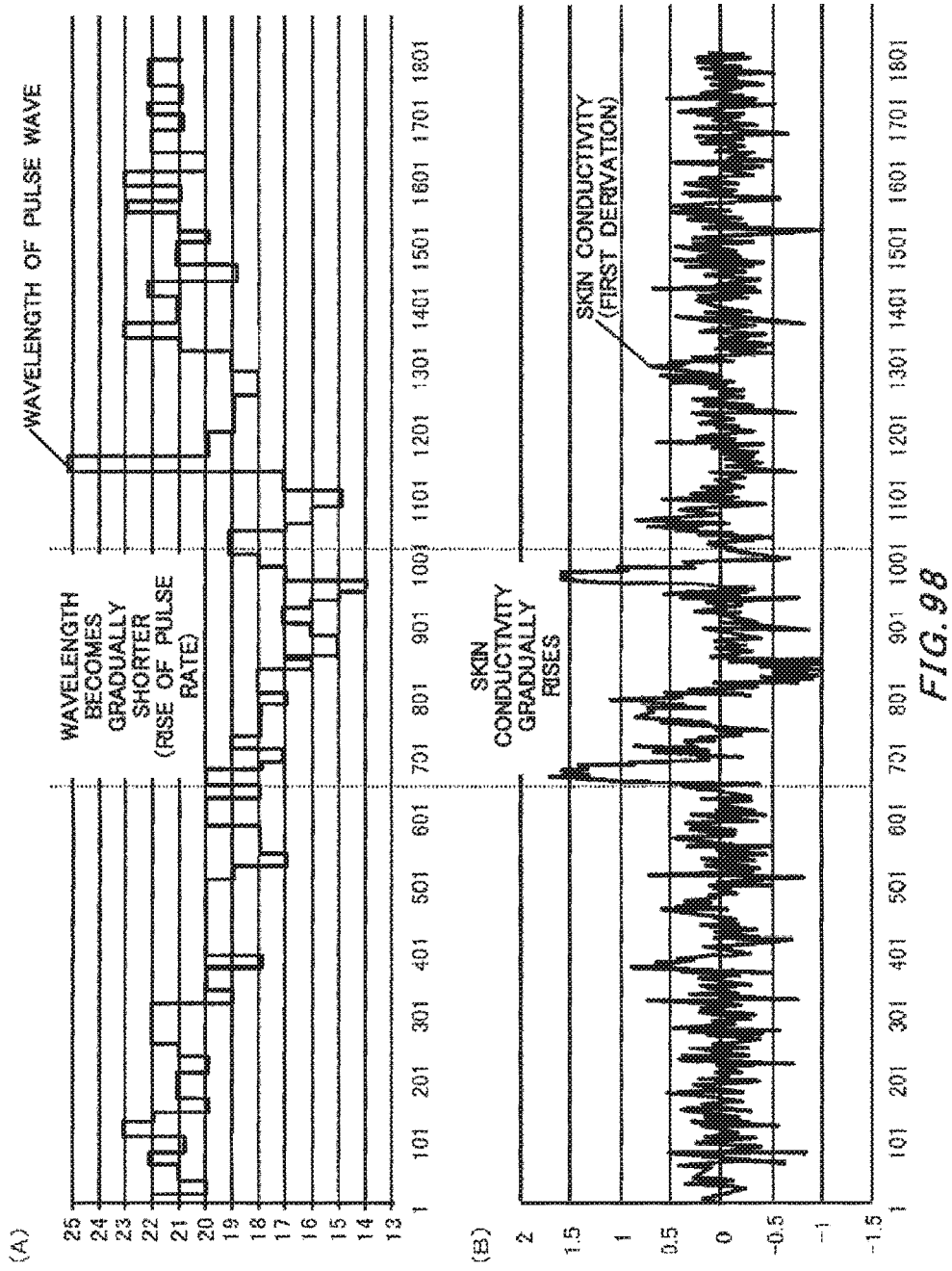
FIG. 98 shows feeling monitoring based on the wavelength of a pulse wave and skin conductivity.

FIG. 98 shows feeling monitoring based on the wavelength of a pulse wave and skin conductivity. A subject in the present example wears a pulse wave sensor on the back side of the right wrist, and wears a skin conductivity sensor on the front side of the left wrist. The graph (A) shows the wavelength of a pulse wave measured by the pulse wave sensor, and the graph (B) shows a first derivation of the measured skin conductivity. The horizontal axes of the graphs (A) and (B) indicate the number of samples of sampling at 20 Hz, and the vertical axes indicate respective signal indexes.

The subject watches a movie of a female singer who has passed a talent finding contest while wearing the respective sensors. In the graph (A), the period during which the wavelength of the pulse wave becomes gradually shorter corresponds to a period during which the pulse rates gradually rises. Referring to the graphs (A) and (B), the period during which the pulse rate gradually rises and the period during which the skin conductivity gradually rises match. That is, in both the sensors, changes are observed at the same timing, and it can be said that the feeling of the subject was detected in both the sensors. Therefore, in the present specification, the pulse wave sensors used for measuring pulses can replace sensors used for measurement of skin conductivity.

Embodiment 25

FIG. 99 shows one example of the empathy detection system 500 according to Embodiment 25. The empathy detection system 500 according to the present example is implemented within a wrist band 336.

A feeling sensor, a vibrator and a communicator are implemented in the one wrist band 336 (including a smart watch), and two users respectively wear the wrist bands 336. When the two feeling sensors detect feeling simultaneously, the vibrators are vibrated to notify the users so as to monitor empathy between the two users. The feeling sensors may monitor changes in the wavelength of pulse wave signals or the number of beats, and furthermore changes in blood pressure computed from pulse wave signals, or may monitor changes in the first derivation of the skin conductivity. Changes in pulse waves are caused by exercising, changes in skin conductivity are caused by deep breathing and changes in signals of these feeling sensors are caused also by contact failures. However, the empathy detection system 500 according to the present example can reduce misjudgments attributable to factors other than feeling by monitoring only empathy.

The vibrator can be realized by oscillators similar to vibrators used in mobile phones in manner mode or vibrators used in controllers of home game consoles. The communicators directly connect the two wrist bands 336 by Bluetooth (registered trademark). Note that although notification means is mainly vibration, notification may be done by using any other means such as the sense of touch, light, sound or temperature.

Also, the communicators can connect the two wrist bands 336 to one smartphone by Bluetooth (registered trademark), and indirectly connect the two wrist bands 336 via the smartphone. Alternatively, one wrist band and one smartphone are connected by Bluetooth (registered trademark), and two smartphones are connected by the Internet through Wi-Fi (registered trademark) so as to enable indirect connection of the two wrist bands.

The present implementation example does not limit the number of users to two, but can be implemented even if the number of users is three or more. In such a case, notification about occurrence of empathy may be done only to users who have contributed to empathy detection, or may be done simultaneously to all users that can be connected wirelessly. For example, by pre-registering the sex of a user or by preparing a wrist band dedicated to each sex, it is possible to devise a method to ignore occurrence of empathy among the same sex.

By plotting, on a map or a facility plan view, a position at which empathy has occurred, a feeling map with less noises can be created. Also, by monitoring the intensity of wireless signals connecting the two wrist bands 336, it is possible to judge the distance from partners, and the technique can be evolved into an application that indicates the distance and direction to the partners so that the two users will not get separated and lost.

Embodiment 26

Figure 100:
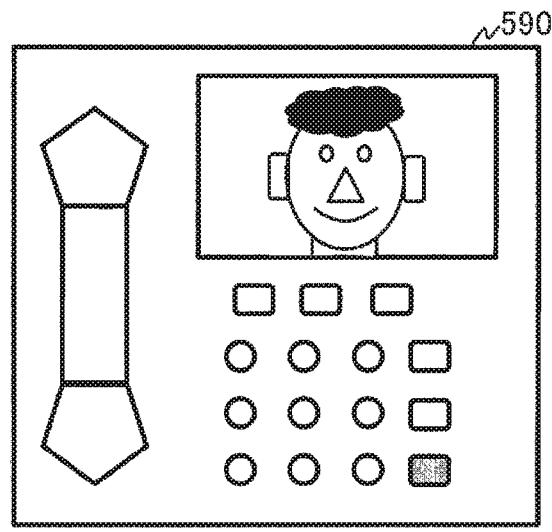
FIG. 100 shows one example of the empathy detection system 500 according to Embodiment 26.

FIG. 100 shows one example of the empathy detection system 500 according to Embodiment 26. The empathy detection system 500 according to the present example is implemented in a videophone 590.

The videophone 590 detects a pulse wave signal from each of an image of the face of a communication partner and an image of the face captured by its own camera. Also, the videophone 590 monitors changes in the wavelength of pulse wave signals, the number of beats or blood pressure to judge whether or not feeling has been detected simultaneously. The videophone 590 displays the judged feeling on a screen to notify a user about occurrence of empathy. The judged feeling may be notified to a user by a vibrator provided to a smartphone as occurrence of empathy. Also, notification about occurrence of empathy may be done by voice or a sound icon (chime) from a speaker of a smartphone. Note that the videophone 590 can share occurrence of empathy with a communication partner by transmitting, in addition to a video and audio, notification information superimposed on the video and audio.

Embodiment 27

Figure 101:
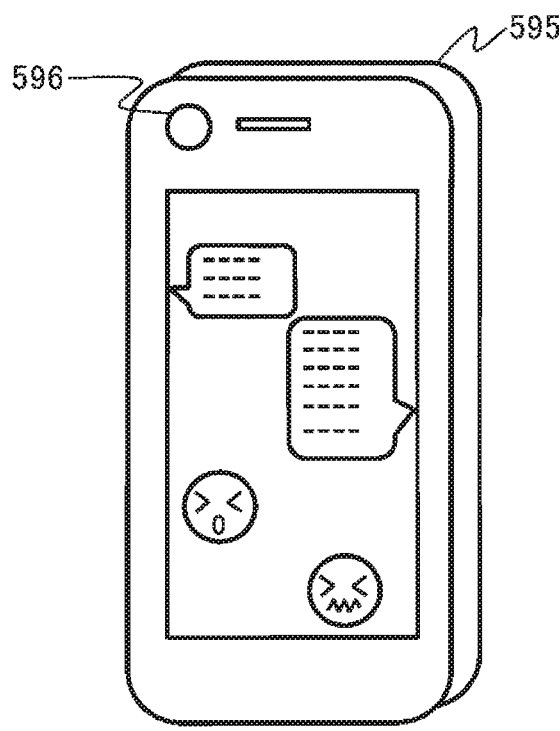
FIG. 101 shows one example of the empathy detection system 500 according to Embodiment 27.

FIG. 101 shows one example of the empathy detection system 500 according to Embodiment 27. The empathy detection system 500 according to the present example is implemented in a smartphone 595.

The smartphone 595 comprises an in-camera 596. The smartphone 595 detects a pulse wave signal from an image of a face captured by the in-camera 596. Changes in the wavelength of pulse wave signals, the number of beats or blood pressure are monitored in the pulse wave signal, and feeling occurrence information is detected. The smartphone 595 transmits detected occurrence of feeling in a social network/message exchange application (examples of which include LINE (registered trademark) and Messenger (registered trademark)). The smartphone 595 detects occurrence of empathy based on feeling occurrence information of its own and feeling occurrence information transmitted from a partner, and notifies occurrence of empathy to users by using decoration functions of a message exchange application (examples which include LINE (registered trademark) stamps, and emojis)

In the present embodiment, feeling felt mutually needs not occur temporally simultaneously. For example, information indicating that feeling has occurred to one of users while he/she is editing a message may be transmitted to a partner together with a message, and feeling may occur to the partner while he/she is editing a reply message. This may be regarded as occurrence of empathy.

Embodiment 28

Figure 102:
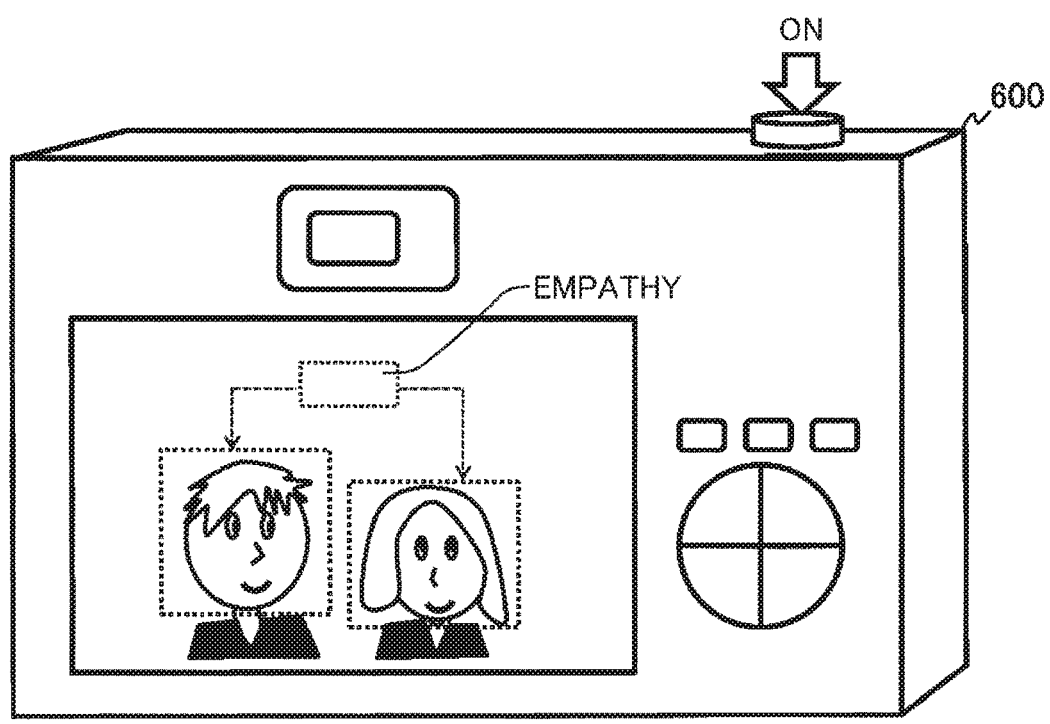
FIG. 102 shows one example of the empathy detection system 500 according to Embodiment 28.

FIG. 102 shows one example of the empathy detection system 500 according to Embodiment 28. The empathy detection system 500 according to the present example is implemented on a camera 600.

The camera 600 detects pulse wave signals from an image of the face of each subject while an image of a plurality of subjects is captured. The camera 600 monitors changes in the wavelength of pulse wave signals, the number of beats or blood pressure to identify a pair of subjects between which empathy has occurred. An image indicating occurrence of empathy and the identified pair is superimposed on a photograph or moving image. The camera 600 may capture an image automatically at the timing of occurrence of empathy irrespective of whether or not the shutter is pressed.

Embodiment 29

Figure 103:
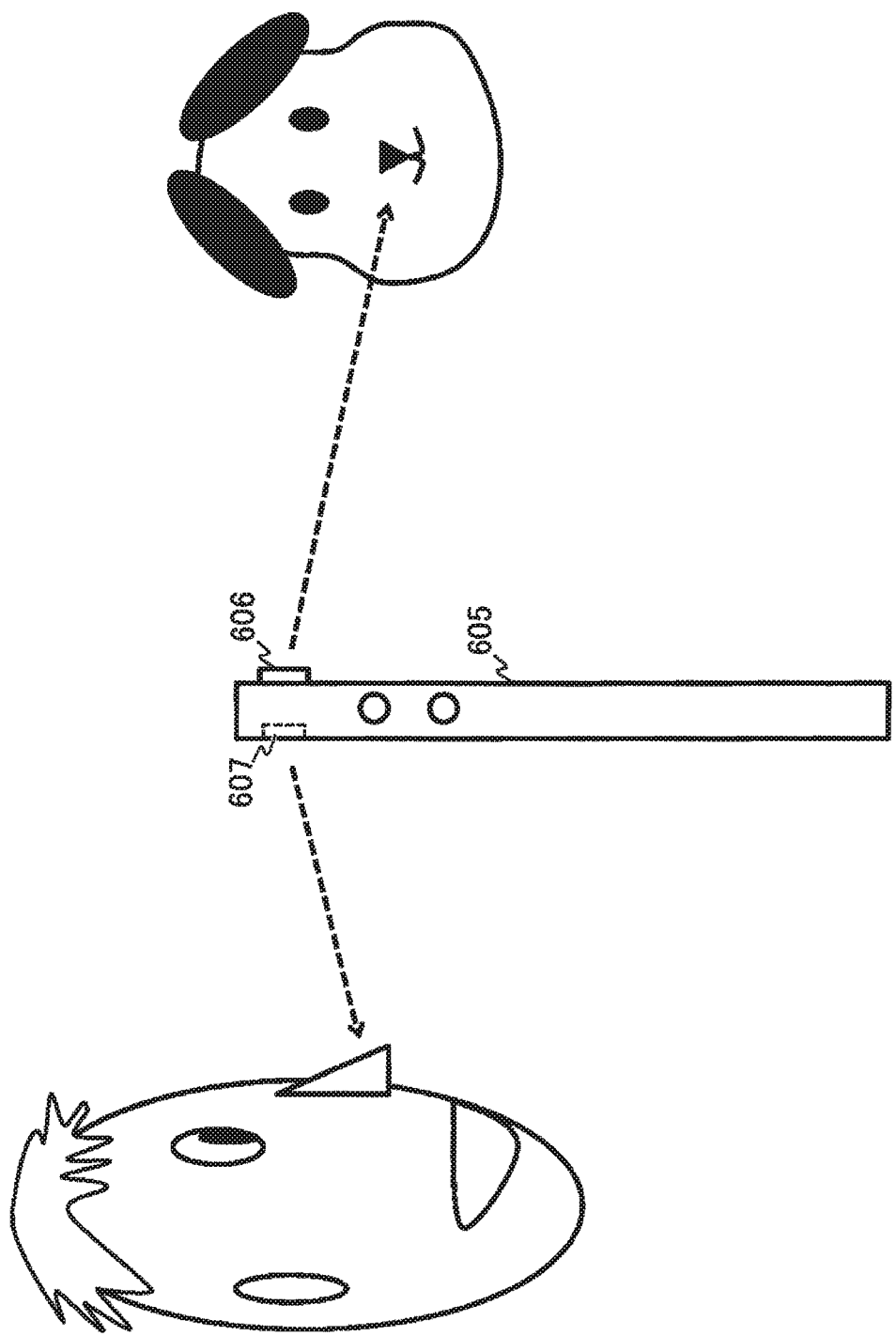
FIG. 103 shows one example of the empathy detection system 500 according to Embodiment 29.

FIG. 103 shows one example of the empathy detection system 500 according to Embodiment 29. The empathy detection system 500 according to the present example is implemented on a smartphone 605 comprising an out-camera 606 and an in-camera 607.

The smartphone 605 detects a pulse wave signal from each of an image of the face of a subject captured by the out-camera 606 and an image of the face of a user captured by the in-camera 607. The subject is not limited to a human being, but may be a pet dog or cat, and the image of the face of the subject may include the noses or tongues of the pets. The smartphone 605 monitors changes in the wavelength of pulse wave signals, the number of beats or blood pressure to judge whether or not feeling has been detected simultaneously. Occurrence of empathy is notified to a user by a vibrator provided to the smartphone 605. Notification of occurrence of empathy may be recorded as a proof of empathy with a user by using an icon or audio (guidance or sound icon) in a photograph or movie captured. Alternatively, a photograph of the face of a user of the in-camera 607 may be superimposed on a part of an image of the out-camera 606 only when empathy has occurred.

The empathy detection system 500 disclosed in the present specification utilizes a phenomenon in which the same living body responses are caused simultaneously when a plurality of users receive the same stimulus so as to reduce misjudgments attributable to noises. For example, a phenomenon in which the same responses of a living body are caused simultaneously may mean a phenomenon in which people cry at the same scene in a movie theater, people are moved by the sudden appearance of a popular character at a theme park, or two people who are physically distant and having a conversation on the phone are moved at the same time.

Due to the empathy detection system 500 disclosed in the present specification, people can know mutual empathy in real-time even in situations where they cannot communicate with each other such as situations where they cannot see facial expressions of one another or cannot have conversations. For example, a situation where people go to a movie theater is considered. While watching a movie, they cannot see faces of his/her company, and feel awkward to talk with them, so they cannot know whether or not the company felt empathy at a certain scene. But by wearing wrist bands comprising biometric sensors on their wrists, and causing the sensors to sense that they felt empathy and to issue notifications by using vibrators similarly provided to the wrist bands, empathy that is felt by the company can be known in real-time without bothering the other audience.

Figure 104:
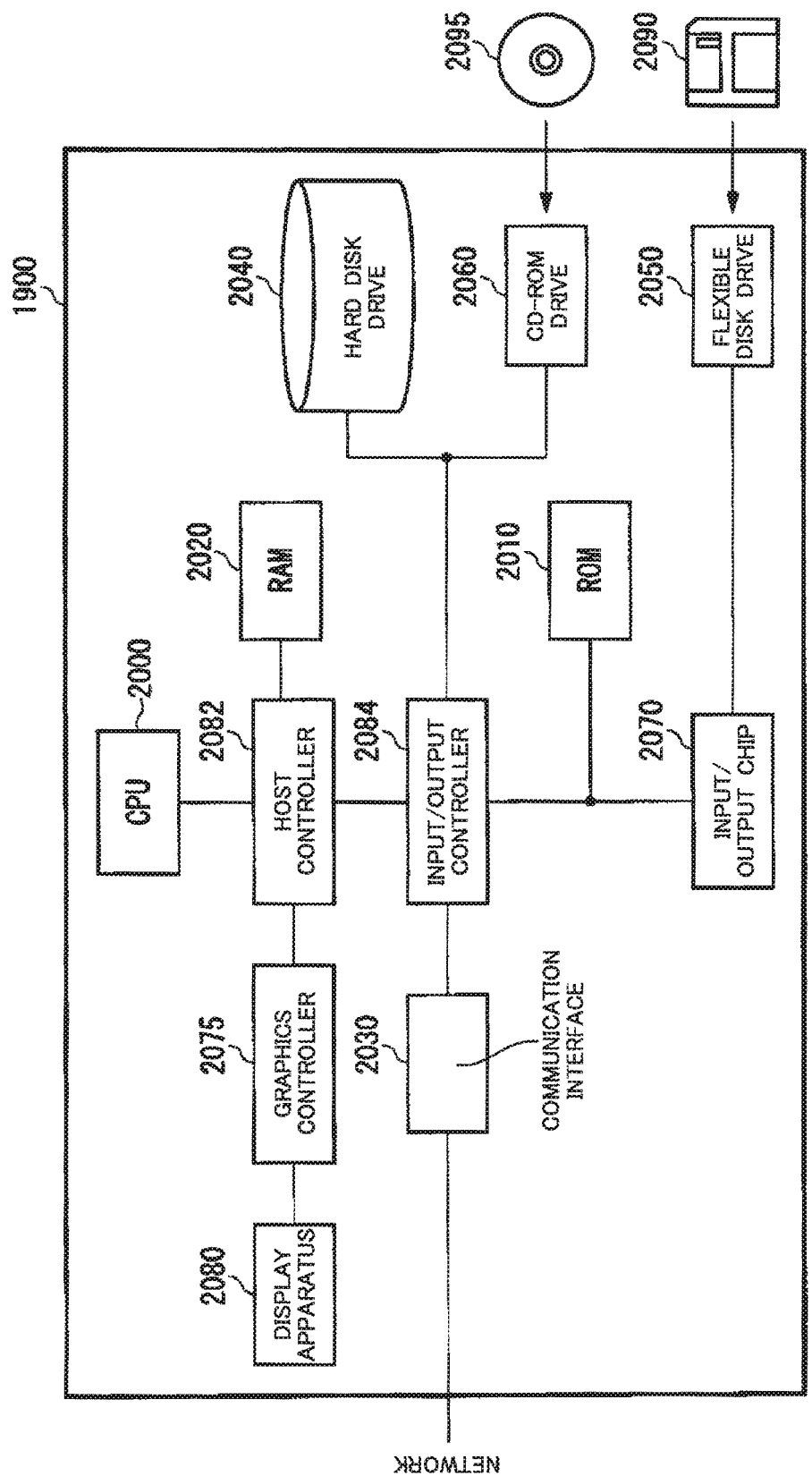
FIG. 104 shows one example of the hardware configuration of a computer 1900.

FIG. 104 shows one example of the hardware configuration of a computer 1900 according to the present embodiment. The computer 1900 according to the present embodiment comprises: a CPU peripheral unit having a CPU 2000, a RAM 2020, a graphics controller 2075 and a display apparatus 2080 that are interconnected by a host controller 2082; an input/output unit having a communication interface 2030, a hard disk drive 2040 and a CD-ROM drive 2060 connected to the host controller 2082 by an input/output controller 2084; and a legacy input/output unit having a ROM 2010, a flexible disk drive 2050 and an input/output chip 2070 connected to the input/output controller 2084.

The host controller 2082 connects the RAM 2020, and the CPU 2000 and graphics controller 2075 that access the RAM 2020 at high transfer rates. The CPU 2000 operates based on a program stored on the ROM 2010 and the RAM 2020, and controls each unit. The graphics controller 2075 acquires image data generated on a frame buffer provided within the RAM 2020 by the CPU 2000 or the like, and displays the image data on the display apparatus 2080. Instead of this, the graphics controller 2075 may include therein a frame buffer that stores image data generated by the CPU 2000 or the like.

The input/output controller 2084 connects the host controller 2082, and the communication interface 2030, hard disk drive 2040 and CD-ROM drive 2060 that are relatively high speed input/output apparatuses. The communication interface 2030 communicates with other apparatuses via a network. The hard disk drive 2040 stores therein a program and data to be used by the CPU 2000 within the computer 1900. The CD-ROM drive 2060 reads out a program or data from the CD-ROM 2095, and provides them to the hard disk drive 2040 via the RAM 2020.

Also, the ROM 2010, and relatively low speed input/output apparatuses of the flexible disk drive 2050 and input/output chip 2070 are connected to the input/output controller 2084. The ROM 2010 stores therein a boot-program that the computer 1900 executes at the time of start-up and/or a program that is dependent on hardware of the computer 1900, or the like. The flexible disk drive 2050 reads out a program or data from the flexible disk 2090, and provides them to the hard disk drive 2040 via the RAM 2020. The input/output chip 2070 connects the flexible disk drive 2050 to the input/output controller 2084, and also connects various types of input/output apparatuses to the input/output controller 2084 via, for example, a parallel port, a serial port, a keyboard port, a mouse port or the like.

A program to be provided to the hard disk drive 2040 via the RAM 2020 is provided by a user by being stored in a recording medium such as the flexible disk 2090, the CD-ROM 2095, an IC card or the like. The program is read out from the recording medium, installed in the hard disk drive 2040 within the computer 1900 via the RAM 2020, and executed in the CPU 2000.

The program installed on the computer 1900 and causes the computer 1900 to function as a blood pressure information output apparatus comprises a video input module, blood pressure information output module and a pulse information calculating module. These programs or modules act on the CPU 2000 or the like to respectively cause the computer 1900 to function as a blood pressure information output apparatus.

The information processing described in the program is read into the computer 1900 to function as the pulse waveform information acquiring unit 21, the blood pressure information output unit 30 and the pulse information calculating unit 40 which are specific means realized by cooperation among software and the above-mentioned various types of hardware resources. By realizing operations or processes on information according to use purposes of the computer 1900 in the present embodiment by means of these specific means, the unique blood pressure information output apparatus 100 and the real-time blood pressure information output apparatus 101 according to the use purposes are constructed.

Also, the program installed on the computer 1900 and causes the computer 1900 to function as a pulse wave measuring apparatus comprises a pulse waveform information acquiring module, a pulse wave feature amount calculating module, and a health information estimating module. The program or modules act on the CPU 2000 or the like to respectively cause the computer 1900 to function as a pulse wave measuring apparatus.

The information processing described in the program is read into the computer 1900 to function as the pulse waveform information acquiring unit 60, the pulse wave feature amount calculating unit 70 and the health information estimating unit 85 which are specific means realized by cooperation among software and the above-mentioned various types of hardware resources. By realizing operations or processes on information according to use purposes of the computer 1900 in the present embodiment by means of these specific means, the unique pulse wave measuring apparatus 102 according to the use purposes is constructed.

In one example, when communication is performed between the computer 1900 and an external apparatus or the like, the CPU 2000 executes a communication program loaded onto the RAM 2020, and based on the processing contents described in the communication program, instructs the communication interface 2030 to perform communication processing. Under control of the CPU 2000, the communication interface 2030 reads out transmitted data memorized in a transmission buffer region or the like provided on a storage such as the RAM 2020, the hard disk drive 2040, the flexible disk 2090 or the CD-ROM 2095 to transmit the data to a network, or writes received data received from a network into a reception buffer region or the like provided on a storage. In this manner, the communication interface 2030 may transfer transmitted/received data between storages by the DMA (direct memory access) system, or instead of this, the CPU 2000 may transfer transmitted/received data by reading out data from a transfer source storage or communication interface 2030, and writing the data into a transfer destination communication interface 2030 or storage.

Also, the CPU 2000 causes all or necessary portions of files, databases or the like stored in an external storage such as the hard disk drive 2040, the CD-ROM drive 2060 (CD-ROM 2095) or the flexible disk drive 2050 (flexible disk 2090) to be read into the RAM 2020 by the DMA transfer or other systems, and performs various types of processing on the data on the RAM 2020. The CPU 2000 writes the data on which processing has been performed back into an external storage by the DMA transfer or other systems. Because in such processing, the RAM 2020 can be regarded as retaining contents of the external storage temporarily, the RAM 2020 and the external storage or the like are collectively called a memory, a storage unit, a storage or the like in the present embodiment. Various types of information such as various types of programs, data, tables, databases or the like in the present embodiment are stored in such a storage, and are subjected to information processing. Note that the CPU 2000 can also retain a portion of the RAM 2020 on a cache memory, and read out from and write in the cache memory. Because in such an embodiment also, the cache memory plays some of the functions of the RAM 2020, in the present embodiment, the cache memory is also regarded as being included in the RAM 2020, a memory and/or a storage unless otherwise they are distinguished from each other.

Also, the CPU 2000 performs, on data read out from the RAM 2020, various types of processing including various types of operation, information processing, conditional judgment, information search/replacement or the like described in the present embodiment that are specified in an instruction sequence of a program, and writes the data back into the RAM 2020. For example, when performing conditional judgment, the CPU 2000 compares various types of variables shown in the present embodiment to judge whether they meet conditions such as being larger than, smaller than, equal to or larger than, equal to or smaller than other variables or constants, and when a condition is met (or when it is not met) branches to a different instruction sequence or calls up a subroutine.

Also, the CPU 2000 can search information stored in files, databases or the like in a storage. For example, when a plurality of entries in which attribute values of a second attribute are respectively associated with attribute values of a first attribute are stored in a storage, the CPU 2000 searches, from among the plurality of entries stored in the storage, an entry whose attribute value of the first attribute matches a specified condition, and reads out the attribute value of the second attribute stored in the entry, thereby obtaining the attribute value of the second attribute associated with the first attribute that meets a predetermined condition.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

The program or module shown above may be stored in an external recording medium. As the recording medium, other than the flexible disk 2090 and the CD-ROM 2095, an optical recording medium such as DVDs or CDs, a magneto-optical recording medium such as MOs, a tape medium, a semiconductor memory such as IC cards or the like may be used. Also, a storage such as a hard disk or a RAM provided to a server system connected to a dedicated communication network or the Internet may be used as the recording medium, and may provide the program to the computer 1900 via a network Implementation Aspects of the embodiments explained above are shown below.

[Implementation Aspect 1]

A blood pressure information output apparatus comprising: a pulse waveform information acquiring unit that optically acquires pulse waveform information from a region of a living body;

a pulse information calculating unit that calculates a pulse rate of the living body by frequency analysis based on the pulse waveform information, and calculates temporal information of a pulse wave of the living body based on the pulse waveform information; and a blood pressure information output unit that estimates and outputs blood pressure information of the living body based on the pulse rate and the temporal information.

[Implementation Aspect 2]

The blood pressure information output apparatus according to Implementation Aspect 1, wherein the temporal information is at least one of rising time of the pulse wave and falling time of the pulse wave.

[Implementation Aspect 3]

The blood pressure information output apparatus according to Implementation Aspect 1 or 2, wherein the region is a nose of the living body.

[Implementation Aspect 4]

The blood pressure information output apparatus according to Implementation Aspect 1 or 2, wherein the region is a fingertip of the living body.

[Implementation Aspect 5]

The blood pressure information output apparatus according to any one of Implementation Aspects 2 to 4, wherein the blood pressure information output unit estimates and outputs the blood pressure information based on a square of the temporal information.

[Implementation Aspect 6]

The blood pressure information output apparatus according to any one of Implementation Aspect 1 to 5, wherein the blood pressure information indicates at least one of a blood pressure, a blood pressure state, arteriosclerosis, a vascular age and a predisposition to stroke.

[Implementation Aspect 7]

The blood pressure information output apparatus according to any one of Implementation Aspects 1 to 6, wherein the pulse information calculating unit calculates the temporal information based on the pulse rate calculated by the frequency analysis and the pulse waveform information.

[Implementation Aspect 8]

A blood pressure information output apparatus comprising:

a video input unit that receives an input of a video of a region of a living body;

a pulse information calculating unit that calculates a pulse rate of the living body and temporal information of a pulse wave of the living body based on the video; and a blood pressure information output unit that estimates and outputs blood pressure information of the living body based on the pulse rate and the temporal information.

[Implementation Aspect 9]

The blood pressure information output apparatus according to Implementation Aspect 8, wherein the temporal information is at least one of rising time of the pulse wave and falling time of the pulse wave.

[Implementation Aspect 10]

The blood pressure information output apparatus according to Implementation Aspect 9, wherein the pulse information calculating unit includes:

a pulse wave component signal extracting unit that extracts a pulse wave component signal of the living body from the video;

a pulse rate calculating unit that calculates a pulse rate of the living body from the pulse wave component signal; and a temporal information calculating unit that calculates at least one of the rising time and the falling time from the pulse wave component signal.

[Implementation Aspect 11]

The blood pressure information output apparatus according to Implementation Aspect 10, wherein the pulse rate calculating unit calculates the pulse rate based on frequency analysis.

[Implementation Aspect 12]

The blood pressure information output apparatus according to Implementation Aspect 11, wherein the frequency analysis is discrete-time analysis, and the number of points of the pulse wave component signal input in the discrete-time analysis is 128 points per window.

[Implementation Aspect 13]

The blood pressure information output apparatus according to Implementation Aspect 12, wherein the frequency analysis is FFT analysis.

[Implementation Aspect 14]

The blood pressure information output apparatus according to Implementation Aspect 12, wherein the frequency analysis is wavelet analysis.

[Implementation Aspect 15]

The blood pressure information output apparatus according to any one of Implementation Aspects 10 to 14, wherein the temporal information calculating unit calculates the temporal information based on first-order differentiation of the pulse wave component signal.

[Implementation Aspect 16]

The blood pressure information output apparatus according to any one of Implementation Aspects 8 to 15, wherein the region is a nose of the living body.

[Implementation Aspect 17]

The blood pressure information output apparatus according to any one of Implementation Aspects 7 to 15, wherein the region is a fingertip of the living body.

[Implementation Aspect 18]

The blood pressure information output apparatus according to any one of Implementation Aspects 8 to 17, wherein the blood pressure information output unit estimates and outputs the blood pressure information based on a square of the temporal information.

[Implementation Aspect 19]

The blood pressure information output apparatus according to any one of Implementation Aspects 8 to 18, wherein the blood pressure information indicates at least one of a blood pressure, a blood pressure state, arteriosclerosis, a vascular age and a predisposition to stroke.

[Implementation Aspect 20]

The blood pressure information output apparatus according to any one of Implementation Aspects 8 to 19, further comprising an information input apparatus to be used when the living body inputs information to the blood pressure information output apparatus, wherein the blood pressure information output unit has a display, and displays the blood pressure information on the display when input to the information input apparatus has not been made for a predetermined length of time.

[Implementation Aspect 21]

The blood pressure information output apparatus according to Implementation Aspect 20, wherein the blood pressure information output unit stops displaying the blood pressure information on the display when information has been input to the information input apparatus.

[Implementation Aspect 22]

The blood pressure information output apparatus according to Implementation Aspect 20 or 21, wherein the information input apparatus is a keyboard or a mouse.

[Implementation Aspect 23]

The blood pressure information output apparatus according to any one of Implementation Aspects 8 to 19, wherein the blood pressure information output unit has a display, and displays, as a screen saver, the blood pressure information on the display.

[Implementation Aspect 24]

A blood pressure information output program that causes a computer to function as the blood pressure information output apparatus according to any one of Implementation Aspects 8 to 23.

[Implementation Aspect 25]

A medium having the blood pressure information output program according to Implementation Aspect 24.

[Implementation Aspect 26]

A blood pressure information output method to be executed by a computer, the method comprising:

acquiring a video of a single region of a living body;

calculating of a pulse rate of the living body and temporal information of a pulse wave of the living body based on the video; and estimating and outputting blood pressure information of the living body based on the pulse rate and the temporal information.

[Implementation Aspect 27]

A blood pressure information output apparatus comprising:

a video input unit that receives an input of a video of a single region of a living body; and a blood pressure information output unit that outputs blood pressure information of the living body based on the video.

[Implementation Aspect 28]

The blood pressure information output apparatus according to Implementation Aspect 27, wherein the video input unit has a camera that captures the video.

[Implementation Aspect 29]

The blood pressure information output apparatus according to Implementation Aspect 27, wherein the blood pressure information output unit has a display that displays the blood pressure information.

[Implementation Aspect 30]

The blood pressure information output apparatus Implementation Aspect 29, further comprising an information input apparatus through which the living body inputs information, wherein the blood pressure information output unit displays the blood pressure information on the display when input to the information input apparatus has not been made for a predetermined length of time.

[Implementation Aspect 31]

The blood pressure information output apparatus according to Implementation Aspect 30, wherein the blood pressure information output unit stops displaying the blood pressure information on the display when information has been input to the information input apparatus.

[Implementation Aspect 32]

The blood pressure information output apparatus according to Implementation Aspect 30, wherein the information input apparatus is a keyboard or a mouse.

[Implementation Aspect 33]

The blood pressure information output apparatus according to Implementation Aspect 29, wherein the blood pressure information output unit displays, as a screen saver, the blood pressure information on the display.

[Implementation Aspect 34]

The blood pressure information output apparatus according to Implementation Aspect 27, wherein the blood pressure information output unit has a speaker that outputs the blood pressure information.

[Implementation Aspect 35]

The blood pressure information output apparatus according to Implementation Aspect 27, wherein the blood pressure information output unit transmits the blood pressure information to electronic equipment.

[Implementation Aspect 36]

The blood pressure information output apparatus according to Implementation Aspect 27, wherein the blood pressure information output unit transmits the blood pressure information to a database at a medical institution.

[Implementation Aspect 37]

The blood pressure information output apparatus according to Implementation Aspect 27, wherein the video is a video of a nose of the living body.

[Implementation Aspect 38]

The blood pressure information output apparatus according to Implementation Aspect 27, wherein the video is a video of a fingertip of the living body.

[Implementation Aspect 39]

A medium having a program that causes a computer to function as the blood pressure information output apparatus according to Implementation Aspect 27.

[Implementation Aspect 40]

A blood pressure information output method to be executed by a computer, the method comprising:

inputting a video of a single region of a living body; and outputting blood pressure information of the living body based on the video.

[Implementation Aspect 41]

The blood pressure information output method according to Implementation Aspect 40, further comprising acquiring the video by a camera.

[Implementation Aspect 42]

The blood pressure information output method according to Implementation Aspect 40, further comprising displaying the blood pressure information on a display.

[Implementation Aspect 43]

The blood pressure information output method according to Implementation Aspect 42, wherein the displaying is to display the blood pressure information on the display when the living body has not input information to the information input apparatus for a predetermined length of time.

[Implementation Aspect 44]

The blood pressure information output method according to Implementation Aspect 43, wherein displaying the blood pressure information on the display is stopped when information has been input to the information input apparatus.

[Implementation Aspect 45]

The blood pressure information output method according to Implementation Aspect 43, wherein the information input apparatus is a keyboard or a mouse.

[Implementation Aspect 46]

The blood pressure information output method according to Implementation Aspect 42, wherein the displaying is to display, as a screen saver, the blood pressure information on the display.

[Implementation Aspect 47]

The blood pressure information output method according to Implementation Aspect 40, further comprising transmitting the blood pressure information to electronic equipment.

[Implementation Aspect 48]

The blood pressure information output method according to Implementation Aspect 40, further comprising transmitting the blood pressure information to a database at a medical institution.

[Implementation Aspect 49]

A real-time blood pressure information output apparatus, comprising:

a facial video input unit that receives an input of a facial video of a living body; and a real-time blood pressure information output unit that outputs real-time blood pressure information of the living body based on the facial video.

[Implementation Aspect 50]

The real-time blood pressure information output apparatus according to Implementation Aspect 49, wherein the facial video input unit has a camera that captures the facial video.

[Implementation Aspect 51]

The real-time blood pressure information output apparatus according to Implementation Aspect 49, wherein the real-time blood pressure information output unit has a display that displays the real-time blood pressure information.

[Implementation Aspect 52]

The real-time blood pressure information output apparatus according to Implementation Aspect 51, further comprising an information input apparatus through which the living body inputs information, wherein the real-time blood pressure information output unit displays the real-time blood pressure information on the display when input to the information input apparatus has not been made for a predetermined length of time.

[Implementation Aspect 53]

The real-time blood pressure information output apparatus according to Implementation Aspect 52, wherein the real-time blood pressure information output unit stops displaying the real-time blood pressure information on the display when information has been input to the information input apparatus.

[Implementation Aspect 54]

The real-time blood pressure information output apparatus according to Implementation Aspect 52, wherein the information input apparatus is a keyboard or a mouse.

[Implementation Aspect 55]

The real-time blood pressure information output apparatus according to Implementation Aspect 51, wherein the blood pressure information output unit displays, as a screen saver, the real-time blood pressure information on the display.

[Implementation Aspect 56]

The real-time blood pressure information output apparatus according to Implementation Aspect 49, wherein the real-time blood pressure information output unit has a speaker that outputs the real-time blood pressure information.

[Implementation Aspect 57]

The real-time blood pressure information output apparatus according to Implementation Aspect 49, wherein the real-time blood pressure information output unit transmits the real-time blood pressure information to electronic equipment.

[Implementation Aspect 58]

The real-time blood pressure information output apparatus according to Implementation Aspect 49, wherein the real-time blood pressure information output unit transmits the real-time blood pressure information to a database at a medical institution.

[Implementation Aspect 59]

The real-time blood pressure information output apparatus according to Implementation Aspect 49, wherein the facial video is a video of a nose of the living body.

[Implementation Aspect 60]

A medium having a program that causes a computer to function as the real-time blood pressure information output apparatus according to Implementation Aspect 49.

[Implementation Aspect 61]

A real-time blood pressure information output method to be executed by a computer, the method comprising:

inputting a facial video of a living body; and outputting real-time blood pressure information of the living body based on the facial video.

[Implementation Aspect 62]

The real-time blood pressure information output method according to Implementation Aspect 61, further comprising acquiring the facial video by a camera.

[Implementation Aspect 63]

The real-time blood pressure information output method according to Implementation Aspect 62, further comprising displaying the real-time blood pressure information on a display.

[Implementation Aspect 64]

The real-time blood pressure information output method according to Implementation Aspect 63, wherein the displaying is to display the real-time blood pressure information on the display when the living body has not input information to an information input apparatus for a predetermined length of time.

[Implementation Aspect 65]

The real-time blood pressure information output method according to Implementation Aspect 64, further comprising stopping displaying the real-time blood pressure information when information has been input to the information input apparatus.

[Implementation Aspect 66]

The real-time blood pressure information output method according to Implementation Aspect 64, wherein the information input apparatus is a keyboard or a mouse.

[Implementation Aspect 67]

The real-time blood pressure information output method according to Implementation Aspect 63, wherein the displaying is to display, as a screen saver, the real-time blood pressure information on the display.

[Implementation Aspect 68]

The real-time blood pressure information output method according to Implementation Aspect 61, further comprising transmitting the real-time blood pressure information to electronic equipment.

[Implementation Aspect 69]

The real-time blood pressure information output method according to Implementation Aspect 61, further comprising transmitting the real-time blood pressure information to a database at a medical institution.

[Implementation Aspect 70]

A healthcare screen saver computer, comprising:

a facial video input unit that receives an input of a facial video of a living body; and a blood pressure information display display that displays, as a screen saver, blood pressure information of the living body based on the facial video.

[Implementation Aspect 71]

A head mount display comprising:

a video input unit that receives an input of a video of a living body; and a blood pressure information display unit that displays blood pressure information based on the video.

[Implementation Aspect 72]

A wristwatch comprising:

a pulse waveform information acquiring unit that acquires pulse waveform information of a living body; and a blood pressure information display unit that displays blood pressure information based on the pulse waveform information.

[Implementation Aspect 73]

A blood pressure information output apparatus comprising:

a video receiving unit that receives a video of a living body acquired by a head mount display; and a blood pressure information output unit that outputs blood pressure information via wireless communication based on the video.

[Implementation Aspect 74]

The blood pressure information output apparatus according to Implementation Aspect 73, wherein the wireless communication is BlueTooth (registered trademark).

[Implementation Aspect 75]

The blood pressure information output apparatus according to Implementation Aspect 74, wherein the wireless communication is Wi-Fi (registered trademark).

[Implementation Aspect 76]

A blood pressure information output apparatus comprising:

a pulse waveform information receiving unit that receives pulse waveform information of a living body acquired by a wristwatch; and a blood pressure information output unit that outputs blood pressure information via wireless communication based on the pulse waveform information.

[Implementation Aspect 77]

The blood pressure information output apparatus according to Implementation Aspect 76, wherein the wireless communication is BlueTooth (registered trademark).

[Implementation Aspect 78]

The blood pressure information output apparatus according to Implementation Aspect 77, wherein the wireless communication is Wi-Fi (registered trademark).

[Implementation Aspect 79]

A blood pressure information output apparatus comprising:

a video input unit that receives an input of a video of a living body;

a video transmitting unit that transmits the video to a network server;

a blood pressure information receiving unit that receives blood pressure information from the network server; and a blood pressure information output unit that outputs the blood pressure information.

[Implementation Aspect 80]

A mood monitor comprising:

a video input unit that receives an input of a video of a living body; and a mood display unit that displays mood information of the living body based on the video.

[Implementation Aspect 81]

The mood monitor according to Implementation Aspect 80, wherein the video input unit receives an input of a video of a plurality of living bodies, and the mood display unit displays mood information of the plurality of living bodies.

[Implementation Aspect 82]

A mirror comprising:

a video input unit that receives an input of a video of a living body; and a blood pressure information display unit that displays blood pressure information of the living body based on the video.

[Implementation Aspect 83]

A health monitor comprising:

a camera that acquires a video of a living body on a bed; and a mobile device that receives the video to output blood pressure information of the living body.

[Implementation Aspect 84]

An operator monitoring system comprising:

an operation control room camera that acquires a video of a vehicle operator; and a physical condition information output computer that receives the video to output physical condition information of the operator.

[Implementation Aspect 85]

The operator monitoring system according to Implementation Aspect 84, further comprising an alarm output unit that receives the physical condition information to output an alarm.

[Implementation Aspect 86]

A player monitor system comprising:

a game controller that has a camera that acquires a video of a game player; and a game console main body that receives the video to transmit information of the game player to a network game server, and game progression of which is controlled by the network game server.

[Implementation Aspect 87]

A viewer monitoring system comprising:

a camera that receives an input of a video of a viewer; and a contents display control television that controls display of contents based on the video.

[Implementation Aspect 88]

The viewer monitoring system according to Implementation Aspect 87, wherein the contents display control television is shut down when the viewer is experiencing photosensitive epilepsy.

[Implementation Aspect 89]

The viewer monitoring system according to Implementation Aspect 87, wherein the contents display control television is shut down when having received contents that are likely to cause photosensitive epilepsy to the viewer.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

As made clear from the above, the embodiments of the present invention can be used to realize a pulse wave measuring device, a mobile device, a medical equipment system and a biological information communication system.

What is claimed is:

1. A pulse wave measuring apparatus comprising:
   a pulse waveform information acquiring unit that has a camera for acquiring video information including pulse waveform information from a region of a living body, configured to optically acquire the pulse waveform information from a video captured by the camera; and
   a pulse wave feature amount calculating unit connected to the pulse waveform information acquiring unit to calculate a pulse wave feature amount based on the pulse waveform information,
   wherein the pulse waveform information acquiring unit corrects a discrepancy of sampling rate of the pulse waveform information generated between a video sampling rate and a fixed sampling rate with the use of a reference signal indicating time, the video sampling rate referring to an actual sampling rate at which the pulse waveform information acquiring unit acquires video information, and the fixed sampling rate referring to an ideal frequency for the pulse waveform information acquiring unit to acquire videos.

2. The pulse wave measuring apparatus according to claim 1, wherein the reference signal is a timestamp included in a frame configuring the video.

3. The pulse wave measuring apparatus according to claim 1, wherein
the video includes light emitted by an illumination driven by an AC power supply, and
the reference signal is a signal according to a luminance frequency of the illumination.

4. The pulse wave measuring apparatus according to claim 1, wherein the pulse wave feature amount includes at least one of a pulse rate, a time interval of feature points of a pulse wave, and an amplitude of feature points of a pulse wave.

5. The pulse wave measuring apparatus according to claim 1, further comprising a health information estimating unit that is connected to the pulse wave feature amount calculating unit and estimates health information of the living body based on the pulse wave feature amount from the pulse wave feature amount calculating unit.

6. The pulse wave measuring apparatus according to claim 5, wherein
the pulse wave feature amount calculating unit has a pulse information calculating unit that calculates a pulse rate of the living body by frequency analysis based on the pulse waveform information, and calculates temporal information of a pulse wave of the living body based on the pulse waveform information, and
the health information estimating unit has a blood pressure information output unit that estimates and outputs blood pressure information of the living body based on the pulse rate and the temporal information.

7. The pulse wave measuring apparatus according to claim 6, wherein the temporal information includes at least one of rising time of the pulse wave, falling time of the pulse wave, and a length of time between any two points of a rising zero-cross point, a falling zero-cross point, a top peak and a bottom peak in a first-order differentiation signal corresponding to one pulse of the pulse wave.

8. The pulse wave measuring apparatus according to claim 6, wherein the temporal information includes at least either of rising time of the pulse wave or falling time of the pulse wave, and
the blood pressure information output unit estimates and outputs the blood pressure information based on a square of the temporal information.

9. The pulse wave measuring apparatus according to claim 6, wherein the pulse information calculating unit calculates the temporal information based on the pulse rate calculated by the frequency analysis and the pulse waveform information.

10. The pulse wave measuring apparatus according to claim 6, wherein the temporal information includes first time, and second time different from the first time, and
the pulse information calculating unit calculates independently each of the first time and the second time.

11. The pulse wave measuring apparatus according to claim 10, wherein the blood pressure information output unit:
estimates a systolic blood pressure of the living body based on the pulse rate and the first time;
estimates a diastolic blood pressure of the living body based on the pulse rate and the second time; and
outputs information indicating the estimated systolic blood pressure and the estimated diastolic blood pressure as the blood pressure information.

12. The pulse wave measuring apparatus according to claim 6, wherein
the temporal information includes rising time of the pulse wave and falling time of the pulse wave, and
the pulse information calculating unit calculates independently each of the rising time and the falling time.

13. The pulse wave measuring apparatus according to claim 12, wherein the blood pressure information output unit:
estimates a systolic blood pressure of the living body based on the pulse rate and the rising time;
estimates a diastolic blood pressure of the living body based on the pulse rate and the falling time; and
outputs information indicating the estimated systolic blood pressure and the estimated diastolic blood pressure as the blood pressure information.

14. The pulse wave measuring apparatus according to claim 13, wherein the blood pressure information output unit:
estimates a systolic blood pressure of the living body based on the pulse rate, the rising time, and a length of time between the rising zero-cross point and the top peak;
estimates a diastolic blood pressure of the living body based on the pulse rate, the falling time, and a length of time between the bottom peak and the rising zero-cross point; and
outputs information indicating the estimated systolic blood pressure and the estimated diastolic blood pressure as the blood pressure information.

15. The pulse wave measuring apparatus according to claim 5, wherein
the pulse wave feature amount calculating unit has a pulse information calculating unit that calculates a pulse rate of the living body and temporal information of a pulse wave of the living body based on the reflected light, and
the health information estimating unit has a blood pressure information output unit that estimates and outputs blood pressure information of the living body based on the pulse rate and the temporal information.

16. The pulse wave measuring apparatus according to claim 15, wherein the temporal information includes at least one of rising time of the pulse wave and falling time of the pulse wave.

17. The pulse wave measuring apparatus according to claim 16, wherein the pulse information calculating unit includes:
a pulse wave component signal extracting unit that extracts a pulse wave component signal of the living body from the reflected light;
a pulse rate calculating unit that calculates a pulse rate of the living body from the pulse wave component signal; and
a temporal information calculating unit that calculates at least one of the rising time and the falling time from the pulse wave component signal.

18. The pulse wave measuring apparatus according to claim 17, wherein the pulse rate calculating unit calculates the pulse rate based on a result of frequency analysis on the pulse wave component signal.

19. The pulse wave measuring apparatus according to claim 18, wherein the frequency analysis is FFT analysis or wavelet analysis.

20. The pulse wave measuring apparatus according to claim 17, wherein the temporal information calculating unit calculates the temporal information based on first-order differentiation of the pulse wave component signal.

21. The pulse wave measuring apparatus according to claim 17, wherein
the temporal information includes first time, and second time different from the first time, and the pulse information calculating unit calculates independently each of the first time and the second time.

22. The pulse wave measuring apparatus according to claim 21, wherein the blood pressure information output unit:
estimates a systolic blood pressure of the living body based on the pulse rate and the first time;
estimates a diastolic blood pressure of the living body based on the pulse rate and the second time, and
outputs information indicating the estimated systolic blood pressure and the estimated diastolic blood pressure as the blood pressure information.

23. The pulse wave measuring apparatus according to claim 17, wherein
the temporal information includes the rising time and the falling time, and
the pulse information calculating unit calculates independently each of the rising time and the falling time.

24. The pulse wave measuring apparatus according to claim 23, wherein the blood pressure information output unit:
estimates a systolic blood pressure of the living body based on the pulse rate and the rising time;
estimates a diastolic blood pressure of the living body based on the pulse rate and the falling time; and
outputs information indicating the estimated systolic blood pressure and the estimated diastolic blood pressure as the blood pressure information.

25. The pulse wave measuring apparatus according to claim 17, wherein
the pulse information calculating unit further calculates a length of time between a rising zero-cross point and a top peak and a length of time between a bottom peak and a rising zero-cross point in a first-order differentiation signal corresponding to one pulse of the pulse wave component signal, and
the blood pressure information output unit estimates and outputs the blood pressure information based further on a length of time between the rising zero-cross point and the top peak and a length of time between the bottom peak and the rising zero-cross point.

26. The pulse wave measuring apparatus according to claim 25, wherein the blood pressure information output unit:
estimates a systolic blood pressure of the living body based on the pulse rate, the rising time, and a length of time between the rising zero-cross point and the top peak:
estimates a diastolic blood pressure of the living body based on the pulse rate, the falling time, and a length of time between the bottom peak and the rising zero-cross point; and
outputs information indicating the estimated systolic blood pressure and the estimated diastolic blood pressure as the blood pressure information.

27. The pulse wave measuring apparatus according to claim 15, wherein the blood pressure information output unit estimates and outputs the blood pressure information based on a square of the temporal information.

28. The pulse wave measuring apparatus according to claim 5, further comprising an attribute information acquiring unit that acquires attribute information of the living body from the pulse waveform information or the video of the region of the living body, wherein
the health information estimating unit estimates health information of the living body based on the attribute information and the pulse wave feature amount.

29. The pulse wave measuring apparatus according to claim 28, wherein the attribute information includes at least one of a sex, an age, a generation, a blood type, a birthplace, a nationality, a mother tongue, a race and a build.

30. A mobile device comprising:
the pulse wave measuring apparatus according to claim 28; and
a display that displays at least either of the attribute information and the health information.

31. The mobile device according to claim 30, wherein
the pulse wave measuring apparatus further has a personal identification information acquiring unit that acquires personal identification information of the living body from the video,
the mobile device further comprises a storage unit that memorizes the personal identification information and past health information of the living body,
health information of the living body is estimated when personal identification information memorized in the storage unit and personal identification information acquired by the personal identification information acquiring unit match, and
health information of the living body is not estimated when the personal identification information memorized in the storage unit and personal identification information acquired by the personal identification information acquiring unit do not match.

32. A medical equipment system comprising:
the pulse wave measuring apparatus according to claim 5; and
medical equipment controlled based on the health information.

33. The medical equipment system according to claim 32, wherein the medical equipment is a dialysis apparatus that controls a dialysis flow rate based on the health information.

34. The medical equipment system according to claim 33, wherein the pulse wave measuring apparatus controls the dialysis flow rate of the dialysis apparatus based on the health information.

35. The medical equipment system according to claim 33, wherein the health information is blood pressure information.

36. The medical equipment system according to claim 33, wherein the pulse wave measuring apparatus or the dialysis apparatus transmits the health information to a data management system at a medical institution.

37. The medical equipment system according to claim 36, wherein the pulse wave measuring apparatus or the dialysis apparatus:
transmits the health information or an alarm to the data management system when the health information is not within a predetermined range, and
does not transmit the health information or an alarm to the data management system when the health information is within the predetermined range.

38. The medical equipment system according to claim 37, wherein upon receiving the health information or the alarm, the data management system outputs an alarm.

39. The medical equipment system according to claim 33, wherein the dialysis apparatus has a display that displays the health information.

40. A biological information communication system, having a plurality of the pulse wave measuring apparatuses according to claim 5 and comprising a correlation judging unit that judges respective correlations of a plurality of pulse wave feature amounts or pieces of health information calculated by the plurality of the pulse wave measuring apparatuses, wherein
when there is a correlation that is higher than a predetermined value among the respective correlations, the correlation judging unit transmits, to a pulse wave measuring apparatus that calculates a corresponding pulse wave feature amount among the plurality of pulse wave feature amounts, information indicating that the correlation is higher than the predetermined value.

41. A biological information communication system having the two pulse wave measuring apparatuses according to claim 5, wherein
at least one of the two pulse wave measuring apparatuses judges a correlation of two pulse wave feature amounts calculated by the two pulse wave measuring apparatuses, and when the correlation is higher than a predetermined value, outputs information indicating that the correlation is higher than the predetermined value.

42. The pulse wave measuring apparatus according to claim 6, wherein the pulse waveform information acquiring unit optically acquires the pulse waveform information from the video of a nose of the living body.

43. The pulse wave measuring apparatus according to claim 6, wherein the pulse waveform information acquiring unit optically acquires the pulse waveform information from the video of a fingertip of the living body.

44. The pulse wave measuring apparatus according to claim 6, wherein the blood pressure information output unit estimates and outputs the blood pressure information that indicates at least one of a blood pressure, a blood pressure state, arteriosclerosis, a vascular age and a predisposition to stroke.

45. The pulse wave measuring apparatus according to claim 1, wherein the pulse waveform information acquiring unit includes:
a transform unit that acquire a video pulse wave signal from the video;
a pulse wave trace signal detector that detects a pulse wave trace signal obtained based on the video pulse wave signal;
a band pass filter that filters the pulse wave trace signal; and
a sampling rate varying unit that varies the sampling rate.

46. The pulse wave measuring apparatus according to claim 1, wherein the reference signal is a timestamp acquired in association with a video of a measurement subject.

47. The pulse wave measuring apparatus according to claim 1, wherein the pulse waveform information acquiring unit corrects the discrepancy of the sampling rate of the pulse waveform information by performing an interpolation to the pulse waveform information.

48. The pulse wave measuring apparatus according to claim 47, wherein the interpolation is one of a spline interpolation, a Lagrange interpolation and a linear interpolation.

49. The pulse wave measuring apparatus according to claim 1, further comprising:
a RGB/YCbCr transform unit configured to transform the video information into video signals, and to acquire a video pulse wave signal from the video signals, and
a pulse wave trace signal detection unit configured to detect a pulse wave trace signal obtained by plotting a value of any clock time based on the video pulse wave signal,
wherein the pulse waveform information is the pulse wave trace signal.

* * * * *